United States Patent
Benatuil et al.

(10) Patent No.: US 10,093,733 B2
(45) Date of Patent: Oct. 9, 2018

(54) LRP-8 BINDING DUAL VARIABLE DOMAIN IMMUNOGLOBULIN PROTEINS

(71) Applicant: AbbVie Inc., North Chicago, IL (US)

(72) Inventors: Lorenzo Benatuil, Northborough, MA (US); Kangwen Deng, Shrewsbury, MA (US); Denise Karaoglu Hanzatian, Natick, MA (US); Maria A. Argiriadi, Southborough, MA (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/967,260

(22) Filed: Dec. 11, 2015

(65) Prior Publication Data

US 2016/0200813 A1 Jul. 14, 2016

Related U.S. Application Data

(60) Provisional application No. 62/090,878, filed on Dec. 11, 2014.

(51) Int. Cl.
| | |
|---|---|
| *C07K 16/28* | (2006.01) |
| *C07K 16/46* | (2006.01) |
| *G01N 33/53* | (2006.01) |
| *C07K 14/705* | (2006.01) |
| *A61K 39/395* | (2006.01) |
| *A61K 45/06* | (2006.01) |
| *G01N 33/566* | (2006.01) |
| *A61K 38/00* | (2006.01) |
| *A61K 47/68* | (2017.01) |
| *A61K 39/00* | (2006.01) |

(52) U.S. Cl.
CPC .............. *C07K 16/28* (2013.01); *A61K 38/00* (2013.01); *A61K 39/3955* (2013.01); *A61K 45/06* (2013.01); *A61K 47/6849* (2017.08); *C07K 14/705* (2013.01); *C07K 16/468* (2013.01); *G01N 33/53* (2013.01); *G01N 33/566* (2013.01); *A61K 2039/505* (2013.01); *C07K 2317/24* (2013.01); *C07K 2317/31* (2013.01); *C07K 2317/33* (2013.01); *C07K 2317/34* (2013.01); *C07K 2317/56* (2013.01); *C07K 2317/565* (2013.01); *C07K 2317/76* (2013.01); *C07K 2317/92* (2013.01); *G01N 2333/705* (2013.01)

(58) Field of Classification Search
None
See application file for complete search history.

(56) References Cited

U.S. PATENT DOCUMENTS

| | | | |
|---|---|---|---|
| 4,526,938 A | 7/1985 | Churchill et al. | |
| 4,554,101 A | 11/1985 | Hopp | |
| 4,699,784 A | 10/1987 | Shih et al. | |
| 4,753,894 A | 6/1988 | Frankel et al. | |
| 4,816,567 A | 3/1989 | Cabilly et al. | |
| 4,880,780 A | 11/1989 | Trainor et al. | |
| 4,943,533 A | 7/1990 | Mendelsohn et al. | |
| 4,946,778 A | 8/1990 | Ladner et al. | |
| 4,980,286 A | 12/1990 | Morgan et al. | |
| 5,006,309 A | 4/1991 | Khalil et al. | |
| 5,063,081 A | 11/1991 | Cozzette et al. | |
| 5,089,424 A | 2/1992 | Khalil et al. | |
| 5,128,326 A | 7/1992 | Balazs et al. | |
| 5,223,409 A | 6/1993 | Ladner et al. | |
| 5,225,539 A | 7/1993 | Winter | |
| 5,258,498 A | 11/1993 | Huston et al. | |
| 5,290,540 A | 3/1994 | Prince et al. | |
| 5,294,404 A | 3/1994 | Grandone et al. | |
| 5,403,484 A | 4/1995 | Ladner et al. | |
| 5,427,908 A | 6/1995 | Dower et al. | |
| 5,500,362 A | 3/1996 | Robinson et al. | |
| 5,516,637 A | 5/1996 | Huang et al. | |
| 5,530,101 A | 6/1996 | Queen et al. | |
| 5,558,864 A | 9/1996 | Bendig et al. | |
| 5,565,332 A | 10/1996 | Hoogenboom et al. | |
| 5,565,352 A | 10/1996 | Hochstrasser et al. | |
| 5,571,698 A | 11/1996 | Ladner et al. | |
| 5,580,717 A | 12/1996 | Dower et al. | |
| 5,585,089 A | 12/1996 | Queen et al. | |
| 5,624,821 A | 4/1997 | Winter et al. | |
| 5,627,052 A | 5/1997 | Schrader | |
| 5,641,870 A | 6/1997 | Rinderknecht et al. | |
| 5,648,260 A | 7/1997 | Winter et al. | |
| 5,656,272 A | 8/1997 | Le et al. | |
| 5,658,727 A | 8/1997 | Barbas et al. | |
| 5,677,171 A | 10/1997 | Hudziak et al. | |
| 5,679,377 A | 10/1997 | Bernstein et al. | |
| 5,693,762 A | 12/1997 | Queen et al. | |
| 5,698,426 A | 12/1997 | Huse | |
| 5,714,350 A | 2/1998 | Co et al. | |
| 5,714,352 A | 2/1998 | Jakobovits | |

(Continued)

FOREIGN PATENT DOCUMENTS

| | | |
|---|---|---|
| CN | 1276428 A | 12/2000 |
| CN | 101058609 A | 10/2007 |

(Continued)

OTHER PUBLICATIONS

"Adalimumab," in *The Merck Index*. 14th Ed., John Wiley & Sons, 2006; pp. 26-27.

(Continued)

*Primary Examiner* — Zachary C Howard

(74) *Attorney, Agent, or Firm* — Sterne, Kessler, Goldstein & Fox P.L.L.C.

(57) ABSTRACT

The disclosure provides binding proteins that specifically bind to LRP-8 and optionally cross the blood brain barrier (BBB), localize to the brain and/or localize to the spinal cord.

25 Claims, 34 Drawing Sheets

Specification includes a Sequence Listing.

(56) References Cited

U.S. PATENT DOCUMENTS

| | | |
|---|---|---|
| 5,723,323 A | 3/1998 | Kauffman et al. |
| 5,733,743 A | 3/1998 | Johnson et al. |
| 5,736,137 A | 4/1998 | Anderson et al. |
| 5,750,753 A | 5/1998 | Kimae et al. |
| 5,763,192 A | 6/1998 | Kauffman et al. |
| 5,766,886 A | 6/1998 | Studnicka et al. |
| 5,776,456 A | 7/1998 | Anderson et al. |
| 5,780,225 A | 7/1998 | Wigler et al. |
| 5,789,554 A | 8/1998 | Leung et al. |
| 5,795,965 A | 8/1998 | Tsuchiya et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,846,765 A | 12/1998 | Matthews et al. |
| 5,849,500 A | 12/1998 | Breitling et al. |
| 5,855,913 A | 1/1999 | Hanes et al. |
| 5,863,765 A | 1/1999 | Berry et al. |
| 5,874,064 A | 2/1999 | Edwards et al. |
| 5,891,996 A | 4/1999 | Mateo de Acosta del Rio et al. |
| 5,912,015 A | 6/1999 | Bernstein et al. |
| 5,916,597 A | 6/1999 | Lee et al. |
| 5,916,771 A | 6/1999 | Hori et al. |
| 5,929,212 A | 7/1999 | Jolliffe et al. |
| 5,934,272 A | 8/1999 | Lloyd et al. |
| 5,939,598 A | 8/1999 | Kucherlapati et al. |
| 5,959,083 A | 9/1999 | Bosslet et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,588 A | 11/1999 | Breitling et al. |
| 5,985,615 A | 11/1999 | Jakobovits et al. |
| 5,989,463 A | 11/1999 | Tracy et al. |
| 5,989,830 A | 11/1999 | Davis et al. |
| 5,998,209 A | 12/1999 | Jokobovits et al. |
| 6,019,968 A | 2/2000 | Platz et al. |
| 6,054,297 A | 4/2000 | Carter et al. |
| 6,057,098 A | 5/2000 | Buechler et al. |
| 6,066,719 A | 5/2000 | Zapata |
| 6,075,181 A | 6/2000 | Kucherlapati et al. |
| 6,090,382 A | 7/2000 | Salfeld et al. |
| 6,091,001 A | 7/2000 | Jakobovits et al. |
| 6,114,598 A | 9/2000 | Kucherlapati et al. |
| 6,127,132 A | 10/2000 | Breitling et al. |
| 6,130,364 A | 10/2000 | Jakobovits et al. |
| 6,180,370 B1 | 1/2001 | Queen et al. |
| 6,204,023 B1 | 3/2001 | Robinson et al. |
| 6,214,984 B1 | 4/2001 | Zapata |
| 6,235,883 B1 | 5/2001 | Jakobovits et al. |
| 6,239,259 B1 | 5/2001 | Davis et al. |
| 6,258,562 B1 | 7/2001 | Salfeld et al. |
| 6,350,861 B1 | 2/2002 | Co et al. |
| 6,387,627 B1 | 5/2002 | Breitling et al. |
| 6,491,916 B1 | 12/2002 | Bluestone et al. |
| 6,506,883 B2 | 1/2003 | Meteo de Acosta del Rio et al. |
| 6,509,015 B1 | 1/2003 | Salfeld et al. |
| 6,639,055 B1 | 10/2003 | Carter et al. |
| 6,660,843 B1 | 12/2003 | Feige et al. |
| 6,699,473 B2 | 3/2004 | Raisch et al. |
| 6,699,658 B1 | 3/2004 | Wittrup et al. |
| 6,730,483 B2 | 5/2004 | Breitling et al. |
| 6,818,392 B2 | 11/2004 | Lou et al. |
| 6,884,879 B1 | 4/2005 | Baca et al. |
| 6,914,128 B1 | 7/2005 | Salfeld et al. |
| 6,986,890 B1 | 1/2006 | Shitara et al. |
| 7,060,269 B1 | 6/2006 | Baca et al. |
| 7,060,808 B1 | 6/2006 | Goldstein et al. |
| 7,070,775 B2 | 7/2006 | Le et al. |
| 7,179,892 B2 | 2/2007 | Basi et al. |
| 7,189,819 B2 | 3/2007 | Basi et al. |
| 7,202,343 B2 | 4/2007 | Gudas et al. |
| 7,241,733 B2 | 7/2007 | Heavner et al. |
| 7,247,301 B2 | 7/2007 | van de Winkel et al. |
| 7,247,304 B2 | 7/2007 | van de Winkel et al. |
| 7,258,857 B2 | 8/2007 | Stern et al. |
| 7,262,028 B2 | 8/2007 | Van Berkel et al. |
| 7,285,269 B2 | 10/2007 | Babcook et al. |
| 7,317,091 B2 | 1/2008 | Lazar et al. |
| 7,419,821 B2 | 9/2008 | Davis et al. |
| 7,429,486 B2 | 9/2008 | Van Berkel et al. |
| 7,438,911 B2 | 10/2008 | Shitara et al. |
| 7,446,175 B2 | 11/2008 | Gram et al. |
| 7,446,179 B2 | 11/2008 | Jensen et al. |
| 7,449,616 B2 | 11/2008 | Pons et al. |
| 7,491,516 B2 | 2/2009 | Collinson et al. |
| 7,528,236 B2 | 5/2009 | Fong et al. |
| 7,566,772 B2 | 7/2009 | Green et al. |
| 7,592,429 B2 | 9/2009 | Paszty et al. |
| 7,612,181 B2 | 11/2009 | Wu et al. |
| 7,682,833 B2 | 3/2010 | Miller et al. |
| 7,727,527 B2 | 6/2010 | Shelton |
| 7,790,858 B2 | 9/2010 | Presta |
| 7,863,419 B2 | 1/2011 | Taylor et al. |
| 7,915,388 B2 | 3/2011 | Wu et al. |
| 7,928,205 B2 | 4/2011 | Dillon et al. |
| 8,187,836 B2 | 5/2012 | Hsieh |
| 8,258,268 B2 | 9/2012 | Wu et al. |
| 8,268,314 B2 | 9/2012 | Baehner et al. |
| 8,388,965 B2 | 3/2013 | Rao et al. |
| 8,389,237 B2 | 3/2013 | Skerry et al. |
| 8,420,783 B2 | 4/2013 | Goldenberg et al. |
| 8,455,219 B2 | 6/2013 | Hsieh |
| 8,586,714 B2 | 11/2013 | Ghayur et al. |
| 8,623,358 B2 | 1/2014 | Benatuil et al. |
| 8,624,002 B2 | 1/2014 | Gu et al. |
| 8,664,367 B2 | 3/2014 | Wu et al. |
| 8,716,450 B2 | 5/2014 | Ghayur et al. |
| 8,722,855 B2 | 5/2014 | Ghayur et al. |
| 8,735,546 B2 | 5/2014 | Ghayur et al. |
| 8,779,101 B2 | 7/2014 | Hsieh et al. |
| 8,822,645 B2 | 9/2014 | Ghayur et al. |
| 8,835,610 B2 | 9/2014 | Hsieh et al. |
| 8,841,417 B2 | 9/2014 | Wu et al. |
| 8,853,365 B2 | 10/2014 | Wu et al. |
| 8,858,941 B2 | 10/2014 | Gurney et al. |
| 8,889,130 B2 | 11/2014 | Kamath |
| 8,987,418 B2 | 3/2015 | Ghayur et al. |
| 9,029,508 B2 | 5/2015 | Ghayur et al. |
| 9,035,027 B2 | 5/2015 | Ghayur et al. |
| 9,045,551 B2 | 6/2015 | Gu et al. |
| 9,046,513 B2 | 6/2015 | Ghayur et al. |
| 9,062,108 B2 | 6/2015 | Ghayur et al. |
| 9,109,026 B2 | 8/2015 | Ghayur et al. |
| 9,115,195 B2 | 8/2015 | Chen et al. |
| 9,120,870 B2 | 9/2015 | Hsieh et al. |
| 9,132,190 B2 | 9/2015 | Benatuil et al. |
| 2002/0004587 A1 | 1/2002 | Miller et al. |
| 2002/0127231 A1 | 9/2002 | Schneck et al. |
| 2002/0136719 A1 | 9/2002 | Shenoy et al. |
| 2002/0137134 A1 | 9/2002 | Gerngross |
| 2003/0039645 A1 | 2/2003 | Adair et al. |
| 2003/0091561 A1 | 5/2003 | van de Winkel et al. |
| 2003/0092059 A1 | 5/2003 | Salfeld et al. |
| 2003/0118583 A1 | 6/2003 | Emery et al. |
| 2003/0165496 A1 | 9/2003 | Basi et al. |
| 2003/0186374 A1 | 10/2003 | Hufton et al. |
| 2003/0206898 A1 | 11/2003 | Fischkoff et al. |
| 2003/0226155 A1 | 12/2003 | Sadeghi et al. |
| 2004/0018577 A1 | 1/2004 | Emerson Campbell et al. |
| 2004/0018590 A1 | 1/2004 | Gerngross et al. |
| 2004/0038339 A1 | 2/2004 | Kufer et al. |
| 2004/0133357 A1 | 7/2004 | Zhong et al. |
| 2004/0162411 A1 | 8/2004 | Lanzavecchia |
| 2004/0219144 A1 | 11/2004 | Shelton |
| 2004/0237124 A1 | 11/2004 | Pons et al. |
| 2004/0241745 A1 | 12/2004 | Honjo et al. |
| 2005/0026881 A1 | 2/2005 | Robinson et al. |
| 2005/0038231 A1 | 2/2005 | Fahrner et al. |
| 2005/0042664 A1 | 2/2005 | Wu et al. |
| 2005/0095246 A1 | 5/2005 | Shafer |
| 2005/0118643 A1 | 6/2005 | Burgess et al. |
| 2005/0147610 A1 | 7/2005 | Ghayur et al. |
| 2005/0215769 A1 | 9/2005 | Breece et al. |

(56) References Cited

U.S. PATENT DOCUMENTS

| | | |
|---|---|---|
| 2005/0260204 A1 | 11/2005 | Allan |
| 2006/0002923 A1 | 1/2006 | Uede et al. |
| 2006/0024300 A1 | 2/2006 | Adams et al. |
| 2006/0041058 A1 | 2/2006 | Yin et al. |
| 2006/0067930 A1 | 3/2006 | Adams et al. |
| 2006/0073141 A1 | 4/2006 | Ignatovich et al. |
| 2006/0078967 A1 | 4/2006 | Medlock et al. |
| 2006/0093599 A1 | 5/2006 | Gazit-Bornstein et al. |
| 2006/0104968 A1 | 5/2006 | Bookbinder et al. |
| 2006/0134105 A1 | 6/2006 | Lazar et al. |
| 2006/0160164 A1 | 7/2006 | Miller et al. |
| 2006/0233791 A1 | 10/2006 | Tedder et al. |
| 2006/0246071 A1 | 11/2006 | Green et al. |
| 2006/0253100 A1 | 11/2006 | Burright et al. |
| 2006/0280747 A1 | 12/2006 | Fuh et al. |
| 2007/0041905 A1 | 2/2007 | Hoffman et al. |
| 2007/0042458 A1 | 2/2007 | DeFrees et al. |
| 2007/0071675 A1 | 3/2007 | Wu et al. |
| 2007/0071745 A1 | 3/2007 | Umana et al. |
| 2007/0072225 A1 | 3/2007 | Alving |
| 2007/0092507 A1 | 4/2007 | Balthasar et al. |
| 2007/0092520 A1 | 4/2007 | Dennis et al. |
| 2007/0110747 A1 | 5/2007 | Paszty et al. |
| 2007/0123479 A1 | 5/2007 | Kufer et al. |
| 2007/0196376 A1 | 8/2007 | Raeber et al. |
| 2007/0232556 A1 | 10/2007 | Montine et al. |
| 2007/0286858 A1 | 12/2007 | Clancy et al. |
| 2007/0292420 A1 | 12/2007 | Giles-Komar et al. |
| 2008/0014196 A1 | 1/2008 | Yan |
| 2008/0015194 A1 | 1/2008 | Errico et al. |
| 2008/0038257 A1 | 2/2008 | Han et al. |
| 2008/0112888 A1 | 5/2008 | Wang |
| 2008/0118506 A1 | 5/2008 | An et al. |
| 2008/0118978 A1 | 5/2008 | Sato et al. |
| 2008/0171014 A1 | 7/2008 | Wu et al. |
| 2008/0175847 A1 | 7/2008 | Yan et al. |
| 2008/0187966 A1 | 8/2008 | Simmons |
| 2008/0193455 A1 | 8/2008 | Stassen et al. |
| 2008/0219971 A1 | 9/2008 | Smith et al. |
| 2008/0241163 A1 | 10/2008 | Burkly et al. |
| 2009/0028851 A1 | 1/2009 | Stuhmer et al. |
| 2009/0030308 A1 | 1/2009 | Bradford et al. |
| 2009/0035308 A1 | 2/2009 | Gill et al. |
| 2009/0042214 A1 | 2/2009 | Cooke et al. |
| 2009/0048122 A1 | 2/2009 | Glaser et al. |
| 2009/0053243 A1 | 2/2009 | Kurosawa et al. |
| 2009/0068195 A1 | 3/2009 | Vugmeyster et al. |
| 2009/0081234 A1 | 3/2009 | Heavner et al. |
| 2009/0148513 A1 | 6/2009 | Fraunhofer et al. |
| 2009/0155257 A1 | 6/2009 | Adams et al. |
| 2009/0155275 A1 | 6/2009 | Wu et al. |
| 2009/0191225 A1 | 7/2009 | Chang et al. |
| 2009/0208490 A1 | 8/2009 | Pavone et al. |
| 2009/0215992 A1 | 8/2009 | Wu et al. |
| 2009/0239259 A1 | 9/2009 | Hsieh |
| 2009/0259026 A1 | 10/2009 | Tomlinson et al. |
| 2009/0304693 A1 | 12/2009 | Ghayur et al. |
| 2009/0311253 A1 | 12/2009 | Ghayur et al. |
| 2010/0028340 A1 | 2/2010 | Mueller et al. |
| 2010/0047239 A1 | 2/2010 | Wu et al. |
| 2010/0056762 A1 | 3/2010 | Old |
| 2010/0076178 A1 | 3/2010 | Ghayur et al. |
| 2010/0104573 A1 | 4/2010 | Burkly et al. |
| 2010/0105569 A1 | 4/2010 | Hsieh et al. |
| 2010/0158901 A1 | 6/2010 | Tedder et al. |
| 2010/0190247 A1 | 7/2010 | Lazar et al. |
| 2010/0210511 A1 | 8/2010 | Carvajal |
| 2010/0233079 A1 | 9/2010 | Jakob et al. |
| 2010/0260668 A1 | 10/2010 | Ghayur et al. |
| 2010/0266531 A1 | 10/2010 | Hsieh et al. |
| 2011/0008766 A1 | 1/2011 | Ghayur et al. |
| 2011/0044980 A1 | 2/2011 | Ghayur et al. |
| 2011/0091463 A1 | 4/2011 | Ghayur et al. |
| 2011/0142761 A1 | 6/2011 | Wu et al. |
| 2011/0150870 A1 | 6/2011 | Rader et al. |
| 2011/0217237 A1 | 9/2011 | Chen et al. |
| 2011/0229476 A1 | 9/2011 | Liu et al. |
| 2011/0263827 A1 | 10/2011 | Ghayur et al. |
| 2011/0318349 A1 | 12/2011 | Ghayur et al. |
| 2012/0014957 A1 | 1/2012 | Ghayur et al. |
| 2012/0087858 A1 | 4/2012 | Ghayur et al. |
| 2012/0201746 A1 | 8/2012 | Liu et al. |
| 2012/0258108 A1 | 10/2012 | Ghayur et al. |
| 2012/0263722 A1 | 10/2012 | Ghayur et al. |
| 2013/0004416 A1 | 1/2013 | Wu et al. |
| 2013/0164256 A1 | 6/2013 | Hsieh et al. |
| 2013/0171059 A1 | 7/2013 | Ghayur et al. |
| 2013/0171096 A1 | 7/2013 | Hsieh et al. |
| 2013/0195871 A1 | 8/2013 | Ghayur et al. |
| 2013/0236458 A1 | 9/2013 | Hsieh et al. |
| 2013/0344537 A1 | 12/2013 | Hsieh |
| 2014/0079705 A1 | 3/2014 | Hsieh et al. |
| 2014/0093521 A1 | 4/2014 | Benatuil et al. |
| 2014/0099671 A1 | 4/2014 | Wu et al. |
| 2014/0134171 A1 | 5/2014 | Ghayur et al. |
| 2014/0134172 A1 | 5/2014 | Gu et al. |
| 2014/0161804 A1 | 6/2014 | Cuff et al. |
| 2014/0161817 A1 | 6/2014 | Siedler et al. |
| 2014/0170152 A1 | 6/2014 | Hsieh et al. |
| 2014/0186377 A1 | 7/2014 | Gu et al. |
| 2014/0212379 A1 | 7/2014 | Wu et al. |
| 2014/0212423 A1 | 7/2014 | Hanzatian et al. |
| 2014/0212925 A1 | 7/2014 | Wu et al. |
| 2014/0213771 A1 | 7/2014 | Ghayur et al. |
| 2014/0213772 A1 | 7/2014 | Ghayur et al. |
| 2014/0219912 A1 | 8/2014 | Ghayur et al. |
| 2014/0219913 A1 | 8/2014 | Ghayur et al. |
| 2014/0220019 A1 | 8/2014 | Ghayur et al. |
| 2014/0220020 A1 | 8/2014 | Wu et al. |
| 2014/0221621 A1 | 8/2014 | Benatuil et al. |
| 2014/0221622 A1 | 8/2014 | Ghayur et al. |
| 2014/0234208 A1 | 8/2014 | Ghayur et al. |
| 2014/0235476 A1 | 8/2014 | Gu et al. |
| 2014/0243228 A1 | 8/2014 | Benatuil et al. |
| 2014/0271457 A1 | 9/2014 | Ghayur et al. |
| 2014/0271458 A1 | 9/2014 | Ghayur et al. |
| 2014/0308286 A1 | 10/2014 | Ghayur et al. |
| 2014/0335014 A1 | 11/2014 | Ghayur et al. |
| 2014/0335564 A1 | 11/2014 | Hsieh et al. |
| 2014/0343267 A1 | 11/2014 | Hsieh et al. |
| 2014/0348834 A1 | 11/2014 | Hsieh et al. |
| 2014/0348835 A1 | 11/2014 | Gu et al. |
| 2014/0348838 A1 | 11/2014 | Tarcsa |
| 2014/0348856 A1 | 11/2014 | Hsieh et al. |
| 2014/0356281 A1 | 12/2014 | Ghayur et al. |
| 2014/0356909 A1 | 12/2014 | Hsieh et al. |
| 2015/0017095 A1 | 1/2015 | Ghayur et al. |
| 2015/0017168 A1 | 1/2015 | Ghayur et al. |
| 2015/0050238 A1 | 2/2015 | Kamath |
| 2015/0104452 A1 | 4/2015 | Ghayur et al. |
| 2015/0183867 A1 | 7/2015 | Ghayur et al. |
| 2015/0291689 A1 | 10/2015 | Padley et al. |
| 2015/0315283 A1 | 11/2015 | Ghayur et al. |
| 2015/0344566 A1 | 12/2015 | Hsieh et al. |
| 2015/0344590 A1 | 12/2015 | Ghayur et al. |
| 2016/0002343 A1 | 1/2016 | Hanzatian et al. |
| 2016/0031986 A1 | 2/2016 | Chen et al. |
| 2016/0032000 A1 | 2/2016 | Ghayur et al. |
| 2016/0060332 A1 | 3/2016 | Benatuil et al. |
| 2016/0122439 A1 | 5/2016 | Gu et al. |

FOREIGN PATENT DOCUMENTS

| | | |
|---|---|---|
| EP | 0 148 075 A2 | 7/1985 |
| EP | 0 517 024 A2 | 12/1992 |
| EP | 0 592 106 A1 | 4/1994 |
| EP | 0 239 400 B1 | 8/1994 |
| EP | 1 176 195 A1 | 1/2002 |
| EP | 1 454 917 A2 | 9/2004 |
| EP | 0 592 106 B1 | 11/2004 |
| EP | 0 519 596 B1 | 2/2005 |
| RU | 2 273 664 C2 | 4/2006 |
| WO | WO 89/06692 A1 | 7/1989 |

(56) References Cited

FOREIGN PATENT DOCUMENTS

| | | |
|---|---|---|
| WO | WO 90/02809 A1 | 3/1990 |
| WO | WO 90/05144 A1 | 5/1990 |
| WO | WO 90/05183 A1 | 5/1990 |
| WO | WO 90/14424 A1 | 11/1990 |
| WO | WO 90/14430 A1 | 11/1990 |
| WO | WO 90/14443 A1 | 11/1990 |
| WO | WO 91/05548 A1 | 5/1991 |
| WO | WO 91/09967 A1 | 7/1991 |
| WO | WO 91/10737 A1 | 7/1991 |
| WO | WO 91/10741 A1 | 7/1991 |
| WO | WO 91/17271 A1 | 11/1991 |
| WO | WO 91/18983 A1 | 12/1991 |
| WO | WO 92/01047 A1 | 1/1992 |
| WO | WO 92/02551 A1 | 2/1992 |
| WO | WO 92/03461 A1 | 3/1992 |
| WO | WO 92/09690 A2 | 6/1992 |
| WO | WO 92/11272 A1 | 7/1992 |
| WO | WO 92/15679 A1 | 9/1992 |
| WO | WO 92/16553 A1 | 10/1992 |
| WO | WO 92/18619 A1 | 10/1992 |
| WO | WO 92/19244 A2 | 11/1992 |
| WO | WO 92/20791 A1 | 11/1992 |
| WO | WO 92/22324 A1 | 12/1992 |
| WO | WO 92/22653 A1 | 12/1992 |
| WO | WO 93/01288 A1 | 1/1993 |
| WO | WO 93/06213 A1 | 4/1993 |
| WO | WO 93/11161 A1 | 6/1993 |
| WO | WO 93/11236 A1 | 6/1993 |
| WO | WO 94/02602 A1 | 2/1994 |
| WO | WO 94/11026 A1 | 5/1994 |
| WO | WO 94/18219 A1 | 8/1994 |
| WO | WO 95/01997 A1 | 1/1995 |
| WO | WO 95/09917 A1 | 4/1995 |
| WO | WO 95/14780 A2 | 6/1995 |
| WO | WO 95/15982 A2 | 6/1995 |
| WO | WO 95/16026 A1 | 6/1995 |
| WO | WO 95/20045 A1 | 7/1995 |
| WO | WO 95/20401 A1 | 8/1995 |
| WO | WO 95/24918 A1 | 9/1995 |
| WO | WO 95/25167 A1 | 9/1995 |
| WO | WO 96/20698 A2 | 7/1996 |
| WO | WO 96/33735 A1 | 10/1996 |
| WO | WO 96/34096 A1 | 10/1996 |
| WO | WO 96/40210 A1 | 12/1996 |
| WO | WO 97/20032 A1 | 6/1997 |
| WO | WO 97/29131 A1 | 8/1997 |
| WO | WO 97/32572 A2 | 9/1997 |
| WO | WO 97/44013 A1 | 11/1997 |
| WO | WO 98/16654 A1 | 4/1998 |
| WO | WO 98/24893 A2 | 6/1998 |
| WO | WO 98/31346 A1 | 7/1998 |
| WO | WO 98/31700 A1 | 7/1998 |
| WO | WO 98/45331 A2 | 10/1998 |
| WO | WO 98/50433 A2 | 11/1998 |
| WO | WO 99/06834 A2 | 2/1999 |
| WO | WO 99/15154 A1 | 4/1999 |
| WO | WO 99/20253 A1 | 4/1999 |
| WO | WO 99/23221 A2 | 5/1999 |
| WO | WO 99/45031 A2 | 9/1999 |
| WO | WO 99/53049 A1 | 10/1999 |
| WO | WO 99/54342 A1 | 10/1999 |
| WO | WO 99/57134 A1 | 11/1999 |
| WO | WO 99/66903 A2 | 12/1999 |
| WO | WO 2000/09560 A2 | 2/2000 |
| WO | WO 2000/37504 A2 | 6/2000 |
| WO | WO 2000/56772 A1 | 9/2000 |
| WO | WO 2000/78815 A1 | 12/2000 |
| WO | WO 2001/00244 A2 | 1/2001 |
| WO | WO 2001/32712 A2 | 5/2001 |
| WO | WO 2001/58956 A2 | 8/2001 |
| WO | WO 2001/62300 A2 | 8/2001 |
| WO | WO 2001/62931 A2 | 8/2001 |
| WO | WO 2001/71005 A2 | 9/2001 |
| WO | WO 2001/77342 A1 | 10/2001 |
| WO | WO 2001/83525 A2 | 11/2001 |
| WO | WO 2001/88138 A1 | 11/2001 |
| WO | WO 2002/02773 A2 | 1/2002 |
| WO | WO 2002/02781 A1 | 1/2002 |
| WO | WO 2002/12502 A2 | 2/2002 |
| WO | WO 2002/16436 A2 | 2/2002 |
| WO | WO 2002/053596 A2 | 7/2002 |
| WO | WO 2002/072636 A2 | 9/2002 |
| WO | WO 2002/097048 A2 | 12/2002 |
| WO | WO 2003/016466 A2 | 2/2003 |
| WO | WO 2003/035835 A2 | 5/2003 |
| WO | WO 2003/039486 A2 | 5/2003 |
| WO | WO 2003/068801 A2 | 8/2003 |
| WO | WO 2003/086458 A1 | 10/2003 |
| WO | WO 2003/089614 A2 | 10/2003 |
| WO | WO 2003/100008 A2 | 12/2003 |
| WO | WO 2003/102132 A2 | 12/2003 |
| WO | WO 2004/003019 A2 | 1/2004 |
| WO | WO 2004/016286 A2 | 2/2004 |
| WO | WO 2004/024866 A2 | 3/2004 |
| WO | WO 2004/050683 A2 | 6/2004 |
| WO | WO 2004/058184 A2 | 7/2004 |
| WO | WO 2004/078140 A2 | 9/2004 |
| WO | WO 2005/016970 A2 | 2/2005 |
| WO | WO 2005/017107 A2 | 2/2005 |
| WO | WO 2005/044853 A2 | 5/2005 |
| WO | WO 2005/061540 A2 | 7/2005 |
| WO | WO 2005/061547 A2 | 7/2005 |
| WO | WO 2005/070965 A2 | 8/2005 |
| WO | WO 2005/100584 A2 | 10/2005 |
| WO | WO 2005/118635 A2 | 12/2005 |
| WO | WO 2005/120557 A2 | 12/2005 |
| WO | WO 2006/001965 A2 | 1/2006 |
| WO | WO 2006/013107 A1 | 2/2006 |
| WO | WO 2006/015373 A2 | 2/2006 |
| WO | WO 2006/020258 A2 | 2/2006 |
| WO | WO 2006/024867 A2 | 3/2006 |
| WO | WO 2006/031370 A2 | 3/2006 |
| WO | WO 2006/044908 A2 | 4/2006 |
| WO | WO 2006/047350 A2 | 5/2006 |
| WO | WO 2006/066171 A1 | 6/2006 |
| WO | WO 2006/089133 A2 | 8/2006 |
| WO | WO 2006/099698 A2 | 9/2006 |
| WO | WO 2006/110883 A2 | 10/2006 |
| WO | WO 2006/116269 A2 | 11/2006 |
| WO | WO 2006/122187 A2 | 11/2006 |
| WO | WO 2006/130374 A2 | 12/2006 |
| WO | WO 2006/130429 A2 | 12/2006 |
| WO | WO 2006/131951 A2 | 12/2006 |
| WO | WO 2006/136159 A2 | 12/2006 |
| WO | WO 2007/005955 A2 | 1/2007 |
| WO | WO 2007/024715 A9 | 3/2007 |
| WO | WO 2007/042261 A2 | 4/2007 |
| WO | WO 2007/048849 A1 | 5/2007 |
| WO | WO 2007/053447 A2 | 5/2007 |
| WO | WO 2007/056470 A2 | 5/2007 |
| WO | WO 2007/059136 A2 | 5/2007 |
| WO | WO 2007/062037 A2 | 5/2007 |
| WO | WO 2007/062852 A2 | 6/2007 |
| WO | WO 2007/077028 A2 | 7/2007 |
| WO | WO 2007/098417 A2 | 8/2007 |
| WO | WO 2007/117749 A2 | 10/2007 |
| WO | WO 2007/120651 A2 | 10/2007 |
| WO | WO 2007/120828 A1 | 10/2007 |
| WO | WO 2007/124299 A2 | 11/2007 |
| WO | WO 2007/143098 A2 | 12/2007 |
| WO | WO 2007/147901 A1 | 12/2007 |
| WO | WO 2008/011348 A2 | 1/2008 |
| WO | WO 2008/022152 A2 | 2/2008 |
| WO | WO 2008/024188 A2 | 2/2008 |
| WO | WO 2008/042236 A2 | 4/2008 |
| WO | WO 2008/057240 A2 | 5/2008 |
| WO | WO 2008/079326 A2 | 7/2008 |
| WO | WO 2008/100624 A2 | 8/2008 |
| WO | WO 2008/145338 A2 | 12/2008 |
| WO | WO 2008/150841 A1 | 12/2008 |
| WO | WO 2009/020654 A1 | 2/2009 |
| WO | WO 2009/052400 A1 | 4/2009 |
| WO | WO 2009/077993 A2 | 6/2009 |
| WO | WO 2009/089004 A1 | 7/2009 |

(56) References Cited

FOREIGN PATENT DOCUMENTS

| | | |
|---|---|---|
| WO | WO 2009/091912 A2 | 7/2009 |
| WO | WO 2009/134776 A2 | 11/2009 |
| WO | WO 2009/136382 A2 | 11/2009 |
| WO | WO 2009/149185 A2 | 12/2009 |
| WO | WO 2009/149189 A2 | 12/2009 |
| WO | WO 2009/155324 A2 | 12/2009 |
| WO | WO 2010/006060 A2 | 1/2010 |
| WO | WO 2010/040508 A1 | 4/2010 |
| WO | WO 2010/065882 A1 | 6/2010 |
| WO | WO 2010/096434 A2 | 8/2010 |
| WO | WO 2010/102251 A2 | 9/2010 |
| WO | WO 2011/039370 A1 | 4/2011 |
| WO | WO 2011/084714 A2 | 7/2011 |
| WO | WO 2011/091304 A1 | 7/2011 |
| WO | WO 2011/143562 A2 | 11/2011 |
| WO | WO 2012/061374 A2 | 5/2012 |
| WO | WO 2012/075037 A1 | 6/2012 |
| WO | WO 2012/088302 A2 | 6/2012 |
| WO | WO 2012/143379 A1 | 10/2012 |
| WO | WO 2013/112922 A1 | 8/2013 |
| WO | WO 2013/177062 A2 | 11/2013 |
| WO | WO 2014/033074 A2 | 3/2014 |
| WO | WO 2014/089209 A2 | 6/2014 |
| WO | WO 2014/151910 A1 | 9/2014 |
| WO | WO 2015/014884 A1 | 2/2015 |

OTHER PUBLICATIONS

"Cetuximab," in *The Merck Index.* 14th Ed., John Wiley & Sons, 2006; p. 335.
"Infliximab," in *The Merck Index.* 14th Ed., John Wiley & Sons, 2006; p. 863.
"Rituximab," in *The Merck Index.* 14th Ed., John Wiley & Sons, 2006; p. 1422.
"Trastuzumab," in *The Merck Index.* 14th Ed., John Wiley & Sons, 2006; p. 1646.
Ahmed et al., "Pharmacokinetics of ABT-122, a Dual TNF- and IL-17A-Targeted DVD-IG™, After Single Dosing in Healthy Volunteers and Multiple Dosing in Subjects with Rheumatoid Arthritis," *Ann. Rheum. Dis.*, 74(Suppl. 2):479, Abstract FRI0156 (2015).
Alderson et al., "Regulation of apoptosis and T cell activation by Fas-specific mAb," *Int. Immunol.*, 6(11): 1799-1806 (1994).
Alegre et al., "An Anti-Murine CD3 Monoclonal Antibody with a Low Affinity for Fcγ Receptors Suppresses Transplantation Responses While Minimizing Acute Toxicity and Immunogenicity," *J. Immunol.*, 155: 1544-1555 (1995).
Alt et al., "Novel tetravalent and bispecific IgG-like antibody molecules combining single-chain diabodies with the immunoglobulin g1 Fc or CH3 region," *FEBS Letters*, 454: 90-94 (1999).
Ames et al., "Conversion of murine Fabs isolated from a combinatorial phage display library to full length immunoglobulins," *J. Immunol. Methods*, 184: 177-186 (1995).
Andrew et al., "Fragmentation of Immunoglobulin G," *Current Protocols in Cell Biology*, 16.4.1-16.4.10 (2000).
Andrew et al., "Fragmentation of Immunoglobulin G," *Current Protocols in Cell Biology*, 2.8.1-2.8.10 (1997).
Aoki et al., "Endothelial Progenitor Cell Capture by Stents Coated with Antibody Against CD34," *J. Am. Coll. Cardiol.*, 45(10): 1574-1579 (2005).
Arancio et al., "RAGE potentiates Aβ-induced perturbation of neuronal function in transgenic mice," *EMBO J.*, 23: 4096-4105 (2004).
Arimura et al., "Prevention of Allergic Inflammation by a Novel Prostaglandin Receptor Antagonist, S-5751," *J. Pharmacol. Exper. Therapeut.*, 298(2): 411-419 (2001).
Arndt et al., "Bispecific Diabodies for Cancer Therapy," *Methods Mol. Biol.*, 207: 305-321 (2003).
Aroonrerk et al., "A sensitive direct ELISA for detection of prostaglandin E2," *J. Immunoassay & Immunochem.*, 28:319-330 (2007).
Atwell et al., "Stable heterodimers from remodeling the domain interface of a homodimer using a phage display library," *J. Mol. Biol.*, 270: 26-35 (1997).
Ayoub et al., "Preferential Formation of MT1/MT2 Melatonin Receptor Heterodimers with Distinct Ligand Interaction Properties Compared with MT2 Homodimers," *Mol. Pharmacol.*, 66(2): 312-321 (2004).
Azzazy et al., "Phage display technology: clinical applications and recent innovations," *Clin. Biochem.*, 35: 425-445 (2002).
Babcook et al., "A novel strategy for generating monoclonal antibodies from single, isolated lymphocytes producing antibodies of defined specificities," *Proc. Natl. Acad. Sci. USA*, 93: 7843-7848 (1996).
Bäckström et al., "Signaling Efficiency of the T Cell Receptor Controlled by a Single Amino Acid in the b Chain Constant Region," *J. Exp. Med.*, 186 (11): 1933-1938 (1997).
Balthasar et al., "High-affinity rabbit antibodies directed against methotrexate: Production, purification, characterization, and pharmacokinetics in the rat," *J. Pharm. Sci.*, 84(1): 2-6 (1995) (Abstract only) (1 page).
Balthasar et al., "Inverse Targeting of Peritoneial Tumors: Selective Alteration of the Disposition of Methotrexate through the Use of Anti-Methotrexate Antibodies and Antibody Fragments," *J. Pharm. Sci.*, 85(10): 1035-1043 (1996).
Barbas et al., "Assembly of combinatorial antibody libraries on phage surfaces: The gene III site," *Proc. Natl. Acad. Sci. USA*, 88: 7978-7982 (1991).
Barbas et al., "In vitro evolution of a neutralizing human antibody to human immunodeficiency virus type 1 to enhance affinity and broaden strain cross-reactivity," *Proc. Natl. Acad. Sci. USA*, 91: 3809-3813 (1994).
Barrios et al., "Length of the antibody heavy chain complementarity determining region 3 as a specificity-determining factor," *J. Mol. Recog.*, 17: 332-338 (2004).
Baslund et al., "Targeting interleukin-15 in patients with rheumatoid arthritis," *Arthritis Rheum.*, 52(9): 2686-2692 (2005).
Baumgartner et al., "Double blind, placebo controlled trial of tumor necrosis factor receptor fusion protein (TNFR:Fc) in active rheumatoid arthritis," Biomedicine '96. Medical Research from Bench to Bedside. Washington, DC, May 3-6, 1996. *J. Invest. Med.*, 44(3):235A (Mar. 1996) (Abstract) (1 page).
Bergman et al. "Pharmacokinetics of IgG and IgM anti-ganglioside antibodies in rats and monkeys after intrathecal administration" *J. Pharmacol. Exp. Ther.*, 284(1): 111-115 (1998).
Berzofsky et al., "Immunogenicity and Antigen Structure," in *Fundamental Immunology.* (Paul, W.E. ed.), New York, NY: Raven Press, 1993; Chapter 8, p. 242 (1 page).
Bessis et al., "Use of hollow fibers filled with cells engineered to secrete IL-4 or IL-13 for treatment of experimental arthritis," (Abstract No. 1681), *Arthritis Rheum.*, 39(9Suppl.): S308 (1996) (1 page).
Better et al., "*Escherichia coli* Secretion of an Active Chimeric Antibody Fragment," *Science*, 240: 1041-1043 (1988).
Biewenga et al., "IgA1 half molecules in human multiple myeloma and the in vitro production of similar fragments from intact IgA1 molecules," *Clin. Exp. Immunol.*, 51: 395-400 (1983).
Bird et al., "Single-Chain Antigen-Binding Proteins," *Science*, 242: 423-426 (1988).
Boado et al., "Fusion Antibody for Alzheimer's Disease with Bidirectional Transport Across the Blood-Brain Barrier and Aβ Fibril Disaggregation," *Bioconj. Chem.*, 18(2): 447-455 (2007).
Bornemann et al., "Aβ—Induced Inflammatory Processes in Microglia Cells of APP23 Transgenic Mice," *Am. J. Pathol.*, 158(1): 63-73 (2001).
Boyce et al., "No audible wheezing: Nuggets and conundrums from mouse asthma models," *J. Exp. Med.*, 201(12): 1869-1873 (2005).
Braen et al., "A 4-week intrathecal toxicity and pharmacokinetic study with trastuzumab in cynomolgus monkeys," *Int. J. Toxicol.*, 29(3): 259-267 (2010).
Brand, D.D., "Rodent Models of Rheumatoid Arthritis," *Comparative Medicine*, 55(2): 114-122 (2005).

(56) References Cited

OTHER PUBLICATIONS

Bree et al., "IL-13 blockade reduces lung inflammation after *Ascaris suum* challenge in cynomolgus monkeys," *J. Allergy Clin. Immunol.*, 119(5): 1251-1257 (2007).
Brennan et al., "Preparation of Bispecific Antibodies by Chemical Recombination of Monoclonal Immunoglobulin $G_1$ Fragments," *Science*, 229: 81-83 (1985).
Brinkmann et al., "Phage display of disulfide-stabilized Fv fragments," *J. Immunol. Methods*, 182: 41-50 (1995).
Bruncko et al., "Studies leading to potent, dual inhibitors of Bcl-2 and Bcl-xL," *J. Med. Chem.*, 50(4): 641-662 (2007).
Brüsselbach et al., "Enzyme recruitment and tumor cell killing in vitro by a secreted bispecific single-chain diabody," *Tumor Targeting*, 4: 115-123 (1999).
Buchwald et al., "Long-term, continuous intravenous heparin administration by an implantable infusion pump in ambulatory patients with recurrent venous thrombosis," *Surgery*, 88: 507-516 (1980).
Buras et al., "Animal Models of Sepsis: Setting the Stage," *Nat. Rev. Drug. Discovery*, 4: 854-865 (2005).
Burke et al., "Zotarolimus (ABT-578) eluting stents," *Adv. Drug Del. Rev.*, 58: 437-446 (2006).
Burton et al., "Human Antibodies from Combinatorial Libraries," *Adv. Immunol.*, 57: 191-280 (1994).
Calandra et al., "Protection from septic shock by neutralization of macrophage migration inhibitory factor," *Nature Med.*, 6(2): 164-170 (2000).
Caron et al., "Chondroprotective Effect of Intraarticular Injections of Interleukin-1 Receptor Antagonist in Experimental Osteoarthritis," *Arthritis Rheum.*, 39: 1535-1544 (1996).
Carroll et al., "The selection of high-producing cell lines using flow cytometry and cell sorting," *Expert Opin. Biol. Ther.*, 4: 1821-1829 (2004).
Carter et al., "Humanization of an anti-p185$^{HER2}$ antibody for human cancer therapy," *Proc. Natl. Acad. Sci. USA*, 89: 4285-4289 (1992).
Casset et al., "A peptide mimetic of an anti-CD4 monoclonal antibody by rational design," *Biochem. Biophys. Res. Commun.*, 307: 198-205 (2003).
Chayen et al., "Protein crystallization: from purified protein to diffraction-quality crystal," *Nature Methods*, 5(2): 147-153 (2008).
Chayen, N.E., "Turning protein crystallisation from an art into a science" *Curr. Opin. Struct. Biol.*, 14: 577-583 (2004).
Chen et al., "Selection and analysis of an optimized anti-VEGF antibody: Crystal structure of an affinity matured Fab in complex with antigen," *J. Mol. Biol.*, 293: 865-881 (1999).
Chikanza et al., "Treatment of patients with rheumatoid arthritis with RP73401 phosphodiesterase Type IV inhibitor," (Abstract No. 1527), *Arthritis Rheum.*, 39(9 Suppl.): S282 (1996) (1 page).
Choi et al., "Recombinant chimeric OKT3 scFv IgM antibodies mediate immune suppression while reducing T cell activation in vitro," *Eur. J. Immunol.*, 31(1): 94-106 (2001).
Chothia et al., "Canonical Structures for the Hypervariable Regions of Immunoglobulins," *J. Mol. Biol.*, 196: 901-917 (1987).
Chothia et al., "Conformations of immunoglobulin hypervariable regions," *Nature*, 342: 877-883 (1989).
Clackson et al., "Making antibody fragments using phage display libraries," *Nature*, 352: 624-628 (1991).
Cleek et al., "Biodegradable Polymeric Carriers for a bFGF Antibody for Cardiovascular Application," *Proceed. Intl. Symp. Control. Rel. Bioact. Mater.*, 24: 853-854 (1997).
Co et al., "Genetically Engineered Deglycosylation of the Variable Domain Increases the Affinity of an Anti-CD33 Monoclonal Antibody," *Mol. Immunol.*, 30(15): 1361-1367 (1993).
Coffman et al., "Nonhuman primate models of asthma," *J. Exp. Med.*, 201(12): 1875-1879 (2005).
Colman, "Effects of amino acid sequence changes on antibody-antigen interactions," *Research in Immunology*, 145:33-36 (1994).
Coloma et al., "Design and production of novel tetravalent bispecific antibodies," *Nature Biotechnol.*, 15: 159-163 (1997).

Coloma et al., "Transport across the primate blood-brain barrier of a genetically engineered chimeric monoclonal antibody to the human insulin receptor," *Pharm. Res.*, 17(3): 266-274 (2000).
Cooper et al., "Variable domain—identical antibodies exhibit IgG subclass-related differences in affinity and kinetic constants as determined by surface plasmon resonance," *Mol. Immunol.*, 31(8): 577-584 (Jun. 1994).
Cot et al., "Production and characterization of highly specific anti-methotrexate monoclonal antibodies," *Hybridoma*, 6(1): 87-95 (1987).
Cox et al., "Measurement of cytokine release at the single cell level using the ELISPOT assay," *Methods*, 38(4): 274-282 (2006).
D'Andrea et al., "Production of Natural Killer Cell Stimulatory Factor (Interleukin 12) by Peripheral Blood Mononuclear Cells," *J. Exp. Med.*, 176: 1387-1398 (1992).
Dahesia et al., "The Interleukin 1β Pathway in the Pathogenesis of Osteoarthritis," *J. Rheumatol.*, 35(12): 2306-2312 (2008).
Dall'Acqua et al., "Contribution of Domain Interface Residues to the Stability of Antibody $C_H3$ Domain Homodimers," *Biochemistry*, 37: 9266-9273 (1998).
Dall'Acqua et al., "Increasing the affinity of a human IgG1 for the neonatal Fc receptor: Biological consequences," *J. Immunol.*, 169(9): 5171-5180 (2002).
Dall'Acqua et al., "Properties of human IgG1s engineered for enhanced binding to the neonatal Fc receptor (FcRn)," *J. Biol. Chem.*, 281: 23514-23524 (2006).
David et al., "Characterization of monoclonal antibodies against prostaglandin $E_2$: Fine specificity and neutralization of biological effects," *Mol. Immunol.*, 22(3): 339-346 (1985).
Dayer et al., "Collagenase Production by Rheumatoid Synovial Cells: Stimulation by a Human Lymphocyte Factor," *Science*, 195: 181-183 (1977).
Dayer et al., "Effects of Prostaglandin E2, Indomethacin, Trifluoperazine and Drugs Affecting the Cytoskeleton on Collagenase Production by Cultured Adherent Rheumatoid Synovial Cells," *Biochem. Pharmacol.*, 33(18): 2893-2899 (1984).
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," *J. Immunol.*, 169: 3076-3084 (2002).
Deane et al., "RAGE mediates amyloid-β peptide transport across the blood-brain barrier and accumulation in brain," *Nature Med.*, 9(7): 907-913 (2003).
DeLuca et al., "Marine and botanical lipids as immunomodulatory and therapeutic agents in the treatment of rheumatoid arthritis," *Rheum. Dis. Clin. North Am.*, 21: 759-777 (1995).
DeScotes, J., "Immunotoxicology of Immunomodulators," *Develop. Biol. Standard*, 77: 99-102 (1992).
DeSmet et al., "Anchor profiles of HLA-specific peptides: analysis by a novel affinity scoring method and experimental validation," *Proteins*, 58: 53-69 (2005).
Desplat-Jego et al., "Anti-TWEAK monoclonal antibodies reduce immune cell infiltration in the central nervous system and severity of experimental autoimmune encephalomyelitis," *Clin. Immunol.*, 117(1): 15-23 (2005).
Dickson, B.J., "Molecular Mechanisms of Axon Guidance," *Science*, 298: 1959-1964 (2002).
DiGiammarino et al., "Ligand association rates to the inner-variable-domain of a dual-variable-domain immunoglobulin are significantly impacted by linker design," *mAbs*, 3(5): 487-494 (2011).
DiNarello et al., "Immunological and Inflammatory Functions of the Interleukin-1 Family," *Annu. Rev. Immunol.*, 27: 519-550 (2009).
DiNarello et al., "Measurement of soluble and membrane-bound interleukin 1 using a fibroblast bioassay," Unit 6.2, in *Current Protocols in Immunology*, pp. 6.21-6.27 (2000) (7 pages).
Dohi et al., "Effect of combination Treatment with TNF-Inhibitor and Anti-TWEAK Antibody in Mouse Colitis Model," *Gastroenterology*, 138(5): S-413, Abstract M1758 (2010).
Domeniconi et al., "Overcoming inhibitors in myelin to promote axonal regeneration," *J. Neurological Sciences*, 233: 43-47 (2005).

(56) References Cited

OTHER PUBLICATIONS

During et al., "Controlled Release of Dopamine from a Polymeric Brain Implant: in Vivo Characterization," *Ann. Neurol.*, 25(4): 351-356 (1989).
Durocher et al., "High-level and high-throughput recombinant protein production by transient transfection of suspension-growing human 293-EBNA1 cells," *Nucl. Acids Res.*, 30(2): e9, (9 pages) (2002).
Economides et al., "Cytokine traps: multi-component, high-affinity blockers of cytokine action," *Nature Med.*, 9(1): 47-52 (2003).
Enrich et al., "Demonstration of selective COX-2 inhibition by MK-966 in humans," (Abstract No. 328), *Arthritis Rheum.*, 39(9 Suppl.): S81 (1996) (1 page).
Enrich et al., "Efficacy of MK-966, a highly selective inhibitor of COX-2, in the treatment of postoperative dental pain," (Abstract No. 329), *Arthritis Rheum.*, 39(9Suppl.): S81 (1996) (1 page).
European Patent Application No. 06813554.0: Supplementary European Search Report and Search Opinion, dated Sep. 21, 2009 (11 pages).
European Patent Application No. 06813554.0: Written Submission in Preparation to Oral Proceedings, dated Jan. 23, 2015 (100 pages).
European Patent Application No. 06813554.0: Minutes of Oral Proceedings, dated Jan. 29, 2015 (7 pages).
European Patent Application No. 06813554.0: Reply to Minutes of Oral Proceedings, dated Jan. 29, 2015 (1 page).
European Patent Application No. 07811045.9: Supplementary European Search Report and Search Opinion, dated Sep. 21, 2009 (7 pages).
European Patent Application No. 09739578.4: Supplementary European Search Report and Search Opinion, dated Mar. 28, 2012 (21 pages).
European Patent Application No. 09759344.6: Supplementary European Search Report and Search Opinion, dated Jun. 13, 2012 (12 pages).
European Patent Application No. 09759348.7: Supplementary European Search Report and Search Opinion, dated Jul. 4, 2012 (11 pages).
European Patent Application No. 09795128.9: Supplementary European Search Report and Search Opinion, dated May 22, 2013 (10 pages).
European Patent Application No. 09831213.5: Supplementary European Search Report and Search Opinion, dated Oct. 21, 2013 (6 pages).
European Patent Application No. 10770441.3 Supplementary European Search Report and Search Opinion, dated Sep. 23, 2013 (16 pages).
European Patent Application No. 10770449.6: Supplementary European Search Report and Search Opinion, dated Jul. 2, 2013 (8 pages).
European Patent Application No. 10805046.9: Supplementary European Search Report and Search Opinion, dated Mar. 26, 2013 (7 pages).
European Patent Application No. 10814433.8: Supplementary European Search Report and Search Opinion, dated Apr. 18, 2013 (11 pages).
European Patent Application No. 10824164.7: Supplementary European Search Report and Search Opinion, dated May 22, 2013 (11 pages).
European Patent Application No. 10825739.5: Supplementary European Search Report and Search Opinion, dated Apr. 29, 2013 (13 pages).
European Patent Application No. 10830460.1: Supplementary European Search Report and Search Opinion, dated Apr. 29, 2013 (15 pages).
European Patent Application No. 11798923.6: Supplementary European Search Report and Search Opinion, dated Jan. 2, 2014 (10 pages).
European Patent Application No. 11804385.0: Supplementary European Search Report and Search Opinion, dated Nov. 20, 2013 (16 pages).
European Patent Application No. 11815172.9: Partial Supplementary European Search Report, dated Nov. 12, 2014 (10 pages).
European Patent Application No. 11815172.9: Supplementary European Search Report and Search Opinion, dated Jan. 21, 2015 (16 pages).
European Patent Application No. 11820654.9: Supplementary European Search Report and Search Opinion, dated Dec. 17, 2013 (17 pages).
European Patent Application No. 11838670.5: Partial Supplementary European Search Report, dated Jun. 24, 2015 (10 pages).
European Patent Application No. 11838670.5: Supplementary European Search Report and Opinion, dated Oct. 13, 2015 (19 pages).
European Patent Application No. 14176206.2 by AbbVie Inc.: Extended European Search Report and Opinion, dated Nov. 12, 2014 (7 pages).
European Patent Application No. 15153941.8 by AbbVie Inc.: Extended European Search Report and Opinion, dated Jun. 10, 2015 (8 pages).
European Patent Application No. 15162013.5 by AbbVie Inc.: Partial European Search Report, dated Jul. 17, 2015 (8 pages).
European Patent Application No. 15162013.5 by AbbVie Inc.: Extended European Search Report, including Search Opinion, dated Nov. 10, 2015 (12 pages).
European Patent Application No. 15162064.8 by AbbVie Inc.: Partial European Search Report, dated Jul. 10, 2015 (8 pages).
European Patent Application No. 15162064.8 by AbbVie Inc.: European Search Report, dated Oct. 9, 2015 (15 pages).
European Patent Application No. 15189272.6 by AbbVie Inc.: Extended European Search Report, including Search Opinion, dated Feb. 16, 2016 (8 pages).
Evans et al., "Efficacy of tumor necrosis factor binding protein (TNF-bp) in the Streptococcal cell wall-induced reactivation model of arthritis," (Abstract No. 1540), *Arthritis Rheum.*, 39(9 Suppl.): S284 (1996) (1 page).
Ewert et al., "Stability improvement of antibodies for extracellular and intracellular applications: CDR grafting to stable frameworks and structure-based framework engineering," *Methods*, 34: 184-199 (2004).
Farr et al., "Sulphasalazine (SASP) in rheumatoid arthritis (RA): A 5 year prospective study," (Abstract No. 1519), *Arthritis Rheum.*, 39(9 Suppl.): S281 (1996) (1 page).
Fernandes et al., "In Vivo Transfer of Interleukin-1 Receptor Antagonist Gene in Osteoarthritic Rabbit Knee Joints," *Am. J. Pathol.*, 154(4): 1159-1169 (1999).
Fiala et al., "IL-17A is increased in the serum and in spinal cord CD8 and mast cells of ALS patients," *J. Neuroinflamm.*, 7:76 (14 pages).
Fiebich et al., "Effects of NSAIDs on IL-1-beta-induced IL-6 mRNA and protein synthesis in human astrocytoma cells," *NeuroReport*, 7: 1209-1213 (1996).
Finnegan et al., "Leflunomide inhibits immunoglobulin production by two separate mechanisms," (Abstract No. 627), *Arthritis Rheum.*, 39(9 (Suppl.): S131 (1996) (1 page).
Finotto, et al., "Asthmatic changes in mice lacking T-bet are mediated by IL-13," *Int. Immunol.*, 17(8): 993-1007 (2005).
Flierl et al., "Adverse functions of IL-17A in experimental sepsis," *FASEB J.*, 22: 2198-2205 (2008).
Friden et al., "Anti-transferrin receptor antibody and antibody-drug conjugates cross the blood-brain barrier," *Proc. Natl. Acad. Sci. USA*, 88:4771-4775 (1991).
Fuchs et al., "Targeting Recombinant Antibodies to the Surface of *Escherichia coli*: Fusion to a Peptidoglycan Associated Lipoprotein," *Bio/Technology*, 9: 1369-1372 (1991).
Fuh et al., "Structure-Function Studies of Two Synthetic Antivascular Endothelial Growth Factor Fabs and Comparison with the Avastin™ Fab," *J. Biol. Chem.*, 281(10): 6625-6631 (2006).
Garber, K., "Targeting vessel abnormalization in cancer," *J. Natl. Canc. Inst.*, 99(13): 991-995 (2007).
Garber, K, "Anti-IL-17 mAbs herald new options in psoriasis," *Nat. Biotechnol.*, 30(6): 475-477 (2012).
Garg et al., "Investigation of the influence of FcRn on the distribution of IgG to the brain," *AAPS J.*, 11(3): 553-557 (2009).

(56) References Cited

OTHER PUBLICATIONS

Garrard et al., "F$_{AB}$ Assembly and Enrichment in a Monovalent Phage Display System," *Bio/Technology*, 9: 1373-1377 (1991).
Gavilondo et al., "Antibody Engineering at the Millennium," *Biotechniques*, 29: 128-145 (2000).
Genain et al., "Creation of a model for multiple sclerosis in *Callithrix jacchus* marmosets," *J. Mol. Med.*, 75(3): 187-197 (1997).
GENBANK Accession No. BAL50004, "Anti-prostaglandin E2 antibody kappa light chain [*Mus musculus*]," Feb. 4, 2012 (2 pages).
GENBANK Accession No. U17870, "Cricetulus migratorius 145. 2c11 kappa light chain mRNA, complete cds," ROD Feb. 7, 1996 (2 pages).
GENBANK Accession No. U17871, "Cricetulus migratorius 145. 2c11 heavy chain mRNA, partial cds," Feb. 7, 1996 (2 pages).
GENBANK Accession No. X99230, "M.musculus mRNA for immunoglobulin heavy chain variable domain, subgroup III," ROD Oct. 8, 1996 (2 pages).
GENBANK Accession No. X99232, "M.musculus mRNA for immunoglobulin light chain variable domain, subgroup III," ROD Oct. 8, 1996 (2 pages).
GENBANK Accession No. Y14283, "Mus musculus mRNA for immunoglobulin heavy chain variable region, subunits VH, DH and JH" ROD May 26, 1998 (2 pages).
GENBANK Accession No. Y14284, "Mus musculus mRNA for immunoglobulin light chain variable region, subunits VL and JL," ROD May 26, 1998 (2 pages).
Genovese et al., "Abatacept for Rheumatoid Arthritis Refractory to Tumor Necrosis Factor α Inhibition," *N. Engl. J. Med.*, 353: 1114-1123 (2005).
GENESEQ™ database, "Mouse anti-hIL13 humanized mAb LC variable region polypeptide SEQ: 71," Thomson Reuters, Philadelphia, USA; Accession No. AZK48805, Dec. 10, 2015 (2 pages).
GENESEQ™ database, "Humanized anti-TNF MAK-199 Ab VH region, SEQ: 91," Thomson Reuters, Philadelphia, USA; Accession No. BAN99936, Dec. 10, 2015 (2 pages).
GENESEQ™ database, "Anti-IL13 antibody heavy chain variable region (VH), SEQ ID: 32," Thomson Reuters, Philadelphia, USA; Accession No. BAQ31976, Dec. 10, 2015 (2 pages).
GENESEQ™ database, "Anti-TNF antibody VL (AB444VL), SEQ ID 49," Thomson Reuters, Philadelphia, USA; Accession No. BBN15100, Dec. 10, 2015 (2 pages).
Germain et al., "Redirecting NK cells mediated tumor cell lysis by a new recombinant bifunctional protein," *Protein Engineering Design and Selection*, 21(11): 665-672 (2008).
Ghetie et al., "Increasing the serum persistence of an IgG fragment by random mutagenesis," *Nature Biotechnol.*, 15(7): 637-640 (1997).
Giegé et al., "An introduction to the crystallogenesis of biological macromolecules," in *Crystallization of Nucleic Acids and Proteins. A Practical Approach*. 2nd ed., (Ducruix and Giegé, eds.), Oxford University Press, New York, 1999; chapter 1, pp. 1-16.
Glennie et al., "Preparation and Performance of Bispecific F(ab' γ.)$_2$ Antibody Containing Thioether-Linked Fab'γ Fragments," *J. Immunol.*, 139(7): 2367-2375 (1987).
Gold and Lühder, "Interleukin-17—Extended Features of a Key Player in Multiple Sclerosis," *Am. J. Pathol.*, 172(1): 8-10 (2008).
Goldring et al., "Interleukin 1 Suppresses Expression of Cartilage-specific Types II and IX Collagens and Increases Types I and III Collagens in Human Chondrocytes," *J. Clin. Investig.*, 82: 2026-2037 (1988).
Goldring et al., "Modulation by Recombinant Interleukin 1 of Synthesis of Types I and III Collagens and Associated Procollagen mRNA Levels in Cultured Human Cells," *J. Biol. Chem.*, 262: 16724-16729 (1987).
Goldspiel et al., "Human Gene Therapy," *Clin. Pharm.*, 12: 488-505 (1993).
Golde et al., "Quantitative and mechanistic studies of Aβ immunotherapy," *CNS Neurol. Disord. Drug Targets*, 8: 31-49 (2009).
Goodson, J.M., "Dental Applications," Chapter 6, in *Medical Applications of Controlled Release, vol. II, Applications and Evaluation*. (Langer and Wise, eds.) (CRC Press, Inc., Boca Raton, 1984), pp. 115-138.
Gracie et al., "A proinflammatory role for IL-18 in rheumatoid arthritis," *J. Clin. Invest.*, 104(10): 1393-1401 (1999).
Gram et al., "In vitro selection and affinity maturation of antibodies from a naive combinatorial immunoglobulin library," *Proc. Natl. Acad. Sci. USA*, 89: 3576-3580 (1992).
Green et al., "Antigen-specific human monoclonal antibodies from mice engineered with human Ig heavy and light chain YACs," *Nature Genetics*, 7: 13-21 (1994).
Green et al., "Regulation of B Cell Development by Variable Gene Complexity in Mice Reconstituted with Human Immunoglobulin Yeast Artificial Chromosomes," *J. Exp. Med.*, 188(3): 483-495 (1998).
Griffin et al., "Blockade of T Cell Activation Using a Surface-Linked Single Chain Antibody to CTLA-4 (CD152)," *J. Immunol.*, 164: 4433-4442 (2000).
Griffiths et al., "Human anti-self antibodies with high specificity from phage display libraries," *EMBO J.*, 12(2): 725-734 (1993).
Grothey and Galanis, "Targeting angiogenesis: progress with anti-VEGF treatment with large molecules," *Nat. Rev. Clin. Oncol.*, 6: 507-518 (2009).
Gu et al., "Generation of Dual-Variable-Domain Immunoglobulin Molecules for Dual-Specific Targeting," *Methods in Enzymology*, 502: 25-41 (2012).
Güssow et al., "Humanization of Monoclonal Antibodies," *Methods Enzymol.*, 203: 99-121 (1991).
Guttadauria, M., "Tenidap in Rheumatoid Arthritis Collaborative International Study (TRACIS): a 6-month interim analysis," (Abstract No. 1516), *Arthritis Rheum.*, 39(9 Suppl.): S280 (1996) (1 page).
Hämmerling et al. (eds.), "Appendix: Production of Antibody-Producing Hybridomas in the Rodent Systems," in *Monoclonal Antibodies and T-Cell Hybridomas. Perspectives and Technical Advances. Research Monographs in Immunology, vol. 3*. Elsevier, New York, 1981; pp. 563-587.
Hanasaki et al., "Binding of Human Plasma Sialoglycoproteins by the B Cell-specific Lectin CD22," *J. Biol. Chem.*, 270(13): 7543-7550 (1995).
Hara et al., "Therapeutic effect of T-614, a new anti-arthritic agent, on rheumatoid arthritis," (Abstract No. 1526), *Arthritis Rheum.*, 39(9 Suppl.): S282 (1996) (1 page).
Harriman et al., "Summary of clinical trials in rheumatoid arthritis using infliximab, an anti-TNFα treatment," *Ann. Rheum. Dis.*, 58(Suppl. I): 161-164 (1999) (4 pages).
Hart et al., "Preclinical efficacy and safety of mepolizumab (SB-240563), a humanized monoclonal antibody to IL-5, in cynomolgus monkeys," *J. Allergy Clin. Immunol.*, 108(2): 250-257 (2001).
Hart et al., "Suppression of Ongoing Disease in a Nonhuman Primate Model of Multiple Sclerosis by a Human-Anti-Human IL-12p40 Antibody," *J. Immunol.*, 175(7): 4761-4768 (2005).
Hawkins et al., "Selection of Phage Antibodies by Binding Affinity. Mimicking Affinity Maturation," *J. Mol. Biol.*, 226: 889-896 (1992).
Hay et al., "Bacteriophage cloning and *Escherichia coli* expression of a human IgM Fab," *Hum. Antibod. Hybridomas*, 3: 81-85 (1992).
Henry et al., "A Prostate-Specific Membrane Antigen Targeted Monoclonal Antibody—Chemotherapeutic Conjugate Designed for the Treatment of Prostate Cancer," *Cancer Res.*, 64: 7995-8001 (2004).
Hezareh et al., "Effector Function Activities of a Panel of Mutants of a Broadly Neutralizing Antibody against Human Immunodeficiency Virus Type 1," *J. Virol.*, 75(24): 12161-12168 (Dec. 2001).
Hibi et al., "Splicing variations in the ligand-binding domain of ApoER2 results in functional differences in the binding properties to Reelin," *Neurosci. Res.*, 63:251-258 (2009).
Hickey et al., "The Rheumatoid Arthritis Azathioprine Registry (RAAR)—interim analysis of malignancy and mortality," (Abstract No. 1521), *Arthritis Rheum.*, 39(9 Suppl.): S281 (1996) (1 page).
Hildebrand et al., "Surface coatings for biological activation and functionalization of medical devices," *Surface & Coatings Technology*, 200: 6318-6324 (2006).

(56) References Cited

OTHER PUBLICATIONS

Hill et al., "Interleukin-17 deficiency improves locomotor recovery and tissue sparing after spinal cord contusion injury in mice," *Neurosci. Lett.*, 487(3): 363-367 (2011).
Hindawi et al., "The development and application of a direct radioimmunoassay for prostaglandin E2 utilising a α-labelled ligand," *Prostaglandins, Leukotrienes and Medicine*, 18: 81-94 (1985).
Hinton et al., "Engineered human IgG antibodies with longer serum half-lives in primates," *J. Biol. Chem.* 279(8): 6213-6216 (2004).
Hirota et al., "Reelin Receptors ApoER2 and VLDLR Are Expressed in Distinct Spatiotemporal Patterns in Developing Mouse Cerebral Cortex" *J. Comp. Neurol.*, 523: 463-478 (2015).
Holliger et al., "'Diabodies': Small bivalent and bispecific antibody fragments," *Proc. Natl. Acad. Sci. USA*, 90: 6444-6448 (1993).
Holliger et al., "Diabodies: Small bispecific antibody fragments," *Cancer Immunol. Immunother.*, 45: 128-130 (1997).
Holm et al., "Functional mapping and single chain construction of the anti-cytokeratin 8 monoclonal antibody TS1 ," *Mol. Immunol.*, 44: 1075-1084 (2007).
Honegger et al., "Yet Another Numbering Scheme for Immunoglobulin Variable Domains: An Automatic Modeling and Analysis Tool," *J. Mol. Biol.*, 309(3): 657-670 (2001).
Honkanen et al., "IL-17 Immunity in Human Type 1 Diabetes," *J. Immunol.*, 185: 1959-1967 (2010).
Honorati et al., "Contribution of interleukin 17 to human cartilage degredation and synovial inflammation in osteoarthritis," *Osteoarthritis and Cartilage*, 10: 799-807 (2002).
Hoogenboom et al., "Multi-subunit proteins on the surface of filamentous phage: Methodologies for displaying antibody (Fab) heavy and light chains," *Nucl. Acids Res.*, 19(15): 4133-4137 (1991).
Hoogenboom et al., "Natural and designer binding sites made by phage display technology," *Immunol. Today*, 21(8): 371-378 (2000).
Hoogenboom, H.R., "Designing and optimizing library selection strategies for generating high-affinity antibodies," *Trends Biotechnol.*, 15: 62-70 (1997).
Hoogenboom, H.R., "Mix and match: Building manifold binding sites," *Nature Biotechnol.*, 15: 125-126 (1997).
Howard et al., "Intracerebral drug delivery in rats with lesion-induced memory deficits," *J. Neurosurg.*, 71: 105-112 (1989).
Hsieh et al., "Discovery and Characterization of ABT-122, an Anti-TNF/IL-17 DVD-Ig™ Molecule as a Potential Therapeutic Candidate for Rheumatoid Arthritis," *Ann. Rheum. Dis.*, 73(Suppl. 2):495, Abstract FRI0303 (2014).
Huber et al., "Crystallographic structure studies of an IgG molecule and an Fc fragment," *Nature*, 264: 415-420 (1976).
Huse et al., "Generation of a Large Combinatorial Library of the Immunoglobulin Repertoire in Phage Lambda," *Science*, 246: 1275-1281 (1989).
Huston et al., "Protein engineering of antibody binding sites: Recovery of specific activity in an anti-digoxin single-chain Fv analogue produced in *Escherichia coli*," *Proc. Natl. Acad. Sci. USA*, 85: 5879-5883 (1988).
Huston et al., "Protein Engineering of Single-Chain Fv Analogs and Fusion Proteins," *Methods Enzymol.*, 203: 46-88 (1991).
Hwang et al., "Cutting Edge: Targeted Ligation of CTLA-4 in Vivo by Membrane-Bound Anti-CTLA-4 Antibody Prevents Rejection of Allogeneic Cells," *J. Immunol.*, 163: 633-637 (2002).
Inter Partes Reexamination (Control No. 95/001,380) of U.S. Pat. No. 7,612,181 (U.S. Appl. No. 11/507,050): Replacement Request, dated Jun. 24, 2010 (62 pages).
Inter Partes Reexamination (Control No. 95/001,380) of U.S. Pat. No. 7,612,181 (U.S. Appl. No. 11/507,050): Order Granting Request for Inter Partes Reexamination, dated Sep. 1, 2010 (18 pages).
Inter Partes Reexamination (Control No. 95/001,380) of U.S. Pat. No. 7,612,181 (U.S. Appl. No. 11/507,050): Reexamination Non-Final Office Action, dated Sep. 1, 2010 (13 pages).
Inter Partes Reexamination (Control No. 95/001,380) of U.S. Pat. No. 7,612,181(U.S. Appl. No. 11/507,050): Response After Non-Final Action—Owner Timely ("Patent Owner's Response Pursuant to 37 CFR § 1.945"), dated Nov. 1, 2010 (71 pages).
Inter Partes Reexamination (Control No. 95/001,380) of U.S. Pat. No. 7,612,181 (U.S. Appl. No. 11/507,050): Third Party Requester Comments After Non-Final Action ("Sanofi's Comments Pursuant to 37 CFR § 1.947"), dated Dec. 1, 2010 (81 pages).
Inter Partes Reexamination (Control No. 95/001,380) of U.S. Pat. No. 7,612,181 (U.S. Appl. No. 11/507,050): Reexamination Non-Final Office Action ("Action Closing Prosecution"), dated Sep. 1, 2011.
Inter Partes Reexamination (Control No. 95/001,380) of U.S. Pat. No. 7,612,181 (U.S. Appl. No. 11/507,050): Patent Owner Comments After Action Closing Prosecution ("Response Pursuant to 37 CFR § 1.951 (a)"), dated Oct. 31, 2011.
Inter Partes Reexamination (Control No. 95/001,380) of U.S. Pat. No. 7,612,181 (U.S. Appl. No. 11/507,050): Third Party Requester Comments after Action Closing Prosecution ("Sanofi's Comments Pursuant to 37 CFR §1.951(a)"), dated Nov. 30, 2011.
Inter Partes Reexamination (Control No. 95/001,380) of U.S. Pat. No. 7,612,181 (U.S. Appl. No. 11/507,050): Right of Appeal Notice (37 CFR 1.953), dated Mar. 7, 2012.
Inter Partes Reexamination (Control No. 95/001,380) of U.S. Pat. No. 7,612,181 (U.S. Appl. No. 11/507,050): Decision on Appeal, dated Mar. 24, 2014.
Inter Partes Reexamination (Control No. 95/001,380) of U.S. Pat. No. 7,612,181 (U.S. Appl. No. 11/507,050): Request to Reopen Prosecution Pursuant to 37 CFR § 41.77(b)(1), dated May 23, 2014.
Inter Partes Reexamination (Control No. 95/001,380) of U.S. Pat. No. 7,612,181 (U.S. Appl. No. 11/507,050): Third Party Requester Comments on Patent Owner Response after Board Decision ("Sanofi's Comments Pursuant to 37 C.F.R. § 41.77(c)"), dated Jun. 22, 2014.
Inter Partes Reexamination (Control No. 95/001,380) of U.S. Pat. No. 7,612,181 (U.S. Appl. No. 11/507,050): Record of Oral Hearing, dated Aug. 4, 2014.
Inter Partes Reexamination (Control No. 95/001,380) of U.S. Pat. No. 7,612,181 (U.S. Appl. No. 11/507,050): Order Reopening Prosecution and Remanding Inter Partes Reexamination Under 37 C.F.R. § 41.77(d) to the Examiner, dated Nov. 20, 2014.
Inter Partes Reexamination (Control No. 95/001,380) of U.S. Pat. No. 7,612,181 (U.S. Appl. No. 11/507,050): Examiner's Determination on Patent Owner Response/Requester Comments After Board Decision, dated Jun. 2, 2015.
Inter Partes Reexamination (Control No. 95/001,380) of U.S. Pat. No. 7,612,181 (U.S. Appl. No. 11/507,050): Patent Owner's Comments on Examiner's Determination after Board Decision ("Patent Owner's Comments Under 37 C.F.R. § 41.77(e)"), dated Jul. 2, 2015.
Inter Partes Reexamination (Control No. 95/001,380) of U.S. Pat. No. 7,612,181 (U.S. Appl. No. 11/507,050): Requester Comments on Patent Owner Response after Board Decision ("Sanofi's Comments Pursuant to 37 C.F.R. § 41.77(e)"), dated Aug. 2, 2015.
Inter Partes Reexamination (Control No. 95/001,380) of U.S. Pat. No. 7,612,181 (U.S. Appl. No. 11/507,050): Patent Owner's Request for Oral Hearing and Petition Under 37 C.F.R. § 1.183 for Oral Hearing, dated Sep. 4, 2015.
Inter Partes Reexamination (Control No. 95/001,380) of U.S. Pat. No. 7,612,181 (U.S. Appl. No. 11/507,050): Decision on Patent Owner's Petition Under 37 C.F.R. § 1.183 for Oral Hearing, dated Mar. 7, 2016.
International Patent Application No. PCT/US2006/032398: International Search Report and Written Opinion, dated Aug. 18, 2008 (14 pages).
International Patent Application No. PCT/US2006/032398: International Preliminary Report on Patentability, dated Jul. 6, 2010 (14 pages).
International Patent Application No. PCT/US2007/017340: International Search Report and Written Opinion, dated Jun. 24, 2008 (5 pages).
International Patent Application No. PCT/US2007/017340: International Preliminary Report on Patentability, dated Nov. 14, 2008 (3 pages).

(56) References Cited

OTHER PUBLICATIONS

International Patent Application No. PCT/US2009/041945: International Search Report and Written Opinion, dated Nov. 2, 2009 (12 pages).
International Patent Application No. PCT/US2009/041945: International Preliminary Report on Patentability, dated Aug. 9, 2010 (12 pages).
International Patent Application No. PCT/US2009/046130: International Search Report and Written Opinion, dated Jan. 11, 2010 (17 pages).
International Patent Application No. PCT/US2009/046130: International Preliminary Report on Patentability, dated Aug. 21, 2010 (13 pages).
International Patent Application No. PCT/US2009/046137: International Search Report and Written Opinion, dated Jan. 12, 2010 (18 pages).
International Patent Application No. PCT/US2009/046137: International Preliminary Report on Patentability, dated Jun. 18, 2010 (14 pages).
International Patent Application No. PCT/US2009/049953: International Search Report and Written Opinion, dated Oct. 29, 2009 (10 pages).
International Patent Application No. PCT/US2009/049954: International Search Report and Written Opinion, dated Mar. 31, 2010 (14 pages).
International Patent Application No. PCT/US2009/049954: International Preliminary Report on Patentability, dated Jul. 2, 2011 (11 pages).
International Patent Application No. PCT/US2009/066815: International Search Report and Written Opinion, dated Mar. 23, 2010 (14 pages).
International Patent Application No. PCT/US2009/066815: International Preliminary Report on Patentability, dated Jan. 6, 2011 (13 pages).
International Patent Application No. PCT/US2010/033231: International Search Report and Written Opinion, dated Nov. 22, 2010 (10 pages).
International Patent Application No. PCT/US2010/033231: International Preliminary Report on Patentability, dated Apr. 27, 2011 (10 pages).
International Patent Application No. PCT/US2010/033246: International Search Report and Written Opinion, dated Nov. 24, 2010 (18 pages).
International Patent Application No. PCT/US2010/033246: International Preliminary Report on Patentability, dated May 4, 2011 (28 pages).
International Patent Application No. PCT/US2010/043716: International Search Report and Written Opinion, dated Feb. 28, 2011 (17 pages).
International Patent Application No. PCT/US2010/043716: International Preliminary Report on Patentability, dated Aug. 31, 2012 (24 pages).
International Patent Application No. PCT/US2010/047543: International Search Report and Written Opinion, dated Feb. 24, 2011 (14 pages).
International Patent Application No. PCT/US2010/052843: International Search Report and Written Opinion, dated Jul. 1, 2011 (21 pages).
International Patent Application No. PCT/US2010/053730: International Search Report and Written Opinion, dated May 6, 2011 (13 pages).
International Patent Application No. PCT/US2010/053730: International Preliminary Report on Patentability, dated Nov. 21, 2011 (12 pages).
International Patent Application No. PCT/US2010/054521: International Search Report and Written Opinion, dated May 26, 2011 (12 pages).
International Patent Application No. PCT/US2010/054521: International Preliminary Report on Patentability, dated Feb. 8, 2012 (12 pages).
International Patent Application No. PCT/US2011/041633: International Search Report and Written Opinion, dated Mar. 13, 2012 (16 pages).
International Patent Application No. PCT/US2011/043297: International Search Report and Written Opinion, dated Feb. 28, 2012 (19 pages).
International Patent Application No. PCT/US2011/046233: International Search Report and Written Opinion, dated Apr. 3, 2012 (17 pages).
International Patent Application No. PCT/US2011/049147: International Search Report and Written Opinion, dated Mar. 21, 2012 (16 pages).
International Patent Application No. PCT/US2011/058769: International Search Report and Written Opinion, dated Jun. 15, 2012 (15 pages).
International Patent Application No. PCT/US2011/059074: International Search Report and Written Opinion, dated Jun. 15, 2012 (18 pages).
International Patent Application No. PCT/US2012/071897: International Search Report and Written Opinion, dated Sep. 3, 2013 (17 pages).
International Patent Application No. PCT/US2012/071929: International Search Report and Written Opinion, dated Sep. 11, 2013 (29 pages).
International Patent Application No. PCT/US2012/072017: International Search Report and Written Opinion, dated Jul. 17, 2013 (24 pages).
International Patent Application No. PCT/US2013/067873: International Search Report and Written Opinion, dated May 8, 2014 (23 pages).
International Patent Application No. PCT/US2013/073114: International Search Report and Written Opinion, dated Jul. 7, 2014 (24 pages).
International Patent Application No. PCT/US2014/028618: Invitation to Pay Additional Fees and Communication Relating to the Results of the Partial International Search, dated Aug. 13, 2014 (8 pages).
International Patent Application No. PCT/US2014/028618: International Search Report and Written Opinion, dated Oct. 28, 2014 (25 pages).
International Patent Application No. PCT/US2014/028646: International Search Report and Written Opinion, dated Oct. 17, 2014 (18 pages).
International Patent Application No. PCT/US2014/028646: Invitation to Pay Additional Fees and Communication Relating to the Results of the Partial International Search, dated Aug. 14, 2014 (10 pages).
International Patent Application No. PCT/US2015/035441: Invitation to Pay Additional Fees, with Communication Relating to the Results of the Partial International Search, dated Oct. 7, 2015 (6 pages).
International Patent Application No. PCT/US2015/035441: International Search Report and Written Opinion, dated Dec. 10, 2015 (18 pages).
International Patent Application No. PCT/US2015/065406: Invitation to Pay Additional Fees, with Communication Relating to the Results of the Partial International Search, dated Apr. 15, 2016 (9 pages).
Ito et al., "Transfer of Severe Experimental Autoimmune Encephalomyelitis by IL-12- and IL-18-Potentiated T Cells is Estrogen Sensitive," *J. Immunol.*, 170(9): 4802-4809 (2003).
Jackson et al., "In Vitro Antibody Maturation, Improvement of a High Affinity, Neutralizing Antibody Against IL-1β," *J. Immunol.*, 154(7): 3310-3319 (1995).
Jakob et al., "Structure reveals function of the dual variable domain immunoglobulin (DVD-Ig™) molecule," *mAbs*, 5(3): 358-363 (2013).
Jakubowski et al., "Dual role for TWEAK in angiogenic regulation," *J. Cell Sci.*, 115(2): 267-274 (2002).
Janelsins et al., "Early correlation of microglial activation with enhanced tumor necrosis factor-alpha and monocyte chemoattractant protein-I expression specifically within the entorhinal cortex of triple transgenic Alzheimer's disease mice," *J. Neuroinflammation*, 2(23): 1-12 (2005).

(56) References Cited

OTHER PUBLICATIONS

Janeway et al., *Immunobiology. The Immune System in Health and Disease*. 3rd Ed. Current Biology Ltd./Garland Publishing Inc., 1997; Chapter 3, pp. 1-11.
Jefferis, R., "Glycosylation of Recombinant Antibody Therapeutics," *Biotechnol. Prog.*, 21: 11-16 (2005).
Jendreyko et al., "Intradiabodies, Bispecific, Tetravalent Antibodies for the Simultaneous Functional Knockout of Two Cell Surface Receptors," *J. Biol. Chem.*, 278(48): 47812-47819 (2003).
Jiang et al., "Regulation of recombinant monoclonal antibody production in Chinese hamster ovary cells: A comparative study of gene copy number, mRNA level, and protein expression," *Biotechnol. Prog.*, 22(1): 313-318 (2006).
Jin et al., "Pharmacokinetic and Pharmacodynamic Effects of High-Dose Monoclonal Antibody Therapy in a Rat Model of Immune Thrombocytopenia," *The AAPS Journal*, 7(4):Article 87, E895-E902 (2006) [online]. Retrieved from: http://www.springerlink.com/content/v6n04672761n9313/fulltext.pdf.
Joachimiak, "High-throughput crystallography for structural genomics" *Curr. Opin. Struct. Biol.*, 19: 573-584 (2009).
Johnsson et al., "Comparison of Methods for Immobilization to Carboxymethyl Dextran Sensor Surfaces by Analysis of the Specific Activity of Monoclonal Antibodies," *J. Mol. Recognit.*, 8: 125-131 (1995).
Johnsson et al., "Immobilization of Proteins to a Carboxymethyldextran—Modified Gold Surface for Biospecific Interaction Analysis in Surface Plasmon Resonance Sensors," *Anal. Biochem.*, 198: 268-277 (1991).
Joliot et al., "Antennapedia homeobox peptide regulates neural morphogenesis," *Proc. Natl. Acad. Sci. USA*, 88: 1864-1868 (1991).
Jones et al., "Replacing the complementarity-determining regions in a human antibody with those from a mouse," *Nature*, 321: 522-525 (1986).
Jones, A.G., "Particle formation and separation in suspension crystallization processes," Chapter 4, in *Process. Solid-Liq. Suspensions*, (P. Ayazi Shamlou, ed.) (Butterworth-Heinemann, Oxford, UK, 1993) pp. 93-117.
Jones, A.J.S., "Analytical methods for the assessment of protein formulations and delivery systems," Chapter 2, in *Formulation and Delivery of Proteins and Peptides*, 1st ed., (Cleland and Langer, eds.) (American Chemical Society, Washington, D.C., 1994) pp. 22-45.
Jones, R., "Rovelizumab—ICOS Corp," *IDrugs*, 3(4): 442-446 (2000).
Jönsson et al., "Introducing a biosensor based technology for real-time biospecific interaction analysis," *Ann. Biol. Clin.*, 51: 19-26 (1993).
Jönsson, et al., "Real-Time Biospecific Interaction Analysis Using Surface Plasmon Resonance and a Sensor Chip Technology," *Bio Techniques*, 11(5): 620-627 (1991).
Joosten et al., "Anticytokine Treatment of Established Type II Collagen-Induced Arthritis in DBA/1 Mice," *Arthritis Rheum.*, 39(5): 797-809 (1996).
Jotanovic et al., "Role of Interleukin-1 Inhibitors in Osteoarthritis," *Drugs Aging*, 29(5): 343-358 (2012).
Ju et al., "Inhibitory effects of nardostachin on nitric oxide, prostaglandin E2, and tumor necrosis factor—alpha production in lipopolysaccharide activated macrophages," *Biol. Pharm. Bull.* 26: 1375-1378 (2003).
Jungbluth et al., "A monoclonal antibody recognizing human cancers with amplification/overexpression of the human epidermal growth factor receptor," *Proc. Natl. Acad. Sci. USA*, 100(2): 639-644 (2003).
Kabat et al., "Attempts to Locate Complementarity-Determining Residues in the Variable Positions of Light and Heavy Chains," *Ann. NY Acad. Sci.*, 190: 382-391 (1971).
Kaine et al., "Results of a multi-dose protocol 7002 using an immunomodulating, non-depleting Primatized™ anti-CD4 monoclonal antibody in rheumatoid arthritis (RA)," (Abstract No. 195), *Arthritis Rheum.*, 38: S185 (1995) (1 page).

Kanda et al., "Establishment of a GDP-mannose 4,6-dehydratase (GMD) knockout host cell line: A new strategy for generating completely non-fucosylated recombinant therapeutics," *J. Biotechnol.*, 130(3): 300-310 (2007).
Kapadia et al., "Soluble TNF binding proteins modulate the negative inotropic properties of TNF-alpha in vitro," *Am. J. Physiol. Heart Circ. Physiol.* 268 (2 Pt. 2): H517-H525 (1995).
Karnezis et al., "The neurite outgrowth inhibitor Nogo A is involved in autoimmune-mediated demyelination," *Nature Neurosci.*, 7: 736-744 (2004).
Karni et al., "IL-18 is linked to raised IFN-$\gamma$ in multiple sclerosis and is induced by activated CD4$^+$ T cells via CD4O-CD40 ligand interactions," *J. Neuroimmunol.*, 125: 134-140 (2002).
Kashmiri et al., "SDR grafting—a new approach to antibody humanization," *Methods*, 36(1): 25-34 (2005).
Kaufman and Sharp, "Amplification and expression of sequences cotransfected with a modular dihydrofolate reductase complementary DNA gene," *J. Mol. Biol.*, 159(4): 601-621 (1982).
Keith Jr., et al., "Recombinant human interleukin eleven decreases arthritis in HLA-B27 transgenic rats," (Abstract No. 1613), *Arthritis Rheum.*, 39(9 Suppl.): S296 (1996) (1 page).
Kellerman et al., "Antibody discovery: The use of transgenic mice to generate human monoclonal antibodies for therapeutics," *Curr. Opin. Biotechnol.*, 13: 593-597 (2002).
Kellner, H., "Targeting interleukin-17 in patients with active rheumatoid arthritis: rationale and clinical potential," *Ther. Adv. Musculoskel. Dis.*, 5(3):141-152 (2013).
Kettleborough et al., "Humanization of a mouse monoclonal antibody by CDR-grafting: the importance of framework residues on loop conformation," *Protein Eng.*, 4(7): 773-783 (1991).
Kettleborough et al., "Isolation of tumor cell-specific single-chain Fv from immunized mice using phage-antibody libraries and the re-construction of whole antibodies from these antibody fragments," *Eur. J. Immunol.*, 24: 952-958 (1994).
Kim and Moalem-Taylor, "Interleukin-17 Contributes to Neuroinflammation and Neuropathic Pain Following Peripheral Nerve Injury in Mice," *J. Pain*, 12(3): 370-383 (2010).
Kim et al., "Identifying amino acid residues that influence plasma clearance of murine IgG1 fragments by site-directed mutagenesis," *Eur. J. Immunol.*, 24: 542-548 (1994).
Kipriyanov et al., "Bispecific CD3×CD19 Diabody for T Cell-Mediated Lysis of Malignant Human B Cells," *Int. J. Cancer*, 77: 763-772 (1998).
Kipriyanov et al., "Generation of recombinant antibodies," *Mol. Biotechnol.*, 12: 173-201 (1999).
Klein, W.L., "A$\beta$ toxicity in Alzheimer's disease: Globular oligomers (ADDLs) as new vaccine and drug targets," *Neurochem. Int.*, 41: 345-352 (2002).
Klyubin et al., "Amyloid $\beta$ protein immunotherapy neutralizes A$\beta$ oligomers that disrupt synaptic plasticity in vivo," *Nature Med.*, 11: 556-561 (2005).
Köhler and Milstein, "Continuous cultures of fused cells secreting antibody of predefined specificity," *Nature*, 256: 495-497 (1975).
Konishi et al., "A simple and sensitive bioassay for the detection of human interleukin-18/ interferon-$\gamma$-inducing factor using human myelomonocytic KG-1 cells," *J. Immunol. Methods*, 209: 187-191 (1997).
Kontermann, R.E., "Recombinant bispecific antibodies for cancer therapy," *Acta Pharmacologica Sinica*, 26(1): 1-9 (2005).
Kostelny et al., "Formation of a Bispecific Antibody by the Use of Leucine Zippers," *J. Immunol.*, 148(5): 1547-1553 (1992).
Kou et al., "A bispecific antibody effectively inhibits tumor growth and metastasis by simultaneous blocking vascular endothelial growth factor A and osteopontin," *Cancer Lett.*, 299: 130-136 (2010).
Kriangkum et al., "Bispecific and bifunctional single chain recombinant antibodies," *Biomol. Eng.*, 18: 31-40 (2001).
Krop et al., "Self-renewal of B-1 lymphocytes is dependent on CD19," *Eur. J. Immunol.*, 26: 238-242 (1996).
Kuby, *Immunology*, 2nd ed., (W.H. Freeman and Company, New York, 1994), p. 115, Fig. 5-6 (1 page).

(56) References Cited

OTHER PUBLICATIONS

Kwong et al., "Generation, affinity maturation, and characterization of a human anti-human NKG2D monoclonal antibody with dual antagonistic and agonistic activity," *J. Mol. Biol.*, 384(5): 1143-1156 (2008).
Kyte et al., "A Simple Method for Displaying the Hydropathic Character of a Protein," *J. Mol. Biol.*, 157: 105-132 (1982).
LaJoie, S. et al., "Complement-mediated regulation of the IL-17A axis is a central genetic determinant of the severity of experimental allergic asthma," *Nat. Immunol.*, 11(10): 928-935 (Oct. 2010).
Lam et al., "Microencapsulation of Recombinant Humanized Monoclonal Antibody for Local Delivery," *Proceed. Intl. Symp. Control Rel. Bioact. Mater.*, 24: 759-760 (1997).
Langer and Peppas, "Chemical and Physical Structure of Polymers as Carriers for Controlled Release of Bioactive Agents: A Review," *J. Macromol. Sci. RMC*, C23(1): 61-126 (1983).
Langer, R., "New Methods of Drug Delivery," *Science*, 249: 1527-1533 (1990).
Laue, T., "Analytical centrifugation: equilibrium approach," in *Current Protocols in Protein Science*, (John Wiley & Sons, Inc., New York, 1999), Supplement 18, Unit 20.3, pp. 20.3.1-20.3.13 (13 pages).
Lazarovici et al., "Cross Talk between the Cardiovascular and Nervous Systems: Neurotrophic Effects of Vascular Endothelial Growth Factor (VEGF) and Angiogenic Effects of Nerve Growth Factor (NGF)—Implications in Drug Development," *Curr. Pharmaceut. Des.*, 12:2609-2622 (2006).
Le Gall et al., "Di-, tri- and tetrameric single chain Fv antibody fragments against human CD19: Effect of valency on cell binding," *FEBS Letters*, 453: 164-168 (1999).
Le Gall et al., "Immunosuppressive properties of anti-CD3 single-chain Fv and diabody," *J. Immunol. Methods*, 285: 111-127 (2004).
Lee et al., "BiP and immunoglobulin light chain cooperate to control the folding of heavy chain and ensure the fidelity of immunoglobulin assembly," *Mol. Biol. Cell*, 10: 2209-2219 (1999).
Lee et al., "Treatment of rheumatoid arthritis (RA) with thalidomide," (Abstract No. 1524), *Arthritis Rheum.*, 39(9 Suppl.): S282 (1996) (1 page).
LeGros et al., "Characterization of an anti-*Borrelia burgdorferi* OspA conformational epitope by limited proteolysis of monoclonal antibody-bound antigen and mass spectrometric peptide mapping," *Protein Science*, 9: 1002-1010 (2000).
Leung et al., "Combined Effects of IL-12 and IL-18 on the Induction of Collagen-Induced Arthritis," *J. Immunol.*, 164(12): 6495-6502 (2000).
Levites et al., "Insights into the mechanisms of action of anti-Aβ antibodies in Alzheimer's disease mouse models," *FASEB J.*, 20(14): 2576-2578 (2006).
Levy et al., "Inhibition of Calcification of Bioprosthetic Heart Valves by Local Controlled-Release Diphosphonate," *Science*, 228: 190-192 (1985).
Li et al., "Structural mutations in the constant region of the T-cell antigen receptor (TCR)β chain and their effect on TCRα and β chain interaction," *Immunology*, 88: 524-530 (1996).
Li et al., "Genetically engineered brain drug delivery vectors: Cloning, expression and in vivo application of an anti-transferrin receptor single chain antibody—streptavidin fusion gene and protein," *Protein Eng.*, 12(9): 787-796 (1999).
Li et al., "Synergistic effects of IL-12 and IL-18 in skewing tumor-reactive T-cell responses towards a type I pattern," *Cancer Res.*, 65(3): 1063-1070 (2005).
Li et al., "Bispecific Antibody to ErbB2 Overcomes Trastuzumab Resistance through Comprehensive Blockade of ErbB2 Heterodimerization," *Cancer Res.*, 73(21): 6471-6483 (2013).
Little et al., "Of mice and men: hybridoma and recombinant antibodies," *Immunol. Today*, 21(8): 364-370 (2000).
Liu et al., "Heterogeneity of Monoclonal Antibodies," *J. Pharm. Sci.*, 97(7): 2426-2447 (2008).
Lloyd et al., "Mouse Models of Allergic Airway Disease," *Adv. Immunol.*, 77: 263-295 (2001).
Lo, B., "Antibody Humanization by CDR Grafting," *Methods Mol. Biol.*, 248: 135-159 (2004).
Lobo et al., "Application of anti-methotrexate Fab fragments for the optimization of intraperitoneal methotrexate therapy in a murine model of peritoneal cancer," *J. Pharma. Sci.*, 94(9): 1957-1964 (2005) (Abstract only) (1 page).
Lobo, "Anti-Methotrexate Fab Fragments for Optimization of Intraperitoneal Methotrexate Chemotherapy," Dissertation, University of New York at Buffalo, Dept. Of Pharmaceutical Sciences, Aug. 2002, pp. 1-243. Available online at: http://www.acsu.buffalo.edu/~jb/Thesis%20080802.pdf.
Lotz et al., "IL-17 promotes cartilage degradation," (Abstract No. 559), *Arthritis Rheum.*, 39(9 Suppl.): S120 (1996) (1 page).
Lu et al., "A Fully Human Recombinant IgG-like Bispecific Antibody to Both the Epidermal Growth Factor Receptor and the Insulin-like Growth Factor Receptor for Enhanced Antitumor Activity," *J. Biol. Chem.*, 280(20): 19665-19672 (2005).
Lu et al., "Di-diabody: A novel tetravalent bispecific antibody molecule by design," *J. Immunol. Methods*, 279: 219-232 (2003).
Lu et al., "Fab-scFv fusion protein: an efficient approach to production of bispecific antibody fragments," *J. Immunol. Methods*, 267: 213-226 (2002).
Lu et al., "Simultaneous Blockade of Both the Epidermal Growth Factor Receptor and the Insulin-like Growth Factor Receptor Signaling Pathways in Cancer Cells with a Fully Human Recombinant Bispecific Antibody," *J. Biol. Chem.*, 279(4): 2856-2865 (2004).
Lublin, F.D., "Relapsing Experimental Allergic Encephalomyelitis. An Autoimmune Model of Multiple Sclerosis," *Springer Semin. Immunopathol.*, 8: 197-208 (1985).
Lund et al., "Human Fc gamma RI and Fc gamma RII interact with distinct but overlapping sites on human IgG," *J. Immunol.*, 147: 2657-2662 (1991).
Luster et al., "Use of animal studies in risk assessment for immunotoxicology," *Toxicology*, 92(1-3): 229-243 (1994).
MacCallum et al., "Antibody-antigen Interactions: Contact Analysis and Binding Site Topography," *J. Mol. Biol.*, 262: 732-745 (1996).
Mack et al., "A small bispecific antibody construct expressed as a functional single-chain molecule with high tumor cell cytotoxicity," *Proc. Natl. Acad. Sci. USA*, 92: 7021-7025 (1995).
Madhusudan et al., "A phase II study of etanercept (Enbrel), a tumor necrosis factor alpha inhibitor in patients with metastatic breast cancer," *Clin. Cancer Res.*, 10(19): 6528-6534 (2004).
Makwana et al., "Molecular mechanisms in successful peripheral regeneration," *FEBS J.*, 272: 2628-2638 (2005).
Malfait et al., "ADAMTS-5 deficient mice do not develop mechanical allodynia associated with osteoarthritis following medial meniscal destabilization," *Osteoarthritis Cartilage*, 18: 572-580 (2010).
Malik-Hall et al., "Primary afferent nociceptor mechanisms mediating NGF-induced mechanical hyperalgesia," *Eur. J. Neurosci.*, 21(12): 3387-3394 (2005).
Mansikka et al., "Safety, Tolerability, and Functional Activity of ABT-122, a Dual TNF- and IL-17a—Targeted DVD-Ig™, Following Single-Dose Administration in Healthy Subjects," *Ann. Rheum. Dis.*, 74(Suppl. 2):482-483 (2015).
Marchalonis et al., "Evolutionary Factors in the Emergence of the Combinatorial Germline Antibody Repertoire," *Adv. Exp. Med. Biol.*, 484: 13-30 (2001).
Margolin et al., "Protein crystals as novel catalytic materials," *Angew. Chem. Int. Ed.*, 40: 2204-2222 (2001).
Mariuzza et al., "The Structural Basis of Antigen-Antibody Recognition," *Annu. Rev. Biophys. Biophys. Chem.*, 16: 139-159 (1987).
Marks et al., "By-Passing Immunization: Building High Affinity Human Antibodies by Chain Shuffling," *BioTechnology*, 10: 779-783 (1992).
Marques et al., "Mediation of the Cytokine Network in the Implantation of Orthopedic Devices," Chapter 21, in *Biodegradable Systems in Tissue Engineering and Regenerative Medicine*, (Reis et al., eds.) (CRC Press LLC, Boca Raton, 2005) pp. 377-397.
Marquina et al., "Inhibition of B cell death causes the development of an IgA nephropathy in (New Zealand White×C57BU6)F1-bcl-2 transgenic mice," *J. Immunol.*, 172(11): 7177-7185 (2004).

(56) References Cited

OTHER PUBLICATIONS

Martin, A.C.R., "Protein Sequence and Structure Analysis of Antibody Variable Domains," Chapter 31, in *Antibody Engineering*. (Kontermann and Dübel, eds.), (Springer-Verlag, Berlin, 2001), pp. 422-439.
Martin et al., "The Emerging Role of IL-17 in the Pathogenesis of Psoriasis: Preclinical and Clinical Findings," *J. Invest. Dermatol.*, 133: 17-26 (2013).
Marvin and Zhu, "Recombinant approaches to IgG-like bispecific antibodies," *Acta Pharmacologica Sinica*, 26(6): 649-658 (2005).
Masliah et al., "Effects of α-Synuclein Immunization in a Mouse Model of Parkinson's Disease," *Neuron*, 46: 857-868 (2005).
Mateo et al., "Humanization of a mouse monoclonal antibody that blocks the epidermal growth factor receptor: recovery of antagonistic activity," *Immunotechnology*, 3: 71-81 (1997).
McCafferty et al., "Phage antibodies: Filamentous phage displaying antibody variable domains," *Nature*, 348: 552-554 (1990).
McDonnell et al., "TNF Antagonism," in *New Drugs for Asthma, Allergy and COPD. Prog Respir Res.*, vol. 31. (Hansel et al., eds.) (Karger, Basel, 2001) pp. 247-250.
McGee et al., "The Nogo-66 receptor: Focusing myelin inhibition of axon regeneration," *Trends in Neurosciences*, 26(4): 193-198 (2003).
McGuire-Goldring et al., "In Vitro Activation of Human Chondrocytes and Synoviocytes by a Human Interleukin-1-Like Factor," *Arthritis Rheum.*, 27(6): 654-662 (1984).
McIntosh et al., "In Vivo Induction of IL-6 by Administration of Exogenous Cytokines and Detection of De Novo Serum Levels of IL-6 in Tumor-Bearing Mice," *J. Immunol.*, 143(1): 162-167 (1989).
McMahon et al., "Does Anti-TNF-Alpha Have a Role in the Treatment of Osteoporosis?" *Bulletin of the NYU Hospital for Joint Diseases*, 66: 280-281 (2008).
Mendez et al., "Functional transplant of megabase human immunoglobulin loci recapitulates human antibody response in mice," *Nature Genet.*, 15: 146-156 (1997).
Merchant et al., "An efficient route to human bispecific IgG," *Nature Biotechnol.*, 16: 677-681 (1998).
Metz et al., "Bispecific antibody derivatives with restricted binding functionalities that are activated by proteolytic processing," *Prot. Engin. Des. Sel.*, 25(10): 571-580 (2012).
Michaelson, J., "Dual Targeting of TNF and TWEAK in Inflammatory Bowel Disease: The Promise of a Bispecific Antibody," Conference, Cytokines & Inflammation, Jan. 28, 2011; Agenda, p. 11. Retrieved from the Internet: http://www.cytokinesandinflammation.com/Index.php?option=com_content&view=article&id=50&itemid=54.
Miller et al., "Design, Construction, and in Vitro Analyses of Multivalent Antibodies," *J. Immunol.*, 170: 4854-4861 (2003).
Milstein et al., "Hybrid hybridomas and their use in immunohistochemistry," *Nature*, 305: 537-540 (1983).
Miossec et al., "Targeting IL-17 and TH17 cells in chronic inflammation," *Nat. Rev. Drug. Disc.*, 11(10): 763-776 (2012).
Mizushima et al., "pEF-BOS, a powerful mammalian expression vector," *Nucl. Acids Res.*, 18(17): 5322 (1990).
Mnich et al., "Characterization of a monoclonal antibody that neutralizes the activity of prostaglandin $E_2$," *J. Immunol.*, 155: 4437-4444 (1995).
Modjtahedi et al., "Antitumor Activity of Combinations of Antibodies Directed Against Different Epitopes on the Extracellular Domain of the Human EGF Receptor," *Cell Biophys.*, 22(1-3): 129-146 (1993).
Modjtahedi et al., "Phase I trial and tumour localisation of the anti-EGFR monoclonal antibody 1CR62 in head and neck or lung cancer," *Br. J. Cancer*, 73: 228-235 (1996).
Modjtahedi et al., "Targeting of Cells Expressing Wild-Type EGFR and Type-III Mutant EGFR (EGFRVIII) by Anti-EGFR MAB ICR62: A Two-Pronged Attack for Tumour Therapy," *Int. J. Cancer*, 105: 273-280 (2003).
Modjtahedi et al., "The human EGF receptor as a target for cancer therapy: Six new rat mAbs against the receptor on the breast carcinoma MDA-MB 468," *Br. J. Cancer*, 67: 247-253 (1993).

Motoi et al., "Apolipoprotein E receptor 2 is involved in neuritic plaque formation in APP sw mice," *Neurosci. Lett.*, 368: 144-147 (2004).
Monnet et al., "Association between the IL-1 family gene cluster and spondyloarthritis," *Ann. Rheum. Dis.*, 71: 885-890 (2012).
Moreland et al., "Soluble tumor necrosis factor receptors (sTNFR): Results of a phase I dose-escalation study in patients with rheumatoid arthritis," (Abstract No. 813), *Arthritis Rheum.*, 37: S295 (1994) (1 page).
Morgan and Anderson, "Human Gene Therapy," *Ann. Rev. Biochem.*, 62: 191-217 (1993).
Morgan et al., "Dissociation of hyperalgesia from fever following intracerebroventricular administration of interleukin-1β in the rat," *Brain Res.*, 1022(1-2): 96-100 (2004).
Morimoto et al., "The Increased Interleukin-13 in Patients with Systemic Lupus Erythematosus: Relations to Other Th1-, Th2-Related Cytokines and Clinical Findings," *Autoimmunity*, 34(1): 19-25 (2001).
Moriuchi et al., "Treatment of established collagen-induced arthritis with PGE1 incorporated in lipid microspheres," (Abstract No. 1528), *Arthritis Rheum.*, 39(9 Suppl.): S282 (1996) (1 page).
Morrison and Schlom, "Recombinant Chimeric Monoclonal Antibodies," Chapter 1, in *Important Advances in Oncology 1990* (J.B. Lippincott Company, Philadelphia, 1990), pp. 3-18.
Morrison et al., "Genetically Engineered Antibody Molecules," *Advances in Immunology*, 44: 65-92 (1989).
Morrison, S., "Two heads are better than one," *Nature Biotech.*, 25(11): 1233-1234 (2007).
Müller et al., "The first constant domain ($C_H1$ and $C_L$) of an antibody used as heterodimerization domain for bispecific miniantibodies," *FEBS Lett.*, 422: 259-264 (1998).
Mulligan, R.C., "The Basic Science of Gene Therapy," *Science*, 260: 926-932 (1993).
Mullinax et al., "Expression of a Heterodimeric Fab Antibody Protein in One Cloning Step," *BioTechniques*, 12(6): 864-869 (1992).
Murthy et al., "Binding of an Antagonistic Monoclonal Antibody to an Intact and Fragmented EGF-Receptor Polypeptide," *Arch. Biochem. Biophys.*, 252(2): 549-560 (1987).
Nakanishi et al., "Interleukin-18 Regulates Both TH1 and TH2 Responses," *Ann. Rev. Immunol.*, 19: 423-474 (2001).
Nalbandian et al., "Interleukin-17 and systemic lupus erythematosus: current concepts," *Clin. Exp. Immunol.*, 157(2): 209-215 (2009).
National Center for Biotechnology Information (NCBI), GenPept Database, "General transcription factor II-I repeat domain-containing protein 1 isoform e [Mus musculus]," Accession No. NP_001074935, ROD Feb. 15, 2015 [online]. Retrieved from the Internet: http://www.ncbi.nlm.nih.gov/protein/NP_001074935 (3 pages).
National Center for Biotechnology Information (NCBI), GenPept Database, "Low-density lipoprotein receptor-related protein 8 isoform 1 precursor [*Homo sapiens*]," Accession No. NP_004622, PRI Nov. 15, 2015 [online]. Retrieved from the Internet: http://www.ncbi.nlm.nih.gov/protein/NP_004622 (7 pages).
National Center for Biotechnology Information (NCBI), GenPept Database, "Low-density lipoprotein receptor-related protein 8 isoform 3 precursor [*Homo sapiens*]," Accession No. NP_059992, PRI Nov. 15, 2015 [online]. Retrieved from the Internet: http://www.ncbi.nlm.nih.gov/protein/NP_059992 (5 pages).
National Center for Biotechnology Information (NCBI), Protein Database, "Chain H, Vascular Endothelial Growth Factor in Complex with a Neutralizing Antibody," Accession No. 1BJ1_H, ROD Jun. 30, 1998 [online]. Retrieved from the Internet: http://www.ncbi.nlm.nih.gov/protein/1BJ1_H (3 pages).
National Center for Biotechnology Information (NCBI), Protein Database, "Chain L, Vascular Endothelial Growth Factor in Complex with a Neutralizing Antibody," Accession No. 1BJ1_L, ROD Jun. 30, 1998 [online]. Retrieved from the Internet: http://www.ncbi.nlm.nih.gov/protein/4389276?sat=11&satkey=3623907 (3 pages).
National Center for Biotechnology Information (NCBI), Protein Database, "Chain H, Structure of the G6 Fab, a Phage Derived Vegf Binding Fab," Accession No. 2FJF_H, PRI Jan. 2, 2006 [online]. Retrieved from the Internet: http://www.ncbi.nlm.nih.gov/protein/90109456?sat=34&satkey=11061854 (2 pages).

(56) References Cited

OTHER PUBLICATIONS

National Center for Biotechnology Information (NCBI), Protein Database, "Chain L, Structure of the G6 Fab, a Phage Derived Vegf Binding Fab," Accession No. 2FJF_L, PRI Jan. 2, 2006 [online]. Retrieved from the Internet: http://www.ncbi.nlm.nih.gov/protein/90109455?sat=34&satkey=11061854 (2 pages).

National Center for Biotechnology Information (NCBI), Protein Database, "Chain H, Structure of the B20-4 Fab, a Phage Derived Fab Fragment, in Complex with Vegf," Accession No. 2FJH_H, PRI Jan. 2, 2006 [online]. Retrieved from the Internet: http://www.ncbi.nlm.nih.gov/protein/90109487?sat=34&satkey=11061856 (2 pages).

National Center for Biotechnology Information (NCBI), Protein Database, "Chain L, Structure of the B20-4 Fab, a Phage Derived Fab Fragment, in Complex with Vegf," Accession No. 2FJH_L, PRI Jan. 2, 2006 [online]. Retrieved from the Internet: http://www.ncbi.nlm.nih.gov/protein/90109486?sat=34&satkey=11061856 (2 pages).

Nelson, R.B. "The Dualistic Nature of Immune Modulation in Alzheimer's Disease: Lessons from the Transgenic Models," *Curr. Pharm. Des.*, 11: 3335-3352 (2005).

Neuman et al., "An ELISA for PGE2 utilizing monoclonal antibody," *J. Immunoassay & Immunochem.*, 9(2): 159-177 (1988).

Ning et al., "Intratumoral radioimmunotherapy of a human colon cancer xenograft using a sustained-release gel," *Radiotherapy Oncol.*, 39: 179-189 (1996).

Nishimoto et al., "Treatment of rheumatoid arthritis with humanized anti-interleukin-6 receptor antibody," *Arthritis Rheum.*, 50(6): 1761-1769 (2004).

O'Connor et al., "Requirement of multiple phage displayed peptide libraries for optimal mapping of a conformational antibody epitope on CCR5," *J. Immunol. Methods*, 299: 21-35 (2005).

Okamoto et al., "Rituximab for Rheumatoid Arthritis," *N. Engl. J. Med.*, 351: 1909 (2004) (1 page).

Onishi and Gaffen, "Interleukin-17 and its target genes: mechanisms of interleukin-17 function in disease," *Immunol.*, 129:311-321 (2010).

Owens et al., "The Immunology of Multiple Sclerosis and Its Animal Model, Experimental Allergic Encephalomyelitis," *Neurol. Clin.*, 13(1): 51-73 (1995).

Pack and Plückthun, "Miniantibodies: Use of Amphipathic Helices to Produce Functional, Flexibly Linked Dimeric $F_V$ Fragments with High Avidity in *Escherichia coli*," *Biochemistry*, 31: 1579-1584 (1992).

Padilla et al., "IL-13 Regulates the Immune Response to Inhaled Antigens," *J. Immunol.*, 174(12): 8097-8105 (2005).

Padlan et al., "Identification of specificity-determining residues in antibodies," *FASEB J.*, 9: 133-139 (1995).

Padlan, E.A., "A Possible Procedure for Reducing the Immunogenicity of Antibody Variable Domains While Preserving Their Ligand-Binding Properties," *Mol. Immunol.*, 28(4/5): 489-498 (1991).

Pardridge, "Blood-brain barrier delivery of protein and non-viral gene therapeutics with molecular Trojan horses," *J. Control Release*, 122(3): 345-348 (2007).

Pardridge, "Biologic TNFα-inhibitors that cross the human blood-brain barrier," *Bioengineered Bugs*, 1(4): 231-234 (2010).

Parikh et al., "Urine NGAL and IL-18 are predictive biomarkers for delayed graft function following kidney transplantation," *Am. J. Transplant.*, 6(7): 1639-1645 (2006).

Park and Lee, "Interleukin-17 regulation: an attractive therapeutic approach for asthma," *Respir. Res.*, 11: 78 (2010).

Park et al., "Generation and characterization of a novel tetravalent bispecific antibody that binds to hepatitis B virus surface antigens," *Molecular Immunol.*, 37: 1123-1130 (2000).

Pearlman and Nguyen, "Analysis of protein drugs," Chapter 6, in *Peptide and Protein Drug Delivery Advances in Parenteral Sciences*, vol. 4. 1st ed. (Lee, ed.) (Marcel Dekker, Inc., New York, 1991), pp. 247-301.

Peipp et al., "Bispecific antibodies targeting cancer cells," *Biochem. Soc. Trans.*, 30(4): 507-511 (2002).

Pelletier et al., "In Vivo Suppression of Early Experimental Osteoarthritis by Interleukin-1 Receptor Antagonist Using Gene Therapy," *Arthritis Rheum.*, 40(6): 1012-1019 (1997).

Peng et al., "Experimental Use of Murine Lupus Models," *Methods Mol. Med.*, 102: 227-272 (2004).

Persic et al., "An integrated vector system for the eukaryotic expression of antibodies or their fragments after seletion from phage display libraries," *Gene*, 187: 9-18 (1997).

Petkova et al., "Enhanced half-life of genetically engineered human IgG1 antibodies in a humanized FcRn mouse model: Potential application in humorally mediated autoimmune disease," *Int. Immunol.*, 18: 1759-1769 (2006).

Petrey et al., "Using multiple structure alignments, fast model building, and energetic analysis in fold recognition and homology modeling," *Proteins*, 53: 430-435 (2003).

Pettiphar et al., "Interleukin 1 induces leukocyte infiltration and cartilage proteoglycan degradation in the synovial joint," *Proc. Natl. Acad. Sci. USA*, 83: 8749-8753 (1986).

Pham, V. et al., "De novo proteomic sequencing of a monoclonal antibody raised against OX40 ligand," *Analytical Biochemistry*, 352: 77-86 (2006).

Piatesi et al., "Immunological Optimization of a Generic Hydrophobic Pocket for High Affinity Hapten Binding and Diels-Alder Activity," *ChemBioChem*, 5: 460-466 (2004).

Pimm et al., "A bispecific monoclonal antibody against methotrexate and a human tumour associated antigen augments cytotoxicity of methotrexate-carrier conjugate," *Br. J. Cancer*, 61: 508-513 (1990).

PIR (Protein Information Resource) Accession No. PC4203, "Ig kappa chain (monoclonal antibody MabA34)—mouse (fragment)," Jan. 11, 2000 (2 pages).

Plückthun et al., "New protein engineering approaches to multivalent and bispecific antibody fragments," *Immunotechnology*, 3: 83-105 (1997).

Poljak, R.J., "Production and structure of diabodies," *Structure*, 2: 1121-1123 (1994).

Portanova et al., "Selective Neutralization of Prostaglandin $E_2$ Blocks Inflammation, Hyperalgesia, and Interleukin 6 Production in Vivo," *J. Exp. Med.*, 184(3): 883-891 (1996).

Portolano et al., "Lack of promiscuity in autoantigen-specific H and L chain combinations as revealed by human H and L chain 'roulette,'" *J. Immunol.*, 150: 880-887 (1993).

Presta et al., "Humanization of an Antibody Directed Against IgE," *Immunol.*, 151(5): 2623-2632 (1993).

Presta, L.G., "Engineering of therapeutic antibodies to minimize immunogenicity and optimize function," *Adv. Drug. Del. Rev.*, 58: 640-656 (2006).

Presta, L.G., "Molecular engineering and design of therapeutic antibodies," *Curr. Opin. Immunol.*, 20: 460-470 (2008).

Presta, L.G., "Selection, design, and engineering of therapeutic antibodies," *J. Allergy Clin. Immunol.*, 116: 731-736 (2005).

Qi et al, "A bispecific antibody against IL-1β and IL-17A is beneficial for experimental rheumatoid arthritis," *Internat'l. Immunopharm.*, 14: 770-778 (2012).

Qu et al., "Bispecific anti-CD20/22 antibodies inhibit B-cell lymphoma proliferation by a unique mechanism of action," *Blood*, 111(4): 2211-2219 (2007).

Quesada et al., "Do Not Say Ever Never More: The Ins and Outs of Antiangiogenic Therapies," *Curr. Pharmaceut. Des.*, 16: 3932-3957 (2010).

Rahman et al., "Association between the interleukin-1 family gene cluster and psoriatic arthritis," *Arthritis Rheum.*, 54(7): 2321-2325 (2006).

Reichert, J.M., "Bispecific antibodies and ADCs. Once and future kings?" *mAbs*, 3(4): 329-330 (2011).

*Remington: The Science and Practice of Pharmacy*. $21^{st}$ ed.(Lippincott Williams & Wilkins, Philadelphia, 2005), pp. 745-747, 802-804, 838, 879-883, 889-890, and 1079-1082 (14 pages).

Reusch et al., "Anti-CD3 x Anti-Epidermal Growth Factor Receptor (EGFR) Bispecific Antibody Redirects T Cell Cytolytic Activity to EGFR—Positive Cancers in vitro and in an Animal Model," *Clin. Cancer Res.*, 12(1): 183-190 (2006).

Ridgway et al., "'Knobs-into-holes' engineering of antibody $C_H3$ domains for heavy chain heterodimerization," *Protein Eng.*, 9(7): 617-621 (1996).

(56) References Cited

OTHER PUBLICATIONS

Ridgway et al., "Inhibition of DII4 signalling inhibits tumour growth by deregulating angiogenesis," *Nature*, 144(7122): 1083-1087 (2006).
Riechmann et al., "Reshaping human antibodies for therapy," *Nature*, 332: 323-327 (1988).
Riemer et al., "Matching of trastuzumab (Herceptin®) epitope mimics onto the surface of Her-2/neu—a new method of epitope definition" *Mol. Immunol.*, 42: 1121-1124 (2005).
Roberts et al., "RNA-peptide fusions for the in vitro selection of peptides and proteins," *Proc. Natl. Acad. Sci. USA*, 94: 12297-12302 (1997).
Robinson, C., "Gene therapy—proceeding from laboratory to clinic," *Trends Biotechnol.*, 11(5): 155 (1993) (1 page).
Rodeck et al., "Interactions Between Growth Factor Receptors and Corresponding Monoclonal Antibodies in Human Tumors," *J. Cell Biochem.*, 35: 315-320 (1987).
Roguska et al., "A comparison of two murine monoclonal antibodies humanized by CDR-grafting and variable domain resurfacing," *Protein Eng.*, 9(10): 895-904 (1996).
Roguska et al., "Humanization of murine monoclonal antibodies through variable domain resurfacing," *Proc. Natl. Acad. Sci. USA*, 91: 969-973 (1994).
Romon et al., "Nerve growth factor promotes breast cancer angiogenesis by activating multiple pathways," *Mol. Cancer*, [online] 9:157 (13 pages) (Jun. 2010). Retrieved from the Internet: http://rd.springer.com/content/pdf/10.1186/1476-4598-9-157.pdf; retrieved on Jul. 1, 2015.
Ronday et al., "Tranexamic acid (TEA), an inhibitor of plasminogen activation, reduces collagen crosslink excretion in arthritis," (Abstract No. 1541), *Arthritis Rheum.*, 39(9 Suppl.): S284 (1996) (1 page).
Ross, J.M., "Sulfasalazine (SSZ) toxicity: An assessment of American College of Rheumatology (ACR) monitoring guidelines for SSZ," (Abstract No. 1520), *Arthritis Rheum.*, 39(9 Suppl.): S281 (1996) (1 page).
Rudikoff et al., "Single amino acid substitution altering antigen-binding specificity," *Proc. Natl. Acad. Sci. USA*, 79: 1979-1983 (1982).
Sainson et al., "Anti-DII4 therapy: can we block tumour growth by increasing angiogenesis?" *TRENDS Mol. Med.*, 13(9): 389-395 (2007).
Sambrook and Russell (eds.), *Molecular Cloning: A Laboratory Manual*. 3rd Ed. Cold Spring Harbor Laboratory Press, Cold Spring Harbor, NY, 2001; pp. 1.10-1.15, 1.84-1.87, 8.18-8.24, 15.54-15.59, and 16.47-16.55 (18 pages).
Santos et al., "Generation and Characterization of a Single Gene-encoded Single-Chain-Tetravalent Antitumor Antibody," *Clin. Cancer Res.*, 5 (Suppl.): 3118s-3123s (1999).
Satoh et al., "Non-fucosylated therapeutic antibodies as next-generation therapeutic antibodies," *Expert Opin. Biol. Ther.*, 6(11): 1161-1173 (2006).
Saudek et al., "A Preliminary Trial of the Programmable Implantable Medication System for Insulin Delivery," *N. Engl. J. Med.*, 321: 574-579 (1989).
Sawai et al., "Direct Production of the Fab Fragment Derived From the Sperm Immobilizing Antibody Using Polymerase Chain Reaction and cDNA Expression Vectors," *Am. J. Reprod. Immunol.*, 34: 26-34 (1995).
Schaefer et al., "Immunoglobulin domain crossover as a generic approach for the production of bispecific IgG antibodies," *PNAS*, 108(27): 11187-11192 (2011).
Schier et al., "Identification of functional and structural amino-acid residues by parsimonious mutagenesis," *Gene*, 169: 147-155 (1996).
Scholz, P., "Inhibition of the production and effect of TNF-alpha by iloprost: possible impact for treatment of rheumatoid arthritis," (Abstract No. 336), *Arthritis Rheum.*, 39(9 Suppl.): S82 (1996).
Sefton, M.V., "Implantable Pumps," *CRC Crit. Rev. Biomed. Eng.*, 14(3): 201-240 (1987).
Seligmann et al., "Immunochemical Study of a Human Myeloma IgG1 Half Molecule," *Ann. Immunol.*, 129 C: 855-870 (1978).

Selkoe, "Clearing the brain's amyloid cobwebs," *Neuron*, 32(2): 177-180 (2001).
Sewell et al., "$DAB_{486}IL-2$ fusion toxin in refractory rheumatoid arthritis," *Arthritis Rheum.*, 36(9): 1223-1233 (Sep. 1993).
Sfikakis et al., "Rituximab anti-B-cell therapy in systemic lupus erythematosus: Pointing to the future," *Curr. Opin. Rheumatol.*, 17: 550-557 (2005).
Shalaby et al., "Development of Humanized Bispecific Antibodies Reactive with Cytotoxic Lymphocytes and Tumor Cells Overexpressing the HER2 Protooncogene," *J. Exp. Med.*, 175: 217-225 (1992).
Shapiro et al., "DNA Target Motifs of Somatic Mutagenesis in Antibody Genes," *Crit. Rev. Immunol.*, 22(3): 183-200 (2002).
Shen et al., "Principles and applicability of CSF sampling for the assessment of CNS drug delivery and pharmacodynamics," *Adv. Drug Deliv. Rev.*, 56(12): 1825-1857 (2004).
Shepherd et al., "Novel 'inflammatory plaque' pathology in presenilin-1 Alzheimer's disease," *Neuropathol. Appl. Neurobiol.*, 31: 503-511 (2005).
Shields et al., "Lack of Fucose on Human IgG1 N-Linked Oligosaccharide Improves Binding to Human $Fc\gamma RIII$ and Antibody-dependent Cellular Toxicity," *J. Biol. Chem.*, 277(30): 26733-26740 (2002).
Shu et al., "Secretion of a single-gene-encoded immunoglobulin from myeloma cells," *Proc. Natl. Acad. Sci. USA*, 90: 7995-7999 (1993).
Shukla et al., "HER2 specific delivery of methotrexate by dendrimer conjugated anti-Her2 mAB," *Nanotechnology*, 19: 295102 (2008) (7 pages).
Sims et al., "A Humanized CD18 Antibody Can Block Function without Cell Destruction," *J. Immunol.*, 151(4): 2296-2308 (1993).
Skerra et al., "Assembly of a Functional Immunoglobulin $F_v$ Fragment in *Escherichia coli*," *Science*, 240: 1038-1041 (1988).
Skripuletz et al., "Cortical demyelination is prominent in the murine cuprizone model and is strain-dependent," *Am. J. Physiol.*, 172(4): 1053-1061 (2008).
Smith and Morrison, "Recombinant Polymeric IgG: An Approach to Engineering More Potent Antibodies," *Bio/Technology*, 12: 683-688 (1994).
Snibson et al., "Airway remodelling and inflammation in sheep lungs after chronic airway challenge with house dust mite," *Clin. Exp. Allergy*, 35: 146-152 (2005).
Soloman, B., "Alzheimer's Disease and Immunotherapy," *Curr. Alzheimer. Res.*, 1: 149-163 (2004).
Song et al., "Antibody Mediated Lung Targeting of Long-Circulating Emulsions," *PDA J. Pharm. Sci. Technol.*, 50(6): 372-377 (1996).
Staerz et al., "Hybrid antibodies can target sites for attack by T cells," *Nature*, 314: 628-631 (1985).
Stamper et al., "Crystal structure of the B7-1/CTLA-4 complex that inhibits human immune responses," *Nature*, 410: 608-611 (2001).
Stancovski et al., "Mechanistic aspects of the opposing effects of monoclonal antibodies to the ERBB2 receptor on tumor growth," *Proc. Natl. Acad. Sci. USA*, 88: 8691-8695 (1991).
Steffen et al., "Basic studies on enzyme therapy of immune complex diseases" *Wien Klin. Wochenschr.*, 97(8): 376-385 (1985) (Abstract only) (1 page).
Steinman et al., "Virtues and pitfalls of EAE for the development of therapies for multiple sclerosis," *Trends Immunol.*, 26(11): 565-571 (2005).
Stickler et al., "CD4+ T-cell epitope determination using unexposed human donor peripheral blood mononuclear cells," *J. Immunotherapy*, 23: 654-660 (2000).
Stolk et al., "Are severe non-hematologic side-effects on azathioprine treatment caused by altered purine enzyme activities?" (Abstract No. 1522), *Arthritis Rheum.*, 39(9 Suppl.): S281 (1996) (1 page).
Streppel et al., "Focal application of neutralizing antibodies to soluble neurotrophic factors reduces collateral axonal branching after peripheral nerve lesion," *Eur. J. Neurosci.*, 15(8): 1327-1342 (2002).
Studnicka et al., "Human-engineered monoclonal antibodies retain full specific binding activity by preserving non-CDR complementarity-modulating residues," *Protein Eng.*, 7(6): 805-814 (1994).

(56) References Cited

OTHER PUBLICATIONS

'T Hart et al., "Suppression of Ongoing Disease in a Nonhuman Primate Model of Multiple Sclerosis by a Human-Anti-Human IL-12p40 Antibody," *J. Immunol.*, 175(7): 4761-4768 (2005).
Taiwan Patent Application No. 095130565: Taiwan Patent Office Search Report, dated Apr. 24, 2009.
Tan et al., "A bispecific antibody against two different epitopes on hepatitis B surface antigen has potent hepatitis B virus neutralizing activity," *mAbs*, 5(6): 946-955 (2013).
Tarsca et al. "Dual-Variable Domain Immunoglobulin (DVD-Ig™ Technology: A Versatile, Novel Format for the Next Generation of Dual-Targeting Biologics," Chapter 10 in *Bispecific Antibodies*. Roland E. Kontermann (ed.), Springer, New York, 2011; pp. 171-185.
Taylor et al., "A transgenic mouse that expresses a diversity of human sequence heavy and light chain immunoglobulins," *Nucl. Acids Res.*, 20: 6287-6295 (1992).
Teng et al., "Nogo Signaling and Non-Physical Injury-Induced Nervous System Pathology," *J. Neuroscience Research*, 79: 273-278 (2005).
Thies et al., "Folding and Association of the Antibody Domain $C_H3$: Prolyl Isomerization Preceeds Dimerization," *J. Mol. Biol.*, 293: 67-79 (1999).
Thoss et al., "Immunomodulation of rat antigen-induced arthritis by leflunomide alone and in combination with cyclosporin A," *Inflamm. Res.*, 45: 103-107 (1996).
Thurston et al., "The Delta paradox: DLL4 blockade leads to more tumour vessels but less tumour growth," *Nat. Rev.: Cancer*, 7(5): 327-331 (2007).
Tol et al., "Chemotherapy, Bevacizumab, and Cetuximab in Metastatic Colorectal Cancer," *N. Engl. J. Med.*, 360(6): 563-572 (2009).
Tolstoshev, P., "Gene Therapy, Concepts, Current Trials and Future Directions," *Ann. Rev. Pharmacol. Toxicol.*, 32: 573-596 (1993).
Torisu et al., "Discovery of a new class of potent, selective, and orally active prostaglandin $D_2$ receptor antagonists," *Bioorg. Med. Chem.*, 12: 5361-5378 (2004).
Torres et al., "The Immunoglobulin Heavy Chain Constant Region Affects Kinetic and Thermodynamic Parameters of Antibody Variable Region Interactions with Antigen," *J. Biol. Chem.*, 282(18): 13917-13927 (May 2007).
Tuohy et al., "Spontaneous Regression of Primary Autoreactivity during Chronic Progression of Experimental Autoimmune Encephalomyelitis and Multiple Sclerosis," *J. Exp. Med.*, 189(7): 1033-1042 (1999).
U.S. Appl. No. 12/431,460, filed Apr. 28, 2009 by Ghayur et al.: Notice of Allowance, dated Jan. 8, 2015.
U.S. Appl. No. 12/431,460, filed Apr. 28, 2009 by Ghayur et al.: Final Office Action, dated Aug. 7, 2014.
U.S. Appl. No. 12/431,460, filed Apr. 28, 2009 by Ghayur et al.: Non-Final Office Action, dated Apr. 4, 2014.
U.S. Appl. No. 12/431,460, filed Apr. 28, 2009 by Ghayur et al.: Final Office Action, dated Nov. 2, 2011.
U.S. Appl. No. 12/431,460, filed Apr. 28, 2009 by Ghayur et al.: Non-Final Office Action, dated Mar. 16, 2011.
U.S. Appl. No. 12/477,668, filed Jun. 3, 2009 by Ghayur et al.: Notice of Allowance, dated Apr. 13, 2015.
U.S. Appl. No. 12/477,668, filed Jun. 3, 2009 by Ghayur et al.: Final Office Action, dated Oct. 14, 2014.
U.S. Appl. No. 12/477,668, filed Jun. 3, 2009 by Ghayur et al.: Non-Final Office Action, dated Mar. 10, 2014.
U.S. Appl. No. 12/477,668, filed Jun. 3, 2009 by Ghayur et al.: Final Office Action, dated May 3, 2012.
U.S. Appl. No. 12/477,668, filed Jun. 3, 2009 by Ghayur et al.: Non-Final Office Action, dated Sep. 8, 2011.
U.S. Appl. No. 12/477,711, filed Jun. 3, 2009 by Ghayur et al.: Notice of Allowance, dated Jan. 27, 2015.
U.S. Appl. No. 12/477,711, filed Jun. 3, 2009 by Ghayur et al.: Non-Final Office Action, dated Jul. 29, 2014.
U.S. Appl. No. 12/477,711, filed Jun. 3, 2009 by Ghayur et al.: Final Office Action, dated Feb. 7, 2014.
U.S. Appl. No. 12/477,711, filed Jun. 3, 2009 by Ghayur et al.: Non-Final Office Action, dated Jul. 17, 2013.
U.S. Appl. No. 12/477,711, filed Jun. 3, 2009 by Ghayur et al.: Final Office Action, dated Dec. 30, 2011.
U.S. Appl. No. 12/477,711, filed Jun. 3, 2009 by Ghayur et al.: Non-Final Office Action, dated Aug. 11, 2011.
U.S. Appl. No. 12/499,652, filed Jul. 8, 2009 by Ghayur et al.: Notice of Allowance, dated Apr. 10, 2014.
U.S. Appl. No. 12/499,652, filed Jul. 8, 2009 by Ghayur et al.: Final Office Action, dated Nov. 3, 2011.
U.S. Appl. No. 12/499,652, filed Jul. 8, 2009 by Ghayur et al.: Non-Final Office Action, dated May 10, 2011.
U.S. Appl. No. 12/605,094, filed Oct. 23, 2009 by Ghayur et al.: Final Office Action, dated Nov. 30, 2011.
U.S. Appl. No. 12/605,094, filed Oct. 23, 2009 by Ghayur et al.: Non-Final Office Action, dated Jun. 29, 2011.
U.S. Appl. No. 12/631,483, filed Dec. 4, 2009 by Jakob et al.: Non-Final Office Action, dated May 27, 2014.
U.S. Appl. No. 12/631,483, filed Dec. 4, 2009 by Jakob et al.: Final Office Action, dated Jul. 6, 2012.
U.S. Appl. No. 12/631,483, filed Dec. 4, 2009 by Jakob et al.: Non-Final Office Action, dated Nov. 23, 2011.
U.S. Appl. No. 12/771,871, filed Apr. 30, 2010 by Ghayur et al.: Non-Final Office Action, dated Apr. 15, 2014.
U.S. Appl. No. 12/771,871, filed Apr. 30, 2010 by Ghayur et al.: Final Office Action, dated May 28, 2013.
U.S. Appl. No. 12/771,871, filed Apr. 30, 2010 by Ghayur et al.: Non-Final Office Action, dated May 16, 2012.
U.S. Appl. No. 12/771,874, filed Apr. 30, 2010 by Ghayur et al.: Final Office Action, dated Nov. 12, 2013.
U.S. Appl. No. 12/771,874, filed Apr. 30, 2010 by Ghayur et al.: Non-Final Office Action, dated Apr. 18, 2013.
U.S. Appl. No. 12/771,874, filed Apr. 30, 2010 by Ghayur et al.: Non-Final Office Action, dated Sep. 7, 2012.
U.S. Appl. No. 12/846,317, filed Jul. 29, 2010 by Ghayur et al.: Final Office Action, dated Nov. 6, 2013.
U.S. Appl. No. 12/846,317, filed Jul. 29, 2010 by Ghayur et al.: Final Office Action, dated May 23, 2013.
U.S. Appl. No. 12/873,926, filed Sep. 1, 2010 by Ghayur et al.: Notice of Allowance, dated Jul. 24, 2013.
U.S. Appl. No. 12/873,926, filed Sep. 1, 2010 by Ghayur et al.: Final Office Action, dated Mar. 12, 2013.
U.S. Appl. No. 12/873,926, filed Sep. 1, 2010 by Ghayur et al.: Non-Final Office Action, dated Aug. 28, 2012.
U.S. Appl. No. 12/905,474, filed Oct. 15, 2010 by Ghayur et al.: Notice of Allowance, dated Jan. 10, 2014.
U.S. Appl. No. 12/905,474, filed Oct. 15, 2010 by Ghayur et al.: Non-Final Office Action, dated May 29, 2013.
U.S. Appl. No. 12/914,614, filed Oct. 28, 2010 by Ghayur et al.: Notice of Allowance, dated Jan. 10, 2014.
U.S. Appl. No. 12/914,614, filed Oct. 28, 2010 by Ghayur et al.: Non-Final Office Action, dated Jun. 6, 2013.
U.S. Appl. No. 13/167,323, filed Jun. 23, 2011 by Ghayur et al.: Final Office Action, dated Nov. 20, 2013.
U.S. Appl. No. 13/167,323, filed Jun. 23, 2011 by Ghayur et al.: Non-Final Office Action, dated Jun. 4, 2013.
U.S. Appl. No. 13/178,641, filed Jul. 8, 2011 by Ghayur et al.: Notice of Allowance, dated May 7, 2015.
U.S. Appl. No. 13/178,641, filed Jul. 8, 2011 by Ghayur et al.: Non-Final Office Action, dated Dec. 17, 2014.
U.S. Appl. No. 13/196,138, filed Aug. 2, 2011 by Ghayur et al.: Notice of Allowance, dated Jan. 16, 2014.
U.S. Appl. No. 13/196,138, filed Aug. 2, 2011 by Ghayur et al.: Non-Final Office Action, dated Nov. 27, 2012.
U.S. Appl. No. 13/217,937, filed Aug. 25, 2011 by Ghayur et al.: Notice of Allowance, dated Feb. 13, 2015.
U.S. Appl. No. 13/217,937, filed Aug. 25, 2011 by Ghayur et al.: Non-Final Office Action, dated Aug. 22, 2014.
U.S. Appl. No. 13/217,937, filed Aug. 25, 2011 by Ghayur et al.: Final Office Action, dated Mar. 20, 2013.
U.S. Appl. No. 13/217,937, filed Aug. 25, 2011 by Ghayur et al.: Non-Final Office Action, dated Sep. 6, 2012.

(56) References Cited

OTHER PUBLICATIONS

U.S. Appl. No. 13/286,707, filed Nov. 1, 2011 by Ghayur et al.: Examiner's Answer to Appeal Brief, dated Sep. 28, 2015.
U.S. Appl. No. 13/286,707, filed Nov. 1, 2011 by Ghayur et al.: Final Office Action, dated Aug. 29, 2014.
U.S. Appl. No. 13/286,707, filed Nov. 1, 2011 by Ghayur et al.: Non-Final Office Action, dated Jan. 29, 2014.
U.S. Appl. No. 13/286,707, filed Nov. 1, 2011 by Ghayur et al.: Final Office Action, dated Jul. 17, 2013.
U.S. Appl. No. 13/286,707, filed Nov. 1, 2011 by Ghayur et al.: Non-Final Office Action, dated Feb. 25, 2013.
U.S. Appl. No. 13/729,353, filed Dec. 28, 2012 by Ghayur et al.: Non-Final Office Action, dated Jun. 2, 2015.
U.S. Appl. No. 13/729,645, filed Dec. 28, 2012 by Hsieh et al.: Notice of Allowance, dated May 1, 2015.
U.S. Appl. No. 14/068,976, filed Oct. 21, 2013 by Gu et al.: Non-Final Office Action, dated Feb. 4, 2015.
U.S. Appl. No. 14/068,976, filed Oct. 21, 2013 by Gu et al.: Notice of Allowance, dated Jun. 11, 2015.
U.S. Appl. No. 14/135,107, filed Dec. 19, 2013 by Ghayur et al.: Non-Final Office Action, dated Dec. 2, 2015.
U.S. Appl. No. 14/135,149, filed Dec. 19, 2013, by Ghayur et al.: Non-Final Office Action, dated Dec. 4, 2015.
U.S. Appl. No. 14/211,604, filed Mar. 14, 2014 by Ghayur et al.: Notice of Allowance, dated Mar. 26, 2015.
U.S. Appl. No. 14/248,223, filed Apr. 8, 2014 by Ghayur et al.: Non-Final Office Action, dated Mar. 24, 2015.
U.S. Appl. No. 14/248,223, filed Apr. 8, 2014 by Ghayur et al.: Final Office Action, dated Jul. 22, 2015.
U.S. Appl. No. 14/301,305, filed Jun. 10, 2014 by Ghayur et al.: Non-Final Office Action, dated May 29, 2015.
U.S. Appl. No. 14/301,546, filed Jun. 11, 2014 by Gu et al.: Notice of Allowance, dated Apr. 9, 2015.
U.S. Appl. No. 14/301,546, filed Jun. 11, 2014 by Gu et al.: Non-Final Office Action, dated Nov. 25, 2014.
U.S. Appl. No. 14/323,627, filed Jul. 3, 2014 by Ghayur et al.: Notice of Allowance, dated Dec. 8, 2014.
Umaña et al., "Engineered glycoforms of an antineuroblastoma IgG1 with optimized antibody-dependent cellular cytotoxic activity," *Nature Biotechnol.*, 17: 176-180 (1999).
Urlaub et al., "Isolation of Chinese hamster cell mutants deficient in dihydrofolate reductase activity," *Proc. Natl. Acad. Sci. USA*, 77: 4216-4220 (1980).
Vaccaro et al., "Divergent activities of an engineered antibody in murine and human systems have implications for therapeutic antibodies," *Proc. Natl. Acad. Sci. USA*, 103: 18709-18714 (2006).
Vajdos et al., "Comprehensive functional maps of the antigen-binding site of an anti-ErbB2 antibody obtained with shotgun scanning mutagenesis," *J. Mol. Biol.*, 320: 415-428 (2002).
Verhoeyen et al., "Reshaping Human Antibodies: Grafting an Antilysozyme Activity," *Science*, 239: 1534-1536 (1988).
Vincent et al., "Clinical associations of serum interleukin-17 in systemic lupus erythematosus," *Arthritis Res. Ther.*, 15: R97 (9 pages).
Voet et al. (Eds.), *Biochemistry*. John Wiley & Sons, Inc., 1999; p. 1100.
Voller et al., "Enzyme immunoassays with special reference to ELISA techniques," *J. Clin. Pathol.*, 31: 507-520 (1978).
Von Mehren et al., "Monoclonal Antibody Therapy for Cancer," *Ann. Rev. Med.*, 54: 343-369 (2003).
Wallick et al., "Glycosylation of a $V_H$ Residue of a Monoclonal Antibody Against α(1→6) Dextran Increases Its Affinity for Antigen," *J. Exp. Med.*, 168: 1099-1109 (1988).
Wang et al., "Antibody Structure, Instability, and Formulation," *J. Pharm. Sci.*, 96(1): 1-26 (2007).
Wang, P. and X. Yang, "Neutralization Efficiency Is Greatly Enhanced by Bivalent Binding of an Antibody to Epitopes in the V4 Region and the Membrane-Proximal External Region within One Trimer of Human Immunodeficiency Virus Type 1 Glycoproteins" *J. Virol.*, 84(14): 7114-7123 (2010).
Ward et al., "Binding activities of a repertoire of single immunoglobulin variable domains secreted from *Escherichia coli*," *Nature*, 341: 544-546 (1989).
West Jr. et al., "Crystal Structure and Immunoglobulin G Binding Properties of the Human Major Histocompatibility Complex-Related Fc Receptor," *Biochemistry*, 39: 9698-9708 (2000).
Wileman et al., "Associations between Subunit Ectodomains Promote T Cell Antigen Receptor Assembly and Protect against Degradation in the ER," *J. Cell Biol.*, 122(1): 67-78 (1993).
Wing et al., "Ex-vivo whole blood cultures for predicting cytokine-release syndrome: Dependence on target antigen and antibody isotype," *Therapeutic Immunol.*, 2(4): 183-190 (1995).
Winkles, J., "The TWEAK-Fn14 cytokine-receptor axis: discovery, biology and therapeutic targeting," *Nature Reviews. Drug Disc.*, 7(5): 411-425 (2008).
Witkowski et al., "Interleukin-17: A mediator of inflammatory responses," *Cell. Mol. Life Sci.*, 61: 567-579 (2004).
Wong et al., "Hyperproduction of IL-23 and IL-17 in patients with systemic lupus erythematosus: Implications for Th17-mediated inflammation in autoimmunity," *Clin. Immunol.*, 127(3): 385-393 (2008).
Wooldridge et al., "Tricks with tetramers: How to get the most from multimeric peptide-MHC," *Immunology*, 126: 147-164 (2009).
Wright et al., "Antibody variable region glycosylation: Position effects on antigen binding and carbohydrate structure," *EMBO J.*, 10(10): 2717-2723 (1991).
Wu and Grainger, "Drug/device combinations for local drug therapies and infection prophylaxis," *Biomaterials*, 27: 2450-2467 (2006).
Wu and Wu, "Delivery systems for gene therapy," *Biotherapy*, 3: 87-95 (1991).
Wu and Wu, "Receptor-mediated in Vitro Gene Transformation by a Soluble DNA Carrier System," *J. Biol. Chem.*, 262(10): 4429-4432 (1987).
Wu et al., "Generation and Characterization of a Dual Variable Domain Immunoglobulin (DVD-Ig™) Molecule," in *Antibody Engineering*, vol. 2. R. Kontermann and S. Dübel (Eds.), Springer-Verlag, 2010; pp. 239-250.
Wu et al., "Humanization of a murine monoclonal antibody by simultaneous optimization of framework and CDR residues," *J. Mol. Biol.*, 294: 151-162 (1999).
Wu et al., "IL-18 receptor β-induced changes in the presentation of IL-18 binding sites affect ligand binding and signal transduction," *J. Immunol.*, 170: 5571-5577 (2003).
Wu et al., "Molecular construction and optimization of anti-human IL-1α/β dual variable domain immunoglobulin (DVD-Ig™) molecules," *mAbs*, 1(4): 339-347 (2009).
Wu et al., "Simultaneous targeting of multiple disease mediators by a dual-variable-domain immunoglobulin," *Nature Biotechnol.*, 25(11): 1290-1297 (2007).
Wu et al., "Simultaneous targeting of multiple disease mediators by a dual-variable-domain immunoglobulin," *Nature Biotechnology* (advance online publication, http://www.nature.com/naturebiotechnology), pp. 1-8 (published online Oct. 14, 2007).
Wu et al., "Tumor localization of anti-CEA single-chain Fvs: Improved targeting by non-covalent dimers," *Immunotechnology*, 2(1): 21-36 (1996).
Wurm, F.M., "Production of recombinant protein therapeutics in cultivated mammalian cells," *Nature Biotechnol.*, 22(11): 1393-1398 (2004).
Wynn et al., "Distinct roles for IL-13 and IL-17 in chronic inflammation and fibrosis," *J. Immunol.*, 184:134.8 (2010).
Xu et al., "Recombinant DNA vaccine encoding multiple domains related to inhibition of neurite outgrowth: A potential strategy for axonal regeneration," *J. Neurochem.*, 91: 1018-1023 (2004).
Yamada et al., "Aβ Immunotherapy: Intracerebral Sequestration of Aβ by an Anti-Aβ Monoclonal Antibody 266 with High Affinity to Soluble Aβ," *J. Neurosci.*, 29(36):11393-11398 (2009).
Yao et al., "Human IL-17: A Novel Cytokine Derived from T Cells," *J. Immunol.*, 155: 5483-5486 (1995).
Yao et al., "Molecular characterization of the human interleukin (IL)-17 receptor," *Cytokine*. 9(11): 794-800 (1997).

(56) References Cited

OTHER PUBLICATIONS

Yelton et al., "Affinity Maturation of the BR96 Anti-Carcinoma Antibody by Codon-Based Mutagenesis," *J. Immunol.*, 155: 1994-2004 (1995).

Yonehara et al., "Involvement of apoptosis antigen Fas in clonal deletion of human thymocytes," *Int. Immunol.*, 6(12): 1849-1856 (1994).

Yu et al., "Boosting Brain Uptake of a Therapeutic Antibody by Reducing Its Affinity for a Transcytosis Target," *Sci. Transl. Med.*, 3(84):84ra44, 8 pages (2011).

Zapata et al., "Engineering linear F(ab')$_2$ fragments for efficient production in *Escherichia coli* and enhanced antiproliferative activity," *Protein Eng.*, 8(10): 1057-1062 (1995).

Zhang and Pardridge, "Delivery of β-Galactosidase to Mouse Brain via the Blood-Brain Barrier Transferrin Receptor," *J. Pharmacol. Exper. Ther.*, 313(5): 1075-1081 (2005).

Zhang et al., "Direct chitosan-mediated gene delivery to the rabbit knee joints in vitro and in vivo," *Biochem. Biophys. Res. Commun.*, 341: 202-208 (2006).

Zhang et al., "Inhibition of Cyclooxygenase-2 Rapidly Reverses Inflammatory Hyperalgesia and Prostaglandin E$_2$ Production," *J. Pharmacol. Exp. Ther.*, 283(3): 1069-1075 (1997).

Zhou et al., "Neuroprotection with a Brain-Penetrating Biologic Tumor Necrosis Factor Inhibitor," *J. Pharmacol. Exp. Therapeut.*, 339(2): 618-623 (2011).

Zola et al., "CD Molecules 2005: Human cell differentiation molecules," *Blood*, 106: 3123-3126 (2005).

Zuo et al., "An efficient route to the production of an IgG-like bispecific antibody," *Protein Eng.*, 13(5): 361-367 (2000).

Atwal, J.K., et al., "A Therapeutic Antibody Targeting BACE1 Inhibits Amyloid-β Production in Vivo," *Science Translational Medicine* 3(84):84ra43, 12 pages, American Association for the Advancement of Science, United States (2011).

Carter, C.J., "Convergence of genes implicated in Alzheimer's disease on the cerebral cholesterol shuttle: APP, cholesterol, lipoproteins, and atherosclerosis," *Neurochemistry International* 50:12-38, Elsevier Ltd., England (2007).

Myant, N.B., "Reelin and apolipoprotein E receptor 2 in the embryonic and mature brain: effects of an evolutionary change in the apoER2 gene," *Proceedings of the Royal Society* 277:345-351, The Royal Society, England (2010).

International Search Report for International Application No. PCT/US2015/065406, European Patent Office, Munich, dated Jun. 30, 2016, 10 pages.

Written Opinion for International Application No. PCT/US2015/065406, European Patent Office, Munich, dated Jun. 30, 2016, 17 pages.

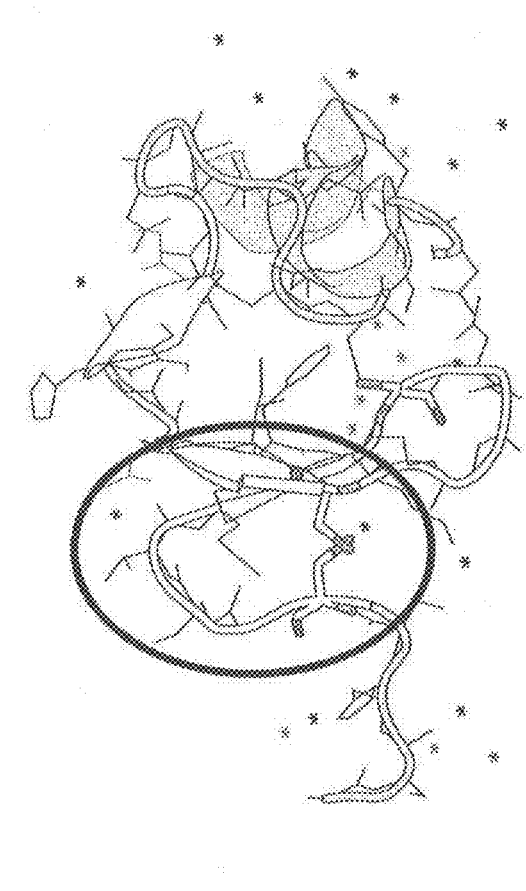

CYNO LRP8 PROTEIN SEQUENCE ALIGNMENT WITH HUMAN AND MOUSE
(FROM BRAIN AND TESTIS TISSUES: TWO DONORS)

```
                          (1)   1        10        20        30        40
HUMANLRP8(NP_059992)      (1)   MGLPEPGPLRLLALLLLLLLLLLQLQHLAAAAAPPLLGGQGPAKDCE
MOUSELRP8(NP_001074935)   (1)   MGRPELGALRPLAL------LLLLIQLQHLSAADPLPGGQGPVKECE
CYNOLRP8 (BRAIN)          (1)   ------------------------MQLQHLAAAAPPLLGGQGPAKECE
CYNOLRP8 (TESTIS)         (1)   ------------------------MQLQHLAAAAPPLLGGQGPAKECE (121) 121      130       140       150       160
HUMANLRP8(NP_059992)    (121)   TCTKQVCPAEKLSCGPTSHKCVPASWRCDGEKDCEGGADEAGCATS-L
MOUSELRP8(NP_001074935)(115)   TCSSECPAEKLSCGPTSHKCVPASWRCDGEKDCEGGADEAGCPTSAP
CYNOLRP8 (BRAIN)       (101)   TCT--------------------------------------------L
CYNOLRP8 (TESTIS)      (101)   TCT--------------------------------------------L (241) 241      250       260       270       280
HUMANLRP8(NP_059992)    (208)   -------LNPCLHNGGCSHICTDLKIGFECTCPAGFQLLDQKTCG
MOUSELRP8(NP_001074935)(235)   SDEPQKVCGLNPCLHNGGCSHICTDLKIGFECTCPAGFQLLDQKTCG
CYNOLRP8 (BRAIN)       (153)   ----RRPRGLNPCLHNGGCSHICTDLKIGFECTCPAGFQLLDQKTCG
CYNOLRP8 (TESTIS)      (153)   ----RRPRGLNPCLHNGGCSHICTDLKIGFECTCPAGFQLLDQKTCG (361) 361      370       380       390       400
HUMANLRP8(NP_059992)    (319)   MLRNVVALDVEVRNRIYWCDLSYRKIYSAYMDKASDPKEQEVLIDEQ
MOUSELRP8(NP_001074935)(355)   MLRNVVALDVEVANRIYWCDLSYRKIYSAHMDKASIPDEQVVLIDRQ
CYNOLRP8 (BRAIN)       (269)   MLRNVVALMEVATNRIYWCDLSYRKIYSAYMDKASDPKEQEVLIDEQ
CYNOLRP8 (TESTIS)      (269)   MLRNVVALMEVATNRIYWCDLSYRKIYSAYMDKASDPKEQEVLIDEQ (481) 481      490       500       510       520
HUMANLRP8(NP_059992)    (439)   SGLNGVDRQTLVSDNIEWPNGITLDLLSQRLYWVDSKLHQLSSIDFSG
MOUSELRP8(NP_001074935)(475)   AGLNGADRQTLVSDNIEWPNGITLDLLGQRLYWVDSKLHQLSSIDFNG
CYNOLRP8 (BRAIN)       (389)   SGLNGVDRQTLVSDNIEWPNGITLDLLSQRLYWVDSKLHQLSSIDFSG
CYNOLRP8 (TESTIS)      (389)   SGLNGVDRQTLVSDNIEWPNGITLDLLSQRLYWVDSKLHQLSSIDFSG (601) 601      610       620       630       640
HUMANLRP8(NP_059992)    (559)   DACELSVQPNGGCEYLCLPAPQISSHSPKYTCACPDTMWLGPDMKRCY
MOUSELRP8(NP_001074935)(595)   DACDLSAQPNGGCEYLCLPAPQISSHSPKYTCACPDTMWLGPDMKRCY
CYNOLRP8 (BRAIN)       (509)   DACKLSVQPNGGCEYLCLPAPQISSHSPKYTCACPDTMWLGPDMKRCY
CYNOLRP8 (TESTIS)      (509)   DACKLSVQPNGGCEYLCLPAPQISSHSPKYTCACPDTMWLGPDMKRCY (721) 721      730       740       750       760
HUMANLRP8(NP_059992)    (606)   ----DANEDKNGSTVTAAVIGIIVPIVVIALLCMSGYLIWRNWKRKN
MOUSELRP8(NP_001074935)(715)   HSQHYGNEGSQNGSTVTAAVIGVIVPIVVIALLCMSGYLIWRNWKRKN
CYNOLRP8 (BRAIN)       (558)   ----DGNEDKKGSTVTAAVIGIIVPIVVIALLCMSGYLIWRNWKRKN
CYNOLRP8 (TESTIS)      (558)   ----DGNEDKKGSTVTAAVIGIIVPIVVIALLCMSGYLIWRNWKRKN
```

*FIG. 2A*

```
                              AB58216 PROTEIN (83-171)
         CR1 PEPTIDE          CR2 PEPTIDE
    50        60        70        80        90        100       110       120
KDQFQCRNERCIPSVWRCDEDDDCLDHSDEDDCPKKTCADSDFTCDNGHCIHERWKCDGEEECPDGSDESEA
EDQFRCRNERCIPLVWRCDEDNDCSDNSDEDDCPKRTCADSDFTCDNGHCIPERWKCDGEEECPDGSDESKA
KDQFQCRNERCIPSVWRCDEDDDCLDHSDEDDCPKKTCADSDFTCDNGHCIHERWKCDGEEECPDGSDESEA
KDQFQCRNERCIPSVWRCDEDDDCLDHSDEDDCPKKTCADSDFTCDNGHCIHERWKCDGEEECPDGSDESEA 170       180       190       200       210       220       230       240
GTCRGDEFQCGDGTCVLAIKHCNQFQDCPDGSDEAGCLQG----------------------------------
GPCRENEFQCGDGTCVLAIKRCNQERDCPDGSDEAGCLQESTCEGPRRFQCKSGECVDGGKVCDDQRDCRDW
GTCHGNEFQCGDGTCVLAIKRCNQFQDCPDGSDEAGCLQVPPTFLGNR---------------------------
GTCHGNEFQCGDGTCVLAIKRCNQFQDCPDGSDEAGCLQVPPTFLGNR---------------------------

290       300       310       320       330       340       350       360
DIDECKDPDACSQICVNYKGYFKCECYPGYEMDLLTKNCKAAANGKSPSLIFTNRHEVRRIDLVKRNYSRLIP
DIDECQDPDACSQICVNYKGYFKCECHPGYEMDTLTKNCKAVAGKSPSLIFTNRHEVRRIDLVKRDYSRLIP
DIDECKDPDACSQICVNYKGYFKCECYPGYEMDLLTKNCKAAAGKSPSLIFTNRHEVRRIDLVKRNYSRLIP
DIDECKDPDACSQICVNYKGYFKCECYPGYEMDLLTKNCKAAAGKSPSLIFTNRHEVRRIDLVKRNYSRLIP 410       420       430       440       450       460       470       480
LHSPEGLAVDWVHKHIYWTDSGNKTISVANLDGRRRTLFSRNLSEPRAIAVDPLRGFMYWSDWGDQAKIEK
LHSPEGLAVDWVHKHIYWTDSGNKTISVATLDGRRRCTLFSRELSEPRAIAVDPLRGFMYWSDWGFQAKIEK
LHSPEGLAVDWVHKHIYWTDSGNKTISVABLDGRRRCTLFSRNLSEPRAIAVDPLQGFMYWSDWGNQAKIEK
LHSPEGLAVDWVHKHIYWTDSGNKTISVATVDGRRRCTLFSRNLSEPRAIAVDPLQGFMYWSDWGNQAKIEK 530       540       550       560       570       580       590       600
GNKKTLISSIDPLSHPEGIAVFDKVFWTDLENEAIFSANRLNGLEISILAENLNPPHDIVIFHELKQPRAP
GNKKMLIFSTDPLSHPFGVAVFDKVFWTDLENEAIFSANRINGLEIARLAENLNNPHDIVIFHELKQPKAA
GNRKMLISSIDPLSHPFGIAVFDKVFWTDLENEAIFSANRLNGLEISILAENLNNPHDIVIFHELKQPRAA
GNRKMLISSIDPLSHPFGIAVFDKVFWTDLENEAIFSANRLNGLEISILAENLNNPHDIVIFHELKQPRAA 650       660       670       680       690       700       710       720
R-------------------------------------------------------------------------
RAPQSTSTTTLASAMTRTVPATTRAPGTTIHDPTYQNHSTETPSQTAAAPHSVNVPRAPSTSPSTPSPATSN
R-------------------------------------------------------------------------
R-------------------------------------------------------------------------

770       780       790       800       810       820       830       840
TKSMNFDNPVYRKTTEEEDEDELHIGRTAQIGHVYP----------------------------------------
TKSMNFDNPVYRKTTEEEDEDELHIGRTAQIGHVYPAAISNYDRPLWAEPCLGETRDLEDPAPALKELFVLP
TKSMNFDNPVYRKTTEEEDEDELHIGRTAQIGHVYP----------------------------------------
TKSMNFDNPVYRKTTEEEDEDELHIGRTAQIGHVYP----------------------------------------
```

AT CR1 AND CR2, PEPTIDES IDENTICAL IN CYNO AND HUMAN LRP8

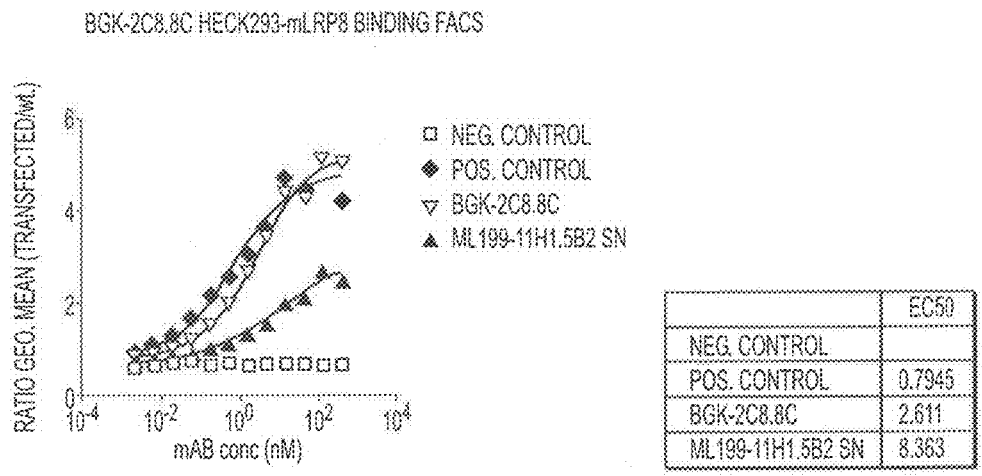
FIG. 12A
FIG. 12B
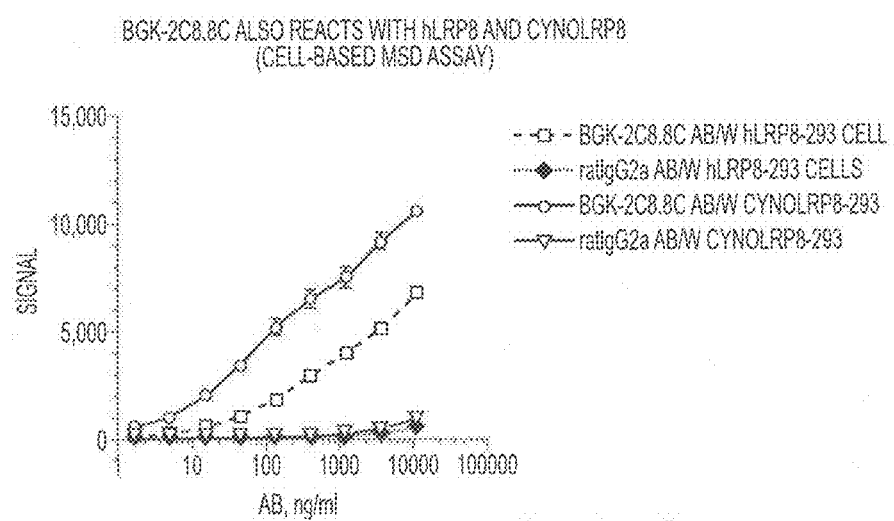
FIG. 12C

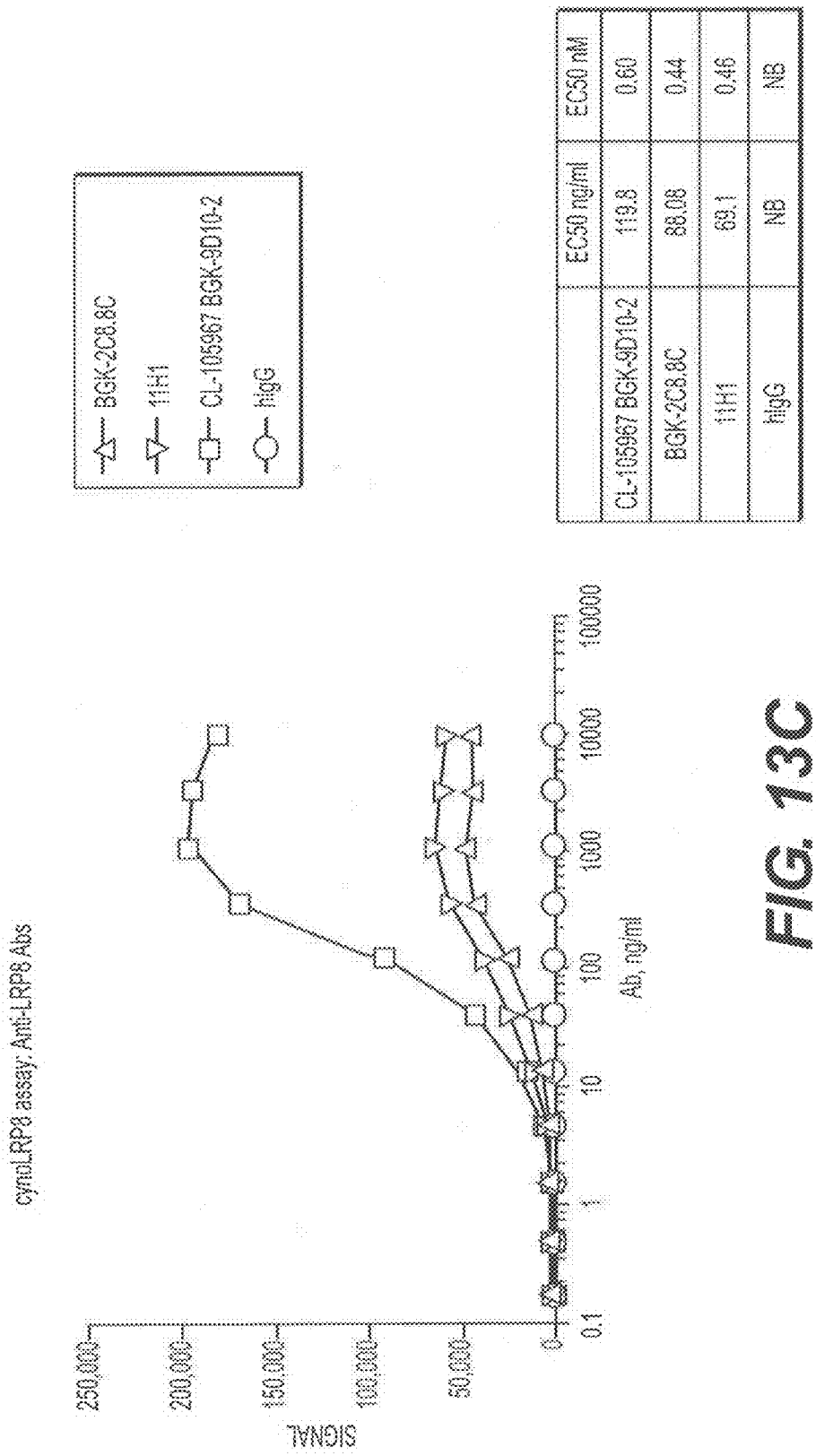

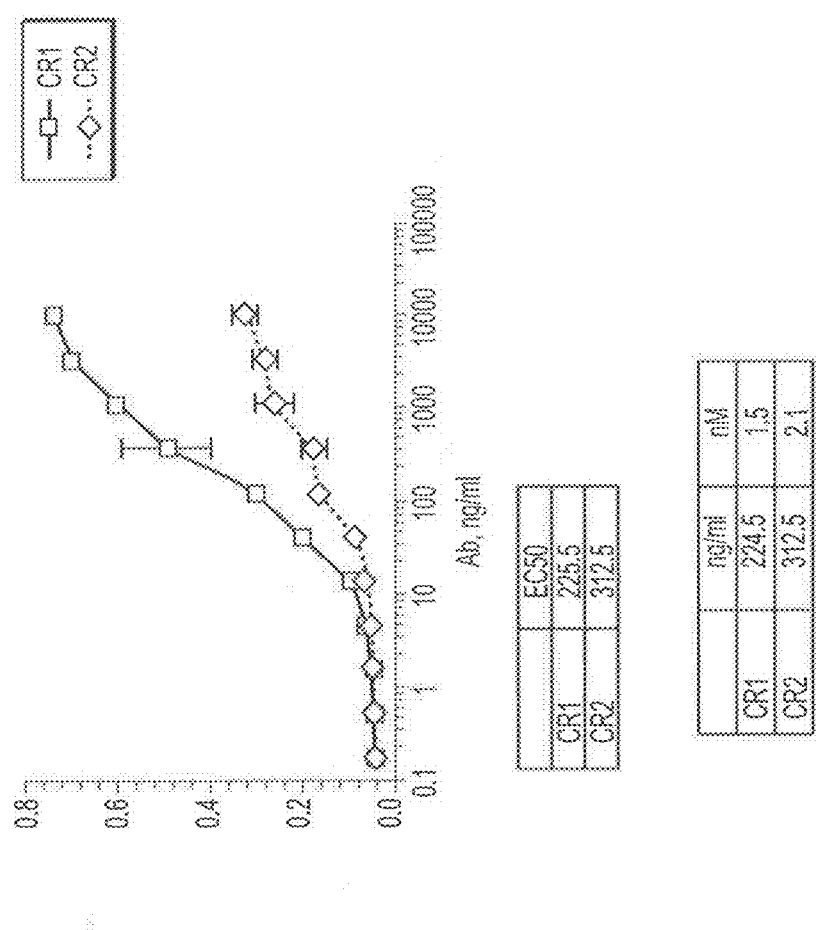

FIG. 17B

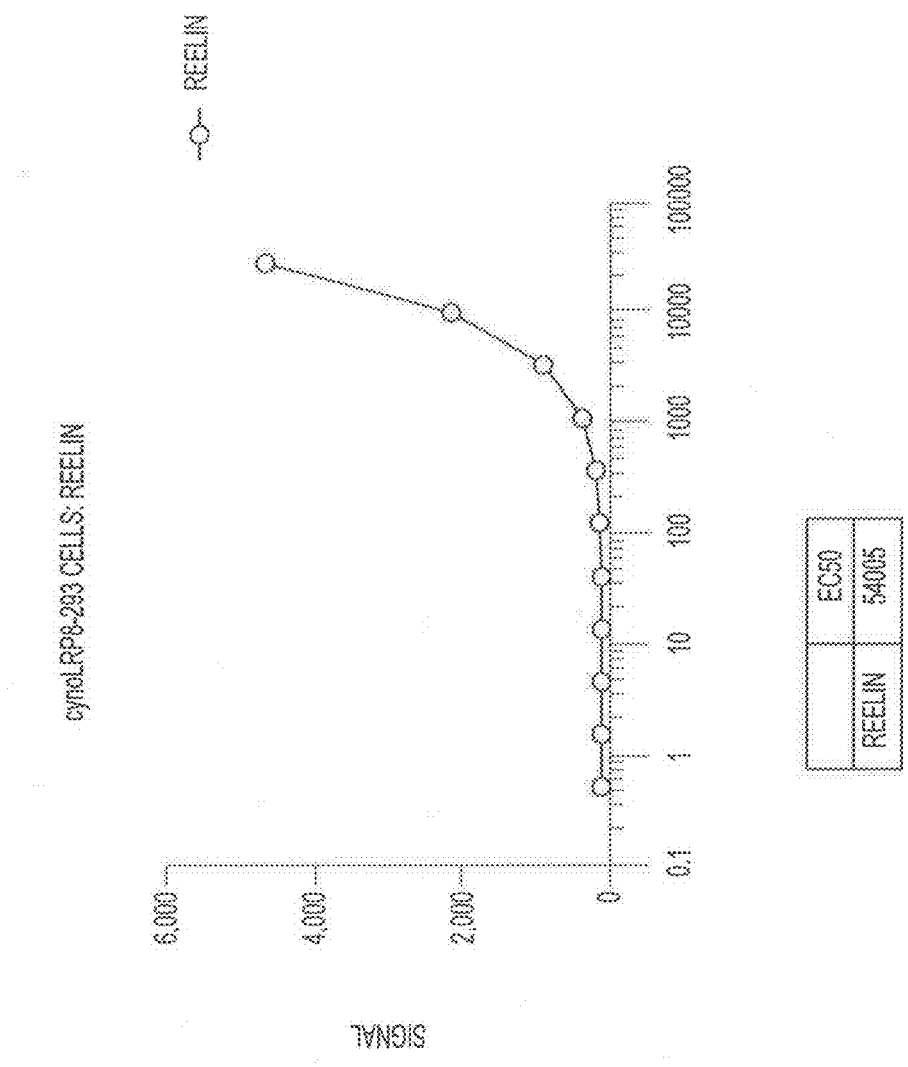

FIG. 22A

VH Alignment of All hLRP6 Antibodies (CDRs were highlighted in bold)

FIG. 22B

VL Alignment of All hLRP6 Antibodies (CDRs were highlighted in bold)

SEQUENCE LISTING

```
<160> NUMBER OF SEQ ID NOS: 232

<210> SEQ ID NO 1
<211> LENGTH: 700
<212> TYPE: PRT
<213> ORGANISM: Homo sapiens

<400> SEQUENCE: 1

Met Gly Leu Pro Glu Pro Gly Pro Leu Arg Leu Leu Ala Leu Leu Leu
```

```
1               5                   10                  15
Leu Leu Leu Leu Leu Leu Leu Leu Gln Leu Gln His Leu Ala Ala Ala
                20                  25                  30
Ala Ala Asp Pro Leu Leu Gly Gly Gln Gly Pro Ala Lys Asp Cys Glu
            35                  40                  45
Lys Asp Gln Phe Gln Cys Arg Asn Glu Arg Cys Ile Pro Ser Val Trp
        50                  55                  60
Arg Cys Asp Glu Asp Asp Cys Leu Asp His Ser Asp Glu Asp Asp
65                  70                  75                  80
Cys Pro Lys Lys Thr Cys Ala Asp Ser Asp Phe Thr Cys Asp Asn Gly
                85                  90                  95
His Cys Ile His Glu Arg Trp Lys Cys Asp Gly Glu Glu Glu Cys Pro
                100                 105                 110
Asp Gly Ser Asp Glu Ser Glu Ala Thr Cys Thr Lys Gln Val Cys Pro
            115                 120                 125
Ala Glu Lys Leu Ser Cys Gly Pro Thr Ser His Lys Cys Val Pro Ala
130                 135                 140
Ser Trp Arg Cys Asp Gly Glu Lys Asp Cys Glu Gly Gly Ala Asp Glu
145                 150                 155                 160
Ala Gly Cys Ala Thr Ser Leu Gly Thr Cys Arg Gly Asp Glu Phe Gln
                165                 170                 175
Cys Gly Asp Gly Thr Cys Val Leu Ala Ile Lys His Cys Asn Gln Glu
            180                 185                 190
Gln Asp Cys Pro Asp Gly Ser Asp Glu Ala Gly Cys Leu Gln Gly Leu
        195                 200                 205
Asn Glu Cys Leu His Asn Asn Gly Gly Cys Ser His Ile Cys Thr Asp
210                 215                 220
Leu Lys Ile Gly Phe Glu Cys Thr Cys Pro Ala Gly Phe Gln Leu Leu
225                 230                 235                 240
Asp Gln Lys Thr Cys Gly Asp Ile Asp Glu Cys Lys Asp Pro Asp Ala
                245                 250                 255
Cys Ser Gln Ile Cys Val Asn Tyr Lys Gly Tyr Phe Lys Cys Glu Cys
            260                 265                 270
Tyr Pro Gly Tyr Glu Met Asp Leu Leu Thr Lys Asn Cys Lys Ala Ala
        275                 280                 285
Ala Gly Lys Ser Pro Ser Leu Ile Phe Thr Asn Arg His Glu Val Arg
290                 295                 300
Arg Ile Asp Leu Val Lys Arg Asn Tyr Ser Arg Leu Ile Pro Met Leu
305                 310                 315                 320
Lys Asn Val Val Ala Leu Asp Val Glu Val Ala Thr Asn Arg Ile Tyr
                325                 330                 335
Trp Cys Asp Leu Ser Tyr Arg Lys Ile Tyr Ser Ala Tyr Met Asp Lys
            340                 345                 350
Ala Ser Asp Pro Lys Glu Gln Glu Val Leu Ile Asp Glu Gln Leu His
        355                 360                 365
Ser Pro Glu Gly Leu Ala Val Asp Trp Val His Lys His Ile Tyr Trp
370                 375                 380
Thr Asp Ser Gly Asn Lys Thr Ile Ser Val Ala Thr Val Asp Gly Gly
385                 390                 395                 400
Arg Arg Arg Thr Leu Phe Ser Arg Asn Leu Ser Glu Pro Arg Ala Ile
                405                 410                 415
Ala Val Asp Pro Leu Arg Gly Phe Met Tyr Trp Ser Asp Trp Gly Asp
            420                 425                 430
```

Gln Ala Lys Ile Glu Lys Ser Gly Leu Asn Gly Val Asp Arg Gln Thr
            435                 440                 445

Leu Val Ser Asp Asn Ile Glu Trp Pro Asn Gly Ile Thr Leu Asp Leu
    450                 455                 460

Leu Ser Gln Arg Leu Tyr Trp Val Asp Ser Lys Leu His Gln Leu Ser
465                 470                 475                 480

Ser Ile Asp Phe Ser Gly Gly Asn Arg Lys Thr Leu Ile Ser Ser Thr
                485                 490                 495

Asp Phe Leu Ser His Pro Phe Gly Ile Ala Val Phe Glu Asp Lys Val
                500                 505                 510

Phe Trp Thr Asp Leu Glu Asn Glu Ala Ile Phe Ser Ala Asn Arg Leu
            515                 520                 525

Asn Gly Leu Glu Ile Ser Ile Leu Ala Glu Asn Leu Asn Asn Pro His
        530                 535                 540

Asp Ile Val Ile Phe His Glu Leu Lys Gln Pro Arg Ala Pro Asp Ala
545                 550                 555                 560

Cys Glu Leu Ser Val Gln Pro Asn Gly Gly Cys Glu Tyr Leu Cys Leu
                565                 570                 575

Pro Ala Pro Gln Ile Ser Ser His Ser Pro Lys Tyr Thr Cys Ala Cys
            580                 585                 590

Pro Asp Thr Met Trp Leu Gly Pro Asp Met Lys Arg Cys Tyr Arg Asp
        595                 600                 605

Ala Asn Glu Asp Ser Lys Met Gly Ser Thr Val Thr Ala Ala Val Ile
610                 615                 620

Gly Ile Ile Val Pro Ile Val Ile Ala Leu Leu Cys Met Ser Gly
625                 630                 635                 640

Tyr Leu Ile Trp Arg Asn Trp Lys Arg Lys Asn Thr Lys Ser Met Asn
                645                 650                 655

Phe Asp Asn Pro Val Tyr Arg Lys Thr Thr Glu Glu Glu Asp Glu Asp
            660                 665                 670

Glu Leu His Ile Gly Arg Thr Ala Gln Ile Gly His Val Tyr Pro Ala
        675                 680                 685

Arg Val Ala Leu Ser Leu Glu Asp Asp Gly Leu Pro
            690                 695                 700

<210> SEQ ID NO 2
<211> LENGTH: 20
<212> TYPE: PRT
<213> ORGANISM: Homo sapiens

<400> SEQUENCE: 2

Cys Glu Lys Asp Gln Phe Gln Cys Arg Asn Glu Arg Cys Ile Pro Ser
1               5                   10                  15

Val Trp Arg Cys
            20

<210> SEQ ID NO 3
<211> LENGTH: 20
<212> TYPE: PRT
<213> ORGANISM: Homo sapiens

<400> SEQUENCE: 3

Cys Ala Asp Ser Asp Phe Thr Cys Asp Asn Gly His Cys Ile His Glu
1               5                   10                  15

Arg Trp Lys Cys
            20

<210> SEQ ID NO 4

<400> SEQUENCE: 4

000

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Cys Glu Lys Asp Gln Phe Gln Ser Arg Asn Glu Arg Cys Ile Pro Ser
1               5                   10                  15

Val Trp Arg Cys
            20
```

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

```
Cys Ala Asp Ser Asp Phe Thr Ser Asp Asn Gly His Cys Ile His Glu
1               5                   10                  15

Arg Trp Lys Cys
            20
```

<210> SEQ ID NO 7
<211> LENGTH: 650
<212> TYPE: PRT
<213> ORGANISM: Macaca fascicularis

<400> SEQUENCE: 7

```
Leu Leu Glu Met Gln Leu Gln His Leu Ala Ala Ala Ala Ala Asp Pro
1               5                   10                  15

Leu Leu Gly Gly Gln Gly Pro Ala Lys Glu Cys Glu Lys Asp Gln Phe
                20                  25                  30

Gln Cys Arg Asn Glu Arg Cys Ile Pro Ser Val Trp Arg Cys Asp Glu
            35                  40                  45

Asp Asp Asp Cys Leu Asp His Ser Asp Glu Asp Asp Cys Pro Lys Lys
        50                  55                  60

Thr Cys Ala Asp Ser Asp Phe Thr Cys Asp Asn Gly His Cys Ile His
65                  70                  75                  80

Glu Arg Trp Lys Cys Asp Gly Glu Glu Glu Cys Pro Asp Gly Ser Asp
                85                  90                  95

Glu Ser Glu Ala Thr Cys Thr Leu Gly Thr Cys His Gly Asn Glu Phe
                100                 105                 110

Gln Cys Gly Asp Gly Thr Cys Val Leu Ala Ile Lys Arg Cys Asn Gln
            115                 120                 125

Glu Gln Asp Cys Pro Asp Gly Ser Asp Glu Ala Gly Cys Leu Gln Val
        130                 135                 140

Pro Pro Thr Phe Leu Gly Asn Arg Arg Pro Arg Gly Leu Asn Glu
145                 150                 155                 160
```

```
Cys Leu His Asn Asn Gly Gly Cys Ser His Ile Cys Thr Asp Leu Lys
                165                 170                 175
Ile Gly Phe Glu Cys Thr Cys Pro Ala Gly Phe Gln Leu Leu Asp Gln
                180                 185                 190
Lys Thr Cys Gly Asp Ile Asp Glu Cys Lys Asp Pro Asp Ala Cys Ser
                195                 200                 205
Gln Ile Cys Val Asn Tyr Lys Gly Tyr Phe Lys Cys Glu Cys Tyr Pro
        210                 215                 220
Gly Tyr Glu Met Asp Leu Leu Thr Lys Asn Cys Lys Ala Ala Ala Gly
225                 230                 235                 240
Lys Ser Pro Ser Leu Ile Phe Thr Asn Arg His Glu Val Arg Arg Ile
                245                 250                 255
Asp Leu Val Lys Arg Asn Tyr Ser Arg Leu Ile Pro Met Leu Lys Asn
                260                 265                 270
Val Val Ala Leu Asp Met Glu Val Ala Thr Asn Arg Ile Tyr Trp Cys
            275                 280                 285
Asp Leu Ser Tyr Arg Lys Ile Tyr Ser Ala Tyr Met Asp Lys Ala Ser
        290                 295                 300
Asp Pro Lys Glu Gln Glu Val Leu Ile Asp Glu Gln Leu His Ser Pro
305                 310                 315                 320
Glu Gly Leu Ala Val Asp Trp Val His Lys His Ile Tyr Trp Thr Asp
                325                 330                 335
Ser Gly Asn Lys Thr Ile Ser Val Ala Thr Val Asp Gly Gly Arg Arg
                340                 345                 350
Cys Thr Leu Phe Ser Arg Asn Leu Ser Glu Pro Arg Ala Ile Ala Val
                355                 360                 365
Asp Pro Leu Gln Gly Phe Met Tyr Trp Ser Asp Trp Gly Asn Gln Ala
        370                 375                 380
Lys Ile Glu Lys Ser Gly Leu Asn Gly Val Asp Arg Gln Thr Leu Val
385                 390                 395                 400
Ser Asp Asn Ile Glu Trp Pro Asn Gly Ile Thr Leu Asp Leu Leu Ser
                405                 410                 415
Gln Arg Leu Tyr Trp Val Asp Ser Lys Leu His Gln Leu Ser Ser Ile
                420                 425                 430
Asp Phe Ser Gly Gly Asn Arg Lys Met Leu Ile Ser Ser Thr Asp Phe
            435                 440                 445
Leu Ser His Pro Phe Gly Ile Ala Val Phe Glu Asp Lys Val Phe Trp
        450                 455                 460
Thr Asp Leu Glu Asn Glu Ala Ile Phe Ser Ala Asn Arg Leu Asn Gly
465                 470                 475                 480
Leu Glu Ile Ser Ile Leu Ala Glu Asn Leu Asn Asn Pro His Asp Ile
                485                 490                 495
Val Ile Phe His Glu Leu Lys Gln Pro Arg Ala Ala Asp Ala Cys Lys
                500                 505                 510
Leu Ser Val Gln Pro Asn Gly Gly Cys Glu Tyr Leu Cys Leu Pro Ala
            515                 520                 525
Pro Gln Ile Ser Ser His Ser Pro Lys Tyr Thr Cys Ala Cys Pro Asp
        530                 535                 540
Thr Met Trp Leu Gly Pro Asp Met Lys Arg Cys Tyr Arg Asp Gly Asn
545                 550                 555                 560
Glu Asp Ser Lys Met Gly Ser Thr Val Thr Ala Ala Val Ile Gly Ile
                565                 570                 575
```

```
Ile Val Pro Ile Val Val Ile Ala Leu Leu Cys Met Ser Gly Tyr Leu
            580                 585                 590

Ile Trp Arg Asn Trp Lys Arg Lys Asn Thr Lys Ser Met Asn Phe Asp
        595                 600                 605

Asn Pro Val Tyr Arg Lys Thr Thr Glu Glu Asp Glu Asp Glu Leu
610                 615                 620

His Ile Gly Arg Thr Ala Gln Ile Gly His Val Tyr Pro Ala Arg Val
625                 630                 635                 640

Ala Leu Ser Leu Glu Asp Asp Gly Leu Pro
                645                 650

<210> SEQ ID NO 8
<211> LENGTH: 650
<212> TYPE: PRT
<213> ORGANISM: Macaca fascicularis

<400> SEQUENCE: 8

Leu Leu Glu Met Gln Leu Gln His Leu Ala Ala Ala Ala Asp Pro
1               5                   10                  15

Leu Leu Gly Gly Gln Gly Pro Ala Lys Glu Cys Glu Lys Asp Gln Phe
            20                  25                  30

Gln Cys Arg Asn Glu Arg Cys Ile Pro Ser Val Trp Arg Cys Asp Glu
        35                  40                  45

Asp Asp Asp Cys Leu Asp His Ser Asp Glu Asp Cys Pro Lys Lys
    50                  55                  60

Thr Cys Ala Asp Ser Asp Phe Thr Cys Asp Asn Gly His Cys Ile His
65                  70                  75                  80

Glu Arg Trp Lys Cys Asp Gly Glu Glu Glu Cys Pro Asp Gly Ser Asp
                85                  90                  95

Glu Ser Glu Ala Thr Cys Thr Leu Gly Thr Cys His Gly Asn Glu Phe
            100                 105                 110

Gln Cys Gly Asp Gly Thr Cys Val Leu Ala Ile Lys Arg Cys Asn Gln
        115                 120                 125

Glu Gln Asp Cys Pro Asp Gly Ser Asp Glu Ala Gly Cys Leu Gln Val
130                 135                 140

Pro Pro Thr Phe Leu Gly Asn Arg Arg Pro Arg Gly Leu Asn Glu
145                 150                 155                 160

Cys Leu His Asn Asn Gly Gly Cys Ser His Ile Ser Thr Asp Leu Lys
                165                 170                 175

Ile Gly Phe Glu Cys Thr Cys Pro Ala Gly Phe Gln Leu Leu Asp Gln
            180                 185                 190

Lys Thr Cys Gly Asp Ile Asp Glu Cys Lys Asp Pro Asp Ala Cys Ser
        195                 200                 205

Gln Ile Cys Val Asn Tyr Lys Gly Tyr Phe Lys Cys Glu Cys Tyr Pro
210                 215                 220

Gly Tyr Glu Met Asp Leu Leu Thr Lys Asn Cys Lys Ala Ala Ala Gly
225                 230                 235                 240

Lys Ser Pro Ser Leu Ile Phe Thr Asn Arg His Glu Val Arg Arg Ile
                245                 250                 255

Asp Leu Val Lys Arg Asn Tyr Ser Arg Leu Ile Pro Met Leu Lys Asn
            260                 265                 270

Val Val Ala Leu Asp Met Glu Val Ala Thr Asn Arg Ile Tyr Trp Cys
        275                 280                 285

Asp Leu Ser Tyr Arg Lys Ile Tyr Ser Ala Tyr Met Asp Lys Ala Ser
290                 295                 300
```

Asp Pro Lys Glu Gln Glu Val Leu Ile Asp Glu Gln Leu His Ser Pro
305                 310                 315                 320

Glu Gly Leu Ala Val Asp Trp Val His Lys His Ile Tyr Trp Thr Asp
                325                 330                 335

Ser Gly Asn Lys Thr Ile Ser Val Ala Thr Val Asp Gly Gly Arg Arg
            340                 345                 350

Cys Thr Leu Phe Ser Arg Asn Leu Ser Glu Pro Arg Ala Ile Ala Val
        355                 360                 365

Asp Pro Leu Gln Gly Phe Met Tyr Trp Ser Asp Trp Gly Asn Gln Ala
    370                 375                 380

Lys Ile Glu Lys Ser Gly Leu Asn Gly Val Asp Arg Gln Thr Leu Val
385                 390                 395                 400

Ser Asp Asn Ile Glu Trp Pro Asn Gly Ile Thr Leu Asp Leu Leu Ser
                405                 410                 415

Gln Arg Leu Tyr Trp Val Asp Ser Lys Leu His Gln Leu Ser Ser Ile
            420                 425                 430

Asp Phe Ser Gly Gly Asn Arg Lys Met Leu Ile Ser Ser Thr Asp Phe
        435                 440                 445

Leu Ser His Pro Phe Gly Ile Ala Val Phe Glu Asp Lys Val Phe Trp
    450                 455                 460

Thr Asp Leu Glu Asn Glu Ala Ile Phe Ser Ala Asn Arg Leu Asn Gly
465                 470                 475                 480

Leu Glu Ile Ser Ile Leu Ala Glu Asn Leu Asn Asn Pro His Asp Ile
                485                 490                 495

Val Ile Phe His Glu Leu Lys Gln Pro Arg Ala Ala Asp Ala Cys Lys
            500                 505                 510

Leu Ser Val Gln Pro Asn Gly Gly Cys Glu Tyr Leu Cys Leu Pro Ala
        515                 520                 525

Pro Gln Ile Ser Ser His Ser Pro Lys Tyr Thr Cys Ala Cys Pro Asp
    530                 535                 540

Thr Met Trp Leu Gly Pro Asp Met Lys Arg Cys Tyr Arg Asp Gly Asn
545                 550                 555                 560

Glu Asp Ser Lys Met Gly Ser Thr Val Thr Ala Ala Val Ile Gly Ile
                565                 570                 575

Ile Val Pro Ile Val Val Ile Ala Leu Leu Cys Met Ser Gly Tyr Leu
            580                 585                 590

Ile Trp Arg Asn Trp Lys Arg Lys Asn Thr Lys Ser Met Asn Phe Asp
        595                 600                 605

Asn Pro Val Tyr Arg Lys Thr Thr Glu Glu Glu Asp Glu Asp Glu Leu
    610                 615                 620

His Ile Gly Arg Thr Ala Gln Ile Gly His Val Tyr Pro Ala Arg Val
625                 630                 635                 640

Ala Leu Ser Leu Glu Asp Asp Gly Leu Pro
                645                 650

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Phe or Tyr

```
<400> SEQUENCE: 9

Arg Phe Thr Phe Ser Asn Xaa Gly Met Ser
1               5                   10

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Ser or His

<400> SEQUENCE: 10

Thr Ile Ser Ser Gly Gly Arg Tyr Thr Tyr Tyr Pro Asp Xaa Val Lys
1               5                   10                  15

Gly

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Gly Gly Ser Gly
1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Gly Ser Gly Gly
1               5

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Gly Gly Gly Gly Ser Gly Gly Gly Gly Ser
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14
```

```
Gly Gly Ser Gly Gly Gly Gly Ser Gly
1               5

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Ser Gly Gly Gly Gly Ser Gly Ser
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Gly Ser Gly Gly Gly Gly Ser Gly Gly Gly Gly Ser
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Gly Gly Gly Ser Gly Gly Gly Gly Ser Gly Gly Gly Gly
1               5                   10

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Gly Gly Ser Gly Gly Gly Gly Ser Gly Gly Gly Gly Ser
1               5                   10                  15

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Ser Thr Lys Gly Pro
1               5

<210> SEQ ID NO 20
<211> LENGTH: 13
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 20

Ala Ser Thr Lys Gly Pro Ser Val Phe Pro Leu Ala Pro
1               5                   10

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Val Ala Ala Pro
1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Arg Thr Val Ala Ala Pro
1               5

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Val Ala Ala Pro Ser Val Phe Ile Phe Pro Pro
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Arg Thr Val Ala Ala Pro Ser Val Phe Ile Phe Pro Pro
1               5                   10

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Lys Thr Thr Pro Lys Leu Glu Glu Gly Glu Phe Ser Glu Ala Arg
1               5                   10                  15
```

```
<210> SEQ ID NO 26
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Lys Thr Thr Pro Lys Leu Glu Glu Gly Glu Phe Ser Glu Ala Arg
1               5                   10                  15

Val

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Lys Thr Thr Pro Lys Leu Gly Gly
1               5

<210> SEQ ID NO 28
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ser Ala Lys Thr Thr Pro Lys Leu Gly Gly
1               5                   10

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ser Ala Lys Thr Thr Pro
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Ala Asp Ala Ala Pro
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 31

Arg Ala Asp Ala Ala Pro Thr Val Ser
1               5

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Arg Ala Asp Ala Ala Ala Ala Gly Gly Pro Gly Ser
1               5                   10

<210> SEQ ID NO 33
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Arg Ala Asp Ala Ala Ala Ala Gly Gly Gly Gly Ser Gly Gly Gly
1               5                   10                  15

Ser Gly Gly Gly Gly Ser Gly Gly Gly Gly Ser
            20                  25

<210> SEQ ID NO 34
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Ala Lys Thr Thr Pro Lys Leu Glu Glu Gly Glu Phe Ser Glu Ala
1               5                   10                  15

Arg Val

<210> SEQ ID NO 35
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Ala Asp Ala Ala Pro
1               5

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Asp Ala Ala Pro Thr Val Ser Ile Phe Pro Pro
```

```
<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Pro Lys Ala Ala Pro
1               5

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Pro Lys Ala Ala Pro Ser Val Thr Leu Phe Pro Pro
1               5                   10

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Lys Thr Thr Pro Pro
1               5

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Lys Thr Thr Pro Pro Ser Val Thr Pro Leu Ala Pro
1               5                   10

<210> SEQ ID NO 41
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ala Lys Thr Thr Ala Pro
1               5

<210> SEQ ID NO 42
<211> LENGTH: 13
<212> TYPE: PRT
<213> ORGANISM: Artificial Sequence
<220> FEATURE:
<223> OTHER INFORMATION: Description of Artificial Sequence: Synthetic
```

```
                                 peptide

<400> SEQUENCE: 42

Ala Lys Thr Thr Ala Pro Ser Val Tyr Pro Leu Ala Pro
1               5                   10

<210> SEQ ID NO 43
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Glu Asn Lys Val Glu Tyr Ala Pro Ala Leu Met Ala Leu Ser
1               5                   10                  15

<210> SEQ ID NO 44
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Pro Ala Lys Glu Leu Thr Pro Leu Lys Glu Ala Lys Val Ser
1               5                   10                  15

<210> SEQ ID NO 45
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly His Glu Ala Ala Ala Val Met Gln Val Gln Tyr Pro Ala Ser
1               5                   10                  15

<210> SEQ ID NO 46
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Asp Tyr Leu Tyr Ala Met Asp Tyr
1               5

<210> SEQ ID NO 47
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Asn, Thr, Arg, Trp or Pro
<220> FEATURE:
<221> NAME/KEY: MOD_RES
<222> LOCATION: (11)..(11)
<223> OTHER INFORMATION: Gly, Glu, Leu or Lys
```

```
<400> SEQUENCE: 47

Arg Ser Ser Gln Ser Leu Val Tyr Ser Xaa Xaa Asn Thr Tyr Leu His
1               5                   10                  15

<210> SEQ ID NO 48
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Lys Val Ser Asn Arg Phe Ser
1               5

<210> SEQ ID NO 49
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Gln Ser Thr His Val Pro Leu Thr
1               5

<210> SEQ ID NO 50
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (63)..(63)
<223> OTHER INFORMATION: Ser or His

<400> SEQUENCE: 50

Glu Val Gln Leu Val Glu Ser Gly Gly Asp Leu Val Lys Pro Gly Gly
1               5                   10                  15

Ser Leu Lys Leu Ser Cys Ala Ala Ser Arg Phe Thr Phe Ser Asn Phe
            20                  25                  30

Gly Met Ser Trp Val Arg Gln Thr Pro Asp Lys Arg Leu Glu Trp Val
        35                  40                  45

Ala Thr Ile Ser Ser Gly Gly Arg Tyr Thr Tyr Tyr Pro Asp Xaa Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Asp Tyr Leu Tyr Ala Met Asp Tyr Trp Gly Gln Gly Thr Ser
            100                 105                 110

Val Thr Val Ser Ser
        115

<210> SEQ ID NO 51
<211> LENGTH: 117
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<221> NAME/KEY: MOD_RES
<222> LOCATION: (63)..(63)
<223> OTHER INFORMATION: Ser or His

<400> SEQUENCE: 51

Glu Val Gln Leu Val Glu Ser Gly Gly Asp Leu Val Lys Pro Gly Gly
1               5                   10                  15

Ser Leu Lys Leu Ser Cys Ala Ala Ser Arg Phe Thr Phe Ser Asn Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Arg Tyr Thr Tyr Tyr Pro Asp Xaa Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg Asp Tyr Leu Tyr Ala Met Asp Tyr Trp Gly Gln Gly Thr Ser
            100                 105                 110

Val Thr Val Ser Ser
        115

<210> SEQ ID NO 52
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Asn, Thr, Arg, Trp or Pro
<220> FEATURE:
<221> NAME/KEY: MOD_RES
<222> LOCATION: (34)..(34)
<223> OTHER INFORMATION: Gly, Glu, Leu or Lys

<400> SEQUENCE: 52

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val Tyr Ser
            20                  25                  30

Xaa Xaa Asn Thr Tyr Leu His Trp Tyr Leu Gln Lys Pro Gly Gln Ser
        35                  40                  45

Pro Lys Val Leu Met Tyr Lys Val Ser Asn Arg Phe Ser Gly Val Ser
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Leu Thr Phe Gly Ala Gly Thr Lys Leu Glu Leu Lys
            100                 105                 110

<210> SEQ ID NO 53
<211> LENGTH: 10
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 53

Gly Phe Thr Val Ser Asp Tyr Tyr Met Ala
1               5                   10

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Ile Ser Tyr Glu Gly Ser Ser Thr Tyr Tyr Gly Asp Ser Val Lys
1               5                   10                  15

Gly

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Pro Leu Arg Tyr Tyr Gly Tyr Asn Tyr Arg Phe Ala Tyr
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Lys Ala Ser Gln Asn Ile His Lys Asn Leu Asp
1               5                   10

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Tyr Thr Asp Asn Leu Gln Thr
1               5

<210> SEQ ID NO 58
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Tyr Gln Tyr Asn Ser Gly Pro Thr
1               5

<210> SEQ ID NO 59
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Val Ser Asp Tyr
            20                  25                  30

Tyr Met Ala Trp Val Arg Gln Ala Pro Lys Lys Gly Leu Glu Trp Val
        35                  40                  45

Ala Ser Ile Ser Tyr Glu Gly Ser Ser Thr Tyr Tyr Gly Asp Ser Val
    50                  55                  60

Lys Gly Arg Phe Thr Ile Ser Arg Asp Asn Ala Lys Ser Ile Leu Tyr
65                  70                  75                  80

Leu Gln Met Asn Ser Leu Arg Ser Glu Asp Thr Ala Thr Tyr Tyr Cys
                85                  90                  95

Ala Arg Pro Leu Arg Tyr Tyr Gly Tyr Asn Tyr Arg Phe Ala Tyr Trp
            100                 105                 110

Gly Gln Gly Thr Leu Val Thr Val Ser Ser
        115                 120

<210> SEQ ID NO 60
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Met Ser Gln Ser Pro Pro Val Leu Ser Ala Ser Val Gly
1               5                   10                  15

Asp Arg Val Thr Leu Ser Cys Lys Ala Ser Gln Asn Ile His Lys Asn
            20                  25                  30

Leu Asp Trp Tyr Gln Gln Lys His Gly Glu Ala Pro Lys Leu Leu Ile
        35                  40                  45

Tyr Tyr Thr Asp Asn Leu Gln Thr Gly Ile Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Val Ala Thr Tyr Tyr Cys Tyr Gln Tyr Asn Ser Gly Pro Thr
                85                  90                  95

Phe Gly Ala Gly Thr Lys Leu Glu Leu Gln
            100                 105

<210> SEQ ID NO 61
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Glu Val Gln Leu Val Glu Ser Gly Gly Asp Leu Val Lys Pro Gly Gly
1               5                   10                  15

Ser Leu Lys Leu Ser Cys Ala Ala Ser Arg Phe Thr Phe Ser Asn Phe
            20                  25                  30

Gly Met Ser Trp Val Arg Gln Thr Pro Asp Lys Arg Leu Glu Trp Val
        35                  40                  45

Ala Thr Ile Ser Ser Gly Gly Arg Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
            85                  90                  95

Ala Arg Asp Tyr Leu Tyr Ala Met Asp Tyr Trp Gly Gln Gly Thr Ser
            100                 105                 110

Val Thr Val Ser Ser
        115

<210> SEQ ID NO 62
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Glu Val Gln Leu Val Glu Ser Gly Gly Asp Leu Val Lys Pro Gly Gly
1               5                   10                  15

Ser Leu Lys Leu Ser Cys Ala Ala Ser Arg Phe Thr Phe Ser Asn Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Arg Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
            85                  90                  95

Ala Arg Asp Tyr Leu Tyr Ala Met Asp Tyr Trp Gly Gln Gly Thr Ser
            100                 105                 110

Val Thr Val Ser Ser
        115

<210> SEQ ID NO 63
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val Tyr Ser
            20                  25                  30

Asn Gly Asn Thr Tyr Leu His Trp Tyr Leu Gln Lys Pro Gly Gln Ser
        35                  40                  45

```
Pro Lys Val Leu Met Tyr Lys Val Ser Asn Arg Phe Ser Gly Val Ser
    50                  55                  60
Asp Arg Phe Ser Gly Ser Gly Ser Gly Thr Asp Phe Thr Leu Lys Ile
65                  70                  75                  80
Ser Arg Val Glu Ala Glu Asp Leu Gly Val Tyr Phe Cys Ser Gln Ser
                85                  90                  95
Thr His Val Pro Leu Thr Phe Gly Ala Gly Thr Lys Leu Glu Leu Lys
                100                 105                 110
```

<210> SEQ ID NO 64
<211> LENGTH: 20
<212> TYPE: PRT
<213> ORGANISM: Homo sapiens

<400> SEQUENCE: 64

```
Cys Glu Lys Asp Gln Ala Gln Ser Arg Asn Glu Arg Cys Ile Pro Ser
1               5                   10                  15
Val Trp Arg Cys
            20
```

<210> SEQ ID NO 65
<211> LENGTH: 20
<212> TYPE: PRT
<213> ORGANISM: Homo sapiens

<400> SEQUENCE: 65

```
Cys Glu Lys Asp Gln Phe Gln Ala Arg Asn Glu Arg Cys Ile Pro Ser
1               5                   10                  15
Val Trp Arg Cys
            20
```

<210> SEQ ID NO 66
<211> LENGTH: 20
<212> TYPE: PRT
<213> ORGANISM: Homo sapiens

<400> SEQUENCE: 66

```
Cys Glu Lys Asp Gln Phe Gln Ser Arg Ala Glu Arg Cys Ile Pro Ser
1               5                   10                  15
Val Trp Arg Cys
            20
```

<210> SEQ ID NO 67
<211> LENGTH: 20
<212> TYPE: PRT
<213> ORGANISM: Homo sapiens

<400> SEQUENCE: 67

```
Cys Glu Lys Asp Gln Ala Gln Ala Arg Ala Glu Arg Cys Ile Pro Ser
1               5                   10                  15
Val Trp Arg Cys
            20
```

<210> SEQ ID NO 68
<211> LENGTH: 959
<212> TYPE: PRT
<213> ORGANISM: Macaca fascicularis

<400> SEQUENCE: 68

```
Met Gly Arg Pro Glu Arg Gly Ala Leu Arg Pro Leu Ala Leu Leu Leu
1               5                   10                  15
```

-continued

Leu Leu Leu Leu Leu Gln Leu Gln His Leu Ala Ala Ala Ala Asp
            20              25              30

Pro Leu Leu Gly Gly Gln Gly Pro Ala Lys Glu Cys Glu Lys Asp Gln
        35              40              45

Phe Gln Cys Arg Asn Glu Arg Cys Ile Pro Ser Val Trp Arg Cys Asp
    50              55              60

Glu Asp Asp Asp Cys Leu Asp His Ser Asp Glu Asp Cys Pro Lys
65              70              75              80

Lys Thr Cys Ala Asp Ser Asp Phe Thr Cys Asp Asn Gly His Cys Ile
            85              90              95

His Glu Arg Trp Lys Cys Asp Gly Glu Glu Cys Pro Asp Gly Ser
        100             105             110

Asp Glu Ser Glu Ala Thr Cys Thr Lys Gln Val Cys Pro Ala Glu Lys
        115             120             125

Leu Ser Cys Gly Pro Thr Ser His Lys Cys Val Pro Ala Ser Trp Arg
    130             135             140

Cys Asp Gly Glu Lys Asp Cys Glu Gly Gly Ala Asp Glu Ala Gly Cys
145             150             155             160

Val Thr Leu Cys Ala Pro His Glu Phe Gln Cys Gly Asn Arg Ser Cys
            165             170             175

Leu Ala Ala Val Phe Val Cys Asp Gly Asp Asp Asp Cys Gly Asp Gly
        180             185             190

Ser Asp Glu Arg Gly Cys Ala Asp Pro Ala Cys Gly Pro Arg Glu Phe
        195             200             205

Arg Cys Gly Arg Asp Gly Gly Ala Cys Ile Pro Glu Arg Trp Val
    210             215             220

Cys Asp Arg Gln Phe Asp Cys Glu Asp Arg Ser Asp Glu Ala Ala Glu
225             230             235             240

Leu Cys Gly Arg Pro Gly Pro Gly Ala Thr Ser Ala Pro Ala Ala Cys
            245             250             255

Ala Thr Ala Ala Gln Phe Ala Cys Arg Ser Gly Glu Cys Val His Leu
        260             265             270

Gly Trp Arg Cys Asp Gly Asp Arg Asp Cys Lys Asp Lys Ser Asp Glu
    275             280             285

Ala Asp Cys Pro Leu Gly Thr Cys His Gly Asn Glu Phe Gln Cys Gly
290             295             300

Asp Gly Thr Cys Val Leu Ala Ile Lys Arg Cys Asn Gln Glu Gln Asp
305             310             315             320

Cys Pro Asp Gly Ser Asp Glu Ala Gly Cys Leu Gln Gly Leu Asn Glu
        325             330             335

Cys Leu His Asn Asn Gly Gly Cys Ser His Ile Cys Thr Asp Leu Lys
        340             345             350

Ile Gly Phe Glu Cys Thr Cys Pro Ala Gly Phe Gln Leu Leu Asp Gln
        355             360             365

Lys Thr Cys Gly Asp Ile Asp Glu Cys Lys Asp Pro Asp Ala Cys Ser
    370             375             380

Gln Ile Cys Val Asn Tyr Lys Gly Tyr Phe Lys Cys Glu Cys Tyr Pro
385             390             395             400

Gly Tyr Glu Met Asp Leu Leu Thr Lys Asn Cys Lys Ala Ala Gly
            405             410             415

Lys Ser Pro Ser Leu Ile Phe Thr Asn Arg His Glu Val Arg Arg Ile
        420             425             430

Asp Leu Val Lys Arg Asn Tyr Ser Arg Leu Ile Pro Met Leu Lys Asn

```
            435                 440                 445
Val Val Ala Leu Asp Val Glu Val Ala Thr Asn Arg Ile Tyr Trp Cys
            450                 455                 460

Asp Leu Ser Tyr Arg Lys Ile Tyr Ser Ala Tyr Met Asp Lys Ala Ser
465                 470                 475                 480

Asp Pro Lys Glu Gln Glu Val Leu Ile Asp Glu Gln Leu His Ser Pro
                485                 490                 495

Glu Gly Leu Ala Val Asp Trp Val His Lys His Ile Tyr Trp Thr Asp
                500                 505                 510

Ser Gly Asn Lys Thr Ile Ser Val Ala Thr Val Asp Gly Gly Arg Arg
                515                 520                 525

Cys Thr Leu Phe Ser Arg Asn Leu Ser Glu Pro Arg Ala Ile Ala Val
            530                 535                 540

Asp Pro Leu Gln Gly Phe Met Tyr Trp Ser Asp Trp Gly Asn Gln Ala
545                 550                 555                 560

Lys Ile Glu Lys Ser Gly Leu Asn Gly Val Asp Arg Gln Thr Leu Val
                565                 570                 575

Ser Asp Asn Ile Glu Trp Pro Asn Gly Ile Thr Leu Asp Leu Leu Ser
                580                 585                 590

Gln Arg Leu Tyr Trp Val Asp Ser Lys Leu His Gln Leu Ser Ser Ile
            595                 600                 605

Asp Phe Ser Gly Gly Asn Arg Lys Met Leu Ile Ser Ser Thr Asp Phe
            610                 615                 620

Leu Ser His Pro Phe Gly Ile Ala Val Phe Glu Asp Lys Val Phe Trp
625                 630                 635                 640

Thr Asp Leu Glu Asn Glu Ala Ile Phe Ser Ala Asn Arg Leu Asn Gly
                645                 650                 655

Leu Glu Ile Ser Ile Leu Ala Glu Asn Leu Asn Asn Pro His Asp Ile
                660                 665                 670

Val Ile Phe His Glu Leu Lys Gln Pro Arg Ala Ala Asp Ala Cys Lys
            675                 680                 685

Leu Ser Val Gln Pro Asn Gly Gly Cys Glu Tyr Leu Cys Leu Pro Ala
            690                 695                 700

Pro Gln Ile Ser Ser His Ser Pro Lys Tyr Thr Cys Ala Cys Pro Asp
705                 710                 715                 720

Thr Met Trp Leu Gly Pro Asp Met Lys Arg Cys Tyr Arg Ala Pro Gln
                725                 730                 735

Ser Thr Ser Thr Thr Thr Leu Pro Ser Thr Thr Arg Thr Gly Pro Ala
                740                 745                 750

Thr Thr Gly Ala Pro Gly Thr Thr Val His Arg Ser Thr Asp Gln Asn
            755                 760                 765

His Ser Thr Glu Thr Pro Asn Leu Ala Ala Ala Val Pro Ser Ser Val
            770                 775                 780

Ser Val Pro Arg Ala Pro Ser Ile Ser Leu Ser Thr Leu Ser Pro Ala
785                 790                 795                 800

Thr Ser Asn His Ser Gln His Tyr Gly Asn Glu Asp Ser Lys Met Gly
                805                 810                 815

Ser Thr Val Thr Ala Ala Val Ile Gly Ile Ile Val Pro Ile Val Val
                820                 825                 830

Ile Ala Leu Leu Cys Met Ser Gly Tyr Leu Ile Trp Arg Asn Trp Lys
            835                 840                 845

Arg Lys Asn Thr Lys Ser Met Asn Phe Asp Asn Pro Val Tyr Arg Lys
850                 855                 860
```

```
Thr Thr Glu Glu Glu Asp Glu Asp Glu Leu His Ile Gly Arg Thr Ala
865                 870                 875                 880

Gln Ile Gly His Val Tyr Pro Ala Ala Ile Ser Ser Phe Asp Arg Pro
            885                 890                 895

Leu Trp Ala Glu Pro Cys Leu Gly Glu Thr Arg Glu Leu Glu Asp Pro
        900                 905                 910

Ala Pro Ala Leu Lys Glu Leu Phe Val Leu Pro Gly Glu Pro Arg Ser
            915                 920                 925

Gln Leu His Gln Leu Pro Arg Asn Pro Leu Ser Glu Leu Pro Val Val
        930                 935                 940

Lys Ser Lys Arg Val Ala Leu Ser Leu Glu Asp Asp Gly Leu Pro
945                 950                 955
```

<210> SEQ ID NO 69
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

```
Asp Val Lys Leu Val Ala Ser Gly Gly Gly Leu Val Lys Pro Gly Gly
1               5                   10                  15

Ser Leu Lys Leu Ser Cys Ala Ala Ser Gly Phe Thr Leu Ser Arg Tyr
            20                  25                  30

Ala Met Ser Trp Val Arg Gln Thr Pro Glu Lys Arg Leu Glu Trp Val
        35                  40                  45

Ala Tyr Ile Arg Asn Gly Gly Asp Tyr Ile Tyr Tyr Ala Asp Thr Val
    50                  55                  60

Lys Gly Arg Phe Thr Ile Ser Arg Asp Asn Ala Arg Asn Thr Leu Tyr
65                  70                  75                  80

Leu Gln Met Ser Ser Leu Lys Ser Glu Asp Thr Ala Met Tyr Tyr Cys
                85                  90                  95

Thr Arg Glu Gly Ser Tyr Tyr Asn Phe Asp Tyr Trp Gly Gln Gly Thr
            100                 105                 110

Thr Leu Thr Val Ser Ser
        115
```

<210> SEQ ID NO 70
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

```
Glu Val Gln Leu Val Glu Ser Gly Gly Gly Leu Val Lys Pro Gly Gly
1               5                   10                  15

Ser Leu Arg Leu Ser Cys Ala Ala Ser Arg Phe Thr Phe Ser Asn Tyr
            20                  25                  30

Gly Met Ser Trp Val Arg Gln Ala Pro Gly Lys Gly Leu Glu Trp Val
        35                  40                  45

Ser Thr Ile Ser Ser Gly Gly Arg Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80
```

Leu Gln Met Asn Ser Leu Arg Ala Glu Asp Thr Ala Val Tyr Tyr Cys
                85                  90                  95

Ala Arg Asp Tyr Leu Tyr Ala Met Asp Tyr Trp Gly Gln Gly Thr Thr
            100                 105                 110

Val Thr Val Ser Ser
        115

<210> SEQ ID NO 71
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Glu Val Gln Leu Val Glu Ser Gly Gly Gly Leu Val Lys Pro Gly Gly
1               5                   10                  15

Ser Leu Arg Leu Ser Cys Ala Ala Ser Arg Phe Thr Phe Ser Asn Tyr
            20                  25                  30

Gly Met Ser Trp Val Arg Gln Ala Pro Gly Lys Gly Leu Glu Trp Val
        35                  40                  45

Ala Thr Ile Ser Ser Gly Gly Arg Tyr Thr Tyr Tyr Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Leu Tyr Ala Met Asp Tyr Trp Gly Gln Gly Thr Thr
            100                 105                 110

Val Thr Val Ser Ser
        115

<210> SEQ ID NO 72
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Glu Ser Gly Gly Gly Leu Val Lys Pro Gly Gly
1               5                   10                  15

Ser Leu Arg Leu Ser Cys Ala Ala Ser Arg Phe Thr Phe Ser Asn Tyr
            20                  25                  30

Gly Met Ser Trp Val Arg Gln Ala Pro Gly Lys Gly Leu Glu Trp Val
        35                  40                  45

Ser Thr Ile Ser Ser Gly Gly Arg Tyr Thr Tyr Tyr Pro Asp His Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Leu Tyr Ala Met Asp Tyr Trp Gly Gln Gly Thr Thr
            100                 105                 110

Val Thr Val Ser Ser
        115

<210> SEQ ID NO 73
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val His Leu Gln Gln Ser Gly Pro Glu Val Val Lys Pro Gly Ala
1               5                   10                  15

Ser Val Lys Ile Ser Cys Lys Ala Ser Gly Tyr Ile Ile Ser Gly Tyr
            20                  25                  30

Phe Leu Asn Trp Val Lys Gln Ser His Gly Lys Ser Leu Glu Trp Val
        35                  40                  45

Gly Arg Ile Asn Pro Tyr Ser Gly Asp Thr Phe Phe Asn Gln Lys Phe
    50                  55                  60

Lys Gly Lys Ala Thr Leu Thr Val Asp Lys Ser Ser Asn Thr Ala His
65                  70                  75                  80

Met Glu Leu Arg Ser Leu Thr Ser Glu Asp Ser Ala Val Phe Tyr Cys
                85                  90                  95

Ala Arg Glu Asp Ile Gly Arg Phe Ala Tyr Trp Gly Gln Gly Thr Leu
            100                 105                 110

Val Thr Val Ser Ala
        115

<210> SEQ ID NO 74
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Gln Val Thr Leu Lys Glu Ser Gly Pro Gly Ile Leu Gln Pro Ser Gln
1               5                   10                  15

Thr Leu Ser Leu Thr Cys Thr Phe Ser Gly Phe Ser Leu Asn Thr Tyr
            20                  25                  30

Gly Met Gly Val Gly Trp Val Arg Gln Pro Ser Gly Lys Gly Leu Glu
        35                  40                  45

Trp Leu Ala Asn Ile Trp Trp Asp Asp Asp Lys Phe Tyr Asn Pro Ser
    50                  55                  60

Leu Lys Asn Arg Leu Thr Val Ser Lys Asp Thr Ser Asn Asn Gln Ala
65                  70                  75                  80

Phe Leu Arg Ile Thr Asn Gly Asp Thr Ala Asp Thr Ala Thr Tyr Phe
                85                  90                  95

Cys Ala Arg Ile Leu Gly Glu Asp Ile Gly Gly Ala Leu Asp Ala Trp
            100                 105                 110

Gly Gln Gly Thr Ser Val Thr Val Ser Ser
        115                 120

<210> SEQ ID NO 75
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Gln Val Gln Leu Arg Glu Thr Gly Pro Asp Leu Val Gln Pro Thr Gln
1               5                   10                  15

Thr Leu Ser Leu Thr Cys Thr Val Ser Gly Phe Ser Leu Thr Asn Tyr
            20                  25                  30

Pro Val Gln Trp Val Arg Gln Pro Pro Gly Ser Gly Leu Glu Trp Leu
        35                  40                  45

Gly Ile Met Trp Pro Ser Gly Ala Ala Asp Phe Asn Pro Ala Leu Lys
    50                  55                  60

Ser Arg Leu Ser Ile Ser Arg Asp Thr Ser Lys Ser Gln Phe Phe Leu
65                  70                  75                  80

Arg Met Asp Asn Leu Gln Thr Asp Asp Thr Ala Ile Tyr Phe Cys Ala
                85                  90                  95

Arg Gly Arg Gly Tyr Ser Ser Pro Tyr Ala Met Asp Ala Trp Gly Gln
            100                 105                 110

Gly Thr Ser Val Thr Val Ser Ser
            115                 120

<210> SEQ ID NO 76
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Val Glu Ser Gly Gly Gly Leu Val Gln Pro Gly Lys
1               5                   10                  15

Ser Leu Lys Leu Ser Cys Ala Ala Ser Gly Phe Thr Phe Ser Asp Tyr
            20                  25                  30

Asn Met Ala Trp Val Arg Gln Ala Pro Lys Lys Gly Leu Glu Trp Val
        35                  40                  45

Ala Thr Ile Met Tyr Asp Gly Ser Arg Thr Phe Tyr Arg Asp Ser Val
    50                  55                  60

Lys Gly Arg Tyr Thr Phe Ser Arg Asp Asn Ala Lys Ser Thr Leu Tyr
65                  70                  75                  80

Leu Gln Met Asp Ser Leu Arg Ser Glu Asp Thr Ala Thr Tyr Tyr Cys
                85                  90                  95

Ala Thr Gly Arg Asn Trp Phe Ala Tyr Trp Gly Gln Gly Thr Leu Val
            100                 105                 110

Thr Val Ser Ser
        115

<210> SEQ ID NO 77
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Val Glu Ser Gly Gly Gly Leu Val Gln Pro Gly Arg
1               5                   10                  15

Ser Met Lys Leu Ser Cys Ala Ala Ser Gly Phe Thr Phe Ser Ser Phe
            20                  25                  30

```
Pro Met Ala Trp Val Arg Gln Ala Pro Thr Lys Gly Leu Glu Trp Val
            35                  40                  45

Ala Thr Val Ser Thr Arg Gly Gly His Thr Tyr Tyr Arg Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ser Glu Asp Thr Ala Thr Tyr Tyr Cys
                 85                  90                  95

Ile Arg Glu Gly Thr Ser Leu Phe Ala Tyr Trp Gly Gln Gly Thr Leu
            100                 105                 110

Val Thr Val Ser Ser
            115

<210> SEQ ID NO 78
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Gln Val Thr Leu Lys Glu Ser Gly Pro Gly Ile Leu Gln Pro Ser Gln
 1               5                  10                  15

Thr Leu Ser Leu Thr Cys Thr Phe Ser Gly Phe Ser Leu Ser Thr Tyr
             20                  25                  30

Gly Met Gly Val Gly Trp Ile Arg Gln Pro Ala Gly Thr Gly Leu Glu
         35                  40                  45

Trp Leu Ala Asn Ile Trp Trp Asp Asp Asp Lys Tyr Tyr Asn Pro Ser
 50                  55                  60

Leu Lys Asn Arg Leu Thr Ile Ser Lys Asp Thr Ser Asn Asn Gln Val
 65                  70                  75                  80

Phe Leu Lys Ile Thr Asn Val Asp Thr Ala Asp Thr Ala Thr Tyr Tyr
             85                  90                  95

Cys Ala Arg Thr Thr Lys Pro Tyr Tyr Phe Asp Tyr Trp Gly Gln Gly
            100                 105                 110

Val Met Val Thr Val Ser Ser
            115

<210> SEQ ID NO 79
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Gln Val Thr Leu Lys Glu Ser Gly Pro Gly Ile Leu Gln Pro Ser Gln
 1               5                  10                  15

Thr Leu Ser Leu Thr Cys Thr Phe Ser Gly Phe Ser Leu Ser Thr Tyr
             20                  25                  30

Gly Leu Gly Val Gly Trp Ile Arg Gln Pro Ser Gly Lys Gly Leu Glu
         35                  40                  45

Trp Leu Ala Asn Ile Trp Trp Asp Asp Ala Lys Tyr Tyr Asn Pro Ser
 50                  55                  60

Leu Lys Asn Arg Leu Thr Ile Ser Lys Asp Thr Ser Asn Asn Gln Ala
 65                  70                  75                  80
```

```
Phe Leu Lys Ile Pro Asn Val Asp Thr Ala Asp Thr Ala Arg Tyr Tyr
                85                  90                  95

Cys Ala Arg Thr Thr Lys Pro Tyr Tyr Phe Asp Tyr Trp Gly Gln Gly
            100                 105                 110

Val Met Val Thr Val Ser Ser
        115

<210> SEQ ID NO 80
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Glu Val Gln Leu Val Glu Ser Gly Gly Gly Leu Val Gln Ser Gly Arg
1               5                   10                  15

Ser Leu Lys Leu Ser Cys Ala Ala Ser Gly Phe Thr Phe Ser Asn Tyr
            20                  25                  30

Tyr Met Ala Trp Val Arg Gln Ala Pro Lys Lys Gly Leu Glu Trp Val
        35                  40                  45

Ala Thr Ile Thr Thr Ser Gly Ser Arg Ser Phe Tyr Pro Asp Ser Val
    50                  55                  60

Lys Gly Arg Phe Thr Ile Ser Arg Asp Asn Ala Lys Ser Ser Leu Tyr
65                  70                  75                  80

Leu Gln Ile Asn Ser Leu Lys Ser Glu Asp Thr Ala Thr Tyr Tyr Cys
                85                  90                  95

Ala Arg Arg Gly Pro Leu Gly Tyr Phe Asp His Trp Gly Arg Gly Val
            100                 105                 110

Met Val Thr Val Ser Ser
        115

<210> SEQ ID NO 81
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Ser Leu Gln Glu Ser Gly Pro Gly Ile Leu Gln Pro Ser Gln
1               5                   10                  15

Thr Leu Ser Leu Thr Cys Thr Phe Ser Gly Phe Ser Leu Ser Thr Phe
            20                  25                  30

Gly Met Gly Val Gly Trp Ile Arg Gln Pro Ser Gly Lys Gly Leu Glu
        35                  40                  45

Trp Leu Ala Asn Ile Trp Trp Asp Asp Asp Lys Tyr Tyr Asn Pro Ser
    50                  55                  60

Leu Lys Asn Arg Leu Thr Ile Ser Lys Asp Thr Ser Asn Asn Gln Ala
65                  70                  75                  80

Phe Leu Lys Ile Thr Asn Val Asp Thr Ala Asp Thr Ala Thr Tyr Tyr
                85                  90                  95

Cys Ala Arg Thr Ala Lys Pro Tyr Tyr Phe Asp Tyr Trp Gly His Gly
            100                 105                 110

Val Met Val Thr Val Ser Ser
        115
```

<210> SEQ ID NO 82
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

Glu Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gln Gly Glu Ile Gly Asn Phe Asp Val Trp Gly Gln Gly
            100                 105                 110

Thr Leu Val Thr Val Ser Ser
        115

<210> SEQ ID NO 83
<211> LENGTH: 120
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Ala Met Ser Trp Val Arg Gln Ala Pro Gly Lys Gly Leu Glu Trp Val
        35                  40                  45

Ser Val Ile Ser Cys Ser Ala Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Ser Val His Glu Glu Phe Pro Phe Asp Val Trp Gly Gln
            100                 105                 110

Gly Thr Leu Val Thr Val Ser Ser
        115                 120

<210> SEQ ID NO 84
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

```
<400> SEQUENCE: 84

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Val Ile Ser Cys Ser Gly Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Gly Gly Gln Phe Asp Leu Trp Gly Gln Gly Thr Leu Val
            100                 105                 110

Thr Val Ser Ser
        115

<210> SEQ ID NO 85
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Phe Thr Leu Ser Arg Tyr Ala Met Ser
1               5                   10

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Tyr Ile Arg Asn Gly Gly Asp Tyr Ile Tyr Tyr Ala Asp Thr Val Lys
1               5                   10                  15

Gly

<210> SEQ ID NO 87
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Glu Gly Ser Tyr Tyr Asn Phe Asp Tyr
1               5

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 88

Arg Phe Thr Phe Ser Asn Phe Gly Met Ser
1               5                   10

<210> SEQ ID NO 89
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Thr Ile Ser Ser Gly Gly Arg Tyr Thr Tyr Tyr Pro Asp Ser Val Lys
1               5                   10                  15

Gly

<210> SEQ ID NO 90
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Asp Tyr Leu Tyr Ala Met Asp Tyr
1               5

<210> SEQ ID NO 91
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Phe Thr Phe Ser Asn Tyr Gly Met Ser
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Arg Phe Thr Phe Ser Asn Tyr Gly Met Ser
1               5                   10

<210> SEQ ID NO 93
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Thr Ile Ser Ser Gly Gly Arg Tyr Thr Tyr Tyr Pro Asp Ser Val Lys
1               5                   10                  15

Gly
```

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Thr Ile Ser Ser Gly Gly Arg Tyr Thr Tyr Tyr Pro Asp His Val Lys
1               5                   10                  15

Gly

<210> SEQ ID NO 95
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Tyr Ile Ile Ser Gly Tyr Phe Leu Asn
1               5                   10

<210> SEQ ID NO 96
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Ile Asn Pro Tyr Ser Gly Asp Thr Phe Phe Asn Gln Lys Phe Lys
1               5                   10                  15

Gly

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Glu Asp Ile Gly Arg Phe Ala Tyr
1               5

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Phe Ser Leu Asn Thr Tyr Gly Met Gly Val Gly
1               5                   10

<210> SEQ ID NO 99
<211> LENGTH: 16
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 99

Asn Ile Trp Trp Asp Asp Lys Phe Tyr Asn Pro Ser Leu Lys Asn
1               5                   10                  15

<210> SEQ ID NO 100
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ile Leu Gly Glu Asp Ile Gly Gly Ala Leu Asp Ala
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Phe Ser Leu Thr Asn Tyr Pro Val Gln
1               5                   10

<210> SEQ ID NO 102
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ile Met Trp Pro Ser Gly Ala Ala Asp Phe Asn Pro Ala Leu Lys Ser
1               5                   10                  15

<210> SEQ ID NO 103
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Arg Gly Tyr Ser Ser Pro Tyr Ala Met Asp Ala
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Phe Thr Phe Ser Asp Tyr Asn Met Ala
1               5                   10
```

<210> SEQ ID NO 105
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Thr Ile Met Tyr Asp Gly Ser Arg Thr Phe Tyr Arg Asp Ser Val Lys
1               5                   10                  15
Gly

<210> SEQ ID NO 106
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Gly Arg Asn Trp Phe Ala Tyr
1               5

<210> SEQ ID NO 107
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Phe Thr Val Ser Asp Tyr Tyr Met Ala
1               5                   10

<210> SEQ ID NO 108
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Ser Ile Ser Tyr Glu Gly Ser Ser Thr Tyr Tyr Gly Asp Ser Val Lys
1               5                   10                  15
Gly

<210> SEQ ID NO 109
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Pro Leu Arg Tyr Tyr Gly Tyr Asn Tyr Arg Phe Ala Tyr
1               5                   10

<210> SEQ ID NO 110
<211> LENGTH: 10
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 110

Gly Phe Thr Phe Ser Ser Phe Pro Met Ala
1               5                   10

<210> SEQ ID NO 111
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Thr Val Ser Thr Arg Gly Gly His Thr Tyr Tyr Arg Asp Ser Val Lys
1               5                   10                  15

Gly

<210> SEQ ID NO 112
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Glu Gly Thr Ser Leu Phe Ala Tyr
1               5

<210> SEQ ID NO 113
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gly Phe Ser Leu Ser Thr Tyr Gly Met Gly Val Gly
1               5                   10

<210> SEQ ID NO 114
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asn Ile Trp Trp Asp Asp Asp Lys Tyr Tyr Asn Pro Ser Leu Lys Asn
1               5                   10                  15

<210> SEQ ID NO 115
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Thr Thr Lys Pro Tyr Tyr Phe Asp Tyr
```

<210> SEQ ID NO 116
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Phe Ser Leu Ser Thr Tyr Gly Leu Gly Val Gly
1               5                   10

<210> SEQ ID NO 117
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asn Ile Trp Trp Asp Asp Ala Lys Tyr Tyr Asn Pro Ser Leu Lys Asn
1               5                   10                  15

<210> SEQ ID NO 118
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Phe Thr Phe Ser Asn Tyr Tyr Met Ala
1               5                   10

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Thr Ile Thr Thr Ser Gly Ser Arg Ser Phe Tyr Pro Asp Ser Val Lys
1               5                   10                  15
Gly

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Arg Gly Pro Leu Gly Tyr Phe Asp His
1               5

<210> SEQ ID NO 121
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 121

Gly Phe Ser Leu Ser Thr Phe Gly Met Gly Val Gly
1               5                   10

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Thr Ala Lys Pro Tyr Tyr Phe Asp Tyr
1               5

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Gly Ser Ile Ser Ser Ser Ser Tyr Tyr Trp Gly
1               5                   10

<210> SEQ ID NO 124
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ser Ile Tyr Tyr Ser Gly Ser Thr Tyr Tyr Asn Pro Ser Leu Lys Ser
1               5                   10                  15

<210> SEQ ID NO 125
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gln Gly Glu Ile Gly Asn Phe Asp Val
1               5

<210> SEQ ID NO 126
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gly Phe Thr Phe Ser Ile Tyr Ala Met Ser
1               5                   10
```

<210> SEQ ID NO 127
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Val Ile Ser Cys Ser Ala Gly Ser Thr Tyr Tyr Ala Asp Ser Val Lys
1               5                   10                  15

Gly

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

His Ser Val His Glu Glu Phe Pro Phe Asp Val
1               5                   10

<210> SEQ ID NO 129
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Gly Phe Thr Phe Ser Ser Tyr Ala Met Ser
1               5                   10

<210> SEQ ID NO 130
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Val Ile Ser Cys Ser Gly Gly Thr Thr Tyr Tyr Ala Asp Ser Val Lys
1               5                   10                  15

Gly

<210> SEQ ID NO 131
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Asn Gly Gly Gln Phe Asp Leu
1               5

<210> SEQ ID NO 132
<211> LENGTH: 112
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 132

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Asn Leu Leu Ile Phe Lys Val Ser Asn Arg Phe Ser Gly Val Pro
50                  55                  60

Asp Arg Phe Ile Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

<210> SEQ ID NO 133
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 133

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Leu Thr Phe Gly Gln Gly Thr Lys Leu Glu Ile Lys
            100                 105                 110

<210> SEQ ID NO 134
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 134

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Gly Asn Thr Tyr Leu His Trp Tyr Leu Gln Lys Pro Gly Gln Ser
        35                  40                  45
```

```
Pro Gln Val Leu Met Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Leu Thr Phe Gly Gln Gly Thr Lys Leu Glu Ile Lys
                100                 105                 110
```

<210> SEQ ID NO 135
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 135

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
                20                  25                  30

Asn Gly Asn Thr Tyr Leu His Trp Tyr Leu Gln Lys Pro Gly Gln Ser
            35                  40                  45

Pro Gln Val Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Leu Thr Phe Gly Gln Gly Thr Lys Leu Glu Ile Lys
                100                 105                 110
```

<210> SEQ ID NO 136
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
                20                  25                  30

Asn Glu Asn Thr Tyr Leu His Trp Tyr Leu Gln Lys Pro Gly Gln Ser
            35                  40                  45

Pro Gln Val Leu Met Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Leu Thr Phe Gly Gln Gly Thr Lys Leu Glu Ile Lys
                100                 105                 110
```

<210> SEQ ID NO 137
<211> LENGTH: 112

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Thr Gly Asn Thr Tyr Leu His Trp Tyr Leu Gln Lys Pro Gly Gln Ser
        35                  40                  45

Pro Gln Val Leu Met Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Leu Thr Phe Gly Gln Gly Thr Lys Leu Glu Ile Lys
            100                 105                 110

<210> SEQ ID NO 138
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Leu Asn Thr Tyr Leu His Trp Tyr Leu Gln Lys Pro Gly Gln Ser
        35                  40                  45

Pro Gln Val Leu Met Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Leu Thr Phe Gly Gln Gly Thr Lys Leu Glu Ile Lys
            100                 105                 110

<210> SEQ ID NO 139
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Lys Asn Thr Tyr Leu His Trp Tyr Leu Gln Lys Pro Gly Gln Ser
```

```
                35                  40                  45
Pro Gln Val Leu Met Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Ser
                 85                  90                  95

Thr His Val Pro Leu Thr Phe Gly Gln Gly Thr Lys Leu Glu Ile Lys
                100                 105                 110

<210> SEQ ID NO 140
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 140

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val Tyr Ser
                 20                  25                  30

Arg Gly Asn Thr Tyr Leu His Trp Tyr Leu Gln Lys Pro Gly Gln Ser
             35                  40                  45

Pro Gln Val Leu Met Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Ser
                 85                  90                  95

Thr His Val Pro Leu Thr Phe Gly Gln Gly Thr Lys Leu Glu Ile Lys
                100                 105                 110

<210> SEQ ID NO 141
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 141

Asp Val Val Met Thr Gln Ser Pro Leu Ser Leu Pro Val Thr Pro Gly
 1               5                  10                  15

Glu Pro Ala Ser Ile Ser Cys Arg Ser Ser Gln Ser Leu Val Tyr Ser
                 20                  25                  30

Trp Gly Asn Thr Tyr Leu His Trp Tyr Leu Gln Lys Pro Gly Gln Ser
             35                  40                  45

Pro Gln Val Leu Met Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Phe Cys Ser Gln Ser
                 85                  90                  95

Thr His Val Pro Leu Thr Phe Gly Gln Gly Thr Lys Leu Glu Ile Lys
                100                 105                 110
```

```
<210> SEQ ID NO 142
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 142

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Pro Gly Asn Thr Tyr Leu His Trp Tyr Leu Gln Lys Pro Gly Gln Ser
        35                  40                  45

Pro Gln Val Leu Met Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Leu Thr Phe Gly Gln Gly Thr Lys Leu Glu Ile Lys
            100                 105                 110

<210> SEQ ID NO 143
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 143

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Ala Pro Pro Thr Phe Gly Gly Gly Thr Lys Leu Glu Ile Lys
            100                 105                 110

<210> SEQ ID NO 144
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 144

Asp Thr Val Leu Thr Gln Ser Pro Ala Leu Ala Val Ser Pro Gly Glu
1               5                   10                  15

Arg Val Ser Ile Ser Cys Arg Ala Ser Glu Gly Val Asn Ser Tyr Met
            20                  25                  30
```

His Trp Tyr Gln Gln Asn Pro Gly Gln Gln Ser Lys Leu Leu Ile Tyr
            35                  40                  45

Arg Thr Ser Asn Leu Ala Ser Gly Val Pro Ala Arg Phe Gly Gly Ser
        50                  55                  60

Gly Ser Gly Thr Asp Phe Thr Leu Thr Ile Asp Pro Val Glu Ala Asp
65                  70                  75                  80

Asp Thr Ala Thr Tyr Phe Cys Gln Gln Ser Trp Asn Asp Pro Pro Thr
                85                  90                  95

Phe Gly Gly Gly Thr Lys Leu Glu Leu Lys
            100                 105

<210> SEQ ID NO 145
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Asp Ile Gln Met Thr Gln Ser Pro Ala Ser Leu Ser Ala Ser Leu Gly
1               5                   10                  15

Glu Thr Val Ser Ile Glu Cys Leu Ala Ser Glu Asp Ile Tyr Asn Asn
            20                  25                  30

Leu Ala Trp Tyr Gln Gln Lys Pro Gly Lys Ser Pro His Leu Leu Ile
        35                  40                  45

His Phe Thr Ser Asn Leu Gln Asp Gly Val Pro Ser Arg Phe Ser Gly
    50                  55                  60

Ser Gly Ser Gly Thr Gln Tyr Ser Leu Lys Ile Asn Ser Leu Glu Ser
65                  70                  75                  80

Glu Asp Gly Ala Thr Tyr Phe Cys Leu Gln Asp Ser Glu Tyr Pro Leu
                85                  90                  95

Thr Phe Gly Ser Gly Thr Lys Leu Glu Ile Lys
            100                 105

<210> SEQ ID NO 146
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Asp Ile Ile Met Thr Gln Ser Pro Ser Ser Leu Ala Val Ser Ala Gly
1               5                   10                  15

Glu Thr Val Thr Ile Asn Cys Lys Ser Ser Gln Ser Leu Leu Ser Ser
            20                  25                  30

Gly Lys Gln Lys Asn Tyr Leu Ala Trp Tyr Gln Gln Lys Pro Gly Gln
        35                  40                  45

Ser Pro Lys Leu Leu Ile Tyr Leu Ala Ser Thr Arg Glu Ser Gly Val
    50                  55                  60

Pro Asp Arg Phe Ile Gly Ser Gly Ser Gly Thr Asp Phe Thr Leu Thr
65                  70                  75                  80

Ile Ser Ser Met Gln Ala Glu Asp Leu Ala Ile Tyr Tyr Cys Gln Gln
                85                  90                  95

His Tyr Asp Thr Pro Leu Thr Phe Gly Ser Gly Thr Lys Leu Glu Ile
            100                 105                 110

Lys

<210> SEQ ID NO 147
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Asp Ile Gln Met Thr Gln Ser Pro Pro Ser Leu Ser Ala Ser Leu Gly
1               5                   10                  15

Glu Thr Val Ser Ile Glu Cys Leu Ala Ser Glu Asp Ile Ser Asn Tyr
            20                  25                  30

Leu Ala Trp Tyr Gln Gln Lys Pro Gly Lys Ser Pro Gln Leu Leu Ile
        35                  40                  45

Tyr Tyr Ala Asn Ser Leu Glu Asp Gly Val Pro Ser Arg Phe Ser Gly
50                  55                  60

Ser Gly Ser Gly Thr Gln Tyr Ser Leu Lys Ile Ser Asn Met Gln Pro
65                  70                  75                  80

Glu Asp Glu Gly Val Tyr His Cys Gln Gln Gly Tyr Asn Tyr Pro Tyr
                85                  90                  95

Thr Phe Gly Ala Gly Thr Lys Leu Glu Leu Lys
            100                 105

<210> SEQ ID NO 148
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 148

His Phe Val Leu Ala Gln Pro Asn Ser Val Ser Thr Asn Leu Gly Ser
1               5                   10                  15

Thr Val Lys Leu Ser Cys Lys Arg Ser Thr Gly Asn Ser Gly Ser Asn
            20                  25                  30

Tyr Val Asn Trp Tyr Gln Gln Tyr Glu Gly Arg Ser Pro Thr Thr Met
        35                  40                  45

Ile Tyr Arg Asp Asp Lys Arg Pro Asp Gly Val Pro Asp Arg Phe Ser
    50                  55                  60

Gly Ser Ile Asp Arg Ser Ser Asn Ser Ala Leu Leu Thr Ile Asn Asn
65                  70                  75                  80

Val Gln Thr Glu Asp Glu Ala Asp Tyr Phe Cys Gln Ser Tyr Ser Ser
                85                  90                  95

Gly Ile Asn Ile Phe Gly Gly Gly Thr Lys Leu Thr Val Leu
            100                 105                 110

<210> SEQ ID NO 149
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 149

His Phe Val Leu Ala Gln Pro Asn Ser Val Ser Thr Asn Leu Gly Ser

```
                1               5                   10                  15
Thr Val Lys Leu Ser Cys Lys Arg Ser Thr Ala Asn Ile Gly Ser Asn
                20                  25                  30

Tyr Val Asn Trp Tyr Gln Gln His Glu Gly Arg Ser Pro Thr Thr Leu
                35                  40                  45

Ile Tyr Arg Asp Asp Arg Arg Pro Asp Gly Val Pro Asp Arg Phe Ser
            50                  55                  60

Gly Ser Ile Asp Arg Ser Ser Asn Ser Ala Leu Leu Thr Ile Asn Asn
65                  70                  75                  80

Val Gln Thr Glu Asp Glu Ala Asp Tyr Phe Cys Gln Ser Tyr Ser Ser
                85                  90                  95

Gly Ile Asn Ile Phe Gly Gly Gly Thr Lys Leu Thr Val Leu
                100                 105                 110
```

<210> SEQ ID NO 150
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 150

```
Asp Ile Gln Met Thr Gln Ser Pro Pro Ser Leu Pro Ala Ser Leu Gly
1               5                   10                  15

Asp Lys Val Thr Ile Thr Cys Gln Ala Ser Gln Asn Ile Asn Lys Tyr
                20                  25                  30

Ile Ala Trp Tyr Gln Gln Lys Pro Gly Lys Ala Pro Arg Leu Leu Ile
                35                  40                  45

Arg Phe Thr Ser Thr Leu Glu Ser Asp Thr Pro Ser Arg Phe Ser Gly
            50                  55                  60

Ser Gly Ser Gly Arg Asp Tyr Ser Phe Ser Ile Ser Asn Val Glu Ser
65                  70                  75                  80

Glu Asp Phe Ala Ser Tyr Tyr Cys Leu His Tyr Asp Asn Leu Pro Pro
                85                  90                  95

Trp Thr Phe Gly Gly Gly Thr Lys Leu Glu Leu Lys
                100                 105
```

<210> SEQ ID NO 151
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 151

```
His Phe Val Leu Ala Gln Pro Asn Ser Val Ser Thr Asn Leu Gly Asn
1               5                   10                  15

Thr Val Lys Leu Ser Cys Lys Arg Ser Thr Gly Asn Ile Gly Ser Asn
                20                  25                  30

Tyr Val Asn Trp Tyr Gln Gln His Glu Gly Arg Ser Pro Thr Thr Leu
                35                  40                  45

Ile Tyr Arg Asp Asp Lys Arg Pro Asp Gly Val Pro Asp Arg Phe Ser
            50                  55                  60

Gly Ser Phe Asp Arg Ser Ser Asn Ser Ala Leu Leu Thr Ile Asn Asn
65                  70                  75                  80

Val Gln Thr Glu Asp Glu Ala Asp Tyr Phe Cys Gln Ser Tyr Asn Ser
```

```
                    85                  90                  95

Gly Ile Asn Phe Phe Gly Gly Gly Thr Lys Leu Thr Val Leu
            100                 105                 110

<210> SEQ ID NO 152
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 152

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Cys
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Val Arg Ser Pro
                85                  90                  95

Ile Thr Phe Gly Gly Gly Thr Lys Val Glu Ile Lys
            100                 105

<210> SEQ ID NO 153
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 153

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ile Pro Pro Leu
                85                  90                  95

Thr Phe Gly Gly Gly Thr Lys Val Glu Ile Lys
            100                 105

<210> SEQ ID NO 154
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154
```

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Cys Thr Tyr
            20                  25                  30

Leu Asn Trp Tyr Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Pro Pro Leu
                85                  90                  95

Thr Phe Gly Gly Gly Thr Lys Val Glu Ile Lys
            100                 105
```

<210> SEQ ID NO 155
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

```
Arg Ser Ser Gln Ser Ile Val His Ser Asn Gly Asn Thr Tyr Leu Glu
1               5                   10                  15
```

<210> SEQ ID NO 156
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

```
Phe Gln Gly Ser His Val Pro Trp Thr
1               5
```

<210> SEQ ID NO 157
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

```
Arg Ser Ser Gln Ser Leu Val Tyr Ser Asn Gly Asn Thr Tyr Leu His
1               5                   10                  15
```

<210> SEQ ID NO 158
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

```
Arg Ser Ser Gln Ser Leu Val Tyr Ser Asn Gly Glu Asn Thr Tyr Leu His
1               5                   10                  15
```

```
<210> SEQ ID NO 159
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Arg Ser Ser Gln Ser Leu Val Tyr Ser Thr Gly Asn Thr Tyr Leu His
1               5                   10                  15

<210> SEQ ID NO 160
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Arg Ser Ser Gln Ser Leu Val Tyr Ser Asn Leu Asn Thr Tyr Leu His
1               5                   10                  15

<210> SEQ ID NO 161
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Arg Ser Ser Gln Ser Leu Val Tyr Ser Asn Lys Asn Thr Tyr Leu His
1               5                   10                  15

<210> SEQ ID NO 162
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Arg Ser Ser Gln Ser Leu Val Tyr Ser Arg Gly Asn Thr Tyr Leu His
1               5                   10                  15

<210> SEQ ID NO 163
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Arg Ser Ser Gln Ser Leu Val Tyr Ser Trp Gly Asn Thr Tyr Leu His
1               5                   10                  15

<210> SEQ ID NO 164
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164
```

Arg Ser Ser Gln Ser Leu Val Tyr Ser Pro Gly Asn Thr Tyr Leu His
1               5                   10                  15

<210> SEQ ID NO 165
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Arg Ser Ser Gln Thr Ile Val His Ser Asn Gly Asn Thr Tyr Leu Glu
1               5                   10                  15

<210> SEQ ID NO 166
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Phe Gln Gly Ser His Ala Pro Pro Thr
1               5

<210> SEQ ID NO 167
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Arg Ala Ser Glu Gly Val Asn Ser Tyr Met His
1               5                   10

<210> SEQ ID NO 168
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Arg Thr Ser Asn Leu Ala Ser
1               5

<210> SEQ ID NO 169
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gln Gln Ser Trp Asn Asp Pro Pro Thr
1               5

<210> SEQ ID NO 170
<211> LENGTH: 11
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 170

Leu Ala Ser Glu Asp Ile Tyr Asn Asn Leu Ala
1               5                   10

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Phe Thr Ser Asn Leu Gln Asp
1               5

<210> SEQ ID NO 172
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Leu Gln Asp Ser Glu Tyr Pro Leu Thr
1               5

<210> SEQ ID NO 173
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Lys Ser Ser Gln Ser Leu Leu Ser Ser Gly Lys Gln Lys Asn Tyr Leu
1               5                   10                  15

Ala

<210> SEQ ID NO 174
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Leu Ala Ser Thr Arg Glu Ser
1               5

<210> SEQ ID NO 175
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Gln Gln His Tyr Asp Thr Pro Leu Thr
```

```
1               5
```

<210> SEQ ID NO 176
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

```
Leu Ala Ser Glu Asp Ile Ser Asn Tyr Leu Ala
1               5                   10
```

<210> SEQ ID NO 177
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

```
Tyr Ala Asn Ser Leu Glu Asp
1               5
```

<210> SEQ ID NO 178
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

```
Gln Gln Gly Tyr Asn Tyr Pro Tyr Thr
1               5
```

<210> SEQ ID NO 179
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

```
Lys Arg Ser Thr Gly Asn Ser Gly Ser Asn Tyr Val Asn
1               5                   10
```

<210> SEQ ID NO 180
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

```
Arg Asp Asp Lys Arg Pro Asp
1               5
```

<210> SEQ ID NO 181
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 181

Gln Ser Tyr Ser Ser Gly Ile Asn Ile
1               5

<210> SEQ ID NO 182
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Lys Arg Ser Thr Ala Asn Ile Gly Ser Asn Tyr Val Asn
1               5                   10

<210> SEQ ID NO 183
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Arg Asp Asp Arg Arg Pro Asp
1               5

<210> SEQ ID NO 184
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Gln Ala Ser Gln Asn Ile Asn Lys Tyr Ile Ala
1               5                   10

<210> SEQ ID NO 185
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Phe Thr Ser Thr Leu Glu Ser
1               5

<210> SEQ ID NO 186
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Leu His Tyr Asp Asn Leu Pro Pro Trp Thr
1               5                   10

<210> SEQ ID NO 187

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Lys Arg Ser Thr Gly Asn Ile Gly Ser Asn Tyr Val Asn
1               5                   10

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gln Ser Tyr Asn Ser Gly Ile Asn Phe
1               5

<210> SEQ ID NO 189
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Arg Ala Ser Gln Ser Val Gly Ser Cys Tyr Leu Ala
1               5                   10

<210> SEQ ID NO 190
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gly Ala Ser Ser Arg Ala Thr
1               5

<210> SEQ ID NO 191
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gln His Tyr Val Arg Ser Pro Ile Thr
1               5

<210> SEQ ID NO 192
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192
```

Arg Ala Ser Gln Ser Ile Gly Ser Tyr Leu Asn
1               5                   10

<210> SEQ ID NO 193
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ala Ala Ser Ser Leu Gln Ser
1               5

<210> SEQ ID NO 194
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Gln Gln Ser Tyr Ile Pro Pro Leu Thr
1               5

<210> SEQ ID NO 195
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Arg Ala Ser Gln Gly Ile Cys Thr Tyr Leu Asn
1               5                   10

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gln Gln Ser Tyr Asn Pro Pro Leu Thr
1               5

<210> SEQ ID NO 197
<211> LENGTH: 330
<212> TYPE: PRT
<213> ORGANISM: Homo sapiens

<400> SEQUENCE: 197

Ala Ser Thr Lys Gly Pro Ser Val Phe Phe Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 198
<211> LENGTH: 330
<212> TYPE: PRT
<213> ORGANISM: Homo sapiens

<400> SEQUENCE: 198

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
                115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 199
<211> LENGTH: 106
<212> TYPE: PRT
<213> ORGANISM: Homo sapiens

<400> SEQUENCE: 199

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 200
<211> LENGTH: 105
<212> TYPE: PRT
<213> ORGANISM: Homo sapiens

<400> SEQUENCE: 200

-continued

```
Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Thr Pro Ser Lys Gln Ser Asn Asn Lys
50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 201
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Any amino acid

<400> SEQUENCE: 201

Phe Gly Xaa Gly
1

<210> SEQ ID NO 202
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(9)
<223> OTHER INFORMATION: Any amino acid

<400> SEQUENCE: 202

Cys Xaa Xaa Xaa Xaa Xaa Xaa Xaa Xaa
1               5

<210> SEQ ID NO 203
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Leu Glu Trp Ile Gly
1               5

<210> SEQ ID NO 204
<211> LENGTH: 4
<212> TYPE: PRT
<213> ORGANISM: Artificial Sequence
<220> FEATURE:
<223> OTHER INFORMATION: Description of Artificial Sequence: Synthetic
```

```
                              peptide
<220> FEATURE:
<221> NAME/KEY: MOD_RES
<222> LOCATION: (3)..(3)
<223> OTHER INFORMATION: Any amino acid

<400> SEQUENCE: 204

Trp Gly Xaa Gly
1

<210> SEQ ID NO 205
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Gly Ser Gly Pro Ala Lys Glu Cys Glu Lys Asp Gln Phe Gln Cys Arg
1               5                   10                  15

Asn Glu Arg Cys Ile Pro Ser Val Trp Arg Cys Asp Glu Asp Asp Asp
            20                  25                  30

Cys Leu Asp His Ser Asp Glu Asp Asp Cys Pro Lys
        35                  40

<210> SEQ ID NO 206
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Cys Glu Lys Asp Gln Phe Gln Ser Arg Asn Glu Arg Cys Ile Pro Ser
1               5                   10                  15

Val Trp Arg

<210> SEQ ID NO 207
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Cys Glu Lys Asp Gln Ala Gln Ser Arg Asn Glu Arg Cys Ile Pro Ser
1               5                   10                  15

Val Trp Arg

<210> SEQ ID NO 208
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Cys Glu Lys Asp Gln Phe Gln Ala Arg Asn Glu Arg Cys Ile Pro Ser
1               5                   10                  15

Val Trp Arg
```

```
<210> SEQ ID NO 209
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Cys Glu Lys Asp Gln Phe Gln Ser Arg Ala Glu Arg Cys Ile Pro Ser
1               5                   10                  15

Val Trp Arg

<210> SEQ ID NO 210
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Cys Glu Lys Asp Gln Ala Gln Ala Arg Ala Glu Arg Cys Ile Pro Ser
1               5                   10                  15

Val Trp Arg

<210> SEQ ID NO 211
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Phe Gln Ser Arg Asn
1               5

<210> SEQ ID NO 212
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Cys Ala Asp Ser Asp Phe Thr Ser Asp Asn Gly His Cys Ile His Glu
1               5                   10                  15

Arg Trp Lys

<210> SEQ ID NO 213
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (62)..(62)
<223> OTHER INFORMATION: Any amino acid except Met, Cys, Asn, Asp or Gln

<400> SEQUENCE: 213

Glu Val Gln Leu Val Glu Ser Gly Gly Gly Leu Val Lys Pro Gly Gly
1               5                   10                  15
```

```
Ser Leu Arg Leu Ser Cys Ala Ala Ser Arg Phe Thr Phe Ser Asn Tyr
            20                  25                  30

Gly Met Ser Trp Val Arg Gln Ala Pro Gly Lys Gly Leu Glu Trp Val
        35                  40                  45

Ser Thr Ile Ser Ser Gly Gly Arg Tyr Thr Tyr Tyr Pro Xaa Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Leu Tyr Ala Met Asp Tyr Trp Gly Gln Gly Thr Thr
            100                 105                 110

Val Thr Val Ser Ser
        115

<210> SEQ ID NO 214
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (63)..(63)
<223> OTHER INFORMATION: Any amino acid except Met, Cys, Gly, Ser, Asn
      or Pro

<400> SEQUENCE: 214

Glu Val Gln Leu Val Glu Ser Gly Gly Gly Leu Val Lys Pro Gly Gly
1               5                   10                  15

Ser Leu Arg Leu Ser Cys Ala Ala Ser Arg Phe Thr Phe Ser Asn Tyr
            20                  25                  30

Gly Met Ser Trp Val Arg Gln Ala Pro Gly Lys Gly Leu Glu Trp Val
        35                  40                  45

Ser Thr Ile Ser Ser Gly Gly Arg Tyr Thr Tyr Tyr Pro Asp Xaa Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Leu Tyr Ala Met Asp Tyr Trp Gly Gln Gly Thr Thr
            100                 105                 110

Val Thr Val Ser Ser
        115

<210> SEQ ID NO 215
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: Any amino acid except Met, Cys, Asn, Asp or Gln

<400> SEQUENCE: 215

Asp Val Val Met Thr Gln Ser Pro Leu Ser Leu Pro Val Thr Pro Gly
1               5                   10                  15
```

Glu Pro Ala Ser Ile Ser Cys Arg Ser Ser Gln Ser Leu Val Tyr Ser
            20                  25                  30

Xaa Gly Asn Thr Tyr Leu His Trp Tyr Leu Gln Lys Pro Gly Gln Ser
        35                  40                  45

Pro Gln Val Leu Met Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Leu Thr Phe Gly Gln Gly Thr Lys Leu Glu Ile Lys
            100                 105                 110

<210> SEQ ID NO 216
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (34)..(34)
<223> OTHER INFORMATION: Any amino acid except Met, Cys, Gly, Ser or Asn

<400> SEQUENCE: 216

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Val Tyr Ser
            20                  25                  30

Asn Xaa Asn Thr Tyr Leu His Trp Tyr Leu Gln Lys Pro Gly Gln Ser
        35                  40                  45

Pro Gln Val Leu Met Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Leu Thr Phe Gly Gln Gly Thr Lys Leu Glu Ile Lys
            100                 105                 110

<210> SEQ ID NO 217
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Cys Glu Lys Asp Gln Phe Gln Cys Arg Asn Gly Arg Cys Ile Pro Ser
1               5                   10                  15

Val Trp Arg Cys Asp Glu Asp Asp Cys Leu Asp His Ser Asp Glu
            20                  25                  30

Asp Asp Cys
        35

<210> SEQ ID NO 218
<211> LENGTH: 38
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 218

Cys Ala Asp Ser Asp Phe Thr Cys Asp Asn Gly His Cys Ile His Glu
1               5                   10                  15

Arg Trp Lys Cys Asp Gly Glu Glu Cys Pro Asp Gly Ser Asp Glu
            20                  25                  30

Ser Glu Ala Thr Cys Thr
        35

<210> SEQ ID NO 219
<211> LENGTH: 43
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Ser His Ser Cys Ser Ser Thr Gln Phe Lys Cys Asn Ser Gly Arg Cys
1               5                   10                  15

Ile Pro Glu His Trp Thr Cys Asp Gly Asp Asn Asp Cys Gly Asp Tyr
            20                  25                  30

Ser Asp Glu Thr His Ala Asn Cys Thr Asn Gln
        35                  40

<210> SEQ ID NO 220
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Gln Val Gln Leu Gln Gln Ser Gly Ala Glu Leu Val Lys Pro Gly Ala
1               5                   10                  15

Ser Val Lys Leu Ser Cys Lys Thr Ser Gly Tyr Thr Phe Gly Asn Tyr
            20                  25                  30

Tyr Met Ser Trp Leu Arg Gln Met Pro Gly Gln Asn Ile Asp Trp Ile
        35                  40                  45

Gly Asn Ile Tyr Gly Gly Asn Gly Gly Ala Ala Tyr Asn Gln Lys Phe
    50                  55                  60

Lys Gly Lys Ala Thr Leu Thr Ile Asp Lys Ser Ser Ser Thr Ala Tyr
65                  70                  75                  80

Met Asp Leu Ser Ser Leu Thr Ser Glu Asp Ser Ala Val Tyr Phe Cys
                85                  90                  95

Ala Arg Val Arg Pro Gly Gly Phe Val Tyr Trp Gly Gln Gly Thr Leu
            100                 105                 110

Val Thr Val Ser Ser
        115

<210> SEQ ID NO 221
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

```
<220> FEATURE:
<221> NAME/KEY: MOD_RES
<222> LOCATION: (82)..(82)
<223> OTHER INFORMATION: Any amino acid

<400> SEQUENCE: 221

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Xaa Val Glu Ala Glu Asp Leu Gly Val Tyr Phe Cys Ser Gln Ser
                85                  90                  95

Thr His Val Pro Trp Thr Phe Gly Gly Thr Lys Leu Glu Ile Lys
            100                 105                 110

<210> SEQ ID NO 222
<211> LENGTH: 687
<212> TYPE: PRT
<213> ORGANISM: Homo sapiens

<400> SEQUENCE: 222

Met Gly Leu Pro Glu Pro Gly Pro Leu Arg Leu Leu Ala Leu Leu Leu
1               5                   10                  15

Leu Leu Leu Leu Leu Leu Leu Leu Gln Leu Gln His Leu Ala Ala Ala
            20                  25                  30

Ala Ala Asp Pro Leu Leu Gly Gly Gln Gly Pro Ala Lys Asp Cys Glu
        35                  40                  45

Lys Asp Gln Phe Gln Cys Arg Asn Glu Arg Cys Ile Pro Ser Val Trp
    50                  55                  60

Arg Cys Asp Glu Asp Asp Asp Cys Leu Asp His Ser Asp Glu Asp Asp
65                  70                  75                  80

Cys Pro Lys Lys Thr Cys Ala Asp Ser Asp Phe Thr Cys Asp Asn Gly
                85                  90                  95

His Cys Ile His Glu Arg Trp Lys Cys Asp Gly Glu Glu Cys Pro
            100                 105                 110

Asp Gly Ser Asp Glu Ser Glu Ala Thr Cys Thr Lys Gln Val Cys Pro
        115                 120                 125

Ala Glu Lys Leu Ser Cys Gly Pro Thr Ser His Lys Cys Val Pro Ala
    130                 135                 140

Ser Trp Arg Cys Asp Gly Glu Lys Asp Cys Glu Gly Gly Ala Asp Glu
145                 150                 155                 160

Ala Gly Cys Ala Thr Ser Leu Gly Thr Cys Arg Gly Asp Glu Phe Gln
                165                 170                 175

Cys Gly Asp Gly Thr Cys Val Leu Ala Ile Lys His Cys Asn Gln Glu
            180                 185                 190

Gln Asp Cys Pro Asp Gly Ser Asp Glu Ala Gly Cys Leu Gln Gly Leu
        195                 200                 205

Asn Glu Cys Leu His Asn Asn Gly Gly Cys Ser His Ile Cys Thr Asp
    210                 215                 220

Leu Lys Ile Gly Phe Glu Cys Thr Cys Pro Ala Gly Phe Gln Leu Leu
```

```
            225                 230                 235                 240

Asp Gln Lys Thr Cys Gly Asp Ile Asp Glu Cys Lys Asp Pro Asp Ala
                        245                 250                 255

Cys Ser Gln Ile Cys Val Asn Tyr Lys Gly Tyr Phe Lys Cys Glu Cys
                        260                 265                 270

Tyr Pro Gly Tyr Glu Met Asp Leu Leu Thr Lys Asn Cys Lys Ala Ala
                        275                 280                 285

Ala Gly Lys Ser Pro Ser Leu Ile Phe Thr Asn Arg His Glu Val Arg
                        290                 295                 300

Arg Ile Asp Leu Val Lys Arg Asn Tyr Ser Arg Leu Ile Pro Met Leu
        305                 310                 315                 320

Lys Asn Val Val Ala Leu Asp Val Glu Val Ala Thr Asn Arg Ile Tyr
                        325                 330                 335

Trp Cys Asp Leu Ser Tyr Arg Lys Ile Tyr Ser Ala Tyr Met Asp Lys
                        340                 345                 350

Ala Ser Asp Pro Lys Glu Gln Glu Val Leu Ile Asp Glu Gln Leu His
                        355                 360                 365

Ser Pro Glu Gly Leu Ala Val Asp Trp Val His Lys His Ile Tyr Trp
                        370                 375                 380

Thr Asp Ser Gly Asn Lys Thr Ile Ser Val Ala Thr Val Asp Gly Gly
        385                 390                 395                 400

Arg Arg Arg Thr Leu Phe Ser Arg Asn Leu Ser Glu Pro Arg Ala Ile
                        405                 410                 415

Ala Val Asp Pro Leu Arg Gly Phe Met Tyr Trp Ser Asp Trp Gly Asp
                        420                 425                 430

Gln Ala Lys Ile Glu Lys Ser Gly Leu Asn Gly Val Asp Arg Gln Thr
                        435                 440                 445

Leu Val Ser Asp Asn Ile Glu Trp Pro Asn Gly Ile Thr Leu Asp Leu
                        450                 455                 460

Leu Ser Gln Arg Leu Tyr Trp Val Asp Ser Lys Leu His Gln Leu Ser
        465                 470                 475                 480

Ser Ile Asp Phe Ser Gly Gly Asn Arg Lys Thr Leu Ile Ser Ser Thr
                        485                 490                 495

Asp Phe Leu Ser His Pro Phe Gly Ile Ala Val Phe Glu Asp Lys Val
                        500                 505                 510

Phe Trp Thr Asp Leu Glu Asn Glu Ala Ile Phe Ser Ala Asn Arg Leu
                        515                 520                 525

Asn Gly Leu Glu Ile Ser Ile Leu Ala Glu Asn Leu Asn Asn Pro His
                        530                 535                 540

Asp Ile Val Ile Phe His Glu Leu Lys Gln Pro Arg Ala Pro Asp Ala
        545                 550                 555                 560

Cys Glu Leu Ser Val Gln Pro Asn Gly Gly Cys Glu Tyr Leu Cys Leu
                        565                 570                 575

Pro Ala Pro Gln Ile Ser Ser His Ser Pro Lys Tyr Thr Cys Ala Cys
                        580                 585                 590

Pro Asp Thr Met Trp Leu Gly Pro Asp Met Lys Arg Cys Tyr Arg Asp
                        595                 600                 605

Ala Asn Glu Asp Ser Lys Met Gly Ser Thr Val Thr Ala Ala Val Ile
                        610                 615                 620

Gly Ile Ile Val Pro Ile Val Ile Ala Leu Leu Cys Met Ser Gly
        625                 630                 635                 640

Tyr Leu Ile Trp Arg Asn Trp Lys Arg Lys Asn Thr Lys Ser Met Asn
                        645                 650                 655
```

Phe Asp Asn Pro Val Tyr Arg Lys Thr Thr Glu Glu Asp Glu Asp
            660                 665                 670

Glu Leu His Ile Gly Arg Thr Ala Gln Ile Gly His Val Tyr Pro
            675                 680                 685

<210> SEQ ID NO 223
<211> LENGTH: 834
<212> TYPE: PRT
<213> ORGANISM: Mus musculus

<400> SEQUENCE: 223

Met Gly Arg Pro Glu Leu Gly Ala Leu Arg Pro Leu Ala Leu Leu
1               5                   10                  15

Leu Leu Leu Leu Gln Leu Gln His Leu Ser Ala Ala Asp Pro Leu Pro
            20                  25                  30

Gly Gly Gln Gly Pro Val Lys Glu Cys Glu Glu Asp Gln Phe Arg Cys
            35                  40                  45

Arg Asn Glu Arg Cys Ile Pro Leu Val Trp Arg Cys Asp Glu Asp Asn
        50                  55                  60

Asp Cys Ser Asp Asn Ser Asp Glu Asp Cys Pro Lys Arg Thr Cys
65                  70                  75                  80

Ala Asp Ser Asp Phe Thr Cys Asp Asn Gly His Cys Ile Pro Glu Arg
                85                  90                  95

Trp Lys Cys Asp Gly Glu Glu Glu Cys Pro Asp Gly Ser Asp Glu Ser
            100                 105                 110

Lys Ala Thr Cys Ser Ser Glu Glu Cys Pro Ala Glu Lys Leu Ser Cys
            115                 120                 125

Gly Pro Thr Ser His Lys Cys Val Pro Ala Ser Trp Arg Cys Asp Gly
        130                 135                 140

Glu Lys Asp Cys Glu Gly Gly Ala Asp Glu Ala Gly Cys Pro Thr Ser
145                 150                 155                 160

Ala Pro Gly Pro Cys Arg Glu Asn Glu Phe Gln Cys Gly Asp Gly Thr
                165                 170                 175

Cys Val Leu Ala Ile Lys Arg Cys Asn Gln Glu Arg Asp Cys Pro Asp
            180                 185                 190

Gly Ser Asp Glu Ala Gly Cys Leu Gln Glu Ser Thr Cys Glu Gly Pro
        195                 200                 205

Arg Arg Phe Gln Cys Lys Ser Gly Glu Cys Val Asp Gly Gly Lys Val
    210                 215                 220

Cys Asp Asp Gln Arg Asp Cys Arg Asp Trp Ser Asp Glu Pro Gln Lys
225                 230                 235                 240

Val Cys Gly Leu Asn Glu Cys Leu His Asn Asn Gly Gly Cys Ser His
                245                 250                 255

Ile Cys Thr Asp Leu Lys Ile Gly Phe Glu Cys Thr Cys Pro Ala Gly
            260                 265                 270

Phe Gln Leu Leu Asp Gln Lys Thr Cys Gly Asp Ile Asp Glu Cys Gln
        275                 280                 285

Asp Pro Asp Ala Cys Ser Gln Ile Cys Val Asn Tyr Lys Gly Tyr Phe
    290                 295                 300

Lys Cys Glu Cys His Pro Gly Tyr Glu Met Asp Thr Leu Thr Lys Asn
305                 310                 315                 320

Cys Lys Ala Val Ala Gly Lys Ser Pro Ser Leu Ile Phe Thr Asn Arg
                325                 330                 335

His Glu Val Arg Arg Ile Asp Leu Val Lys Arg Asp Tyr Ser Arg Leu

```
                  340                 345                 350
Ile Pro Met Leu Lys Asn Val Val Ala Leu Asp Val Glu Val Ala Thr
            355                 360                 365

Asn Arg Ile Tyr Trp Cys Asp Leu Ser Tyr Arg Lys Ile Tyr Ser Ala
        370                 375                 380

His Met Asp Lys Ala Ser Ile Pro Asp Glu Gln Val Val Leu Ile Asp
385                 390                 395                 400

Glu Gln Leu His Ser Pro Glu Gly Leu Ala Val Asp Trp Val His Lys
                405                 410                 415

His Ile Tyr Trp Thr Asp Ser Gly Asn Lys Thr Ile Ser Val Ala Thr
            420                 425                 430

Thr Asp Gly Arg Arg Cys Thr Leu Phe Ser Arg Glu Leu Ser Glu
                435                 440                 445

Pro Arg Ala Ile Ala Val Asp Pro Leu Arg Gly Phe Met Tyr Trp Ser
        450                 455                 460

Asp Trp Gly Phe Gln Ala Lys Ile Glu Lys Ala Gly Leu Asn Gly Ala
465                 470                 475                 480

Asp Arg Gln Thr Leu Val Ser Asp Asn Ile Glu Trp Pro Asn Gly Ile
                485                 490                 495

Thr Leu Asp Leu Leu Ser Gln Arg Leu Tyr Trp Val Asp Ser Lys Leu
            500                 505                 510

His Gln Leu Ser Ser Ile Asp Phe Asn Gly Gly Asn Arg Lys Met Leu
        515                 520                 525

Ile Phe Ser Thr Asp Phe Leu Ser His Pro Phe Gly Val Ala Val Phe
        530                 535                 540

Glu Asp Lys Val Phe Trp Thr Asp Leu Glu Asn Glu Ala Ile Phe Ser
545                 550                 555                 560

Ala Asn Arg Leu Asn Gly Leu Glu Ile Ala Ile Leu Ala Glu Asn Leu
                565                 570                 575

Asn Asn Pro His Asp Ile Val Ile Phe His Glu Leu Lys Gln Pro Lys
            580                 585                 590

Ala Ala Asp Ala Cys Asp Leu Ser Ala Gln Pro Asn Gly Gly Cys Glu
        595                 600                 605

Tyr Leu Cys Leu Pro Ala Pro Gln Ile Ser Ser His Ser Pro Lys Tyr
        610                 615                 620

Thr Cys Ala Cys Pro Asp Thr Met Trp Leu Gly Pro Asp Met Lys Arg
625                 630                 635                 640

Cys Tyr Arg Ala Pro Gln Ser Thr Ser Thr Thr Leu Ala Ser Ala
                645                 650                 655

Met Thr Arg Thr Val Pro Ala Thr Thr Arg Ala Pro Gly Thr Thr Ile
                660                 665                 670

His Asp Pro Thr Tyr Gln Asn His Ser Thr Glu Thr Pro Ser Gln Thr
            675                 680                 685

Ala Ala Ala Pro His Ser Val Asn Val Pro Arg Ala Pro Ser Thr Ser
        690                 695                 700

Pro Ser Thr Pro Ser Pro Ala Thr Ser Asn His Ser Gln His Tyr Gly
705                 710                 715                 720

Asn Glu Gly Ser Gln Met Gly Ser Thr Val Thr Ala Ala Val Ile Gly
                725                 730                 735

Val Ile Val Pro Ile Val Val Ile Ala Leu Leu Cys Met Ser Gly Tyr
            740                 745                 750

Leu Ile Trp Arg Asn Trp Lys Arg Lys Asn Thr Lys Ser Met Asn Phe
        755                 760                 765
```

```
Asp Asn Pro Val Tyr Arg Lys Thr Thr Glu Glu Glu Glu Asp Glu
            770                 775                 780

Leu His Ile Gly Arg Thr Ala Gln Ile Gly His Val Tyr Pro Ala Ala
785                 790                 795                 800

Ile Ser Asn Tyr Asp Arg Pro Leu Trp Ala Glu Pro Cys Leu Gly Glu
                    805                 810                 815

Thr Arg Asp Leu Glu Asp Pro Ala Pro Ala Leu Lys Glu Leu Phe Val
                820                 825                 830

Leu Pro

<210> SEQ ID NO 224
<211> LENGTH: 637
<212> TYPE: PRT
<213> ORGANISM: Macaca fascicularis

<400> SEQUENCE: 224

Leu Leu Glu Met Gln Leu Gln His Leu Ala Ala Ala Ala Asp Pro
1               5                   10                  15

Leu Leu Gly Gly Gln Gly Pro Ala Lys Glu Cys Glu Lys Asp Gln Phe
                20                  25                  30

Gln Cys Arg Asn Glu Arg Cys Ile Pro Ser Val Trp Arg Cys Asp Glu
            35                  40                  45

Asp Asp Asp Cys Leu Asp His Ser Asp Glu Asp Cys Pro Lys Lys
        50                  55                  60

Thr Cys Ala Asp Ser Asp Phe Thr Cys Asp Asn Gly His Cys Ile His
65                  70                  75                  80

Glu Arg Trp Lys Cys Asp Gly Glu Glu Glu Cys Pro Asp Gly Ser Asp
                85                  90                  95

Glu Ser Glu Ala Thr Cys Thr Leu Gly Thr Cys His Gly Asn Glu Phe
            100                 105                 110

Gln Cys Gly Asp Gly Thr Cys Val Leu Ala Ile Lys Arg Cys Asn Gln
        115                 120                 125

Glu Gln Asp Cys Pro Asp Gly Ser Asp Glu Ala Gly Cys Leu Gln Val
    130                 135                 140

Pro Pro Thr Phe Leu Gly Asn Arg Arg Arg Pro Arg Gly Leu Asn Glu
145                 150                 155                 160

Cys Leu His Asn Asn Gly Gly Cys Ser His Ile Cys Thr Asp Leu Lys
                165                 170                 175

Ile Gly Phe Glu Cys Thr Cys Pro Ala Gly Phe Gln Leu Leu Asp Gln
            180                 185                 190

Lys Thr Cys Gly Asp Ile Asp Glu Cys Lys Asp Pro Asp Ala Cys Ser
        195                 200                 205

Gln Ile Cys Val Asn Tyr Lys Gly Tyr Phe Lys Cys Glu Cys Tyr Pro
    210                 215                 220

Gly Tyr Glu Met Asp Leu Leu Thr Lys Asn Cys Lys Ala Ala Ala Gly
225                 230                 235                 240

Lys Ser Pro Ser Leu Ile Phe Thr Asn Arg His Glu Val Arg Arg Ile
                245                 250                 255

Asp Leu Val Lys Arg Asn Tyr Ser Arg Leu Ile Pro Met Leu Lys Asn
            260                 265                 270

Val Val Ala Leu Asp Met Glu Val Ala Thr Asn Arg Ile Tyr Trp Cys
        275                 280                 285

Asp Leu Ser Tyr Arg Lys Ile Tyr Ser Ala Tyr Met Asp Lys Ala Ser
    290                 295                 300
```

Asp Pro Lys Glu Gln Glu Val Leu Ile Asp Glu Gln Leu His Ser Pro
305                 310                 315                 320

Glu Gly Leu Ala Val Asp Trp Val His Lys His Ile Tyr Trp Thr Asp
            325                 330                 335

Ser Gly Asn Lys Thr Ile Ser Val Ala Thr Val Asp Gly Gly Arg Arg
        340                 345                 350

Cys Thr Leu Phe Ser Arg Asn Leu Ser Glu Pro Arg Ala Ile Ala Val
    355                 360                 365

Asp Pro Leu Gln Gly Phe Met Tyr Trp Ser Asp Trp Gly Asn Gln Ala
370                 375                 380

Lys Ile Glu Lys Ser Gly Leu Asn Gly Val Asp Arg Gln Thr Leu Val
385                 390                 395                 400

Ser Asp Asn Ile Glu Trp Pro Asn Gly Ile Thr Leu Asp Leu Leu Ser
            405                 410                 415

Gln Arg Leu Tyr Trp Val Asp Ser Lys Leu His Gln Leu Ser Ser Ile
        420                 425                 430

Asp Phe Ser Gly Gly Asn Arg Lys Met Leu Ile Ser Ser Thr Asp Phe
    435                 440                 445

Leu Ser His Pro Phe Gly Ile Ala Val Phe Glu Asp Lys Val Phe Trp
450                 455                 460

Thr Asp Leu Glu Asn Glu Ala Ile Phe Ser Ala Asn Arg Leu Asn Gly
465                 470                 475                 480

Leu Glu Ile Ser Ile Leu Ala Glu Asn Leu Asn Asn Pro His Asp Ile
            485                 490                 495

Val Ile Phe His Glu Leu Lys Gln Pro Arg Ala Ala Asp Ala Cys Lys
        500                 505                 510

Leu Ser Val Gln Pro Asn Gly Gly Cys Glu Tyr Leu Cys Leu Pro Ala
    515                 520                 525

Pro Gln Ile Ser Ser His Ser Pro Lys Tyr Thr Cys Ala Cys Pro Asp
530                 535                 540

Thr Met Trp Leu Gly Pro Asp Met Lys Arg Cys Tyr Arg Asp Gly Asn
545                 550                 555                 560

Glu Asp Ser Lys Met Gly Ser Thr Val Thr Ala Ala Val Ile Gly Ile
            565                 570                 575

Ile Val Pro Ile Val Val Ile Ala Leu Leu Cys Met Ser Gly Tyr Leu
        580                 585                 590

Ile Trp Arg Asn Trp Lys Arg Lys Asn Thr Lys Ser Met Asn Phe Asp
    595                 600                 605

Asn Pro Val Tyr Arg Lys Thr Thr Glu Glu Glu Asp Glu Asp Glu Leu
610                 615                 620

His Ile Gly Arg Thr Ala Gln Ile Gly His Val Tyr Pro
625                 630                 635

<210> SEQ ID NO 225
<211> LENGTH: 637
<212> TYPE: PRT
<213> ORGANISM: Macaca fascicularis

<400> SEQUENCE: 225

Leu Leu Glu Met Gln Leu Gln His Leu Ala Ala Ala Ala Asp Pro
1               5                   10                  15

Leu Leu Gly Gly Gln Gly Pro Ala Lys Glu Cys Glu Lys Asp Gln Phe
            20                  25                  30

Gln Cys Arg Asn Glu Arg Cys Ile Pro Ser Val Trp Arg Cys Asp Glu

```
                35                  40                  45
Asp Asp Asp Cys Leu Asp His Ser Asp Glu Asp Cys Pro Lys Lys
         50                  55                  60
Thr Cys Ala Asp Ser Asp Phe Thr Cys Asp Asn Gly His Cys Ile His
 65                  70                  75                  80
Glu Arg Trp Lys Cys Asp Gly Glu Glu Cys Pro Asp Gly Ser Asp
                 85                  90                  95
Glu Ser Glu Ala Thr Cys Thr Leu Gly Thr Cys His Gly Asn Glu Phe
                    100                 105                 110
Gln Cys Gly Asp Gly Thr Cys Val Leu Ala Ile Lys Arg Cys Asn Gln
                115                 120                 125
Glu Gln Asp Cys Pro Asp Gly Ser Asp Glu Ala Gly Cys Leu Gln Val
                130                 135                 140
Pro Pro Thr Phe Leu Gly Asn Arg Arg Pro Arg Gly Leu Asn Glu
145                 150                 155                 160
Cys Leu His Asn Asn Gly Gly Cys Ser His Ile Ser Thr Asp Leu Lys
                    165                 170                 175
Ile Gly Phe Glu Cys Thr Cys Pro Ala Gly Phe Gln Leu Leu Asp Gln
                180                 185                 190
Lys Thr Cys Gly Asp Ile Asp Glu Cys Lys Asp Pro Asp Ala Cys Ser
                195                 200                 205
Gln Ile Cys Val Asn Tyr Lys Gly Tyr Phe Lys Cys Glu Cys Tyr Pro
210                 215                 220
Gly Tyr Glu Met Asp Leu Leu Thr Lys Asn Cys Lys Ala Ala Ala Gly
225                 230                 235                 240
Lys Ser Pro Ser Leu Ile Phe Thr Asn Arg His Glu Val Arg Arg Ile
                245                 250                 255
Asp Leu Val Lys Arg Asn Tyr Ser Arg Leu Ile Pro Met Leu Lys Asn
                260                 265                 270
Val Val Ala Leu Asp Met Glu Val Ala Thr Asn Arg Ile Tyr Trp Cys
                275                 280                 285
Asp Leu Ser Tyr Arg Lys Ile Tyr Ser Ala Tyr Met Asp Lys Ala Ser
                290                 295                 300
Asp Pro Lys Glu Gln Glu Val Leu Ile Asp Glu Gln Leu His Ser Pro
305                 310                 315                 320
Glu Gly Leu Ala Val Asp Trp Val His Lys His Ile Tyr Trp Thr Asp
                325                 330                 335
Ser Gly Asn Lys Thr Ile Ser Val Ala Thr Val Asp Gly Gly Arg Arg
                340                 345                 350
Cys Thr Leu Phe Ser Arg Asn Leu Ser Glu Pro Arg Ala Ile Ala Val
                355                 360                 365
Asp Pro Leu Gln Gly Phe Met Tyr Trp Ser Asp Trp Gly Asn Gln Ala
                370                 375                 380
Lys Ile Glu Lys Ser Gly Leu Asn Gly Val Asp Arg Gln Thr Leu Val
385                 390                 395                 400
Ser Asp Asn Ile Glu Trp Pro Asn Gly Ile Thr Leu Asp Leu Leu Ser
                    405                 410                 415
Gln Arg Leu Tyr Trp Val Asp Ser Lys Leu His Gln Leu Ser Ser Ile
                420                 425                 430
Asp Phe Ser Gly Gly Asn Arg Lys Met Leu Ile Ser Ser Thr Asp Phe
                435                 440                 445
Leu Ser His Pro Phe Gly Ile Ala Val Phe Glu Asp Lys Val Phe Trp
                450                 455                 460
```

```
Thr Asp Leu Glu Asn Glu Ala Ile Phe Ser Ala Asn Arg Leu Asn Gly
465                 470                 475                 480

Leu Glu Ile Ser Ile Leu Ala Glu Asn Leu Asn Asn Pro His Asp Ile
                485                 490                 495

Val Ile Phe His Glu Leu Lys Gln Pro Arg Ala Ala Asp Ala Cys Lys
            500                 505                 510

Leu Ser Val Gln Pro Asn Gly Gly Cys Glu Tyr Leu Cys Leu Pro Ala
        515                 520                 525

Pro Gln Ile Ser Ser His Ser Pro Lys Tyr Thr Cys Ala Cys Pro Asp
    530                 535                 540

Thr Met Trp Leu Gly Pro Asp Met Lys Arg Cys Tyr Arg Asp Gly Asn
545                 550                 555                 560

Glu Asp Ser Lys Met Gly Ser Thr Val Thr Ala Val Ile Gly Ile
                565                 570                 575

Ile Val Pro Ile Val Val Ile Ala Leu Leu Cys Met Ser Gly Tyr Leu
            580                 585                 590

Ile Trp Arg Asn Trp Lys Arg Lys Asn Thr Lys Ser Met Asn Phe Asp
                595                 600                 605

Asn Pro Val Tyr Arg Lys Thr Thr Glu Glu Asp Glu Asp Glu Leu
610                 615                 620

His Ile Gly Arg Thr Ala Gln Ile Gly His Val Tyr Pro
625                 630                 635

<210> SEQ ID NO 226
<211> LENGTH: 963
<212> TYPE: PRT
<213> ORGANISM: Homo sapiens

<400> SEQUENCE: 226

Met Gly Leu Pro Glu Pro Gly Pro Leu Arg Leu Leu Ala Leu Leu Leu
1               5                   10                  15

Leu Leu Leu Leu Leu Leu Leu Leu Gln Leu Gln His Leu Ala Ala Ala
            20                  25                  30

Ala Ala Asp Pro Leu Leu Gly Gly Gln Gly Pro Ala Lys Asp Cys Glu
        35                  40                  45

Lys Asp Gln Phe Gln Cys Arg Asn Glu Arg Cys Ile Pro Ser Val Trp
    50                  55                  60

Arg Cys Asp Glu Asp Asp Asp Cys Leu Asp His Ser Asp Glu Asp Asp
65                  70                  75                  80

Cys Pro Lys Lys Thr Cys Ala Asp Ser Asp Phe Thr Cys Asp Asn Gly
                85                  90                  95

His Cys Ile His Glu Arg Trp Lys Cys Asp Gly Glu Glu Glu Cys Pro
            100                 105                 110

Asp Gly Ser Asp Glu Ser Glu Ala Thr Cys Thr Lys Gln Val Cys Pro
        115                 120                 125

Ala Glu Lys Leu Ser Cys Gly Pro Thr Ser His Lys Cys Val Pro Ala
    130                 135                 140

Ser Trp Arg Cys Asp Gly Glu Lys Asp Cys Glu Gly Gly Ala Asp Glu
145                 150                 155                 160

Ala Gly Cys Ala Thr Leu Cys Ala Pro His Glu Phe Gln Cys Gly Asn
                165                 170                 175

Arg Ser Cys Leu Ala Ala Val Phe Val Cys Asp Gly Asp Asp Cys
            180                 185                 190

Gly Asp Gly Ser Asp Glu Arg Gly Cys Ala Asp Pro Ala Cys Gly Pro
```

```
            195                 200                 205
Arg Glu Phe Arg Cys Gly Gly Asp Gly Gly Ala Cys Ile Pro Glu
210                 215                 220

Arg Trp Val Cys Asp Arg Gln Phe Asp Cys Glu Asp Arg Ser Asp Glu
225                 230                 235                 240

Ala Ala Glu Leu Cys Gly Arg Pro Gly Pro Gly Ala Thr Ser Ala Pro
                245                 250                 255

Ala Ala Cys Ala Thr Ala Ser Gln Phe Ala Cys Arg Ser Gly Glu Cys
                260                 265                 270

Val His Leu Gly Trp Arg Cys Asp Gly Asp Arg Asp Cys Lys Asp Lys
                275                 280                 285

Ser Asp Glu Ala Asp Cys Pro Leu Gly Thr Cys Arg Gly Asp Glu Phe
290                 295                 300

Gln Cys Gly Asp Gly Thr Cys Val Leu Ala Ile Lys His Cys Asn Gln
305                 310                 315                 320

Glu Gln Asp Cys Pro Asp Gly Ser Asp Glu Ala Gly Cys Leu Gln Gly
                325                 330                 335

Leu Asn Glu Cys Leu His Asn Asn Gly Gly Cys Ser His Ile Cys Thr
                340                 345                 350

Asp Leu Lys Ile Gly Phe Glu Cys Thr Cys Pro Ala Gly Phe Gln Leu
                355                 360                 365

Leu Asp Gln Lys Thr Cys Gly Asp Ile Asp Glu Cys Lys Asp Pro Asp
370                 375                 380

Ala Cys Ser Gln Ile Cys Val Asn Tyr Lys Gly Tyr Phe Lys Cys Glu
385                 390                 395                 400

Cys Tyr Pro Gly Tyr Glu Met Asp Leu Leu Thr Lys Asn Cys Lys Ala
                405                 410                 415

Ala Ala Gly Lys Ser Pro Ser Leu Ile Phe Thr Asn Arg His Glu Val
                420                 425                 430

Arg Arg Ile Asp Leu Val Lys Arg Asn Tyr Ser Arg Leu Ile Pro Met
                435                 440                 445

Leu Lys Asn Val Val Ala Leu Asp Val Glu Val Ala Thr Asn Arg Ile
450                 455                 460

Tyr Trp Cys Asp Leu Ser Tyr Arg Lys Ile Tyr Ser Ala Tyr Met Asp
465                 470                 475                 480

Lys Ala Ser Asp Pro Lys Glu Gln Glu Val Leu Ile Asp Glu Gln Leu
                485                 490                 495

His Ser Pro Glu Gly Leu Ala Val Asp Trp Val His Lys His Ile Tyr
                500                 505                 510

Trp Thr Asp Ser Gly Asn Lys Thr Ile Ser Val Ala Thr Val Asp Gly
                515                 520                 525

Gly Arg Arg Arg Thr Leu Phe Ser Arg Asn Leu Ser Glu Pro Arg Ala
                530                 535                 540

Ile Ala Val Asp Pro Leu Arg Gly Phe Met Tyr Trp Ser Asp Trp Gly
545                 550                 555                 560

Asp Gln Ala Lys Ile Glu Lys Ser Gly Leu Asn Gly Val Asp Arg Gln
                565                 570                 575

Thr Leu Val Ser Asp Asn Ile Glu Trp Pro Asn Gly Ile Thr Leu Asp
                580                 585                 590

Leu Leu Ser Gln Arg Leu Tyr Trp Val Asp Ser Lys Leu His Gln Leu
                595                 600                 605

Ser Ser Ile Asp Phe Ser Gly Gly Asn Arg Lys Thr Leu Ile Ser Ser
                610                 615                 620
```

Thr Asp Phe Leu Ser His Pro Phe Gly Ile Ala Val Phe Glu Asp Lys
625                 630                 635                 640

Val Phe Trp Thr Asp Leu Glu Asn Glu Ala Ile Phe Ser Ala Asn Arg
            645                 650                 655

Leu Asn Gly Leu Glu Ile Ser Ile Leu Ala Glu Asn Leu Asn Asn Pro
                660                 665                 670

His Asp Ile Val Ile Phe His Glu Leu Lys Gln Pro Arg Ala Pro Asp
            675                 680                 685

Ala Cys Glu Leu Ser Val Gln Pro Asn Gly Gly Cys Glu Tyr Leu Cys
690                 695                 700

Leu Pro Ala Pro Gln Ile Ser Ser His Ser Pro Lys Tyr Thr Cys Ala
705                 710                 715                 720

Cys Pro Asp Thr Met Trp Leu Gly Pro Asp Met Lys Arg Cys Tyr Arg
                725                 730                 735

Ala Pro Gln Ser Thr Ser Thr Thr Leu Ala Ser Thr Met Thr Arg
                740                 745                 750

Thr Val Pro Ala Thr Thr Arg Ala Pro Gly Thr Thr Val His Arg Ser
            755                 760                 765

Thr Tyr Gln Asn His Ser Thr Glu Thr Pro Ser Leu Thr Ala Ala Val
770                 775                 780

Pro Ser Ser Val Ser Val Pro Arg Ala Pro Ser Ile Ser Pro Ser Thr
785                 790                 795                 800

Leu Ser Pro Ala Thr Ser Asn His Ser Gln His Tyr Ala Asn Glu Asp
                805                 810                 815

Ser Lys Met Gly Ser Thr Val Thr Ala Ala Val Ile Gly Ile Ile Val
            820                 825                 830

Pro Ile Val Val Ile Ala Leu Leu Cys Met Ser Gly Tyr Leu Ile Trp
            835                 840                 845

Arg Asn Trp Lys Arg Lys Asn Thr Lys Ser Met Asn Phe Asp Asn Pro
850                 855                 860

Val Tyr Arg Lys Thr Thr Glu Glu Glu Asp Glu Asp Glu Leu His Ile
865                 870                 875                 880

Gly Arg Thr Ala Gln Ile Gly His Val Tyr Pro Ala Ala Ile Ser Ser
                885                 890                 895

Phe Asp Arg Pro Leu Trp Ala Glu Pro Cys Leu Gly Glu Thr Arg Glu
                900                 905                 910

Pro Glu Asp Pro Ala Pro Ala Leu Lys Glu Leu Phe Val Leu Pro Gly
            915                 920                 925

Glu Pro Arg Ser Gln Leu His Gln Leu Pro Lys Asn Pro Leu Ser Glu
            930                 935                 940

Leu Pro Val Val Lys Ser Lys Arg Val Ala Leu Ser Leu Glu Asp Asp
945                 950                 955                 960

Gly Leu Pro

<210> SEQ ID NO 227
<211> LENGTH: 955
<212> TYPE: PRT
<213> ORGANISM: Macaca fascicularis

<400> SEQUENCE: 227

Glu Arg Gly Ala Leu Arg Pro Leu Ala Leu Leu Leu Leu Leu Leu Leu
1               5                   10                  15

Leu Gln Leu Gln His Leu Ala Ala Ala Ala Asp Pro Leu Leu Gly
            20                  25                  30

```
Gly Gln Gly Pro Ala Lys Glu Cys Glu Lys Asp Gln Phe Gln Cys Arg
         35                  40                  45

Asn Glu Arg Cys Ile Pro Ser Val Trp Arg Cys Asp Glu Asp Asp
 50                  55                  60

Cys Leu Asp His Ser Asp Glu Asp Cys Pro Lys Lys Thr Cys Ala
 65                  70                  75                  80

Asp Ser Asp Phe Thr Cys Asp Asn Gly His Cys Ile His Glu Arg Trp
                 85                  90                  95

Lys Cys Asp Gly Glu Glu Cys Pro Asp Gly Ser Asp Glu Ser Glu
                100                 105                 110

Ala Thr Cys Thr Lys Gln Val Cys Pro Ala Glu Lys Leu Ser Cys Gly
         115                 120                 125

Pro Thr Ser His Lys Cys Val Pro Ala Ser Trp Arg Cys Asp Gly Glu
         130                 135                 140

Lys Asp Cys Glu Gly Gly Ala Asp Glu Ala Gly Cys Val Thr Leu Cys
145                 150                 155                 160

Ala Pro His Glu Phe Gln Cys Gly Asn Arg Ser Cys Leu Ala Ala Val
                 165                 170                 175

Phe Val Cys Asp Gly Asp Asp Asp Cys Gly Asp Gly Ser Asp Glu Arg
                 180                 185                 190

Gly Cys Ala Asp Pro Ala Cys Gly Pro Arg Glu Phe Arg Cys Gly Arg
         195                 200                 205

Asp Gly Gly Gly Ala Cys Ile Pro Glu Arg Trp Val Cys Asp Arg Gln
         210                 215                 220

Phe Asp Cys Glu Asp Arg Ser Asp Glu Ala Ala Glu Leu Cys Gly Arg
225                 230                 235                 240

Pro Gly Pro Gly Ala Thr Ser Ala Pro Ala Ala Cys Ala Thr Ala Ala
                 245                 250                 255

Gln Phe Ala Cys Arg Ser Gly Glu Cys Val His Leu Gly Trp Arg Cys
         260                 265                 270

Asp Gly Asp Arg Asp Cys Lys Asp Lys Ser Asp Glu Ala Asp Cys Pro
         275                 280                 285

Leu Gly Thr Cys His Gly Asn Glu Phe Gln Cys Gly Asp Gly Thr Cys
         290                 295                 300

Val Leu Ala Ile Lys Arg Cys Asn Gln Glu Gln Asp Cys Pro Asp Gly
305                 310                 315                 320

Ser Asp Glu Ala Gly Cys Leu Gln Gly Leu Asn Glu Cys Leu His Asn
                 325                 330                 335

Asn Gly Gly Cys Ser His Ile Cys Thr Asp Leu Lys Ile Gly Phe Glu
                 340                 345                 350

Cys Thr Cys Pro Ala Gly Phe Gln Leu Leu Asp Gln Lys Thr Cys Gly
         355                 360                 365

Asp Ile Asp Glu Cys Lys Asp Pro Asp Ala Cys Ser Gln Ile Cys Val
         370                 375                 380

Asn Tyr Lys Gly Tyr Phe Lys Cys Glu Cys Tyr Pro Gly Tyr Glu Met
385                 390                 395                 400

Asp Leu Leu Thr Lys Asn Cys Lys Ala Ala Gly Lys Ser Pro Ser
                 405                 410                 415

Leu Ile Phe Thr Asn Arg His Glu Val Arg Arg Ile Asp Leu Val Lys
                 420                 425                 430

Arg Asn Tyr Ser Arg Leu Ile Pro Met Leu Lys Asn Val Val Ala Leu
         435                 440                 445
```

```
Asp Val Glu Val Ala Thr Asn Arg Ile Tyr Trp Cys Asp Leu Ser Tyr
    450                 455                 460

Arg Lys Ile Tyr Ser Ala Tyr Met Asp Lys Ala Ser Asp Pro Lys Glu
465                 470                 475                 480

Gln Glu Val Leu Ile Asp Glu Gln Leu His Ser Pro Glu Gly Leu Ala
                485                 490                 495

Val Asp Trp Val His Lys His Ile Tyr Trp Thr Asp Ser Gly Asn Lys
            500                 505                 510

Thr Ile Ser Val Ala Thr Val Asp Gly Arg Arg Cys Thr Leu Phe
        515                 520                 525

Ser Arg Asn Leu Ser Glu Pro Arg Ala Ile Ala Val Asp Pro Leu Gln
530                 535                 540

Gly Phe Met Tyr Trp Ser Asp Trp Gly Asn Gln Ala Lys Ile Glu Lys
545                 550                 555                 560

Ser Gly Leu Asn Gly Val Asp Arg Gln Thr Leu Val Ser Asp Asn Ile
                565                 570                 575

Glu Trp Pro Asn Gly Ile Thr Leu Asp Leu Leu Ser Gln Arg Leu Tyr
            580                 585                 590

Trp Val Asp Ser Lys Leu His Gln Leu Ser Ser Ile Asp Phe Ser Gly
        595                 600                 605

Gly Asn Arg Lys Met Leu Ile Ser Ser Thr Asp Phe Leu Ser His Pro
610                 615                 620

Phe Gly Ile Ala Val Phe Glu Asp Lys Val Phe Trp Thr Asp Leu Glu
625                 630                 635                 640

Asn Glu Ala Ile Phe Ser Ala Asn Arg Leu Asn Gly Leu Glu Ile Ser
                645                 650                 655

Ile Leu Ala Glu Asn Leu Asn Asn Pro His Asp Ile Val Ile Phe His
            660                 665                 670

Glu Leu Lys Gln Pro Arg Ala Ala Asp Ala Cys Lys Leu Ser Val Gln
        675                 680                 685

Pro Asn Gly Gly Cys Glu Tyr Leu Cys Leu Pro Ala Pro Gln Ile Ser
    690                 695                 700

Ser His Ser Pro Lys Tyr Thr Cys Ala Cys Pro Asp Thr Met Trp Leu
705                 710                 715                 720

Gly Pro Asp Met Lys Arg Cys Tyr Arg Ala Pro Gln Ser Thr Ser Thr
                725                 730                 735

Thr Thr Leu Pro Ser Thr Thr Arg Thr Gly Pro Ala Thr Thr Gly Ala
            740                 745                 750

Pro Gly Thr Thr Val His Arg Ser Thr Asp Gln Asn His Ser Thr Glu
        755                 760                 765

Thr Pro Asn Leu Ala Ala Val Pro Ser Ser Val Ser Val Pro Arg
770                 775                 780

Ala Pro Ser Ile Ser Leu Ser Thr Leu Ser Pro Ala Thr Ser Asn His
785                 790                 795                 800

Ser Gln His Tyr Gly Asn Glu Asp Ser Lys Met Gly Ser Thr Val Thr
                805                 810                 815

Ala Ala Val Ile Gly Ile Ile Val Pro Ile Val Ile Ala Leu Leu
            820                 825                 830

Cys Met Ser Gly Tyr Leu Ile Trp Arg Asn Trp Lys Arg Lys Asn Thr
        835                 840                 845

Lys Ser Met Asn Phe Asp Asn Pro Val Tyr Arg Lys Thr Thr Glu Glu
    850                 855                 860

Glu Asp Glu Asp Glu Leu His Ile Gly Arg Thr Ala Gln Ile Gly His
```

```
                865                 870                 875                 880
Val Tyr Pro Ala Ala Ile Ser Ser Phe Asp Arg Pro Leu Trp Ala Glu
                    885                 890                 895

Pro Cys Leu Gly Glu Thr Arg Glu Leu Glu Asp Pro Ala Pro Ala Leu
                900                 905                 910

Lys Glu Leu Phe Val Leu Pro Gly Pro Arg Ser Gln Leu His Gln
                915                 920                 925

Leu Pro Arg Asn Pro Leu Ser Glu Leu Pro Val Val Lys Ser Lys Arg
                930                 935                 940

Val Ala Leu Ser Leu Glu Asp Asp Gly Leu Pro
945                 950                 955

<210> SEQ ID NO 228
<211> LENGTH: 938
<212> TYPE: PRT
<213> ORGANISM: Macaca fascicularis

<400> SEQUENCE: 228

Gln Leu Gln His Leu Ala Ala Ala Ala Asp Pro Leu Leu Gly Gly
1               5                   10                  15

Gln Gly Pro Ala Lys Glu Cys Glu Lys Asp Gln Phe Gln Cys Arg Asn
                20                  25                  30

Glu Arg Cys Ile Pro Ser Val Trp Arg Cys Asp Glu Asp Asp Cys
            35                  40                  45

Leu Asp His Ser Asp Glu Asp Cys Pro Lys Lys Thr Cys Ala Asp
        50                  55                  60

Ser Asp Phe Thr Cys Asp Asn Gly His Cys Ile His Glu Arg Trp Lys
65                  70                  75                  80

Cys Asp Gly Glu Glu Glu Cys Pro Asp Gly Ser Asp Glu Ser Glu Ala
                85                  90                  95

Thr Cys Thr Lys Gln Val Cys Pro Ala Glu Lys Leu Ser Cys Gly Pro
                100                 105                 110

Thr Ser His Lys Cys Val Pro Ala Ser Trp Arg Cys Asp Gly Glu Lys
                115                 120                 125

Asp Cys Glu Gly Gly Ala Asp Glu Ala Gly Cys Val Thr Leu Cys Ala
        130                 135                 140

Pro His Glu Phe Gln Cys Gly Asn Arg Ser Cys Leu Ala Ala Val Phe
145                 150                 155                 160

Val Cys Asp Gly Asp Asp Cys Gly Asp Gly Ser Asp Glu Arg Gly
                    165                 170                 175

Cys Ala Asp Pro Ala Cys Gly Pro Arg Glu Phe Arg Cys Gly Arg Asp
                180                 185                 190

Gly Gly Gly Ala Cys Ile Pro Glu Arg Trp Val Cys Asp Arg Gln Phe
        195                 200                 205

Asp Cys Glu Asp Arg Ser Asp Glu Ala Ala Glu Leu Cys Gly Arg Pro
    210                 215                 220

Gly Pro Gly Ala Thr Ser Ala Pro Ala Ala Cys Ala Thr Ala Ala Gln
225                 230                 235                 240

Phe Ala Cys Arg Ser Gly Glu Cys Val His Leu Gly Trp Arg Cys Asp
                245                 250                 255

Gly Asp Arg Asp Cys Lys Asp Lys Ser Asp Glu Ala Asp Cys Pro Leu
            260                 265                 270

Gly Thr Cys His Gly Asn Glu Phe Gln Cys Gly Asp Gly Thr Cys Val
                275                 280                 285
```

```
Leu Ala Ile Lys Arg Cys Asn Gln Glu Gln Asp Cys Pro Asp Gly Ser
    290                 295                 300
Asp Glu Ala Gly Cys Leu Gln Gly Leu Asn Glu Cys Leu His Asn Asn
305                 310                 315                 320
Gly Gly Cys Ser His Ile Cys Thr Asp Leu Lys Ile Gly Phe Glu Cys
                325                 330                 335
Thr Cys Pro Ala Gly Phe Gln Leu Leu Asp Gln Lys Thr Cys Gly Asp
            340                 345                 350
Ile Asp Glu Cys Lys Asp Pro Asp Ala Cys Ser Gln Ile Cys Val Asn
        355                 360                 365
Tyr Lys Gly Tyr Phe Lys Cys Glu Cys Tyr Pro Gly Tyr Glu Met Asp
    370                 375                 380
Leu Leu Thr Lys Asn Cys Lys Ala Ala Gly Lys Ser Pro Ser Leu
385                 390                 395                 400
Ile Phe Thr Asn Arg His Glu Val Arg Arg Ile Asp Leu Val Lys Arg
                405                 410                 415
Asn Tyr Ser Arg Leu Ile Pro Met Leu Lys Asn Val Val Ala Leu Asp
            420                 425                 430
Val Glu Val Ala Thr Asn Arg Ile Tyr Trp Cys Asp Leu Ser Tyr Arg
        435                 440                 445
Lys Ile Tyr Ser Ala Tyr Met Asp Lys Ala Ser Asp Pro Lys Glu Gln
    450                 455                 460
Glu Val Leu Ile Asp Glu Gln Leu His Ser Pro Glu Gly Leu Ala Val
465                 470                 475                 480
Asp Trp Val His Lys His Ile Tyr Trp Thr Asp Ser Gly Asn Lys Thr
                485                 490                 495
Ile Ser Val Ala Thr Val Asp Gly Gly Arg Arg Cys Thr Leu Phe Ser
            500                 505                 510
Arg Asn Leu Ser Glu Pro Arg Ala Ile Ala Val Asp Pro Leu Gln Gly
        515                 520                 525
Phe Met Tyr Trp Ser Asp Trp Gly Asn Gln Ala Lys Ile Glu Lys Ser
    530                 535                 540
Gly Leu Asn Gly Val Asp Arg Gln Thr Leu Val Ser Asp Asn Ile Glu
545                 550                 555                 560
Trp Pro Asn Gly Ile Thr Leu Asp Leu Leu Ser Gln Arg Leu Tyr Trp
                565                 570                 575
Val Asp Ser Lys Leu His Gln Leu Ser Ser Ile Asp Phe Ser Gly Gly
            580                 585                 590
Asn Arg Lys Met Leu Ile Ser Ser Thr Asp Phe Leu Ser His Pro Phe
        595                 600                 605
Gly Ile Ala Val Phe Glu Asp Lys Val Phe Trp Thr Asp Leu Glu Asn
    610                 615                 620
Glu Ala Ile Phe Ser Ala Asn Arg Leu Asn Gly Leu Glu Ile Ser Ile
625                 630                 635                 640
Leu Ala Glu Asn Leu Asn Asn Pro His Asp Ile Val Ile Phe His Glu
                645                 650                 655
Leu Lys Gln Pro Arg Ala Ala Asp Ala Cys Lys Leu Ser Val Gln Pro
            660                 665                 670
Asn Gly Gly Cys Glu Tyr Leu Cys Leu Pro Ala Pro Gln Ile Ser Ser
        675                 680                 685
His Ser Pro Lys Tyr Thr Cys Ala Cys Pro Asp Thr Met Trp Leu Gly
    690                 695                 700
Pro Asp Met Lys Arg Cys Tyr Arg Ala Pro Gln Ser Thr Ser Thr Thr
```

```
                705                 710                 715                 720
            Thr Leu Pro Ser Thr Thr Arg Thr Gly Pro Ala Thr Thr Gly Ala Pro
                            725                 730                 735
            Gly Thr Thr Val His Arg Ser Thr Asp Gln Asn His Ser Thr Glu Thr
                            740                 745                 750
            Pro Asn Leu Ala Ala Ala Val Pro Ser Ser Val Ser Pro Arg Ala
                            755                 760                 765
            Pro Ser Ile Ser Leu Ser Thr Leu Ser Pro Ala Thr Ser Asn His Ser
                770                 775                 780
            Gln His Tyr Gly Asn Glu Asp Ser Lys Met Gly Ser Thr Val Thr Ala
            785                 790                 795                 800
            Ala Val Ile Gly Ile Ile Val Pro Ile Val Val Ile Ala Leu Leu Cys
                            805                 810                 815
            Met Ser Gly Tyr Leu Ile Trp Arg Asn Trp Lys Arg Lys Asn Thr Lys
                            820                 825                 830
            Ser Met Asn Phe Asp Asn Pro Val Tyr Arg Lys Thr Thr Glu Glu Glu
                            835                 840                 845
            Asp Glu Asp Glu Leu His Ile Gly Arg Thr Ala Gln Ile Gly His Val
            850                 855                 860
            Tyr Pro Ala Ala Ile Ser Ser Phe Asp Arg Pro Leu Trp Ala Glu Pro
            865                 870                 875                 880
            Cys Leu Gly Glu Thr Arg Glu Leu Glu Asp Pro Ala Pro Ala Leu Lys
                            885                 890                 895
            Glu Leu Phe Val Leu Pro Gly Glu Pro Arg Ser Gln Leu His Gln Leu
                            900                 905                 910
            Pro Arg Asn Pro Leu Ser Glu Leu Pro Val Val Lys Ser Lys Arg Val
                            915                 920                 925
            Ala Leu Ser Leu Glu Asp Asp Gly Leu Pro
                            930                 935

<210> SEQ ID NO 229
            <211> LENGTH: 929
            <212> TYPE: PRT
            <213> ORGANISM: Macaca fascicularis

<400> SEQUENCE: 229

Ala Asp Pro Leu Leu Gly Gly Gln Gly Pro Ala Lys Glu Cys Glu Lys
            1               5                   10                  15
            Asp Gln Phe Gln Cys Arg Asn Glu Arg Cys Ile Pro Ser Val Trp Arg
                            20                  25                  30
            Cys Asp Glu Asp Asp Asp Cys Leu Asp His Ser Asp Glu Asp Asp Cys
                        35                  40                  45
            Pro Lys Lys Thr Cys Ala Asp Ser Asp Phe Thr Cys Asp Asn Gly His
                50                  55                  60
            Cys Ile His Glu Arg Trp Lys Cys Asp Gly Glu Glu Glu Cys Pro Asp
            65                  70                  75                  80
            Gly Ser Asp Glu Ser Glu Ala Thr Cys Thr Lys Gln Val Cys Pro Ala
                            85                  90                  95
            Glu Lys Leu Ser Cys Gly Pro Thr Ser His Lys Cys Val Pro Ala Ser
                        100                 105                 110
            Trp Arg Cys Asp Gly Glu Lys Asp Cys Glu Gly Gly Ala Asp Glu Ala
                    115                 120                 125
            Gly Cys Val Thr Leu Cys Ala Pro His Glu Phe Gln Cys Gly Asn Arg
                130                 135                 140
```

```
Ser Cys Leu Ala Ala Val Phe Val Cys Asp Gly Asp Asp Cys Gly
145                 150                 155                 160

Asp Gly Ser Asp Glu Arg Gly Cys Ala Asp Pro Ala Cys Gly Pro Arg
                165                 170                 175

Glu Phe Arg Cys Gly Arg Asp Gly Gly Ala Cys Ile Pro Glu Arg
            180                 185                 190

Trp Val Cys Asp Arg Gln Phe Asp Cys Glu Asp Arg Ser Asp Glu Ala
        195                 200                 205

Ala Glu Leu Cys Gly Arg Pro Gly Pro Gly Ala Thr Ser Ala Pro Ala
    210                 215                 220

Ala Cys Ala Thr Ala Ala Gln Phe Ala Cys Arg Ser Gly Glu Cys Val
225                 230                 235                 240

His Leu Gly Trp Arg Cys Asp Gly Asp Arg Asp Cys Lys Asp Lys Ser
                245                 250                 255

Asp Glu Ala Asp Cys Pro Leu Gly Thr Cys His Gly Asn Glu Phe Gln
                260                 265                 270

Cys Gly Asp Gly Thr Cys Val Leu Ala Ile Lys Arg Cys Asn Gln Glu
            275                 280                 285

Gln Asp Cys Pro Asp Gly Ser Asp Glu Ala Gly Cys Leu Gln Gly Leu
    290                 295                 300

Asn Glu Cys Leu His Asn Asn Gly Gly Cys Ser His Ile Cys Thr Asp
305                 310                 315                 320

Leu Lys Ile Gly Phe Glu Cys Thr Cys Pro Ala Gly Phe Gln Leu Leu
                325                 330                 335

Asp Gln Lys Thr Cys Gly Asp Ile Asp Glu Cys Lys Asp Pro Asp Ala
                340                 345                 350

Cys Ser Gln Ile Cys Val Asn Tyr Lys Gly Tyr Phe Lys Cys Glu Cys
            355                 360                 365

Tyr Pro Gly Tyr Glu Met Asp Leu Leu Thr Lys Asn Cys Lys Ala Ala
        370                 375                 380

Ala Gly Lys Ser Pro Ser Leu Ile Phe Thr Asn Arg His Glu Val Arg
385                 390                 395                 400

Arg Ile Asp Leu Val Lys Arg Asn Tyr Ser Arg Leu Ile Pro Met Leu
                405                 410                 415

Lys Asn Val Val Ala Leu Asp Val Glu Val Ala Thr Asn Arg Ile Tyr
            420                 425                 430

Trp Cys Asp Leu Ser Tyr Arg Lys Ile Tyr Ser Ala Tyr Met Asp Lys
        435                 440                 445

Ala Ser Asp Pro Lys Glu Gln Glu Val Leu Ile Asp Glu Gln Leu His
450                 455                 460

Ser Pro Glu Gly Leu Ala Val Asp Trp Val His Lys His Ile Tyr Trp
465                 470                 475                 480

Thr Asp Ser Gly Asn Lys Thr Ile Ser Val Ala Thr Val Asp Gly Gly
                485                 490                 495

Arg Arg Cys Thr Leu Phe Ser Arg Asn Leu Ser Glu Pro Arg Ala Ile
            500                 505                 510

Ala Val Asp Pro Leu Gln Gly Phe Met Tyr Trp Ser Asp Trp Gly Asn
        515                 520                 525

Gln Ala Lys Ile Glu Lys Ser Gly Leu Asn Gly Val Asp Arg Gln Thr
    530                 535                 540

Leu Val Ser Asp Asn Ile Glu Trp Pro Asn Gly Ile Thr Leu Asp Leu
545                 550                 555                 560

Leu Ser Gln Arg Leu Tyr Trp Val Asp Ser Lys Leu His Gln Leu Ser
```

```
            565                 570                 575

Ser Ile Asp Phe Ser Gly Gly Asn Arg Lys Met Leu Ile Ser Ser Thr
            580                 585                 590

Asp Phe Leu Ser His Pro Phe Gly Ile Ala Val Phe Glu Asp Lys Val
        595                 600                 605

Phe Trp Thr Asp Leu Glu Asn Glu Ala Ile Phe Ser Ala Asn Arg Leu
    610                 615                 620

Asn Gly Leu Glu Ile Ser Ile Leu Ala Glu Asn Leu Asn Asn Pro His
625                 630                 635                 640

Asp Ile Val Ile Phe His Glu Leu Lys Gln Pro Arg Ala Ala Asp Ala
                645                 650                 655

Cys Lys Leu Ser Val Gln Pro Asn Gly Gly Cys Glu Tyr Leu Cys Leu
            660                 665                 670

Pro Ala Pro Gln Ile Ser Ser His Ser Pro Lys Tyr Thr Cys Ala Cys
        675                 680                 685

Pro Asp Thr Met Trp Leu Gly Pro Asp Met Lys Arg Cys Tyr Arg Ala
    690                 695                 700

Pro Gln Ser Thr Ser Thr Thr Leu Pro Ser Thr Thr Arg Thr Gly
705                 710                 715                 720

Pro Ala Thr Thr Gly Ala Pro Gly Thr Thr Val His Arg Ser Thr Asp
                725                 730                 735

Gln Asn His Ser Thr Glu Thr Pro Asn Leu Ala Ala Val Pro Ser
            740                 745                 750

Ser Val Ser Val Pro Arg Ala Pro Ser Ile Ser Leu Ser Thr Leu Ser
        755                 760                 765

Pro Ala Thr Ser Asn His Ser Gln His Tyr Gly Asn Glu Asp Ser Lys
    770                 775                 780

Met Gly Ser Thr Val Thr Ala Ala Val Ile Gly Ile Val Pro Ile
785                 790                 795                 800

Val Val Ile Ala Leu Leu Cys Met Ser Gly Tyr Leu Ile Trp Arg Asn
                805                 810                 815

Trp Lys Arg Lys Asn Thr Lys Ser Met Asn Phe Asp Asn Pro Val Tyr
            820                 825                 830

Arg Lys Thr Thr Glu Glu Asp Glu Asp Glu Leu His Ile Gly Arg
        835                 840                 845

Thr Ala Gln Ile Gly His Val Tyr Pro Ala Ala Ile Ser Ser Phe Asp
    850                 855                 860

Arg Pro Leu Trp Ala Glu Pro Cys Leu Gly Glu Thr Arg Glu Leu Glu
865                 870                 875                 880

Asp Pro Ala Pro Ala Leu Lys Glu Leu Phe Val Leu Pro Gly Glu Pro
                885                 890                 895

Arg Ser Gln Leu His Gln Leu Pro Arg Asn Pro Leu Ser Glu Leu Pro
            900                 905                 910

Val Val Lys Ser Lys Arg Val Ala Leu Ser Leu Glu Asp Asp Gly Leu
        915                 920                 925

Pro

<210> SEQ ID NO 230
<211> LENGTH: 938
<212> TYPE: PRT
<213> ORGANISM: Macaca fascicularis

<400> SEQUENCE: 230

Gln Leu Gln His Leu Ala Ala Ala Ala Ala Asp Pro Leu Leu Gly Gly
```

-continued

```
1               5                   10                  15
Gln Gly Pro Ala Lys Glu Cys Glu Lys Asp Gln Phe Gln Cys Arg Asn
            20                  25                  30

Glu Arg Cys Ile Pro Ser Val Trp Arg Cys Asp Glu Asp Asp Cys
        35                  40                  45

Leu Asp His Ser Asp Glu Asp Cys Pro Lys Lys Thr Cys Ala Asp
50                  55                  60

Ser Asp Phe Thr Cys Asp Asn Gly His Cys Ile His Glu Arg Trp Lys
65                  70                  75                  80

Cys Asp Gly Glu Glu Glu Cys Pro Asp Gly Ser Asp Glu Ser Glu Ala
                85                  90                  95

Thr Cys Thr Lys Gln Val Cys Pro Ala Glu Lys Leu Ser Cys Gly Pro
            100                 105                 110

Thr Ser His Lys Cys Val Pro Ala Ser Trp Arg Cys Asp Gly Glu Lys
        115                 120                 125

Asp Cys Glu Gly Gly Ala Asp Glu Ala Gly Cys Val Thr Leu Cys Ala
130                 135                 140

Pro His Glu Phe Gln Cys Gly Asn Arg Ser Cys Leu Ala Ala Val Phe
145                 150                 155                 160

Val Cys Asp Gly Asp Asp Cys Gly Asp Gly Ser Asp Glu Arg Gly
                165                 170                 175

Cys Ala Asp Pro Ala Cys Gly Pro Arg Glu Phe Ser Cys Gly Arg Asp
            180                 185                 190

Gly Gly Gly Ala Cys Ile Pro Glu Arg Trp Val Cys Asp Arg Gln Phe
        195                 200                 205

Asp Cys Glu Asp Arg Ser Asp Glu Ala Ala Glu Leu Cys Gly Arg Pro
210                 215                 220

Gly Pro Gly Ala Thr Ser Ala Pro Ala Ala Cys Ala Thr Ala Ala Gln
225                 230                 235                 240

Phe Ala Cys Arg Ser Gly Glu Cys Val His Leu Gly Trp Arg Cys Asp
                245                 250                 255

Gly Asp Arg Asp Cys Lys Asp Lys Ser Asp Glu Ala Asp Cys Pro Leu
            260                 265                 270

Gly Thr Cys His Gly Asn Glu Phe Gln Cys Gly Asp Gly Thr Cys Val
        275                 280                 285

Leu Ala Ile Lys Arg Cys Asn Gln Glu Gln Asp Cys Pro Asp Gly Ser
290                 295                 300

Asp Glu Ala Gly Cys Leu Gln Gly Leu Asn Glu Cys Leu His Asn Asn
305                 310                 315                 320

Gly Gly Cys Ser His Ile Cys Thr Asp Leu Lys Ile Gly Phe Glu Cys
                325                 330                 335

Thr Cys Pro Ala Gly Phe Gln Leu Leu Asp Gln Lys Thr Cys Gly Asp
            340                 345                 350

Ile Asp Glu Cys Lys Asp Pro Asp Ala Cys Ser Gln Ile Cys Val Asn
        355                 360                 365

Tyr Lys Gly Tyr Phe Lys Cys Glu Cys Tyr Pro Gly Tyr Glu Met Asp
370                 375                 380

Leu Leu Thr Lys Asn Cys Lys Ala Ala Gly Lys Ser Pro Ser Leu
385                 390                 395                 400

Ile Phe Thr Asn Arg His Glu Val Arg Arg Ile Asp Leu Val Lys Arg
                405                 410                 415

Asn Tyr Ser Arg Leu Ile Pro Met Leu Lys Asn Val Val Ala Leu Asp
            420                 425                 430
```

```
Val Glu Val Ala Thr Asn Arg Ile Tyr Trp Cys Asp Leu Ser Tyr Arg
            435                 440                 445

Lys Ile Tyr Ser Ala Tyr Met Asp Lys Ala Ser Asp Pro Lys Glu Gln
        450                 455                 460

Glu Val Leu Ile Asp Glu Gln Leu His Ser Pro Glu Gly Leu Ala Val
465                 470                 475                 480

Asp Trp Val His Lys His Ile Tyr Trp Thr Asp Ser Gly Asn Lys Thr
                485                 490                 495

Ile Ser Val Ala Thr Val Asp Gly Gly Arg Arg Cys Thr Leu Phe Ser
            500                 505                 510

Arg Asn Leu Ser Glu Pro Arg Ala Ile Ala Val Asp Pro Leu Gln Gly
        515                 520                 525

Phe Met Tyr Trp Ser Asp Trp Gly Asn Gln Ala Lys Ile Glu Lys Ser
530                 535                 540

Gly Leu Asn Gly Val Asp Arg Gln Thr Leu Val Ser Asp Asn Ile Glu
545                 550                 555                 560

Trp Pro Asn Gly Ile Thr Leu Asp Leu Leu Ser Gln Arg Leu Tyr Trp
                565                 570                 575

Val Asp Ser Lys Leu His Gln Leu Ser Ser Ile Asp Phe Ser Gly Gly
            580                 585                 590

Asn Arg Lys Met Leu Ile Ser Ser Thr Asp Phe Leu Ser His Pro Phe
        595                 600                 605

Gly Ile Ala Val Phe Glu Asp Lys Val Phe Trp Thr Asp Leu Glu Asn
610                 615                 620

Glu Ala Ile Phe Ser Ala Asn Arg Leu Asn Gly Leu Glu Ile Ser Ile
625                 630                 635                 640

Leu Ala Glu Asn Leu Asn Asn Pro His Asp Ile Val Ile Phe His Glu
                645                 650                 655

Leu Lys Gln Pro Arg Ala Ala Asp Ala Cys Lys Leu Ser Val Gln Pro
            660                 665                 670

Asn Gly Gly Cys Glu Tyr Leu Cys Leu Pro Ala Pro Gln Ile Ser Ser
        675                 680                 685

His Ser Pro Lys Tyr Thr Cys Ala Cys Pro Asp Thr Met Trp Leu Gly
690                 695                 700

Pro Asp Met Lys Arg Cys Tyr Arg Ala Pro Gln Ser Thr Ser Thr Thr
705                 710                 715                 720

Thr Leu Pro Ser Thr Thr Arg Thr Gly Pro Ala Thr Thr Gly Ala Pro
                725                 730                 735

Gly Thr Thr Val His Arg Ser Thr Asp Gln Asn His Ser Thr Glu Thr
            740                 745                 750

Pro Asn Leu Ala Ala Ala Val Pro Ser Ser Val Ser Val Pro Arg Ala
        755                 760                 765

Pro Ser Ile Ser Leu Ser Thr Leu Ser Pro Ala Thr Ser Asn His Ser
770                 775                 780

Gln His Tyr Gly Asn Glu Asp Ser Lys Met Gly Ser Thr Val Thr Ala
785                 790                 795                 800

Ala Val Ile Gly Ile Ile Val Pro Ile Val Ile Ala Leu Leu Cys
                805                 810                 815

Met Ser Gly Tyr Leu Ile Trp Arg Asn Trp Lys Arg Lys Asn Thr Lys
            820                 825                 830

Ser Met Asn Phe Asp Asn Pro Val Tyr Arg Lys Thr Thr Glu Glu Glu
        835                 840                 845
```

```
Asp Glu Asp Glu Leu His Ile Gly Arg Thr Ala Gln Ile Gly His Val
850                 855                 860

Tyr Pro Ala Ala Ile Ser Ser Phe Asp Arg Pro Leu Trp Ala Glu Pro
865                 870                 875                 880

Cys Leu Gly Glu Thr Arg Glu Leu Glu Asp Pro Ala Pro Ala Leu Lys
                885                 890                 895

Glu Leu Phe Val Leu Pro Gly Glu Pro Arg Ser Gln Leu His Gln Leu
            900                 905                 910

Pro Arg Asn Pro Leu Ser Glu Leu Pro Val Val Lys Ser Lys Arg Val
                915                 920                 925

Ala Leu Ser Leu Glu Asp Asp Gly Leu Pro
930                 935

<210> SEQ ID NO 231
<211> LENGTH: 949
<212> TYPE: PRT
<213> ORGANISM: Macaca fascicularis

<400> SEQUENCE: 231

Glu Arg Gly Ala Leu Arg Pro Leu Ala Leu Leu Leu Leu Leu Leu Leu
1               5                   10                  15

Leu Gln Leu Gln His Leu Ala Ala Ala Ala Asp Pro Leu Leu Gly
            20                  25                  30

Gly Gln Gly Pro Ala Lys Glu Cys Glu Lys Asp Gln Phe Gln Cys Arg
        35                  40                  45

Asn Glu Arg Cys Ile Pro Ser Val Trp Arg Cys Asp Glu Asp Asp Asp
    50                  55                  60

Cys Leu Asp His Ser Asp Glu Asp Cys Pro Lys Lys Thr Cys Ala
65              70                  75                  80

Asp Ser Asp Phe Thr Cys Asp Asn Gly His Cys Ile His Glu Arg Trp
                85                  90                  95

Lys Cys Asp Gly Glu Glu Glu Cys Pro Asp Gly Ser Asp Glu Ser Glu
            100                 105                 110

Ala Thr Cys Thr Lys Gln Val Cys Pro Ala Glu Lys Leu Ser Cys Gly
        115                 120                 125

Pro Thr Ser His Lys Cys Val Pro Ala Ser Trp Arg Cys Asp Gly Glu
    130                 135                 140

Lys Asp Cys Glu Gly Gly Ala Asp Glu Ala Gly Cys Val Thr Leu Cys
145                 150                 155                 160

Ala Pro His Glu Phe Gln Cys Gly Asn Arg Ser Cys Leu Ala Ala Val
                165                 170                 175

Phe Val Cys Asp Gly Asp Asp Cys Gly Asp Gly Ser Asp Glu Arg
            180                 185                 190

Gly Cys Ala Asp Pro Ala Cys Gly Pro Arg Glu Phe Arg Cys Gly Arg
        195                 200                 205

Asp Gly Gly Gly Ala Cys Ile Pro Glu Arg Trp Val Cys Asp Arg Gln
    210                 215                 220

Phe Asp Cys Glu Asp Arg Ser Asp Glu Ala Ala Glu Leu Cys Gly Arg
225                 230                 235                 240

Pro Gly Pro Gly Ala Thr Ser Ala Pro Ala Ala Cys Ala Thr Ala Ala
                245                 250                 255

Gln Phe Ala Cys Arg Ser Gly Glu Cys Val His Leu Gly Trp Arg Cys
            260                 265                 270

Asp Gly Asp Arg Asp Glu Ala Cys Pro Leu Gly Thr Cys His Gly
        275                 280                 285
```

```
Asn Glu Phe Gln Cys Gly Asp Gly Thr Cys Val Leu Ala Ile Lys Arg
    290                 295                 300
Cys Asn Gln Glu Gln Asp Cys Pro Asp Gly Ser Asp Glu Ala Gly Cys
305                 310                 315                 320
Leu Gln Gly Leu Asn Glu Cys Leu His Asn Asn Gly Gly Cys Ser His
                325                 330                 335
Ile Cys Thr Asp Leu Lys Ile Gly Phe Glu Cys Thr Cys Pro Ala Gly
            340                 345                 350
Phe Gln Leu Leu Asp Gln Lys Thr Cys Gly Asp Ile Asp Glu Cys Lys
        355                 360                 365
Asp Pro Asp Ala Cys Ser Gln Ile Cys Val Asn Tyr Lys Gly Tyr Phe
    370                 375                 380
Lys Cys Glu Cys Tyr Pro Gly Tyr Glu Met Asp Leu Leu Thr Lys Asn
385                 390                 395                 400
Cys Lys Ala Ala Ala Gly Lys Ser Pro Ser Leu Ile Phe Thr Asn Arg
                405                 410                 415
His Glu Val Arg Arg Ile Asp Leu Val Lys Arg Asn Tyr Ser Arg Leu
            420                 425                 430
Ile Pro Met Leu Lys Asn Val Val Ala Leu Asp Val Glu Val Ala Thr
        435                 440                 445
Asn Arg Ile Tyr Trp Cys Asp Leu Ser Tyr Arg Lys Ile Tyr Ser Ala
    450                 455                 460
Tyr Met Asp Lys Ala Ser Asp Pro Lys Glu Gln Glu Val Leu Ile Asp
465                 470                 475                 480
Glu Gln Leu His Ser Pro Glu Gly Leu Ala Val Asp Trp Val His Lys
                485                 490                 495
His Ile Tyr Trp Thr Asp Ser Gly Asn Lys Thr Ile Ser Val Ala Thr
            500                 505                 510
Val Asp Gly Gly Arg Arg Cys Thr Leu Phe Ser Arg Asn Leu Ser Glu
        515                 520                 525
Pro Arg Ala Ile Ala Val Asp Pro Leu Gln Gly Phe Met Tyr Trp Ser
    530                 535                 540
Asp Trp Gly Asn Gln Ala Lys Ile Glu Lys Ser Gly Leu Asn Gly Val
545                 550                 555                 560
Asp Arg Gln Thr Leu Val Ser Asp Asn Ile Glu Trp Pro Asn Gly Ile
                565                 570                 575
Thr Leu Asp Leu Leu Ser Gln Arg Leu Tyr Trp Val Asp Ser Lys Leu
            580                 585                 590
His Gln Leu Ser Ser Ile Asp Phe Ser Gly Gly Asn Arg Lys Met Leu
        595                 600                 605
Ile Ser Ser Thr Asp Phe Leu Ser His Pro Phe Gly Ile Ala Val Phe
    610                 615                 620
Glu Asp Lys Val Phe Trp Thr Asp Leu Glu Asn Glu Ala Ile Phe Ser
625                 630                 635                 640
Ala Asn Arg Leu Asn Gly Leu Glu Ile Ser Ile Leu Ala Glu Asn Leu
                645                 650                 655
Asn Asn Pro His Asp Ile Val Ile Phe His Glu Leu Lys Gln Pro Arg
            660                 665                 670
Ala Ala Asp Ala Cys Lys Leu Ser Val Gln Pro Asn Gly Gly Cys Glu
        675                 680                 685
Tyr Leu Cys Leu Pro Ala Pro Gln Ile Ser Ser His Ser Pro Lys Tyr
    690                 695                 700
```

Thr Cys Ala Cys Pro Asp Thr Met Trp Leu Gly Pro Asp Met Lys Arg
705                 710                 715                 720

Cys Tyr Arg Ala Pro Gln Ser Thr Ser Thr Thr Thr Leu Pro Ser Thr
            725                 730                 735

Thr Arg Thr Gly Pro Ala Thr Thr Gly Ala Pro Gly Thr Thr Val His
            740                 745                 750

Arg Ser Thr Asp Gln Asn His Ser Thr Glu Thr Pro Asn Leu Ala Ala
            755                 760                 765

Ala Val Pro Ser Ser Val Ser Val Pro Arg Ala Pro Ser Ile Ser Leu
            770                 775                 780

Ser Thr Leu Ser Pro Ala Thr Ser Asn His Ser Gln His Tyr Gly Asn
785                 790                 795                 800

Glu Asp Ser Lys Met Gly Ser Thr Val Thr Ala Ala Val Ile Gly Ile
                805                 810                 815

Ile Val Pro Ile Val Val Ile Ala Leu Leu Cys Met Ser Gly Tyr Leu
                820                 825                 830

Ile Trp Arg Asn Trp Lys Arg Lys Asn Thr Lys Ser Met Asn Phe Asp
            835                 840                 845

Asn Pro Val Tyr Arg Lys Thr Thr Glu Glu Asp Glu Asp Glu Leu
850                 855                 860

His Ile Gly Arg Thr Ala Gln Ile Gly His Val Tyr Pro Ala Ala Ile
865                 870                 875                 880

Ser Ser Phe Asp Arg Pro Leu Trp Ala Glu Pro Cys Leu Gly Glu Thr
            885                 890                 895

Arg Glu Leu Glu Asp Pro Ala Pro Ala Leu Lys Glu Leu Phe Val Leu
            900                 905                 910

Pro Gly Glu Pro Arg Ser Gln Leu His Gln Leu Pro Arg Asn Pro Leu
            915                 920                 925

Ser Glu Leu Pro Val Val Lys Ser Lys Arg Val Ala Leu Ser Leu Glu
            930                 935                 940

Asp Asp Gly Leu Pro
945

<210> SEQ ID NO 232
<211> LENGTH: 931
<212> TYPE: PRT
<213> ORGANISM: Macaca fascicularis

<400> SEQUENCE: 232

Ala Ala Ala Asp Pro Leu Leu Gly Gly Gln Gly Pro Ala Lys Glu Cys
1               5                   10                  15

Glu Lys Asp Gln Phe Gln Cys Arg Asn Glu Arg Cys Ile Pro Ser Val
            20                  25                  30

Trp Arg Cys Asp Glu Asp Asp Asp Cys Leu Asp His Ser Asp Glu Asp
            35                  40                  45

Asp Cys Pro Lys Lys Thr Cys Ala Asp Ser Asp Phe Thr Cys Asp Asn
            50                  55                  60

Gly His Cys Ile His Glu Arg Trp Lys Cys Asp Gly Glu Glu Glu Cys
65                  70                  75                  80

Pro Asp Gly Ser Asp Glu Ser Glu Ala Thr Cys Thr Lys Gln Val Cys
                85                  90                  95

Pro Ala Glu Lys Leu Ser Cys Gly Pro Thr Ser His Lys Cys Val Pro
            100                 105                 110

Ala Ser Trp Arg Cys Asp Gly Glu Lys Asp Cys Glu Gly Gly Ala Asp
            115                 120                 125

```
Glu Ala Gly Cys Val Thr Leu Cys Ala Pro His Glu Phe Gln Cys Gly
    130                 135                 140

Asn Arg Ser Cys Leu Ala Val Phe Val Cys Asp Gly Asp Asp Asp
145                 150                 155                 160

Cys Gly Asp Gly Ser Asp Glu Arg Gly Cys Ala Asp Pro Ala Cys Gly
                    165                 170                 175

Pro Arg Glu Phe Arg Cys Gly Arg Asp Gly Gly Ala Cys Ile Pro
                180                 185                 190

Glu Arg Trp Val Cys Asp Arg Gln Phe Asp Cys Glu Asn Arg Ser Asp
            195                 200                 205

Glu Ala Ala Glu Leu Cys Gly Arg Pro Gly Pro Gly Ala Thr Ser Ala
            210                 215                 220

Pro Ala Ala Cys Ala Thr Ala Ala Gln Phe Ala Cys Arg Ser Gly Glu
225                 230                 235                 240

Cys Val His Leu Gly Trp Arg Cys Asp Gly Asp Arg Asp Cys Lys Asp
                245                 250                 255

Lys Ser Asp Glu Ala Asp Cys Pro Leu Gly Thr Cys His Gly Asn Glu
                260                 265                 270

Phe Gln Cys Gly Asp Gly Thr Cys Val Leu Ala Ile Lys Arg Cys Asn
            275                 280                 285

Gln Glu Gln Asp Cys Pro Asp Gly Ser Asp Glu Ala Gly Cys Leu Gln
            290                 295                 300

Gly Leu Asn Glu Cys Leu His Asn Asn Gly Gly Cys Ser His Ile Cys
305                 310                 315                 320

Thr Asp Leu Lys Ile Gly Phe Glu Cys Thr Cys Pro Ala Gly Phe Gln
                325                 330                 335

Leu Leu Asp Gln Lys Thr Cys Gly Asp Ile Asp Glu Cys Lys Asp Pro
                340                 345                 350

Asp Ala Cys Ser Gln Ile Cys Val Asn Tyr Lys Gly Tyr Phe Lys Cys
            355                 360                 365

Glu Cys Tyr Pro Gly Tyr Glu Met Asp Leu Leu Thr Lys Asn Cys Lys
            370                 375                 380

Ala Ala Ala Gly Lys Ser Pro Ser Leu Ile Phe Thr Asn Arg His Glu
385                 390                 395                 400

Val Arg Arg Ile Asp Leu Val Lys Arg Asn Tyr Ser Arg Leu Ile Pro
                405                 410                 415

Met Leu Lys Asn Val Val Ala Leu Asp Val Glu Val Ala Thr Asn Arg
                420                 425                 430

Ile Tyr Trp Cys Asp Leu Ser Tyr Arg Lys Ile Tyr Ser Ala Tyr Met
            435                 440                 445

Asp Lys Ala Ser Asp Pro Lys Glu Gln Glu Val Leu Ile Asp Glu Gln
            450                 455                 460

Leu His Ser Pro Glu Gly Leu Ala Val Asp Trp Val His Lys His Ile
465                 470                 475                 480

Tyr Trp Thr Asp Ser Gly Asn Lys Thr Ile Ser Val Ala Thr Val Asp
                485                 490                 495

Gly Gly Arg Arg Cys Thr Leu Phe Ser Arg Asn Leu Ser Glu Pro Arg
                500                 505                 510

Ala Ile Ala Val Asp Pro Leu Gln Gly Phe Met Tyr Trp Ser Asp Trp
            515                 520                 525

Gly Asn Gln Ala Lys Ile Glu Lys Ser Gly Leu Asn Gly Val Asp Arg
530                 535                 540
```

-continued

```
Gln Thr Leu Val Ser Asp Asn Ile Glu Trp Pro Asn Gly Ile Thr Leu
545                 550                 555                 560
Asp Leu Leu Ser Gln Arg Leu Tyr Trp Val Asp Ser Lys Leu His Gln
                565                 570                 575
Leu Ser Ser Ile Asp Phe Ser Gly Gly Asn Arg Lys Met Leu Ile Ser
                580                 585                 590
Ser Thr Asp Phe Leu Ser His Pro Phe Gly Ile Ala Val Phe Glu Asp
            595                 600                 605
Lys Val Phe Trp Thr Asp Leu Glu Asn Glu Ala Ile Phe Ser Ala Asn
        610                 615                 620
Arg Leu Asn Gly Leu Glu Ile Ser Ile Leu Ala Glu Asn Leu Asn Asn
625                 630                 635                 640
Pro His Asp Ile Val Ile Phe His Glu Leu Lys Gln Pro Arg Ala Ala
                645                 650                 655
Asp Ala Cys Lys Leu Ser Val Gln Pro Asn Gly Gly Cys Glu Tyr Leu
                660                 665                 670
Cys Leu Pro Ala Pro Gln Ile Ser Ser His Ser Pro Lys Tyr Thr Cys
            675                 680                 685
Ala Cys Pro Asp Thr Met Trp Leu Gly Pro Asp Met Lys Arg Cys Tyr
690                 695                 700
Arg Ala Pro Gln Ser Thr Ser Thr Thr Thr Leu Pro Ser Thr Thr Arg
705                 710                 715                 720
Thr Gly Pro Ala Thr Thr Gly Ala Pro Gly Thr Thr Val His Arg Ser
                725                 730                 735
Thr Asp Gln Asn His Ser Thr Glu Thr Pro Asn Leu Ala Ala Ala Val
            740                 745                 750
Pro Ser Ser Val Ser Val Pro Arg Ala Pro Ser Ile Ser Leu Ser Thr
            755                 760                 765
Leu Ser Pro Ala Thr Ser Asn His Ser Gln His Tyr Gly Asn Glu Asp
    770                 775                 780
Ser Lys Met Gly Ser Thr Val Thr Ala Ala Val Ile Gly Ile Ile Val
785                 790                 795                 800
Pro Ile Val Val Ile Ala Leu Leu Cys Met Ser Gly Tyr Leu Ile Trp
                805                 810                 815
Arg Asn Trp Lys Arg Lys Asn Thr Lys Ser Met Asn Phe Asp Asn Pro
                820                 825                 830
Val Tyr Arg Lys Thr Thr Glu Glu Glu Asp Glu Asp Glu Leu His Ile
            835                 840                 845
Gly Arg Thr Ala Gln Ile Gly His Val Tyr Pro Ala Ala Ile Ser Ser
850                 855                 860
Phe Asp Arg Pro Leu Trp Ala Glu Pro Cys Leu Gly Glu Thr Arg Glu
865                 870                 875                 880
Leu Glu Asp Pro Ala Pro Ala Leu Lys Glu Leu Phe Val Leu Pro Gly
                885                 890                 895
Glu Pro Arg Ser Gln Leu His Gln Leu Pro Arg Asn Pro Leu Ser Glu
            900                 905                 910
Leu Pro Val Val Lys Ser Lys Arg Val Ala Leu Ser Leu Glu Asp Asp
            915                 920                 925
Gly Leu Pro
930
```

LRP-8 BINDING DUAL VARIABLE DOMAIN IMMUNOGLOBULIN PROTEINS

This application claims priority to U.S. Provisional Application No. 62/090,878, filed Dec. 11, 2014, which is incorporated herein by reference in its entirety.

SEQUENCE LISTING

The instant application contains a Sequence Listing which has been submitted electronically in ASCII format and is hereby incorporated by reference in its entirety. Said ASCII copy, created on Feb. 18, 2016, is named 12252.0195-00000_SL.txt and is 215,639 bytes in size.

FIELD

The present disclosure provides LRP-8 binding proteins, including those that can participate in endocytosis, transcytosis, and/or crossing the blood brain barrier (BBB).

BACKGROUND

Low density lipoprotein receptor-related protein 8 (LRP-8) (also called ApoER2) is a cell surface receptor and is a member of the LDL receptor family. LRP-8 is abundant in the brain and placenta. LRP-8 ligands include reelin, ApoE, selenoprotein P and endoplasmic reticulum resident receptor-associated protein (RAP). LRP-8 plays a role in endocytosis, transcytosis and signal transduction, in particular in embryonic neuronal migration and postnatal long-term potentiation. LRP-8 isoform 1 consists of 963 amino acids and is separated into a ligand binding domain of eight ligand binding regions (Accession No: Q14114.4). While all LDL receptor family proteins consist of a cytoplasmic tail, LRP-8 is unique in that it contains a proline-rich 59 amino acid insert encoded by the alternatively spliced exon 19. This insert allows for protein interactions that are unable to occur with other LDL receptors and also diminishes the function of LRP-8 in lipoprotein endocytosis (Myant (2010) Proc. Biol. Sci. 277(1680): 345-51).

Through interactions with one of its ligands, reelin, LRP-8 also plays a critical role in the migration of neurons during development. Another LDL family member, VLDLR, also interacts with reelin, and together these two receptors modulate brain development and function. LRP-8 also functions as a receptor for the cholesterol transport protein apolipoprotein E. Decreased expression of LRP-8 is thus associated with certain neurological diseases. For instance, studies show that manipulation of LRP-8 can lead to Alzheimer's disease. A decrease in LRP8 expression is observed in patients with Alzheimer's disease. LRP-8 synthesis can lead to increased gamma secretase activity, a protease which cleaves LRP-8 as well as amyloid precursor protein (APP) into amyloid β (Aβ), resulting in degrading products that control the expression of a tau protein, which ultimately leads to Alzheimer's disease (Carter (2007) Neurochem Int. 50(1): 12-38). LRP-8 activity has also been linked to antiphospholipid syndrome and major depressive disorder (MDD).

The blood-brain barrier (BBB) is a highly selective permeability barrier formed by brain endothelial cells that separates circulating blood from the brain extracellular fluid. It acts to effectively protect the brain from many common bacterial infections. While the BBB allows for the passage of water, some gases, and selective molecules, the BBB severely limits the penetration of large molecule drugs into the brain. Antibodies are generally too large to cross the BBB, and only certain antibiotics are able to cross. In some cases, a drug must be administered directly into the cerebrospinal fluid. However, drugs delivered directly to the cerebrospinal fluid often do not effectively penetrate into the brain tissue itself.

Several mechanisms have been developed for drug targeting in the brain that involve going "through" or "behind" the BBB. One of the strategies devised to overcome this obstacle includes utilizing transcytosis trafficking pathways of endogenous receptors expressed at the brain capillary endothelium. Recombinant proteins, such as monoclonal antibodies, have been designed against these receptors to enable receptor-mediated drug delivery. Recent studies suggest that antibodies with low affinity to BBB receptors, such as the transferrin receptor (TfR), offer the potential to substantially increase BBB transport and CNS retention of associated therapeutic moieties/molecules compared with high-affinity antibodies. These low affinity antibodies maximize brain uptake while minimizing reverse transcytosis back to the blood and also maximize the extent of accumulation after therapeutic dosing (Atwal et al. (2011) Sci. Transl. Med. 3: 84ra43; Yu et al. (2011) Sci. Transl. Med. 3(84): 84ra44). Yet, the safety of administering such antibodies and conjugates is not well known.

Other BBB receptors used for binding an antibody to mediate transport across the BBB include the insulin receptor, insulin-like growth factor receptor (IGF receptor), LRP-8, low density lipoprotein receptor-related protein 1 (LRP1), glucose transporter 1 (Glut1) and heparin-binding epidermal growth factor-like growth factor (HB-EGF). Antibodies and binding proteins that target some of these receptors and transport therapeutic agents across the BBB have been proposed.

Moreover, engineered proteins, such as antibodies, fragments, and multispecific binding proteins capable of binding two or more antigens, are known in the art. Such multispecific binding proteins can be generated using cell fusion, chemical conjugation, or recombinant DNA techniques. There are a variety of multispecific binding protein structures known in the art and many structures and methods have distinct advantages or disadvantages.

Bispecific antibodies have been produced, for instance, using quadroma technology. Bispecific antibodies can also be produced by chemical conjugation of two different mAbs. Other approaches include coupling of two parental antibodies with a hetero-bifunctional crosslinker, production of tandem single-chain Fv molecules, diabodies, bispecific diabodies, single-chain diabodies, and di-diabodies. In addition, a multivalent antibody construct comprising two Fab repeats in the heavy chain of an IgG and capable of binding four antigen molecules has been described (see PCT Publication No. WO 01/77342 and Miller et al. (2003) J. Immunol. 170(9):4854-61).

U.S. Pat. No. 7,612,181 (incorporated herein by reference in its entirety) provides a novel family of binding proteins capable of binding two or more antigens with high affinity, which are called dual variable domain binding proteins (DVD-Ig binding protein) or dual variable domain immunoglobulins (DVD-Ig). DVD-Ig molecules are binding proteins that may be used to bind two distinct epitopes on the same molecule or two different molecules simultaneously. DVD-Ig molecules are unique binding proteins comprised of two variable domains fused to N-terminal constant regions. The variable domains may be directly fused to one another or connected via synthetic peptide linkers of assorted length and amino acid composition. DVD-Ig binding proteins may be engineered with intact and functional Fc domains, or otherwise modified constant domains, allowing them to mediate appropriate effector functions and exhibit other desired properties. The DVD-Ig format, due to its flexibility of choice of variable domain pair, orientation of two antigen-binding domains, and the length of the linker that joins them, may provide novel therapeutic modalities.

There remains a need for constructs, including multispecific constructs, exhibiting better targeting, efficiency, and/or efficacy in binding to LRP-8, and/or improved transport and delivery of therapeutic agents across the blood brain barrier. Improved targeting of LRP-8 may lead to improvements in, e.g., preventing, diagnosing, and/or treating disorders such as brain disorders, neurological diseases, and/or brain cancers. Also, while a variety of structures have been provided in the art, with various advantages and disadvantages, new variable domain sequences can further improve the properties of binding proteins targeting LRP-8, or their cognate receptors.

SUMMARY

This disclosure provides proteins that bind LRP-8. Binding proteins of the disclosure include but are not limited to antibodies, antigen binding portions thereof, and multivalent and/or multispecific binding proteins such as dual variable domain immunoglobulin (DVD-Ig) binding proteins that can bind LRP-8. The disclosure also provides methods and compositions for targeting an LRP-8 binding protein to the brain and/or spinal cord and/or across the blood brain barrier (BBB), as well as pharmaceutically relevant animal models.

In one aspect, the disclosure provides a binding protein that specifically binds to human LRP-8. In certain aspects, the disclosure provides a binding protein that specifically binds to human and/or cynomolgus LRP-8. In certain aspects, the binding proteins bind LRP-8 expressed on brain vascular endothelium of a subject and facilitate uptake of a composition into the brain of the subject.

In certain embodiments, the binding protein also specifically binds to mouse and/or rat LRP-8. In certain aspects the binding protein undergoes endocytosis into HEK293 cells expressing LRP-8 at a rate between 1.5 and 2.5 times the endocytosis of control IgG into HEK293 cells expressing LRP-8. In other embodiments, the binding protein undergoes transcytosis across a Caco-2 cell monolayer expressing LRP-8 at a rate between 1.5 and 2.0 times the transcytosis of control IgG across a Caco-2 cell monolayer.

In certain embodiments, the binding protein specifically binds to residues 33-622 of human LRP-8 isoform 3. In certain embodiments, the binding protein specifically binds to one or both of an amino acid sequence comprising the sequence of CR1 (SEQ ID NO:2) and an amino acid sequence comprising the sequence of CR2 (SEQ ID NO:3).

In certain embodiments, disclosed herein are binding proteins comprising first and second polypeptide chains forming a binding domain for LRP-8, wherein each polypeptide chain comprises 1, 2, or 3 CDRs from, or at least 80% homology to, a VH or VL sequence listed in any one of Tables 2-7. In some embodiments, a binding protein comprises a first polypeptide chain comprising three CDRs from a VH sequence listed in any one of Tables 2-7, and a second polypeptide chain comprising three CDRs from the corresponding VL sequence listed in any one of Tables 2-7. In some embodiments, a binding protein comprises a first polypeptide chain comprising a VH sequence listed in any one of Tables 2-7, and a second polypeptide chain comprising the corresponding VL sequence listed in any one of Tables 2-7.

In certain embodiments, the LRP-8 binding protein comprises six CDRs: CDR-H1, CDR-H2, CDR-H3, CDR-L1, CDR-L2, and CDR-L3, as defined below:

CDR-H1: RFTFSNX1GMS (SEQ ID NO: 9), wherein X1 is F or Y;
CDR-H2: TISSGGRYTYYPDX2VKG (SEQ ID NO: 10), wherein X2 is S or H;
CDR-H3: DYLYAMDY (SEQ ID NO: 46);
CDR-L1: RSSQSLVYSX3X4NTYLH (SEQ ID NO: 47), wherein X3 is N, T, R, W or P, and wherein X4 is G, E, L or K;
CDR-L2: KVSNRFS (SEQ ID NO: 48); and
CDR-L3: SQSTHVPLT (SEQ ID NO: 49).

In certain embodiments, the LRP-8 binding protein comprises a heavy chain variable domain and a light chain variable domain, wherein the heavy chain variable domain comprises the sequence of (SEQ ID NO: 50)
EVQLVESGGDLVKPGGSLKLSCAASRFTFSNFGMSWVRQTPDKRLEWVAT

ISSGGRYTYYPDX$_1$VKGRFTISRDNAKNTLYLQMSSLRSEDTAMYYCARD

YLYAMDYWGQGTSVTVSS,
or (SEQ ID NO: 51)
EVQLVESGGDLVKPGGSLKLSCAASRFTFSNYGMSWVRQTPDKRLEWVAT

ISSGGRYTYYPDX$_1$VKGRFTISRDNAKNTLYLQMSSLRSEDTAMYYCARD

YLYAMDYWGQGTSVTVSS, wherein X1 is S or H, and
wherein the light chain variable domain comprises the sequence of (SEQ ID NO: 52)
DVVMTQTPLSLPVSLGDQASISCRSSQSLVYSX$_2$X$_3$NTYLHWYLQKPGQ

SPKVLMYKVSNRFSGVSDRFSGSGSGTDFTLKISRVEAEDLGVYFCSQS

THVPLTFGAGTKLELK, wherein X2 is N, T, R, W or P and X3 is G, E, L or K.

In certain embodiments, the LRP-8 binding protein comprises six CDRs: CDR-H1, CDR-H2, CDR-H3, CDR-L1, CDR-L2, and CDR-L3, as defined below:

CDR-H1:
(SEQ ID NO: 53)
GFTVSDYYMA;

CDR-H2:
(SEQ ID NO: 54)
SISYEGSSTYYGDSVKG;

CDR-H3:
(SEQ ID NO: 55)
PLRYYGYNYRFAY;

CDR-L1:
(SEQ ID NO: 56)
KASQNIHKNLD;

CDR-L2:
(SEQ ID NO: 57)
YTDNLQT;

and

CDR-L3:

(SEQ ID NO: 58)
YQYNSGPT.

In certain embodiments, the LRP-8 binding protein comprises a heavy chain variable domain and a light chain variable domain, wherein the heavy chain variable domain comprises the sequence of (SEQ ID NO: 59)
EVQLVESGGGLVQPGRSLKLSCAASGFTVSDYYMAWVRQAPKKGLEW

VASISYEGSSTYYGDSVKGRFTISRDNAKSILYLQMNSLRSEDTATY

YCARPLRYYGYNYRFAYWGQGTLVTVSS and wherein the light chain variable domain comprises the sequence of (SEQ ID NO: 60)
DIQMSQSPPVLSASVGDRVTLSCKASQNIHKNLDWYQQKHGEAPKLLI

YYTDNLQTGIPSRFSGSGSGTDYTLTISSLQPEDVATYYCYQYNSGPT

FGAGTKLELQ, wherein the bold portions are CDR-H1, CDR-H2, CDR-H3, CDR-L1, CDR-L2, and CDR-L3, respectively.

In another aspect, the disclosure provides dual variable domain (DVD-Ig) binding proteins that specifically bind to LRP-8. In certain aspects, the DVD-Ig binding proteins bind LRP-8 expressed on brain vascular endothelium of a subject and facilitate uptake of a composition into the brain of the subject.

In an embodiment, the LRP-8 binding protein comprises a heavy chain polypeptide, wherein the polypeptide comprises VD1-(X1)n-VD2-C-(X2)n, wherein VD1 is a first heavy chain variable domain; VD2 is a second heavy chain variable domain; C is a heavy chain constant domain; X1 is a linker with the proviso that it is not CH1; X2 is an Fc region; and n is independently 0 or 1. In some embodiments, the VD1 and/or VD2 comprises three CDRs: CDR-H1, CDR-H2, CDR-H3, as defined below: CDR-H1: RFTFSNX1GMS (SEQ ID NO: 9), wherein X1 is F or Y or GFTVSDYYMA (SEQ ID NO: 53); CDR-H2: TISSGGRYTYYPDX2VKG (SEQ ID NO: 10), wherein X2 is S or H or SISYEGSSTYYGDSVKG (SEQ ID NO: 54); and CDR-H3: DYLYAMDY (SEQ ID NO: 46) or PLRYYGYNYRFAY (SEQ ID NO: 55).

In some embodiments, VD1 and/or VD2 on the heavy chain polypeptide comprises an amino acid sequence of (SEQ ID NO: 50)
EVQLVESGGDLVKPGGSLKLSCAASRFTFSNFGMSWVRQTPDKRLEWV

ATISSGGRYTYYPDX1VKGRFTISRDNAKNTLYLQMSSLRSEDTAMYY

CARDYLYAMDYWGQGTSVTVSS,
or (SEQ ID NO: 51)
EVQLVESGGDLVKPGGSLKLSCAASRFTFSNYGMSWVRQTPDKRLEWV

ATISSGGRYTYYPDX1VKGRFTISRDNAKNTLYLQMSSLRSEDTAMYY

CARDYLYAMDYWGQGTSVTVSS, wherein X1 is R or S; or (SEQ ID NO: 59)
EVQLVESGGGLVQPGRSLKLSCAASGFTVSDYYMAWVRQAPKKGLEWV

ASISYEGSSTYYGDSVKGRFTISRDNAKSILYLQMNSLRSEDTATYYC

ARPLRYYGYNYRFAYWGQGTLVTVSS, wherein the CDRs are bolded.

In some embodiments, VD1 and/or VD2 on the heavy chain polypeptide comprises an amino acid sequence of (SEQ ID NO: 61)
EVQLVESGGDLVKPGGSLKLSCAASRFTFSNFGMSWVRQTPDKRLEWV

ATISSGGRYTYYPDSVKGRFTISRDNAKNTLYLQMSSLRSEDTAMYYC

ARDYLYAMDYWGQGTSVTVSS,
or (SEQ ID NO: 62)
EVQLVESGGDLVKPGGSLKLSCAASRFTFSNYGMSWVRQTPDKRLEWV

ATISSGGRYTYYPDSVKGRFTISRDNAKNTLYLQMSSLRSEDTAMYYC

ARDYLYAMDYWGQGTSVTVSS, wherein the CDRs are bolded.

In some embodiments, the LRP-8 binding protein comprises a light chain polypeptide, wherein the polypeptide comprises VD1-(X1)n-VD2-C, wherein VD1 is a first light chain variable domain; VD2 is a second light chain variable domain; C is a light chain constant domain; X1 is a linker with the proviso that it is not CL; and n is 0 or 1. In some embodiments, the polypeptide chain does not comprise an Fc region. In some embodiments, the VD1 and/or VD2 comprises three CDRs: CDR-L1, CDR-L2, CDR-L3, as defined below: CDR-L1: RSSQSLVYSX3X4NTYLH (SEQ ID NO: 47), wherein X3 is N, T, R, W or P, and wherein X4 is G, E, L or K or KASQNIHKNLD (SEQ ID NO: 56); CDR-L2: KVSNRFS (SEQ ID NO: 48) or YTDNLQT (SEQ ID NO: 57); and CDR-L3: SQSTHVPLT (SEQ ID NO: 49) or YQYNSGPT (SEQ ID NO: 58).

In another embodiment, VD1 and/or VD2 on the light chain polypeptide comprises an amino acid sequence of (SEQ ID NO: 52)
DVVMTQTPLSLPVSLGDQASISCRSSQSLVYSX2X3NTYLHWYLQKPG

QSPKVLMYKVSNRFSGVSDRFSGSGSGTDFTLKISRVEAEDLGVYFCS

QSTHVPLTFGAGTKLELK, wherein X2 is N, T, R, W or P and X3 is G, E, L or K; or (SEQ ID NO: 60)
DIQMSQSPPVLSASVGDRVTLSCKASQNIHKNLDWYQQKHGEAPKLLI

YYTDNLQTGIPSRFSGSGSGTDYTLTISSLQPEDVATYYCYQYNSGPT

FGAGTKLELQ, wherein the CDRs are bolded.

In another embodiment, VD1 and/or VD2 on the light chain polypeptide comprises an amino acid sequence of (SEQ ID NO: 63)
DVVMTQTPLSLPVSLGDQASISCRSSQSLVYSNGNTYLHWYLQKPGQS

PKVLMYKVSNRFSGVSDRFSGSGSGTDFTLKISRVEAEDLGVYFCSQS

THVPLTFGAGTKLELK, wherein the CDRs are bolded.

In an embodiment, the binding proteins disclosed herein comprise a heavy chain polypeptide as discussed above and a light chain polypeptide as discussed above.

In certain embodiments, the LRP-8 binding protein comprises first and second polypeptide chain, wherein each polypeptide chain comprises VD1-(X1)n-VD2-C-(X2)n, wherein VD1 is a first variable domain; VD2 is a second variable domain; C is a constant domain; X1 is a linker; X2 is an Fc region on the first polypeptide chain and X2 is absent on the second polypeptide chain (i.e., n is 0 for (X2)n on the second chain); n is independently 0 or 1 on the first and second chains; wherein the VD1 domains on the first and second polypeptide chains form a first functional target binding site; and wherein the VD2 domains on the first and second polypeptide chains form a second functional target binding site. In some embodiments, the antigen target for the binding site formed by the VD1 and/or VD2 domains on the first and second polypeptide chains is LRP-8. In some embodiments, the VD1 and/or VD2 domains on the first and second polypeptide chains comprise the CDRs and/or variable domains from clone ML199.11H1.5B2. In some embodiments, the VD1 and/or VD2 domains on the first and second polypeptide chains comprise the CDRs and/or variable domains from clone BGK-2C8.8C. In some embodiments, the VD1 and/or VD2 domains on the first and second polypeptide chains comprise the CDRs and/or variable domains from clone ML201-8F3.3D7. In some embodiments, the VD1 and/or VD2 domains on the first and second polypeptide chains comprise the CDRs and/or variable domains from clone BGK.9D10-2. In some embodiments, the VD1 and/or VD2 domains on the first and second polypeptide chains comprise the CDRs and/or variable domains from clone CL-105967. In some embodiments, the VD1 and/or VD2 domains on the first polypeptide chain comprise a CDR-H1 of RFTFSNX1GMS (SEQ ID NO: 9), wherein X1 is F or Y or GFTVSDYYMA (SEQ ID NO: 53); a CDR-H2 of TISSGGRYTYYPDX2VKG (SEQ ID NO: 10), wherein X2 is S or H or SISYEGSSTYYGDSVKG (SEQ ID NO: 54); and a CDR-H3 of DYLYAMDY (SEQ ID NO: 46) or PLRYYGYNYRFAY (SEQ ID NO: 55); and the VD1 and/or VD2 domains on the second polypeptide chain comprise a CDR-L1 of RSSQSLVYSX3X4NTYLH (SEQ ID NO: 47), wherein X3 is N, T, R, W or P, and wherein X4 is G, E, L or K or KASQNIHKNLD (SEQ ID NO: 56); a CDR-L2 of KVSNRFS (SEQ ID NO: 48) or YTDNLQT (SEQ ID NO: 57); and a CDR-L3 of SQSTHVPLT (SEQ ID NO: 49) or YQYNSGPT (SEQ ID NO: 58). In certain embodiments, the LRP-8 binding protein comprises heavy chain polypeptide and a light chain polypeptide, wherein the heavy chain polypeptide comprises VD1-(X1)n-VD2-C-(X2)n, wherein VD1 is a first heavy chain variable domain; VD2 is a second heavy chain variable domain; C is a heavy chain constant domain; X1 is a linker with the proviso that it is not CH1; X2 is an Fc region; n is independently 0 or 1; and wherein the light chain polypeptide comprises VD1-(X1)n-VD2-C, wherein VD1 is a first light chain variable domain; VD2 is a second light chain variable domain; C is a light chain constant domain; X1 is a linker with a proviso that it is not CL; X2 is an Fc region; n is 0 or 1; and wherein the light chain polypeptide does not comprise an Fc region. In some embodiments, the VD1 domains on the heavy and light chain polypeptides form a first functional target binding site; and wherein the VD2 domains on the heavy and light chain polypeptides form a second functional target binding site. In some embodiments, the antigen target for the binding site formed by the VD1 and/or VD2 domains is LRP-8. In some embodiments, the VD1 and/or VD2 domains on the heavy and light chain polypeptides comprise the CDRs and/or variable domains from clone ML199.11H1.5B2. In some embodiments, the VD1 and/or VD2 domains on the heavy and light chain polypeptides comprise the CDRs and/or variable domains from clone BGK-2C8.8C. In some embodiments, the VD1 and/or VD2 domains on the heavy and light chain polypeptides comprise the CDRs and/or variable domains from clone ML201-8F3.3D7. In some embodiments, the VD1 and/or VD2 domains on the heavy and light chain polypeptides comprise the CDRs and/or variable domains from clone BGK.9D10-2. In some embodiments, the VD1 and/or VD2 domains on the heavy and light chain polypeptides comprise the CDRs and/or variable domains from clone CL-105967. In some embodiments, the VD1 and/or VD2 domains on the heavy chain polypeptide comprise a CDR-H1 of RFTFSNX1GMS (SEQ ID NO: 9), wherein X1 is F or Y or GFTVSDYYMA (SEQ ID NO: 53); a CDR-H2 of TISSGGRYTYYPDX2VKG (SEQ ID NO: 10), wherein X2 is S or H or SISYEGSSTYYGDSVKG (SEQ ID NO: 54); and a CDR-H3 of DYLYAMDY (SEQ ID NO: 46) or PLRYYGYNYRFAY (SEQ ID NO: 55); and the VD1 and/or VD2 domains on the light chain polypeptide comprise a CDR-L1 of RSSQSLVYSX3X4NTYLH (SEQ ID NO: 47), wherein X3 is N, T, R, W or P, and wherein X4 is G, E, L or K or KASQNIHKNLD (SEQ ID NO: 56); a CDR-L2 of KVSNRFS (SEQ ID NO: 48) or YTDNLQT (SEQ ID NO: 57); and a CDR-L3 of SQSTHVPLT (SEQ ID NO: 49) or YQYNSGPT (SEQ ID NO: 58).

In certain embodiments, the LRP-8 binding protein can also bind a brain antigen which benefits from transport to the brain via binding of the LRP-8 binding domain to that antigen.

In certain embodiments, the binding protein comprises two first polypeptide chains and two second polypeptide chains. In another embodiment, the Fc region comprises a variant sequence Fc region. In another embodiment, the Fc region comprises an Fc region selected from the group consisting of IgG1, IgG2, IgG3, IgG4, IgA, IgM, IgE, and IgD.

In another aspect, the disclosure provides a binding protein conjugate comprising a binding protein as described herein, the binding protein conjugate further comprising an immunoadhesion molecule, an imaging agent, a therapeutic agent, or a cytotoxic agent.

In one embodiment, the imaging agent is a radiolabel, an enzyme, a fluorescent label, a luminescent label, a bioluminescent label, a magnetic label, or biotin. In certain embodiments, the imaging agent is $^3$H, $^{14}$C, $^{35}$S, $^{99}$Y, $^{99}$Tc, $^{111}$In, $^{125}$I, $^{131}$I, $^{177}$Lu, $^{166}$Ho, or $^{153}$Sm.

In one aspect, the disclosure provides an isolated nucleic acid encoding the amino acid sequence of a polypeptide chain or both polypeptide chains of a binding protein described herein. In another embodiment, a vector or vectors (e.g., pcDNA, pTT, pTT3, pEFBOS, pBV, pJV, pcDNA3.1 TOPO, pEF6 TOPO, pHybE, pBOS or pBJ) is provided encoding the isolated nucleic acid sequence or sequences that encode a binding protein disclosed herein.

In another aspect, a host cell is transformed with the vector(s) disclosed herein. In certain embodiments, the host cell is a prokaryotic cell. In an embodiment, the host cell is E. Coli. In some embodiments, the host cell is a eukaryotic cell. In certain embodiments, the eukaryotic cell is selected from the group consisting of a protist cell, animal cell, plant cell, and fungal cell. In yet another embodiment, the host cell is a mammalian cell including, but not limited to, CHO, COS, NSO, SP2, PER.C6, or a fungal cell such as *Saccharomyces cerevisiae*, or an insect cell such as Sf9.

In another aspect, the disclosure provides a method of producing a binding protein, comprising culturing a host cell described herein in culture medium under conditions sufficient to produce the binding protein.

In another aspect, the disclosure provides a binding protein produced by a method of culturing a host cell described herein in culture medium under conditions sufficient to produce the binding protein.

In another aspect, the disclosure provides a pharmaceutical composition comprising a binding protein described herein, and a pharmaceutically acceptable carrier.

In one embodiment, the pharmaceutical composition includes at least one additional agent. In certain embodiments, the additional agent is an imaging agent, a cytotoxic agent, an angiogenesis inhibitor, a kinase inhibitor, a co-stimulation molecule blocker, an adhesion molecule blocker, an anti-cytokine antibody or functional fragment thereof, a detectable label or reporter, an antirheumatic, a muscle relaxant, a narcotic, a non-steroid anti-inflammatory drug (NSAID), an analgesic, an anesthetic, a sedative, a neuromuscular blocker, an antimicrobial, an antipsoriatic, a corticosteriod, an anabolic steroid, an erythropoietin, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, a cytokine antagonist, budenoside, epidermal growth factor, a corticosteroid, cyclosporin, sulfasalazine, an aminosalicylate, 6-mercaptopurine, azathioprine, metronidazole, a lipoxygenase inhibitor, mesalamine, olsalazine, balsalazide, an antioxidant, a thromboxane inhibitor, a growth factor, an elastase inhibitor, a pyridinylimidazole compound, an antibody, antagonist or agonist of TNF, LT, IL-1, IL-1R, IL-2, IL-4, IL-6, IL-6R, IL-7, IL-8, IL-10, IL-11, IL-12, IL-13, IL-15, IL-16, IL-18, IL-23, TGF-β, EMAP-II, GM-CSF, FGF, PDGF, CD2, CD3, CD4, CD8, CD-19, CD25, CD28, CD30, CD40, CD45, CD69, CD90 or a ligand thereof, methotrexate, FK506, rapamycin, mycophenolate mofetil, leflunomide, ibuprofen, prednisolone, a phosphodiesterase inhibitor, an adenosine agonist, an antithrombotic agent, a complement inhibitor, an adrenergic agent, IRAK, NIK, IKK, p38, a MAP kinase inhibitor, an IL-1β converting enzyme inhibitor, a TNFα-converting enzyme inhibitor, a T-cell signaling inhibitor, a metalloproteinase inhibitor, an angiotensin converting enzyme inhibitor, a soluble cytokine receptor, a soluble p55 TNF receptor, a soluble p75 TNF receptor, sIL-1RI, sIL-1RII, sIL-6R or combinations thereof.

In one aspect, the disclosure provides an LRP-8 binding protein or composition as described herein for use in therapy. In certain embodiments, the disclosure provides a binding protein for use in treating a subject for a disease or a disorder. In some embodiments, the binding protein may be used for treatment by administering to the subject the binding protein such that treatment is achieved. In an embodiment, the LRP-8 binding proteins of the disclosure are used to deliver a drug or other therapeutic agent to the brain. In certain embodiments, the LRP-8 binding protein binds a target in the brain that is associated with a disease.

In various embodiments, the binding proteins disclosed herein are used in the treatment of brain disorders, e.g., an autoimmune or inflammatory disease of the brain, an infectious disorder of the brain, a neurological disorder, a neurodegenerative disorder, a brain cancer, or a brain metastasis. In certain embodiments, the disorder is Huntington's chorea, Parkinson's disease, Alzheimer's disease, dementia, acute or chronic spinal cord injury, multiple sclerosis, stroke, mental disorders, depression, schizophrenia, acute pain or chronic pain.

In another embodiment, the binding protein is administered or suitable for administration to a subject by a parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathecal, intrathoracic, intrauterine, intravesical, bolus, epidural, vaginal, rectal, buccal, sublingual, intranasal, or transdermal route.

In another aspect, the disclosure provides an isolated polypeptide, comprising an amino acid sequence of human LRP-8 CR1 peptide (SEQ ID NO:2) or human LRP-8 CR2 peptide (SEQ ID NO:3). In some embodiments, the peptide is a cyclic peptide. In some aspects, the disclosure also provides a method of generating an LRP-8 binding protein by immunizing a mammal with an isolated polypeptide described herein.

In another aspect, the disclosure provides methods of determining the presence of LRP-8 or fragment thereof in a test sample by an immunoassay, comprising contacting the sample with the LRP-8 binding protein described herein.

BRIEF DESCRIPTION OF THE DRAWINGS

FIG. 1A shows a high resolution structure of CR7 from LRP as presented previously (Simonovic et al. (2001) Biochemistry 40(50): 15127-34, PDB:1J8E). This structure shows a loop/turn motif that is stabilized by a disulfide linkage (circled).

FIG. 1B shows a multiple sequence alignment of two complement-like repeat regions in LRP-8: CR1 and CR2. Figure discloses SEQ ID NOS 217-219 and 5-6, respectively, in order of appearance.

FIGS. 2A and 2B show a multiple sequence alignment of mouse (SEQ ID NO: 223), human (SEQ ID NO: 222), and cynomolgus (SEQ ID NOS 224 and 225, respectively, in order of appearance) LRP-8 isoform 3 sequences.

FIGS. 2C, 2D, and 2E show a multiple sequence alignment of human (SEQ ID NO: 226) and cynomolgus (SEQ ID NOS 68 and 227-232, respectively, in order of appearance) LRP-8 isoform 1 sequences.

FIG. 12A shows FACS data for LRP-8-transfected HEK293 cells versus wild type HEK293 cells (ordinate) as a function of antibody concentration (abscissa) for antibodies BGK-2C8.8c and ML199-11H1.5B2 SN. A positive control antibody and an anti-mIgG negative control antibody were also analyzed.

FIG. 12B shows the EC50 (nM) binding data for the antibodies of FIG. 12A.

FIG. 12C shows binding of LRP-8 antibody BGK-2C8.8c to cells overexpressing human LRP-8 and cyno LRP-8 in a MSD-ECL assay.

FIG. 13C shows binding of LRP-8 antibodies ML1991.11H1.5B2, BGK-2C8.8C, and BGT-9D10-2 to cells overexpressing cyno LRP-8 variant 1 in a MSD-ECL assay.

FIG. 17A shows binding of anti-LRP-8 ML199.11H1.5B2 antibody to CR1 and CR2 peptides.

FIG. 17B shows the sequence alignment between CR1 and CR2 peptides (SEQ ID NOS 5 and 6, respectively) and indicates alanine mutants introduced in variants of CR1 peptide (SEQ ID NO: 5) (CR1.1, CR1.2, CR1.3, and CR1.4 (SEQ ID NOS 64-67, respectively)).

FIG. 21A shows the reelin count in cynoLRP8-293 cells.

FIG. 22A and FIG. 22B show heavy chain and light chain sequence alignment of all hLRP8 antibodies. FIG. 22A discloses SEQ ID NOS 77-81, 61-62, 74-76, 59, 220, 73, and 82-84, respectively, in order of appearance. FIG. 22B discloses SEQ ID NOS 147-151, 63, 63, 144-146, 60, 221, 143, and 152-154, respectively, in order of appearance.

DETAILED DESCRIPTION

Figure 2C:
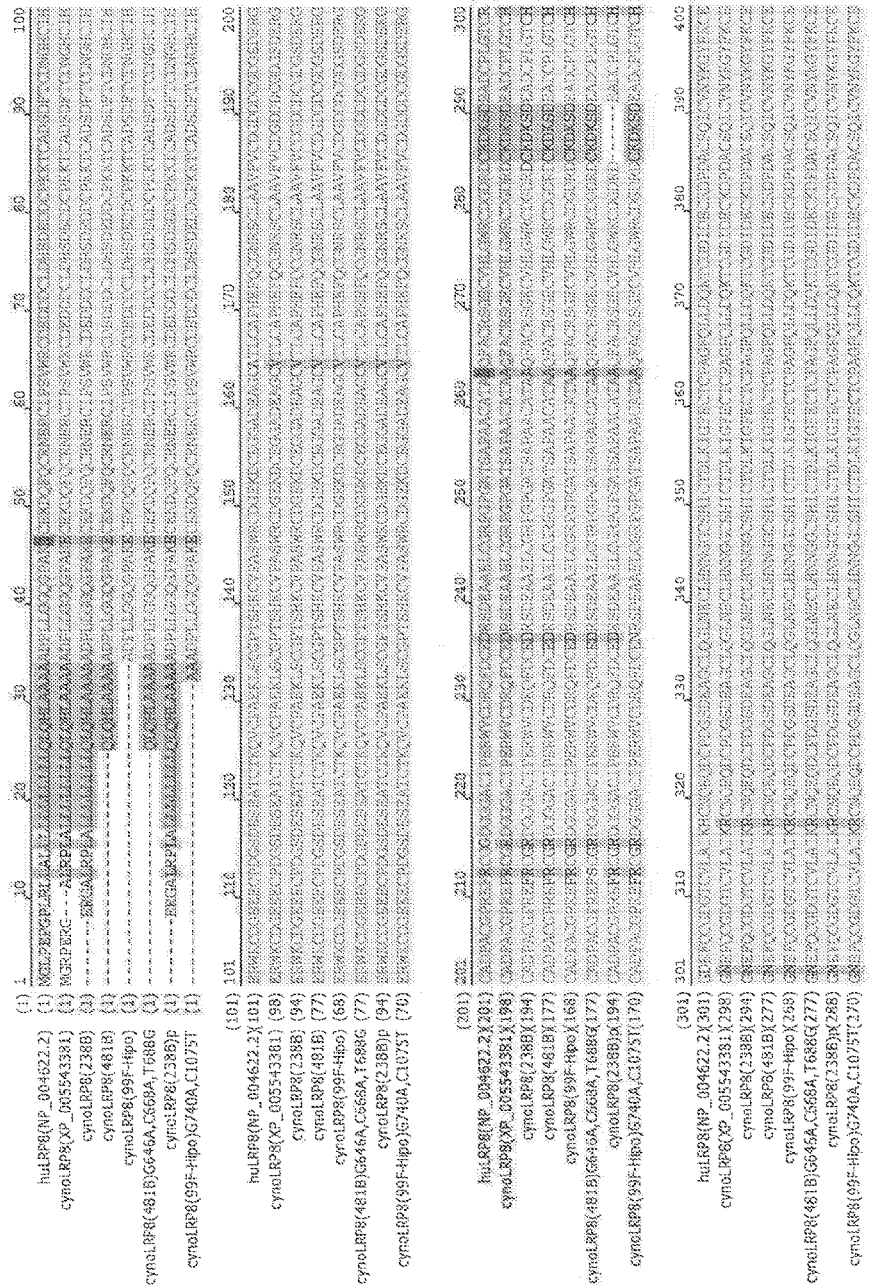

This disclosure provides low density Lipoprotein Receptor-Related Protein 8 (LRP-8) binding proteins, including, but not limited to, anti-LRP-8 antibodies or antigen-binding portions thereof that bind LRP-8, and multivalent, multi-specific binding proteins such as dual variable domain immunoglobulin (DVD-Ig) binding proteins that bind LRP- 8. Various aspects of the disclosure relate to LRP-8 antibodies, multispecific molecules, antibody fragments, and pharmaceutical compositions thereof, as well as nucleic acids, recombinant expression vectors and host cells for making such LRP-8 binding proteins. Methods of using the LRP-8 binding proteins of the disclosure to cross the BBB, mediate localization to the brain and/or mediate localization to the spinal cord are also encompassed by the disclosure. The disclosure also encompasses any binding protein or antibody capable of binding to the same epitope bound by any of the antibodies and binding proteins disclosed herein, as well as any binding protein or antibody capable of competing for binding to LRP-8 with a binding protein described herein. In certain aspects of the disclosure, an LRP-8 binding protein has one or more of the following properties: 1) binds to an extracellular domain of LRP-8; 2) binds to LRP-8 with minimal interruption of natural ligand binding; 3) internalizes as part of a binding protein-receptor complex; 4) transcytoses to the albuminal side of endothelial cells; 5) increases binding protein uptake to targeted tissue; 6) comprises a DVD-Ig; and/or 7) is cross-reactive with LRP-8 in a non-human mammal (e.g., one or any combination of cynomolgus monkey, rat or mouse). In some embodiments, a cross-reactive binding protein is one that exhibits at least about 50% of the binding affinity to a second species as observed for a first species (e.g., at least about 50% of the affinity to mouse LRP-8 as observed for human LRP-8).

According to certain embodiments, an LRP-8 binding protein binds to LRP-8 (e.g., human LRP-8 and/or cyno LRP-8). In certain embodiments, an LRP-8 binding protein binds to an epitope between about amino acids 1 and 120 of human LRP-8 (SEQ ID NO:1). In certain embodiments, an LRP-8 binding protein binds to one or both of human LRP-8 CR1 peptide (SEQ ID NO:2) or human LRP-8 CR2 peptide (SEQ ID NO:3). In other embodiments, an LRP-8 binding protein binds to one or both of conjugated human LRP-8 CR1 peptide (SEQ ID NO:5) or conjugated human LRP-8 CR2 peptide (SEQ ID NO:6). In other embodiments, an LRP-8 binding protein binds to a CR1/CR2 consensus sequence (SEQ ID NO:4). In some embodiments, an LRP-8 binding protein binds to one or more of CR1, CR1.1, CR1.2, CR1.3, CR1.4, and CR2 (sequences provided in Table 1). In some embodiments, an LRP-8 binding protein binds to CR1, CR1.2, CR1.3, and CR2, but does not bind to CR1.1 and/or CR1.4 (sequences provided in Table 1). In certain embodiments, an LRP-8 binding protein binds to an epitope in LRP-8 comprising or consisting of amino acid residues 47-57 and 60 of human LRP-8 (SEQ ID NO:1). In certain embodiments, an LRP-8 binding protein binds to an epitope in LRP-8 comprising or consisting of amino acid residues 47-66 of human LRP-8 (SEQ ID NO:1), or comprising or consisting of four or more, or five or more, amino acid residues from within that amino acid stretch of human LRP-8. In certain embodiments, an LRP-8 binding protein binds to a conformational epitope, consisting of or comprising discontinues residues of human LRP-8 (SEQ ID NO: 1). In certain embodiments, an LRP-8 binding protein binds to an epitope in LRP-8 comprising one or more amino acid residues selected from 52(F), 56(C), and 56(N), or all three amino acid residues of human LRP-8 (SEQ ID NO:1). In certain embodiments, an LRP-8 binding protein binds to an epitope in LRP-8 comprising one or more amino acid residues selected from 47(C), 52(F), 54(C), 56(N), 59(C), 60(I), 64(W), and 66(C) of human LRP-8 (SEQ ID NO:1). In various embodiments, the epitope is a conformational epitope and comprises portions of human LRP-8 (SEQ ID NO:1) contacted by the antibody in addition to those listed above. In various embodiments, the binding protein comprises clone ML199.11H1.5B2, or the CDR and/or variable domains from that clone. In some embodiments, the binding protein exhibits cross-reactivity with LRP-8 in a non-human mammal (e.g., one or any combination of cynomolgus monkey, rat or mouse).

In various embodiments, an epitope is determined by obtaining an X-ray crystal structure of an antibody: antigen complex and determining which residues on LRP-8 are within a specified distance of residues on the antibody of interest, wherein the specified distance is, 5 Å or less, e.g., 5 Å, 4 Å, 3 Å, 2 Å, 1 Å or any distance in between. In some embodiments, the epitope is defined as a stretch of 8 or more contiguous amino acid residues along the LRP-8 sequence in which at least 50%, 70% or 85% of the residues are within the specified distance of the antibody or binding protein in the X-ray crystal structure.

In various embodiments, the binding proteins disclosed herein are capable of binding LRP-8 (e.g., human, cyno, and/or mouse LRP-8). In various embodiments, the binding proteins disclosed herein are capable of binding LRP-8 without disrupting one or more biological function of LRP-8. The biological functions of LRP-8 include, for example, the recognition of a natural ligand such as reelin, ApoE, selenoprotein P and RAP, and the activation of downstream signaling pathways including PI3K pathway (see e.g., Herz et al. (2009) Curr. Opin. Lipidol. 20(3): 190-196; and Kurokawa et al. (2014) J. Biol. Chem. 289(13): 9195-9207). In some embodiments, binding to LRP-8 without disrupting one or more biological function allows for targeting of binding proteins to the brain/nervous system and crossing the blood-brain barrier (e.g., for delivery of a second agent, multispecific binding protein, or conjugate) without disrupting the natural functions of LRP-8 functions. In some embodiments, the binding protein comprises clone ML199.11H1.5B2, or the CDR and/or variable domains from that clone. In various embodiments, a binding protein comprising an LRP-8 binding domain disclosed herein is able to cross the blood-brain barrier in either a monospecific or multispecific format, or both. In various embodiments, the binding proteins disclosed herein exhibit an effective affinity, epitope, charge, and/or valency to enhance uptake across the blood-brain barrier.

In various embodiments, the binding protein is capable of binding LRP-8, and comprises clone ML199.11H1.5B2. In various embodiments, the binding protein is capable of binding LRP-8, and comprises the CDR and/or variable domain amino acid sequences of clone ML199.11H1.5B2. In various embodiments, the binding protein is capable of binding LRP-8, and comprises clone 11H1. In various embodiments, the binding protein is capable of binding LRP-8, and comprises the CDR and/or variable domain amino acid sequences of clone 11H1. In various embodiments, the binding protein is capable of binding LRP-8, and comprises clone BGK-2C8.8C. In various embodiments, the binding protein is capable of binding LRP-8, and comprises the CDR and/or variable domain amino acid sequences of clone BGK-2C8.8C. In various embodiments, the binding protein is capable of binding LRP-8, and comprises clone ML201-8F3.3D7. In various embodiments, the binding protein is capable of binding LRP-8, and comprises the CDR and/or variable domain amino acid sequences of clone ML201-8F3.3D7. In various embodiments, the binding protein is capable of binding LRP-8, and comprises clone BGK.9D10-2. In various embodiments, the binding protein is capable of binding LRP-8, and comprises the CDR and/or variable domain amino acid sequences of clone BGK.9D10-

2. In an embodiment, the binding protein is capable of binding LRP-8, and comprises CL-105967.

In some embodiments, the binding protein exhibits cross-reactivity with LRP-8 in a non-human mammal (e.g., one or any combination of cynomolgus monkey, rat or mouse).

Table 1 shows amino acid sequences of LRP-8 proteins, including various complement-like repeat regions of LRP-8 ("CR," also know as ligand binding repeats) and variant CR regions, as well as conserved regions across species.

TABLE 1

LRP-8 Protein Amino Acid Sequences

| Protein | Sequence Identifier | Sequence<br>12345678901234567890123456789 0 |
|---|---|---|
| Human LRP-8 Protein | SEQ ID NO: 1 | MGLPEPGPLRLLALLLLLLLLLLQLQHLA<br>AAAADPLLGGQGPAKDCEKDQFQCRNERCI<br>PSVWRCDEDDDCLDHSDEDDCPKKTCADSD<br>FTCDNGHCIHERWKCDGEEECPDGSDESEA<br>TCTKQVCPAEKLSCGPTSHKCVPASWRCDG<br>EKDCEGGADEAGCATSLGTCRGDEFQCGDG<br>TCVLAIKHCNQEQDCPDGSDEAGCLQGLNE<br>CLHNNGGCSHICTDLKIGFECTCPAGFQLL<br>DQKTCGDIDECKDPDACSQICVNYKGYFKC<br>ECYPGYEMDLLTKNCKAAAGKSPSLIFTNR<br>HEVRRIDLVKRNYSRLIPMLKNVVALDVEV<br>ATNRIYWCDLSYRKIYSAYMDKASDPKEQE<br>VLIDEQLHSPEGLAVDWVHKHIYWTDSGNK<br>TISVATVDGGRRRTLFSRNLSEPRAIAVDP<br>LRGFMYWSDWGDQAKIEKSGLNGVDRQTLV<br>SDNIEWPNGITLDLLSQRLYWVDSKLHQLS<br>SIDFSGGNRKTLISSTDFLSHPFGIAVFED<br>KVFWTDLENEAIFSANRLNGLEISILAENL<br>NNPHDIVIFHELKQPRAPDACELSVQPNGG<br>CEYLCLPAPQISSHSPKYTCACPDTMWLGP<br>DMKRCYRDANEDSKMGSTVTAAVIGIIVPI<br>VVIALLCMSGYLIWRNWKRKNTKSMNFDNP<br>VYRKTTEEEDEDELHIGRTAQIGHVYPARV<br>ALSLEDDGLP |
| Human LRP-8 CR1 Peptide | SEQ ID NO: 2 | CEKDQFQCRNERCIPSVWRC |
| Human LRP-8 CR1.1 Variant Peptide | SEQ ID NO: 64 | CEKDQAQSRNERCIPSVWRC |
| Human LRP-8 CR1.2 Variant Peptide | SEQ ID NO: 65 | CEKDQFQARNERCIPSVWRC |
| Human LRP-8 CR1.3 Variant Peptide | SEQ ID NO: 66 | CEKDQFQSRAERCIPSVWRC |
| Human LRP-8 CR1.4 Variant Peptide | SEQ ID NO: 67 | CEKDQAQARAERCIPSVWRC |
| Human LRP-8 CR2 Peptide | SEQ ID NO: 3 | CADSDFTCDNGHCIHERWKC |
| Conjugated Human LRP-8 CR1 Peptide | SEQ ID NO: 5 | CEKDQFQSRNERCIPSVWRC |
| Conjugated Human LRP-8 CR2 Peptide | SEQ ID NO: 6 | CADSDFTSDNGHCIHERWKC |
| cynoLRP-8 (brain) | SEQ ID NO: 7 | LLEMQLQHLAAAAADPLLGGQGPAKECEKD<br>QFQCRNERCIPSVWRCDEDDDCLDHSDEDD<br>CPKKTCADSDFTCDNGHCIHERWKCDGEEE<br>CPDGSDESEATCTLGTCHGNEFQCGDGTCV<br>LAIKRCNQEQDCPDGSDEAGCLQVPPTFLG<br>NRRRPRGLNECLHNNGGCSHICTDLKIGFE<br>CTCPAGFQLLDQKTCGDIDECKDPDACSQI<br>CVNYKGYFKCECYPGYEMDLLTKNCKAAAG<br>KSPSLIFTNRHEVRRIDLVKRNYSRLIPML<br>KNVVALDMEVATNRIYWCDLSYRKIYSAYM<br>DKASDPKEQEVLIDEQLHSPEGLAVDWVHK<br>HIYWTDSGNKTISVATVDGGRRCTLFSRNL<br>SEPRAIAVDPLQGFMYWSDWGNQAKIEKSG |

TABLE 1-continued

LRP-8 Protein Amino Acid Sequences

| Protein | Sequence Identifier | Sequence<br>12345678901234567890123456789 0 |
|---|---|---|
| | | LNGVDRQTLVSDNIEWPNGITLDLLSQRLY<br>WVDSKLHQLSSIDFSGGNRKMLISSTDFLS<br>HPFGIAVFEDKVFWTDLENEAIFSANRLNG<br>LEISILAENLNNPHDIVIFHELKQPRAADA<br>CKLSVQPNGGCEYLCLPAPQISSHSPKYTC<br>ACPDTMWLGPDMKRCYRDGNEDSKMGSTVT<br>AAVIGIIVPIVVIALLCMSGYLIWRNWKRK<br>NTKSMNFDNPVYRKTTEEEDEDELHIGRTA<br>QIGHVYPARVALSLEDDGLP |
| cynoLRP-8<br>(testis) | SEQ ID NO: 8 | LLEMQLQHLAAAAADPLLGGQGPAKECEKD<br>QFQCRNERCIPSVWRCDEDDDCLDHSDEDD<br>CPKKTCADSDFTCDNGHCIHERWKCDGEEE<br>CPDGSDESEATCTLGTCHGNEFQCGDGTCV<br>LAIKRCNQEQDCPDGSDEAGCLQVPPTFLG<br>NRRRPRGLNECLHNNGGCSHISTDLKIGFE<br>CTCPAGFQLLDQKTCGDIDECKDPDACSQI<br>CVNYKGYFKCECYPGYEMDLLTKNCKAAAG<br>KSPSLIFTNRHEVRRIDLVKRNYSRLIPML<br>KNVVALDMEVATNRIYWCDLSYRKIYSAYM<br>DKASDPKEQEVLIDEQLHSPEGLAVDWVHK<br>HIYWTDSGNKTISVATVDGGRRCTLFSRNL<br>SEPRAIAVDPLQGFMYWSDWGNQAKIEKSG<br>LNGVDRQTLVSDNIEWPNGITLDLLSQRLY<br>WVDSKLHQLSSIDFSGGNRKMLISSTDFLS<br>HPFGIAVFEDKVFWTDLENEAIFSANRLNG<br>LEISILAENLNNPHDIVIFHELKQPRAADA<br>CKLSVQPNGGCEYLCLPAPQISSHSPKYTC<br>ACPDTMWLGPDMKRCYRDGNEDSKMGSTVT<br>AAVIGIIVPIVVIALLCMSGYLIWRNWKRK<br>NTKSMNFDNPVYRKTTEEEDEDELHIGRTA<br>QIGHVYPARVALSLEDDGLP |
| Cyno LRP-8<br>isoform 1* | SEQ ID NO: 68 | <u>MGRPERGALRPLALLLLLLLLQLQHLAAAA</u><br>ADPLLGGQGPAKECEKDQFQCRNERCIPSV<br>WRCDEDDDCLDHSDEDDCPKKTCADSDFTC<br>DNGHCIHERWKCDGEEECPDGSDESEATCT<br>KQVCPAEKLSCGPTSHKCVPASWRCDGEKD<br>CEGGADEAGCVTLCAPHEFQCGNRSCLAAV<br>FVCDGDDDCGDGSDERGCADPACGPREFRC<br>GRDGGGACIPERWVCDRQFDCEDRSDEAAE<br>LCGRPGPGATSAPAACATAAQFACRSGECV<br>HLGWRCDGDRDCKDKSDEADCPLGTCHGNE<br>FQCGDGTCVLAIKRCNQEQDCPDGSDEAGC<br>LQGLNECLHNNGGCSHICTDLKIGFECTCP<br>AGFQLLDQKTCGDIDECKDPDACSQICVNY<br>KGYFKCECYPGYEMDLLTKNCKAAAGKSPS<br>LIFTNRHEVRRIDLVKRNYSRLIPMLKNVV<br>ALDVEVATNRIYWCDLSYRKIYSAYMDKAS<br>DPKEQEVLIDEQLHSPEGLAVDWVHKHIYW<br>TDSGNKTISVATVDGGRRCTLFSRNLSEPR<br>AIAVDPLQGFMYWSDWGNQAKIEKSGLNGV<br>DRQTLVSDNIEWPNGITLDLLSQRLYWVDS<br>KLHQLSSIDFSGGNRKMLISSTDFLSHPFG<br>IAVFEDKVFWTDLENEAIFSANRLNGLEIS<br>ILAENLNNPHDIVIFHELKQPRAADACKLS<br>VQPNGGCEYLCLPAPQISSHSPKYTCACPD<br>TMWLGPDMKRCYRAPQSTSTTTLPSTTRTG<br>PATTGAPGTTVHRSTDQNHSTETPNLAAAV<br>PSSVSVPRAPSISLSTLSPATSNHSQHYGN<br>EDSKMGSTVTAAVIGIIVPIVVIALLCMSG<br>YLIWRNWKRKNTKSMNFDNPVYRKTTEEED<br>EDELHIGRTAQIGHVYPAAISSFDRPLWAE<br>PCLGETRELEDPAPALKELFVLPGEPRSQL<br>HQLPRNPLSELPVVKSKRVALSLEDDGLP |

*Predicted cyno LRP-8 isoform 1 signal peptide is underline

In certain embodiments, this disclosure provides binding proteins that specifically bind LRP-8. In some embodiments, a binding protein, including a DVD-Ig binding protein, antibody, or fragment thereof, is capable of binding LRP-8 and has a heavy or light chain comprising at least about 80%, 90%, 95%, 99%, or 100% homology to CDRs 1-3 or to the full variable domains of any of the sequences in Tables 2-7 or 18. As used herein, the term percent (%) homology defines the percentage of residues in an amino acid sequence that are identical to a reference sequence after aligning the sequences and introducing gaps and other spacing, e.g., using the BLAST alignment software.

In certain embodiments, the binding proteins disclosed herein have at least about 80% homology to the VH and VL domains of antibodies or binding proteins that specifically bind LRP-8, e.g., binding proteins or antibodies LRP-8 comprising CDRs and/or variable domains selected from those identified in Tables 2-7. Each VH and VL domain of a binding protein contains three CDR domains: CDR-H1, CDR-H2, CDR-H3, and CDR-L1, CDR-L2, and CDR-L3. According to certain embodiments, a binding protein described herein can contain 1, 2, or 3 CDRs having at least 80% homology to the CDRs in a VH or VL sequence listed in any one of Tables 2-7. In some embodiments, a binding protein described herein can comprise 1, 2, 3, 4, 5, or 6 CDRs having at least 80% homology to the CDRs in a VH domain and its paired VL domain disclosed in any one of Tables 2-7. In some embodiments, the binding proteins disclosed herein have sequences that have at least 80% homology to a VH domain and its paired VL domain disclosed in any one of Tables 2-7.

In certain embodiments, a binding protein disclosed herein can compete for binding with an antibody or binding protein that specifically bind LRP-8. In certain embodiments, a binding protein disclosed herein can compete for binding with an antibody or binding protein comprising CDRs and/or variable domains selected from those identified in Tables 2-7. In certain embodiments, a binding protein disclosed herein can compete for binding with clone ML199.11H1.5B2. In certain embodiments, a binding protein disclosed herein can compete for binding with clone 11H1. In certain embodiments, a binding protein disclosed herein can compete for binding with clone BGK-2C8.8C. In certain embodiments, a binding protein disclosed herein can compete for binding with clone ML201-8F3.3D7. In certain embodiments, a binding protein disclosed herein can compete for binding with clone BGK.9D10-2. In certain embodiments, a binding protein disclosed herein can compete for binding with clone CL-105967.

In certain embodiments, competitive binding can be evaluated using routine cross-blocking assays, such as the assay described in ANTIBODIES, A LABORATORY MANUAL, Cold Spring Harbor Laboratory, Ed Harlow and David Lane (1st edition 1988, 2nd edition 2014). In some embodiments, competitive binding is identified when a test antibody or binding protein reduces binding of a reference antibody or binding protein (e.g., a binding protein comprising CDRs and/or variable domains selected from those identified in Tables 2-7) to LRP-8 by at least about 50% in the cross-blocking assay (e.g., 50%, 60%, 70%, 80%, 90%, 95%, 99%, 99.5%, or more, or any percentage in between), and/or vice versa. In some embodiments, competitive binding can be due to shared or similar (e.g., partially overlapping) epitopes, or due to steric hindrance where antibodies or binding proteins bind at nearby epitopes. See, e.g., Tzartos, Methods in Molecular Biology, vol. 66, Epitope Mapping Protocols, pages 55-66, Humana Press Inc. (1998) ("only marked mutual crosscompetition should be taken as unequivocal evidence of overlapping epitopes, since weak or one-way inhibition may simply reflect a decrease in affinity owing to steric or allosteric effects. Therefore, we completely ignored cases of weak inhibition (<25%) and essentially only considered inhibition of >50%"). In some embodiments, competitive binding can be used to sort groups of binding proteins that share similar epitopes, e.g., those that compete for binding can be "binned" as a group of binding proteins that have overlapping or nearby epitopes, while those that do not compete are placed in a separate group of binding proteins that do not have overlapping or nearby epitopes.

In various embodiments, the VH and VL domains disclosed herein are 80%, 85%, 90%, 91%, 92%, 93%, 94%, 95%, 96%, 97%, 98%, 99% or 100% identical (i.e., they share the specified percent homology) to one or more of those shown in Tables 2-7. According to certain embodiments, an LRP-8 binding protein can have one or more heavy chain variable domains and/or one or more light chain variable domains as set forth in any one of Tables 2-7. In certain embodiments, an LRP-8 binding protein can have CDR sequences selected from one or more of the heavy chain variable domains and/or one or more light chain variable domains as set forth in any one of Tables 2-7. In some embodiments, a binding protein disclosed herein comprises heavy chain CDR sequences and/or a heavy chain variable domain and its paired light chain CDR sequences and/or a paired light chain variable domain selected from Tables 2-7.

TABLE 2

LRP-8 Binding Protein Heavy Chain Variable Domain Amino Acid Sequences (CDRs In Bold)

| SEQ ID NO: | Clone | Heavy Chain Variable Domain (CDRs in bold) 12345678901234567890123456789012345678901234567890 |
|---|---|---|
| 69 | CL-33867 (ML201-2B4.2B1.2H10) | DVKLVASGGGLVKPGGSLKLSCAASGFTLSRYAMSWVRQTPEKRLEWVAYIRNGGDYIYYADTVKGRFTISRDNARNTLYLQMSSLKSEDTAMYYCTREGSYYNFDYWGQGTTLTVSS |
| 61 | CL-33866 (ML201-8F3.3D7) | EVQLVESGGDLVKPGGSLKLSCAASRFTFSNFGMSWVRQTPDKRLEWVATISSGGRYTYYPDSVKGRFTISRDNAKNTLYLQMSSLRSEDTAMYYCARDYLYAMDYWGQGTSVTVSS |
| 62 | CL-33865 (ML199-11H1.5B2) | EVQLVESGGDLVKPGGSLKLSCAASRFTFSNYGMSWVRQTPDKRLEWVATISSGGRYTYYPDSVKGRFTISRDNAKNTLYLQMSSLRSEDTAMYYCARDYLYAMDYWGQGTSVTVSS |
| 70 | hML199-11H1-5B2.VH.1 | EVQLVESGGGLVKPGGSLRLSCAASRFTFSNYGMSWVRQAPGKGLEWVSTISSGGRYTYYPDSVKGRFTISRDNAKNSLYLQMNSLRAEDTAVYYCARDYLYAMDYWGQGTTVTVSS |
| 71 | hML199-11H1-5B2.VH.1a | EVQLVESGGGLVKPGGSLRLSCAASRFTFSNYGMSWVRQAPGKGLEWVATISSGGRYTYYPDSVKGRFTISRDNAKNSLYLQMNSLRAEDTAVYYCARDYLYAMDYWGQGTTVTVSS |

TABLE 2-continued

LRP-8 Binding Protein Heavy Chain Variable Domain Amino Acid Sequences (CDRs In Bold)

| SEQ ID NO: | Clone | Heavy Chain Variable Domain (CDRs in bold) 12345678901234567890123456789012345678901234567890 |
|---|---|---|
| 72 | ML199.11H1.5B2.1A.15 | EVQLVESGGGLVKPGGSLRLSCAASRFTFSNYGMSWVRQAPGKGLEWVST ISSGGRYTYYPDHVKGRFTISRDNAKNSLYLQMNSLRAEDTAVYYCARDY LYAMDYWGQGTTVTVSS |
| 72 | ML199.11H1.5B2.1A.16 | EVQLVESGGGLVKPGGSLRLSCAASRFTFSNYGMSWVRQAPGKGLEWVST ISSGGRYTYYPDHVKGRFTISRDNAKNSLYLQMNSLRAEDTAVYYCARDY LYAMDYWGQGTTVTVSS |
| 72 | ML199.11H1.5B2.1A.17 | EVQLVESGGGLVKPGGSLRLSCAASRFTFSNYGMSWVRQAPGKGLEWVST ISSGGRYTYYPDHVKGRFTISRDNAKNSLYLQMNSLRAEDTAVYYCARDY LYAMDYWGQGTTVTVSS |
| 72 | ML199.11H1.5B2.1A.18 | EVQLVESGGGLVKPGGSLRLSCAASRFTFSNYGMSWVRQAPGKGLEWVST ISSGGRYTYYPDHVKGRFTISRDNAKNSLYLQMNSLRAEDTAVYYCARDY LYAMDYWGQGTTVTVSS |
| 72 | ML199.11H1.5B2.1A.19 | EVQLVESGGGLVKPGGSLRLSCAASRFTFSNYGMSWVRQAPGKGLEWVST ISSGGRYTYYPDHVKGRFTISRDNAKNSLYLQMNSLRAEDTAVYYCARDY LYAMDYWGQGTTVTVSS |
| 72 | ML199.11H1.5B2.1A.20 | EVQLVESGGGLVKPGGSLRLSCAASRFTFSNYGMSWVRQAPGKGLEWVST ISSGGRYTYYPDHVKGRFTISRDNAKNSLYLQMNSLRAEDTAVYYCARDY LYAMDYWGQGTTVTVSS |
| 72 | ML199.11H1.5B2.1A.21 | EVQLVESGGGLVKPGGSLRLSCAASRFTFSNYGMSWVRQAPGKGLEWVST ISSGGRYTYYPDHVKGRFTISRDNAKNSLYLQMNSLRAEDTAVYYCARDY LYAMDYWGQGTTVTVSS |
| 73 | ab58216 | EVHLQQSGPEVVKPGASVKISCKASGYIISGYFLNWVKQSHGKSLEWVGR INPYSGDTFFNQKFKGKATLTVDKSSNTAHMELRSLTSEDSAVFYCARED IGRFAYWGQGTLVTVSA |
| 74 | BGK-2C8.E6.D3 | QVTLKESGPGILQPSQTLSLTCTFSGFSLNTYGMGVGWVRQPSGKGLEWLA NIWWDDDKFYNPSLKNRLTVSKDTSNNQAFLRITNGDTADTATYFCARIL GEDIGGALDAWGQGTSVTVSS |
| 75 | BGK-5D10-E4 | QVQLRETGPDLVQPTQTLSLTCTVSGFSLTNYPVQWVRQPPGSGLEWLGI MWPSGAADFNPALKSRLSISRDTSKSQFFLRMDNLQTDDTAIYFCARGRG YSSPYAMDAWGQGTSVTVSS |
| 76 | BGK-6E3-F4 | EVQLVESGGGLVQPGKSLKLSCAASGFTFSDYNMAWVRQAPKKGLEWVAT IMYDGSRTFYRDSVKGRYTFSRDNAKSTLYLQMDSLRSEDTATYYCATGR NWFAYWGQGTLVTVSS |
| 59 | BGK-2C8.8C | EVQLVESGGGLVQPGRSLKLSCAASGFTVSDYYMAWVRQAPKKGLEWVAS ISYEGSSTYYGDSVKGRFTISRDNAKSILYLQMNSLRSEDTATYYCARPL RYYGYNYRFAYWGQGTLVTVSS |
| 77 | CL-105945 (BGK-2H4) | EVQLVESGGGLVQPGRSMKLSCAASGFTFSSFPMAWVRQAPTKGLEWVAT VSTRGGHTYYRDSVKGRFTISRDNAKNTLYLQMNSLRSEDTATYYCIREG TSLFAYWGQGTLVTVSS |
| 78 | CL-105959 (BGK-7A11) | QVTLKESGPGILQPSQTLSLTCTFSGFSLSTYGMGVGWIRQPAGTGLEWLA NIWWDDDKYYNPSLKNRLTISKDTSNNQVFLKITNVDTADTATYYCART TKPYYFDYWGQGVMVTVSS |
| 79 | CL-105960 (BGK-7F7) | QVTLKESGPGILQPSQTLSLTCTFSGFSLSTYGLGVGWIRQPSGKGLEWLA NIWWDDAKYYNPSLKNRLTISKDTSNNQAFLKIPNVDTADTARYYCART TKPYYFDYWGQGVMVTVSS |
| 80 | CL-105967 (BGK-9D10-2) | EVQLVESGGGLVQSGRSLKLSCAASGFTFSNYYMAWVRQAPKKGLEWVAT ITTSGSRSFYPDSVKGRFTISRDNAKSSLYLQINSLKSEDTATYYCARRG PLGYFDHWGRVMVTVSS |
| 81 | CL-105969 (BGK-6B5-2) | QVSLQESGPGILQPSQTLSLTCTFSGFSLSTFGMGVGWIRQPSGKGLEWLA NIWWDDDKYYNPSLKNRLTISKDTSNNQAFLKITNVDTADTATYYCART AKPYYFDYWGHGVMVTVSS |
| 82 | CL-134994 | ELQLQESGPGLVKPSETLSLTCTVSGGSISSSSYYWGWIRQPPGKGLEWIG SIYYSGSTYYNPSLKSRVTISVDTSKNQFSLKLSSVTAADTAVYYCARQ GEIGNFDVWGQGTLVTVSS |

TABLE 2-continued

LRP-8 Binding Protein Heavy Chain Variable Domain Amino Acid Sequences (CDRs In Bold)

| SEQ ID NO: | Clone | Heavy Chain Variable Domain (CDRs in bold)<br>123456789012345678901234567890123456789012345678901234567890 |
|---|---|---|
| 83 | CL-135325 | EVQLVQSGGGLVQPGGSLRLSCAASGFTFSIYAMSWVRQAPGKGLEWVSV<br>ISCSAGSTYYADSVKGRFTISRDNSKNTLYLQMNSLRAEDTAVYYCARHS<br>VHEEFPFDVWGQGTLVTVSS |
| 84 | CL-135359 | EVQLVQSGGGLVQPGGSLRLSCAASGFTFSSYAMSWVRQAPGKGLEWVSV<br>ISCSGGTTYYADSVKGRFTISRDNSKNTLYLQMNSLRAEDTAVYYCARNG<br>GQFDLWGQGTLVTVSS |

In certain embodiments, an LRP-8 binding protein can comprise CDR sequences selected from one or more of the following heavy chain CDR sequences in Table 3. In some embodiments, an LRP-8 binding protein can include a set of heavy chain CDR sequences (e.g., an HCDR1, HCDR2, and HCDR3) selected from any of the sets shown below. In some embodiments, a binding protein can comprise a heavy chain CDR set selected from Table 3 and any light chain CDR set selected from Table 6. In some embodiments, a binding protein can comprise a heavy chain CDR set selected from Table 3 and its paired light chain CDR set in Table 6 (e.g., the heavy chain CDR set from clone ML199-11H1.5B2 paired with the light chain CDR set from clone ML199-11H1.5B2).

TABLE 3

LRP-8 Binding Protein Heavy Chain CDR Amino Acid Sequences

| Clone | HCDR1 | HCDR2 | HCDR3 |
|---|---|---|---|
| CL-33867<br>(ML201-2B4.2B1.2H10) | GFTLSRYAMS<br>(SEQ ID NO: 85) | YIRNGGDYIYYADTVKG<br>(SEQ ID NO: 86) | EGSYYNFDY<br>(SEQ ID NO: 87) |
| CL-33866<br>(ML201-8F3.3D7) | RFTFSNFGMS<br>(SEQ ID NO: 88) | TISSGGRYTYYPDSVKG<br>(SEQ ID NO: 89) | DYLYAMDY<br>(SEQ ID NO: 90) |
| CL-33865<br>(ML199-11H1.5B2) | RFTFSNYGMS<br>(SEQ ID NO: 91) | TISSGGRYTYYPDSVKG<br>(SEQ ID NO: 89) | DYLYAMDY<br>(SEQ ID NO: 90) |
| hML199-11H1-5B2.VH.1 | RFTFSNYGMS<br>(SEQ ID NO: 92) | TISSGGRYTYYPDSVKG<br>(SEQ ID NO: 93) | DYLYAMDY<br>(SEQ ID NO: 46) |
| hML199-11H1-5B2.VH.1a | RFTFSNYGMS<br>(SEQ ID NO: 92) | TISSGGRYTYYPDSVKG<br>(SEQ ID NO: 93) | DYLYAMDY<br>(SEQ ID NO: 46) |
| ML199.11H1.5B2.1A.15 | RFTFSNYGMS<br>(SEQ ID NO: 92) | TISSGGRYTYYPDHVKG<br>(SEQ ID NO: 94) | DYLYAMDY<br>(SEQ ID NO: 46) |
| ML199.11H1.5B2.1A.16 | RFTFSNYGMS<br>(SEQ ID NO: 92) | TISSGGRYTYYPDHVKG<br>(SEQ ID NO: 94) | DYLYAMDY<br>(SEQ ID NO: 46) |
| ML199.11H1.5B2.1A.17 | RFTFSNYGMS<br>(SEQ ID NO: 92) | TISSGGRYTYYPDHVKG<br>(SEQ ID NO: 94) | DYLYAMDY<br>(SEQ ID NO: 46) |
| ML199.11H1.5B2.1A.18 | RFTFSNYGMS<br>(SEQ ID NO: 92) | TISSGGRYTYYPDHVKG<br>(SEQ ID NO: 94) | DYLYAMDY<br>(SEQ ID NO: 46) |
| ML199.11H1.5B2.1A.19 | RFTFSNYGMS<br>(SEQ ID NO: 92) | TISSGGRYTYYPDHVKG<br>(SEQ ID NO: 94) | DYLYAMDY<br>(SEQ ID NO: 46) |
| ML199.11H1.5B2.1A.20 | RFTFSNYGMS<br>(SEQ ID NO: 92) | TISSGGRYTYYPDHVKG<br>(SEQ ID NO: 94) | DYLYAMDY<br>(SEQ ID NO: 46) |
| ML199.11H1.5B2.1A.21 | RFTFSNYGMS<br>(SEQ ID NO: 92) | TISSGGRYTYYPDHVKG<br>(SEQ ID NO: 94) | DYLYAMDY<br>(SEQ ID NO: 46) |
| ab58216 | GYIISGYFLN<br>(SEQ ID NO: 95) | RINPYSGDTFFNQKFKG<br>(SEQ ID NO: 96) | EDIGRFAY<br>(SEQ ID NO: 97) |
| BGK-2C8.E6.D3 | GFSLNTYGMGVG<br>(SEQ ID NO: 98) | NIWWDDDKFYNPSLKN<br>(SEQ ID NO: 99) | ILGEDIGGALDA<br>(SEQ ID NO: 100) |
| BGK-5D10-E4 | GFSLTNYPVQ<br>(SEQ ID NO: 101) | IMWPSGAADFNPALKS<br>(SEQ ID NO: 102) | GRGYSSPYAMDA<br>(SEQ ID NO: 103) |

TABLE 3-continued

LRP-8 Binding Protein Heavy Chain CDR Amino Acid Sequences

| Clone | HCDR1 | HCDR2 | HCDR3 |
|---|---|---|---|
| BGK-6E3-F4 | GFTFSDYNMA (SEQ ID NO: 104) | TIMYDGSRTFYRDSVKG (SEQ ID NO: 105) | GRNWFAY (SEQ ID NO: 106) |
| BGK-2C8.8C | GFTVSDYYMA (SEQ ID NO: 107) | SISYEGSSTYYGDSVKG (SEQ ID NO: 108) | PLRYYGYNYRFAY (SEQ ID NO: 109) |
| CL-105945 (BGK-2H4) | GFTFSSFPMA (SEQ ID NO: 110) | TVSTRGGHTYYRDSVKG (SEQ ID NO: 111) | EGTSLFAY (SEQ ID NO: 112) |
| CL-105959 (BGK-7A11) | GFSLSTYGMGVG (SEQ ID NO: 113) | NIWWDDDKYYNPSLKN (SEQ ID NO: 114) | TTKPYYFDY (SEQ ID NO: 115) |
| CL-105960 (BGK-7F7) | GFSLSTYGLGVG (SEQ ID NO: 116) | NIWWDDAKYYNPSLKN (SEQ ID NO: 117) | TTKPYYFDY (SEQ ID NO: 115) |
| CL-105967 (BGK-9D10-2) | GFTFSNYYMA (SEQ ID NO: 118) | TITTSGSRSFYPDSVKG (SEQ ID NO: 119) | RGPLGYFDH (SEQ ID NO: 120) |
| CL-105969 (BGK-6B5-2) | GFSLSTFGMGVG (SEQ ID NO: 121) | NIWWDDDKYYNPSLKN (SEQ ID NO: 114) | TAKPYYFDY (SEQ ID NO: 122) |
| CL-134994 | GGSISSSSYYWG (SEQ ID NO: 123) | SIYYSGSTYYNPSLKS (SEQ ID NO: 124) | QGEIGNFDV (SEQ ID NO: 125) |
| CL-135325 | GFTFSIYAMS (SEQ ID NO: 126) | VISCSAGSTYYADSVKG (SEQ ID NO: 127) | HSVHEEFPFDV (SEQ ID NO: 128) |
| CL-135359 | GFTFSSYAMS (SEQ ID NO: 129) | VISCSGGTTYYADSVKG (SEQ ID NO: 130) | NGGQFDL (SEQ ID NO: 131) |

In certain embodiments, an LRP-8 binding protein can comprise a heavy chain variable domain sequence selected from any of the following sequences in Table 4. In some embodiments, a binding protein can comprise a heavy chain variable domain sequence selected from Table 4 and any light chain variable domain sequence selected from Table 7.

In some embodiments, a binding protein can comprise a heavy chain variable domain sequence selected from Table 4 and its paired light chain variable domain sequence in Table 6 (e.g., the heavy chain variable domain from clone ML199-11H1.5B2 paired with the light chain variable domain from clone ML199-11H1.5B2).

TABLE 4

LRP-8 Binding Protein Heavy Chain Variable Domain Amin Acid Sequences (CDRs in bold, gaps introduced to align frameworks; also depicted in FIG. 22A)

| SEQ ID NO: | Clone | Heavy Chain Variable Domain (CDRs in bold, gaps introduced to align frameworks) |
|---|---|---|
| 69 | CL-33867 (ML201-2B4.2B1.2H10) | DVKLVASGGGLVKPGGSLKLSCAASGFTLSRY--AMSWVRQTPEKRLEWVAYIRNGGDYIYYADTVKGRFTISRDNARNTLYLQMSSLKSEDTAMYYCTREGS-----YYNFDYWGQGTTLTVSS |
| 61 | CL-33866 (ML201-8F3.3D7) | EVQLVESGGDLVKPGGSLKLSCAASRFTFSNF--GMSWVRQTPDKRLEWVATISSGGRYTYYPDSVKGRFTISRDNAKNTLYLQMSSLRSEDTAMYYCAR-DY-----LYAMDYWGQGTSVTVSS |
| 62 | CL-33865 (ML199-11H1.5B2) | EVQLVESGGDLVKPGGSLKLSCAASRFTFSNY--GMSWVRQTPDKRLEWVATISSGGRYTYYPDSVKGRFTISRDNAKNTLYLQMSSLRSEDTAMYYCAR-DY-----LYAMDYWGQGTSVTVSS |
| 70 | hML199-11H1-5B2.VH.1 | EVQLVESGGGLVKPGGSLRLSCAASRFTFSNY--GMSWVRQAPGKGLEWVSTISSGGRYTYYPDSVKGRFTISRDNAKNSLYLQMNSLRAEDTAVYYCAR-DY-----LYAMDYWGQGTTVTVSS |
| 71 | hML199-11H1-5B2.VH.1a | EVQLVESGGGLVKPGGSLRLSCAASRFTFSNY--GMSWVRQAPGKGLEWVATISSGGRYTYYPDSVKGRFTISRDNAKNSLYLQMNSLRAEDTAVYYCAR-DY-----LYAMDYWGQGTTVTVSS |
| 72 | ML199.11H1.5B2.1A.15 | EVQLVESGGGLVKPGGSLRLSCAASRFTFSNY--GMSWVRQAPGKGLEWVSTISSGGRYTYYPDHVKGRFTISRDNAKNSLYLQMNSLRAEDTAVYYCAR-DY-----LYAMDYWGQGTTVTVSS |

TABLE 4-continued

LRP-8 Binding Protein Heavy Chain Variable Domain Amin Acid
Sequences (CDRs in bold, gaps introduced to align frameworks;
also depicted in FIG. 22A)

| SEQ ID NO: | Clone | Heavy Chain Variable Domain (CDRs in bold, gaps introduced to align frameworks) |
|---|---|---|
| 72 | ML199.11H1.5B2.1 A.16 | EVQLVESGGGLVKPGGSLRLSCAASRFTFSNY--GMSWVRQAPGKGLEWVSTISSGGRYTYYPDHVKGRFTISRDNAKNSLYLQMNSLRAEDTAVYYCAR-DY-----LYAMDYWGQGTTVTVSS |
| 72 | ML199.11H1.5B2.1 A.17 | EVQLVESGGGLVKPGGSLRLSCAASRFTFSNY--GMSWVRQAPGKGLEWVSTISSGGRYTYYPDHVKGRFTISRDNAKNSLYLQMNSLRAEDTAVYYCAR-DY-----LYAMDYWGQGTTVTVSS |
| 72 | ML199.11H1.5B2.1 A.18 | EVQLVESGGGLVKPGGSLRLSCAASRFTFSNY--GMSWVRQAPGKGLEWVSTISSGGRYTYYPDHVKGRFTISRDNAKNSLYLQMNSLRAEDTAVYYCAR-DY-----LYAMDYWGQGTTVTVSS |
| 72 | ML199.11H1.5B2.1 A.19 | EVQLVESGGGLVKPGGSLRLSCAASRFTFSNY--GMSWVRQAPGKGLEWVSTISSGGRYTYYPDHVKGRFTISRDNAKNSLYLQMNSLRAEDTAVYYCAR-DY-----LYAMDYWGQGTTVTVSS |
| 72 | ML199.11H1.5B2.1 A.20 | EVQLVESGGGLVKPGGSLRLSCAASRFTFSNY--GMSWVRQAPGKGLEWVSTISSGGRYTYYPDHVKGRFTISRDNAKNSLYLQMNSLRAEDTAVYYCAR-DY-----LYAMDYWGQGTTVTVSS |
| 72 | ML199.11H1.5B2.1 A.21 | EVQLVESGGGLVKPGGSLRLSCAASRFTFSNY--GMSWVRQAPGKGLEWVSTISSGGRYTYYPDHVKGRFTISRDNAKNSLYLQMNSLRAEDTAVYYCAR-DY-----LYAMDYWGQGTTVTVSS |
| 73 | ab58216 | EVHLQQSGPEVVKPGASVKISCKASGYIISGY--FLNWVKQSHGKSLEWVGRINPYSGDTFFNQKFKGKATLTVDKSSNTAHMELRSLTSEDSAVFYCAREDI------GRFAYWGQGTLVTVSA |
| 74 | BGK-2C8.E6.D3 | QVTLKESGPGILQPSQTLSLTCTFSGFSLNTYGMGVGWVRQPSGKGLEWLANIWWDDDK-FYNPSLKNRLTVSKDTSNNQAFLRITNGDTADTATYFCARILG--EDIGGALDAWGQGTSVTVSS |
| 75 | BGK-5D10-E4 | QVQLRETGPDLVQPTQTLSLTCTVSGFSLTNY--PVQWVRQPPGSGLEWLGIMWPSGAA-DFNPALKSRLSISRDTSKSQFFLRMDNLQTDDTAIYFCARGRG--YSSPYAMDAWGQGTSVTVSS |
| 76 | BGK-6E3-F4 | EVQLVESGGGLVQPGKSLKLSCAASGFTFSDY--NMAWVRQAPKKGLEWVATIMYDGSRTFYRDSVKGRYTFSRDNAKSTLYLQMDSLRSEDTATYYCAT-------GRNWFAYWGQGTLVTVSS |
| 59 | BGK-2C8.8C | EVQLVESGGGLVQPGRSLKLSCAASGFTVSDY--YMAWVRQAPKKGLEWVASISYEGSSTYYGDSVKGRFTISRDNAKSILYLQMNSLRSEPTATYYCARPLR-YYGYNYRFAYWGQGTLVTVSS |
| 77 | CL-105945 (BGK-2H4) | EVQLVESGGGLVQPGRSMKLSCAASGFTFSSF--PMAWVRQAPTKGLEWVATVSTRGGHTYYRDSVKGRFTISRDNAKNTLYLQMNSLRSEDTATYYCIREG------TSLFAYWGQGTLVTVSS |
| 78 | CL-105959 (BGK-7A11) | QVTLKESGPGILQPSQTLSLTCTFSGFSLSTYGMGVGWIRQPAGTGLEWLANIWWDDDK-YYNPSLKNRLTISKDTSNNQVFLKITNVDTADTATYYCARTTK--PYY---FDYWGQGVMVTVSS |
| 79 | CL-105960 (BGK-7F7) | QVTLKESGPGILQPSQTLSLTCTFSGFSLSTYGLGVGWIRQPSGKGLEWLANIWWDDAK-YYNPSLKNRLTISKDTSNNQAFLKIPNVDTADTARYYCARTTK--PYY---FDYWGQGVMVTVSS |
| 80 | CL-105967 (BGK-9D10-2) | EVQLVESGGGLVQSGRSLKLSCAASGFTFSNY--YMAWVRQAPKKGLEWVATITTSGSRSFYPDSVKGRFTISRDNAKSSLYLQINSLKSEDTATYYCARR-----GPLGYFDHWGRGVMVTVSS |
| 81 | CL-105969 (BGK-6B5-2) | QVSLQESGPGILQPSQTLSLTCTFSGFSLSTFGMGVGWIRQPSGKGLEWLANIWWDDDK-YYNPSLKNRLTISKDTSNNQAFLKITNVDTADTATYYCARTAK--PYY---FDYWGHGVMVTVSS |
| 82 | CL-134994 | ELQLQESGPGLVKPSETLSLTCTVSGGSISSSSYYWGWIRQPPGKGLEWIGSIYYSGST-YYNPSLKSRVTISVDTSKNQFSLKLSSVTAADTAVYYCARQGEIGN-----FDVWGQGTLVTVSS |

TABLE 4-continued

LRP-8 Binding Protein Heavy Chain Variable Domain Amin Acid Sequences (CDRs in bold, gaps introduced to align frameworks; also depicted in FIG. 22A)

| SEQ ID NO: | Clone | Heavy Chain Variable Domain (CDRs in bold, gaps introduced to align frameworks) |
|---|---|---|
| 83 | CL-135325 | EVQLVQSGGGLVQPGGSLRLSCAASGFTFSIYA--<br>MSWVRQAPGKGLEWVSVISCSAGSTYYADSVKGRFTISRDNSKNTLYLQMNSL<br>RAEDTAVYYCARHSVH---EEFPFDVWGQGTLVTVSS |
| 84 | CL-135359 | EVQLVQSGGGLVQPGGSLRLSCAASGFTFSSYA--<br>MSWVRQAPGKGLEWVSVISCSGGTTYYADSVKGRFTISRDNSKNTLYLQMNSL<br>RAEDTAVYYCARN-------GGQFDLWGQGTLVTVSS |

According to certain embodiments, an LRP-8 binding protein can comprise one or more light chain variable domains as set forth in Table 5.

TABLE 5

LRP-8 Binding Protein Light Chain Variable Domain Sequences (CDRs In Bold)

| SEQ ID NO: | Clone | Light Chain Variable Domain (CDRs in bold)<br>12345678901234567890123456789012345678901234567890 |
|---|---|---|
| 132 | CL-33867<br>(ML201-2B4.2B1.2H10) | DVLMTQTPLSLPVSLGDQASISCRSSQSIVHSNGNTYLEWYLQKPGQSPN<br>LLIFKVSNRFSGVPDRFIGSGSGTDFTLKISRVEAEDLGVYYCFQGSHVP<br>WTFGGGTKLEIK |
| 63 | CL-33866<br>(ML201-8F3.3D7) | DVVMTQTPLSLPVSLGDQASISCRSSQSLVYSNGNTYLHWYLQKPGQSPK<br>VLMYKVSNRFSGVSDRFSGSGSGTDFTLKISRVEAEDLGVYFCSQSTHVP<br>LTFGAGTKLELK |
| 63 | CL-33865<br>(ML199-11H1.5B2) | DVVMTQTPLSLPVSLGDQASISCRSSQSLVYSNGNTYLHWYLQKPGQSPK<br>VLMYKVSNRFSGVSDRFSGSGSGTDFTLKISRVEAEDLGVYFCSQSTHVP<br>LTFGAGTKLELK |
| 133 | hML199-11H1-5B2VL.1 | DIVMTQSPLSLPVTPGEPASISCRSSQSLVYSNGNTYLHWYLQKPGQSPQ<br>LLIYKVSNRFSGVPDRFSGSGSGTDFTLKISRVEAEDVGVYYCSQSTHVP<br>LTFGQGTKLEIK |
| 134 | hML199-11H1-5B2VL.1a | DVVMTQSPLSLPVTPGEPASISCRSSQSLVYSNGNTYLHWYLQKPGQSPQ<br>VLMYKVSNRFSGVPDRFSGSGSGTDFTLKISRVEAEDVGVYFCSQSTHVP<br>LTFGQGTKLEIK |
| 135 | hML199-11H1-5B2VL.1b | DVVMTQSPLSLPVTPGEPASISCRSSQSLVYSNGNTYLHWYLQKPGQSPQ<br>VLIYKVSNRFSGVPDRFSGSGSGTDFTLKISRVEAEDVGVYYCSQSTHVP<br>LTFGQGTKLEIK |
| 136 | ML199.11H1.5B2.1A.15 | DVVMTQSPLSLPVTPGEPASISCRSSQSLVYSNENTYLHWYLQKPGQSPQ<br>VLMYKVSNRFSGVPDRFSGSGSGTDFTLKISRVEAEDVGVYFCSQSTHVP<br>LTFGQGTKLEIK |
| 137 | ML199.11H1.5B2.1A.16 | DVVMTQSPLSLPVTPGEPASISCRSSQSLVYSTGNTYLHWYLQKPGQSPQ<br>VLMYKVSNRFSGVPDRFSGSGSGTDFTLKISRVEAEDVGVYFCSQSTHVP<br>LTFGQGTKLEIK |
| 138 | ML199.11H1.5B2.1A.17 | DVVMTQSPLSLPVTPGEPASISCRSSQSLVYSNLNTYLHWYLQKPGQSPQ<br>VLMYKVSNRFSGVPDRFSGSGSGTDFTLKISRVEAEDVGVYFCSQSTHVP<br>LTFGQGTKLEIK |
| 139 | ML199.11H1.5B2.1A.18 | DVVMTQSPLSLPVTPGEPASISCRSSQSLVYSNKNTYLHWYLQKPGQSPQ<br>VLMYKVSNRFSGVPDRFSGSGSGTDFTLKISRVEAEDVGVYFCSQSTHVP<br>LTFGQGTKLEIK |
| 140 | ML199.11H1.5B2.1A.19 | DVVMTQSPLSLPVTPGEPASISCRSSQSLVYSRGNTYLHWYLQKPGQSPQ<br>VLMYKVSNRFSGVPDRFSGSGSGTDFTLKISRVEAEDVGVYFCSQSTHVP<br>LTFGQGTKLEIK |
| 141 | ML199.11H1.5B2.1A.20 | DVVMTQSPLSLPVTPGEPASISCRSSQSLVYSWGNTYLHWYLQKPGQSPQ<br>VLMYKVSNRFSGVPDRFSGSGSGTDFTLKISRVEAEDVGVYFCSQSTHVP<br>LTFGQGTKLEIK |

TABLE 5-continued

LRP-8 Binding Protein Light Chain Variable Domain Sequences (CDRs In Bold)

| SEQ ID NO: | Clone | Light Chain Variable Domain (CDRs in bold) 12345678901234567890123456789012345678901234567890 |
|---|---|---|
| 142 | ML199.11H1.5B2.1A.21 | DVVMTQSPLSLPVTPGEPASISCRSSQSLVYSPGNTYLHWYLQKPGQSPQ VLMYKVSNRFSGVPDRFSGSGSGTDFTLKISRVEAEDVGVYFCSQSTHVP LTFGQGTKLEIK |
| 143 | ab58216 | DVLMTQTPLSLPVSLGDQASISCRSSQTIVHSNGNTYLEWYLQKPGQSPK LLIYKVSNRFSGVPDRFSGSGSGTDFTLKISRVEAEDLGVYYCFQGSHAP PTFGGGTKLEIK |
| 144 | BGK-2C8.E6.D3 | DTVLTQSPALAVSPGERVSISCRASEGVNSYMHWYQQNPGQQSKLLIYRT SNLASGVPARFGGSGSGTDFTLTIDPVEADDTATYFCQQSWNDPPTFGGG TKLELK |
| 145 | BGK-5D10-E4 | DIQMTQSPASLSASLGETVSIECLASEDIYNNLAWYQQKPGKSPHLLIHF TSNLQDGVPSRFSGSGSGTQYSLKINSLESEDGATYFCLQDSEYPLTFGS GTKLEIK |
| 146 | BGK-6E3-F4 | DIIMTQSPSSLAVSAGETVTINCKSSQSLLSSGKQKNYLAWYQQKPGQSP KLLIYLASTRESGVPDRFIGSGSGTDFTLTISSMQAEDLAIYYCQQHYDT PLTFGSGTKLEIK |
| 60 | BGK-2C8.8C | DIQMSQSPPVLSASVGDRVTLSCKASQNIHKNLDWYQQKHGEAPKLLIYYT DNLQTGIPSRFSGSGSGTDYTLTISSLQPEDVATYYCYQYNSGPTFGAG TKLELQ |
| 147 | CL-105945 (BGK-2H4) | DIQMTQSPPSLSASLGETVSIECLASEDISNYLAWYQQKPGKSPQLLIYYA NSLEDGVPSRFSGSGSGTQYSLKISNMQPEDEGVYHCQQGYNYPYTFGA GTKLELK |
| 148 | CL-105959 (BGK-7A11) | HFVLAQPNSVSTNLGSTVKLSCKRSTGNSGSNYVNWYQQYEGRSPTTMIYR DDKRPDGVPDRFSGSIDRSSNSALLTINNVQTEDEADYFCQSYSSGINI FGGGTKLTVL |
| 149 | CL-105960 (BGK-7F7) | HFVLAQPNSVSTNLGSTVKLSCKRSTANIGSNYVNWYQQHEGRSPTTLIYR DDRRPDGVPDRFSGSIDRSSNSALLTINNVQTEDEADYFCQSYSSGINI FGGGTKLTVL |
| 150 | CL-105967 (BGK-9D10-2) | DIQMTQSPPSLPASLGDKVTITCQASQNINKYIAWYQQKPGKAPRLLIRF TSTLESDTPSRFSGSGSGRDYSFSISNVESEDFASYYCLHYDNLPPWTFG GGTKLELK |
| 151 | CL-105969 (BGK-6B5-2) | HFVLAQPNSVSTNLGNTVKLSCKRSTGNIGSNYVNWYQQHEGRSPTTLIYR DDKRPDGVPDRFSGSFDRSSNSALLTINNVQTEDEADYFCQSYNSGINF FGGGTKLTVL |
| 152 | CL-134994 | EIVLTQSPGTLSLSPGERATLSCRASQSVGSCYLAWYQQKPGQAPRLLIYG ASSRATGIPDRFSGSGSGTDFTLTISRLEPEDFAVYYCQHYVRSPITFG GGTKVEIK |
| 153 | CL-135325 | DIQMTQSPSSLSASVGDRVTITCRASQSIGSYLNWYQQKPGKAPKLLIYAA SSLQSGVPSRFSGSGSGTDFTLTISSLQPEDFATYYCQQSYIPPLTFGG GTKVEIK |
| 154 | CL-135359 | DIQMTQSPSSLSASVGDRVTITCRASQGICTYLNWYQQKPGKAPKLLIYAA SSLQSGVPSRFSGSGSGTDFTLTISSLQPEDFATYYCQQSYNPPLTFGG GTKVEIK |

According to certain embodiments, an LRP-8 binding protein can comprise one or more sequences selected from or homologous to the following light chain CDR sequences in Table 6.

TABLE 6

LRP-8 Binding Protein Light Chain CDR Sequences

| Clone | LCDR1 | LCDR2 | LCDR3 |
|---|---|---|---|
| CL-33867 (ML201-2B4.2B1.2H10) | RSSQSIVHSNGNTYLE (SEQ ID NO: 155) | KVSNRFS (SEQ ID NO: 48) | FQGSHVPWT (SEQ ID NO: 156) |

TABLE 6-continued

LRP-8 Binding Protein Light Chain CDR Sequences

| Clone | LCDR1 | LCDR2 | LCDR3 |
| --- | --- | --- | --- |
| CL-33866 (ML201-8F3.3D7) | RSSQSLVYSNGNTYLH (SEQ ID NO: 157) | KVSNRFS (SEQ ID NO: 48) | SQSTHVPLT (SEQ ID NO: 49) |
| CL-33865 (ML199-11H1.5B2) | RSSQSLVYSNGNTYLH (SEQ ID NO: 157) | KVSNRFS (SEQ ID NO: 48) | SQSTHVPLT (SEQ ID NO: 49) |
| hML199-11H1-5B2VL.1 | RSSQSLVYSNGNTYLH (SEQ ID NO: 157) | KVSNRFS (SEQ ID NO: 48) | SQSTHVPLT (SEQ ID NO: 49) |
| hML199-11H1-5B2VL.1a | RSSQSLVYSNGNTYLH (SEQ ID NO: 157) | KVSNRFS (SEQ ID NO: 48) | SQSTHVPLT (SEQ ID NO: 49) |
| hML199-11H1-5B2VL.1b | RSSQSLVYSNGNTYLH (SEQ ID NO: 157) | KVSNRFS (SEQ ID NO: 48) | SQSTHVPLT (SEQ ID NO: 49) |
| ML199.11H1.5B2.1A.15 | RSSQSLVYSNENTYLH (SEQ ID NO: 158) | KVSNRFS (SEQ ID NO: 48) | SQSTHVPLT (SEQ ID NO: 49) |
| ML199.11H1.5B2.1A.16 | RSSQSLVYSTGNTYLH (SEQ ID NO: 159) | KVSNRFS (SEQ ID NO: 48) | SQSTHVPLT (SEQ ID NO: 49) |
| ML199.11H1.5B2.1A.17 | RSSQSLVYSNLNTYLH (SEQ ID NO: 160) | KVSNRFS (SEQ ID NO: 48) | SQSTHVPLT (SEQ ID NO: 49) |
| ML199.11H1.5B2.1A.18 | RSSQSLVYSNKNTYLH (SEQ ID NO: 161) | KVSNRFS (SEQ ID NO: 48) | SQSTHVPLT (SEQ ID NO: 49) |
| ML199.11H1.5B2.1A.19 | RSSQSLVYSRGNTYLH (SEQ ID NO: 162) | KVSNRFS (SEQ ID NO: 48) | SQSTHVPLT (SEQ ID NO: 49) |
| ML199.11H1.5B2.1A.20 | RSSQSLVYSWGNTYLH (SEQ ID NO: 163) | KVSNRFS (SEQ ID NO: 48) | SQSTHVPLT (SEQ ID NO: 49) |
| ML199.11H1.5B2.1A.21 | RSSQSLVYSPGNTYLH (SEQ ID NO: 164) | KVSNRFS (SEQ ID NO: 48) | SQSTHVPLT (SEQ ID NO: 49) |
| ab58216 | RSSQTIVHSNGNTYLE (SEQ ID NO: 165) | KVSNRFS (SEQ ID NO: 48) | FQGSHAPPT (SEQ ID NO: 166) |
| BGK-2C8.E6.D3 | RASEGVNSYMH (SEQ ID NO: 167) | RTSNLAS (SEQ ID NO: 168) | QQSWNDPPT (SEQ ID NO: 169) |
| BGK-5D10-E4 | LASEDIYNNLA (SEQ ID NO: 170) | FTSNLQD (SEQ ID NO: 171) | LQDSEYPLT (SEQ ID NO: 172) |
| BGK-6E3-F4 | KSSQSLLSSGKQKNYLA (SEQ ID NO: 173) | LASTRES (SEQ ID NO: 174) | QQHYDTPLT (SEQ ID NO: 175) |
| BGK-2C8.8C | KASQNIHKNLD (SEQ ID NO: 56) | YTDNLQT (SEQ ID NO: 57) | YQYNSGPT (SEQ ID NO: 58) |
| CL-105945 (BGK-2H4) | LASEDISNYLA (SEQ ID NO: 176) | YANSLED (SEQ ID NO: 177) | QQGYNYPYT (SEQ ID NO: 178) |
| CL-105959 (BGK-7A11) | KRSTGNSGSNYVN (SEQ ID NO: 179) | RDDKRPD (SEQ ID NO: 180) | QSYSSGINI (SEQ ID NO: 181) |

TABLE 6-continued

LRP-8 Binding Protein Light Chain CDR Sequences

| Clone | LCDR1 | LCDR2 | LCDR3 |
|---|---|---|---|
| CL-105960 (BGK-7F7) | KRSTANIGSNYVN (SEQ ID NO: 182) | RDDRRPD (SEQ ID NO: 183) | QSYSSGINI (SEQ ID NO: 181) |
| CL-105967 (BGK-9D10-2) | QASQNINKYIA (SEQ ID NO: 184) | FTSTLES (SEQ ID NO: 185) | LHYDNLPPWT (SEQ ID NO: 186) |
| CL-105969 (BGK-6B5-2) | KRSTGNIGSNYVN (SEQ ID NO: 187) | RDDKRPD (SEQ ID NO: 180) | QSYNSGINF (SEQ ID NO: 188) |
| CL-134994 | RASQSVGSCYLA (SEQ ID NO: 189) | GASSRAT (SEQ ID NO: 190) | QHYVRSPIT (SEQ ID NO: 191) |
| CL-135325 | RASQSIGSYLN (SEQ ID NO: 192) | AASSLQS (SEQ ID NO: 193) | QQSYIPPLT (SEQ ID NO: 194) |
| CL-135359 | RASQGICTYLN (SEQ ID NO: 195) | AASSLQS (SEQ ID NO: 193) | QQSYNPPLT (SEQ ID NO: 196) |

According to certain embodiments, an LRP-8 binding protein can comprise one or more light chain variable domains as set forth in Table 7.

TABLE 7

LRP-8 Binding Protein Light Chain Variable Domain Amino Acid Sequences (CDRs in bold, gaps introduced to align frameworks; also depicted in FIG. 22B)

| SEQ ID NO: | Clone | Light Chain Variable Domain (CDRs in bold, gaps introduced to align frameworks) |
|---|---|---|
| 132 | CL-33867 (ML201-2B4.2B1.2H10) | DVLMTQTPLSLPVSLGDQASISCRSSQSIVHSNGN-TYLEWYLQKPGQSPNLLIFKVSNRFSGVPDRFIGSG--SGTDFTLKISRVEAEDLGVYYCFQGSHVP-WTFGGGTKLEIK |
| 63 | CL-33866 (ML201-8F3.3D7) | DVVMTQTPLSLPVSLGDQASISCRSSQSLVYSNGN-TYLHWYLQKPGQSPKVLMYKVSNRFSGVSDRFSGSG--SGTDFTLKISRVEAEDLGVYFCSQSTHVP-LTFGAGTKLELK |
| 63 | CL-33865 (ML199-11H1.5B2) | DVVMTQTPLSLPVSLGDQASISCRSSQSLVYSNGN-TYLHWYLQKPGQSPKVLMYKVSNRFSGVSDRFSGSG--SGTDFTLKISRVEAEDLGVYFCSQSTHVP-LTFGAGTKLELK |
| 133 | hML199-11H1-5B2VL.1 | DIVMTQSPLSLPVTPGEPASISCRSSQSLVYSNGN-TYLHWYLQKPGQSPQLLIYKVSNRFSGVPDRFSGSG--SGTDFTLKISRVEAEDVGVYYCSQSTHVP-LTFGQGTKLEIK |
| 134 | hML199-11H1-5B2VL.1a | DVVMTQSPLSLPVTPGEPASISCRSSQSLVYSNGN--TYLHWYLQKPGQSPQVLMYKVSNRFSGVPDRFSGSG--SGTDFTLKISRVEAEDVGVYFCSQSTHVP-LTFGQGTKLEIK |
| 135 | hML199-11H1-5B2VL.1b | DVVMTQSPLSLPVTPGEPASISCRSSQSLVYSNGN--TYLHWYLQKPGQSPQVLIYKVSNRFSGVPDRFSGSG--SGTDFTLKISRVEAEDVGVYYCSQSTHVP-LTFGQGTKLEIK |
| 136 | ML199.11H1.5B2.1A.15 | DVVMTQSPLSLPVTPGEPASISCRSSQSLVYSNEN--TYLHWYLQKPGQSPQVLMYKVSNRFSGVPDRFSGSG--SGTDFTLKISRVEAEDVGVYFCSQSTHVP-LTFGQGTKLEIK |
| 137 | ML199.11H1.5B2.1A.16 | DVVMTQSPLSLPVTPGEPASISCRSSQSLVYSTGN--TYLHWYLQKPGQSPQVLMYKVSNRFSGVPDRFSGSG--SGTDFTLKISRVEAEDVGVYFCSQSTHVP-LTFGQGTKLEIK |
| 138 | ML199.11H1.5B2.1A.17 | DVVMTQSPLSLPVTPGEPASISCRSSQSLVYSNLN--TYLHWYLQKPGQSPQVLMYKVSNRFSGVPDRFSGSG--SGTDFTLKISRVEAEDVGVYFCSQSTHVP-LTFGQGTKLEIK |

TABLE 7-continued

LRP-8 Binding Protein Light Chain Variable Domain Amino Acid Sequences (CDRs in bold, gaps introduced to align frameworks; also depicted in FIG. 22B)

| SEQ ID NO: | Clone | Light Chain Variable Domain (CDRs in bold, gaps introduced to align frameworks) |
|---|---|---|
| 139 | ML199.11H1.5B2.1A.18 | DVVMTQSPLSLPVTPGEPASISCRSSQSLVYSNKN--TYLHWYLQKPGQSPQVLMYKVSNRFSGVPDRFSGSG--SGTDFTLKISRVEAEDVGVYFCSQSTHVP-LTFGQGTKLEIK |
| 140 | ML199.11H1.5B2.1A.19 | DVVMTQSPLSLPVTPGEPASISCRSSQSLVYSRGN--TYLHWYLQKPGQSPQVLMYKVSNRFSGVPDRFSGSG--SGTDFTLKISRVEAEDVGVYFCSQSTHVP-LTFGQGTKLEIK |
| 141 | ML199.11H1.5B2.1A.20 | DVVMTQSPLSLPVTPGEPASISCRSSQSLVYSWGN--TYLHWYLQKPGQSPQVLMYKVSNRFSGVPDRFSGSG--SGTDFTLKISRVEAEDVGVYFCSQSTHVP-LTFGQGTKLEIK |
| 142 | ML199.11H1.5B2.1A.21 | DVVMTQSPLSLPVTPGEPASISCRSSQSLVYSPGN--TYLHWYLQKPGQSPQVLMYKVSNRFSGVPDRFSGSG--SGTDFTLKISRVEAEDVGVYFCSQSTHVP-LTFGQGTKLEIK |
| 143 | ab58216 | DVLMTQTPLSLPVSLGDQASISCRSSQTIVHSNGN-TYLEWYLQKPGQSPKLLIYKVSNRFSGVPDRFSGSG--SGTDFTLKISRVEAEDLGVYYCFQGSHAP-PTFGGGTKLEIK |
| 144 | BGK-2C8.E6.D3 | DTVLTQSP-ALAVSPGERVSISCRAS-----EGVN-SYMHWYQQNPGQQSKLLIYRTSNLASGVPARFGGSG--SGTDFTLTIDPVEADDTATYFCQQSWNDP-PTFGGGTKLELK |
| 145 | BGK-5D10-E4 | DIQMTQSPASLSASLGETVSIECLASEDIY------NNLAWYQQKPGKSPHLLIHFTSNLQDGVPSRFSGSG--SGTQYSLKINSLESEDGATYFCLQDSEYP-LTFGSGTKLEIK |
| 146 | BGK-6E3-F4 | DIIMTQSPSSLAVSAGETVTINCKSSQSLLSSGKQKNYLAWYQQKPGQSPKLLIYLASTRESGVPDRFIGSG--SGTDFTLTISSMQAEDLAIYYCQQHYDTP-LTFGSGTKLEIK |
| 60 | BGK-2C8.8C | DIQMSQSPPVLSASVGDRVTLSCKASQNIH------KNLDWYQQKHGEAPKLLIYYTDNLQTGIPSRFSGSG--SGTDYTLTISSLQPEDVATYYCYQYNSG--PTFGAGTKLELQ |
| 147 | CL-105945 (BGK-2H4) | DIQMTQSPPSLSASLGETVSIECLASEDIS------NYLAWYQQKPGKSPQLLIYYANSLEDGVPSRFSGSG--SGTQYSLKISNMQPEDEGVYHCQQGYNYP-YTFGAGTKLELK |
| 148 | CL-105959 (BGK-7A11) | -HFVLAQPNSVSTNLGSTVKLSCKRSTGNS----GSNYVNWYQQYEGRSPTTMIYRDDKRPDGVPDRFSGSIDRSSNSALLTINNVQTEDEADYFCQSYSSGI-NIFGGGTKLTVL |
| 149 | CL-105960 (BGK-7F7) | -HFVLAQPNSVSTNLGSTVKLSCKRSTANI----GSNYVNWYQQHEGRSPTTLIYRDDRRPDGVPDRFSGSIDRSSNSALLTINNVQTEDEADYFCQSYSSGI-NIFGGGTKLTVL |
| 150 | CL-105967 (BGK-9D10-2) | DIQMTQSPPSLPASLGDKVTITCQASQNIN------KYIAWYQQKPGKAPRLLIRFTSTLESDTPSRFSGSG--SGRDYSFSISNVESEDFASYYCLHYDNLPPWTFGGGTKLELK |
| 151 | CL-105969 (BGK-6B5-2) | -HFVLAQPNSVSTNLGNTVKLSCKRSTGNI----GSNYVNWYQQHEGRSPTTLIYRDDKRPDGVPDRFSGSFDRSSNSALLTINNVQTEDEADYFCQSYNSGI-NFFGGGTKLTVL |
| 152 | CL-134994 | EIVLTQSPGTLSLSPGERATLSCRAS---QSVGS-CYLAWYQQKPGQAPRLLIYGASSRATGIPDRFSGSG--SGTDFTLTISRLEPEDFAVYYCQHYVRSP-ITFGGGTKVEIK |
| 153 | CL-135325 | DIQMTQSPSSLSASVGDRVTITCRAS---QSIG---SYLNWYQQKPGKAPKLLIYAASSLQSGVPSRFSGSGS--GTDFTLTISSLQPEDFATYYCQQSYIPP-LTFGGGTKVEIK |
| 154 | CL-135359 | DIQMTQSPSSLSASVGDRVTITCRAS---QGIC---TYLNWYQQKPGKAPKLLIYAASSLQSGVPSRFSGSGS--GTDFTLTISSLQPEDFATYYCQQSYNPP-LTFGGGTKVEIK |

In some embodiments, the LRP-8 binding protein can include sequences that are at least about 80%, 90%, 95%, 99%, or 100% homologous to sequences in Tables 2-7. In certain embodiments, the binding proteins described herein contain two or more sequences identical to or with homology to two or more VH sequences or fragments thereof. In certain embodiments, each of the VH sequences specifically binds to the same proteins. In this situation, the two VH sequences can bind to the same or different epitopes on the same protein. In other embodiments, the binding proteins described herein contain two or more sequences identical to or homologous with two or more VL sequences or fragments thereof. In certain embodiments, each of the VL sequences specifically binds to the same proteins. In this situation, the two VL sequences can bind to the same or different epitopes on the same protein. In certain embodiments, each of the VL sequences specifically binds to different proteins.

For example, the binding protein may be a bispecific or multispecific construct. The bispecific or multispecific construct may be monovalent or bivalent. Various bispecific or multispecific constructs are known in the art (see e.g., Spiess et al. (2015) Mol. Immunol. 67; 95-106). The bispecific or multispecific constructs include, but are not limited to, an asymmetric bispecific antibody, an asymmetric bispecific IgG4, a CrossMab binding protein, a DAF (dual action Fab antibody; two-in-one), a DAF (dual action Fab antibody; four-in-one), a DutaMab, a DT-IgG, a knobs-in-holes binding protein, a Charge pair binding protein, a Fab-arm exchange binding protein, a SEEDbody, a Triomab (Triomab quadroma bispecific or removab bispecific), a LUZ-Y, a Fcab, a κλ-body, an iMab (innovative multimer), and an Orthogonal Fab. In some embodiments, the bispecific or multispecific construct is a DVD-Ig binding protein, an IgG(H)-scFv, an scFv-(H)IgG, an IgG(L)-scFv, an scFv-(L)IgG, an IgG(L, H)-Fv, an IgG(H)-V, a V(H)-IgG, an IgG(L)-V, a V(L)-IgG, a KIH IgG-scFab, a 2scFv-IgG, an IgG-2scFv, an scFv4-Ig, a Zybody, or a DVI-IgG (four-in-one). The bispecific or multispecific construct also can be a nanobody (or VHH), a bispecific tandem nanobody, a bispecific trivalent tandem nanobody, a nanobody-HSA, a BiTE (bispecific T-cell engager) binding protein, a Diabody, a DART (dual affinity retargeting) binding protein, a TandAb (tetravalent bispecific tandem antibody), an scDiabody, an scDiabody-CH3, a Diabody-CH3, a Triple Body, a Miniantibody, a Minibody, a TriBi minibody, an scFv-CH3 KIH, a Fab-scFv, an scFv-CH-CL-scFv, a F(ab')2, a F(ab')2 scFv2, an scFv-KIH, a Fab-scFv-Fc, a Tetravalent HCAb, an scDiabody-Fc, a Diabody-Fc, a Tandem scFv-Fc, a Fabsc, a bsFc-1/2, a CODV-Ig (cross-over dual variable immunoglobulin), a biclonics antibody or an Intrabody. The bispecific or multispecific constructs also include, for example, a Dock and Lock binding protein, an ImmTAC, an HSAbody, an scDiabody-HSA, a Tandem scFv-Toxin, an IgG-IgG binding protein, a Cov-X-Body, and an scFv1-PEG-scFv2. In some embodiments, the bispecific or multispecific construct is a DVD-Ig binding protein, a CrossMab binding protein, a diabody, a tandem single-chain Fv molecule, a bispecific diabody, a single-chain diabody molecule, or a di-diabody. In some embodiments, the binding protein is a DVD-Ig binding protein. See, e.g., U.S. Pat. No. 7,612,181 (incorporated herein by reference in its entirety). The bispecific or multispecific construct may comprise one or more binding sites for LRP-8. The bispecific or multispecific construct may comprise binding sites only for LRP-8, or may comprise additional binding sites for other antigen targets. The bispecific or multispecific construct may comprise binding sites for more than one epitope on LRP-8, e.g., using different CDR sets or variable domains from Tables 2-7 to form binding sites targeting different epitopes on LRP-8.

The binding proteins described herein can also be larger protein structures including three or more VH and/or VL domains, for example a triple variable domain immunoglobulin (TVD-Ig) binding protein.

The blood-brain-barrier (BBB) is layer of tightly packed endothelial cells that make up the walls of brain capillaries and prevent substances in the blood from diffusing freely into the brain. The instant disclosure improves upon the art by providing, in certain embodiments, binding proteins capable of binding a BBB antigen (LRP-8) and transcytosing into mouse and monkey brains, thereby facilitating critical preclinical testing, and would be expected to also exhibit similar activity in human brain. In certain aspects, the disclosure provides high molecular weight multivalent binding proteins (e.g., a DVD-Ig or other bispecific binding proteins) comprising at least one binding domain targeting an LRP-8 antigen combined with one or more second binding domains directed against a therapeutically relevant target. Unlike other binding proteins, the binding proteins of the disclosure may have one or more binding domains (e.g., one, two, or three binding domains) that are unoccupied upon BBB uptake such that they remain available for binding to the therapeutically relevant target molecule present in the brain. Additionally or alternatively, one or more of the binding domains may be pre-loaded with a therapeutic agent (e.g., an endogenous or exogenous therapeutic protein) to facilitate delivery of the agent to the brain. Accordingly, the binding proteins of the disclosure are well-suited for the treatment of brain and CNS diseases including, but not limited to, Alzheimer's disease (AD), Parkinson's disease (PD) or multiple sclerosis (MS). In some embodiments, the binding proteins are used to treat brain and CNS diseases including, but not limited to, Alzheimer's disease (AD), Parkinson's disease (PD) or multiple sclerosis (MS).

Also disclosed herein are methods for treating a disease or condition (e.g., a neurological and/or brain condition) in a human subject. Such methods comprise administering to an individual (human or other mammal) one or more binding proteins that bind LRP-8 or a portion thereof (e.g., CR1 and CR2), and another target.

Dual variable domain ("DVD-Ig") binding proteins of the disclosure comprise two or more antigen binding sites and may be tetravalent or multivalent binding proteins. DVDs may be monospecific, i.e., capable of binding one antigen, or multispecific, i.e., capable of binding two or more antigens. A DVD-Ig binding protein comprising two heavy chain DVD polypeptides and two light chain DVD polypeptides is referred to as a "DVD immunoglobulin" or "DVD-Ig". Each half of a DVD-Ig comprises a heavy chain DVD polypeptide and a light chain DVD polypeptide, and two or more antigen binding sites. Each binding site comprises a heavy chain variable domain and a light chain variable domain with a total of six CDRs involved in antigen binding per antigen binding site. A description of the design, expression, and characterization of DVD-Ig molecules is provided in U.S. Pat. No. 7,612,181 and Wu et al. (2007) Nature Biotechnol. 25:1290-1297. An example of such DVD-Ig molecules comprises a heavy chain that comprises the structural formula VD1-(X1)n-VD2-C-(X2)n, wherein VD1 is a first heavy chain variable domain, VD2 is a second heavy chain variable domain, C is a heavy chain constant domain, X1 is a linker with the proviso that it is not CH1, X2 is an Fc region, and n is 0 or 1, but preferably 1; and a light chain that comprises the structural formula VD1-(X1)n-VD2-C-(X2)n, wherein VD1 is a first light chain variable domain, VD2 is a second light chain variable domain, C is a light chain constant domain, X1 is a linker with the proviso that it is not CH1, and X2 does not comprise an Fc region; and n is 0 or 1, but preferably 1. Such a DVD-Ig may comprise two such heavy chains and two such light chains, wherein each chain comprises variable domains linked in tandem without an intervening constant region between the variable domains, wherein a heavy chain and a light chain associate to form tandem functional antigen binding sites, and a pair of heavy and light chains may associate with another pair of heavy and light chains to form a tetrameric binding protein with four functional antigen binding sites. In another example, a DVD-Ig molecule may comprise heavy and light chains that each comprise three variable domains (VD1, VD2, VD3) linked in tandem without an intervening constant region between variable domains, wherein a pair of heavy and light chains may associate to form three antigen binding sites, and wherein a pair of heavy and light chains may associate with another pair of heavy and light chains to form a tetrameric binding protein with six antigen binding sites.

For example, the DVD-Ig binding protein can bind to an amino acid comprising the sequence of SEQ ID NO: 2 or a portion thereof. In various embodiments, the DVD-Ig binding protein binds to an amino acid comprising the sequence of SEQ ID NO: 3 or a portion thereof. In various embodiments the DVD-Ig binding proteins binds an amino acid comprising both of the sequences of SEQ ID NO:2 and SEQ ID NO: 3. A DVD-Ig binding protein may bind one or more epitopes of LRP-8, such as the CR1 region of SEQ ID NO:2. In an embodiment, a DVD-Ig binding protein may bind an epitope of LRP-8 and an epitope of a second target antigen other than an LRP-8 polypeptide.

Also disclosed herein are methods for reducing one or more symptoms of a condition associated with the brain (e.g., a condition affecting neuronal or vascular tissues) in an individual comprising administering to the individual a binding protein that binds LRP-8 or a portion thereof and also another target. In some embodiments, the binding protein is a DVD-Ig binding protein including a variable heavy chain and/or a variable light chain comprising an amino acid sequence selected from the sequences described herein, whereby one or more symptoms of the condition is reduced.

In various embodiments, a binding protein comprising an LRP-8 binding domain as described herein can be linked to a second binding domain or a second active agent (e.g., a cytotoxic agent) via a linker sequence. The linker sequence may be a single amino acid or a linker polypeptide comprising two or more amino acid residues joined by peptide bonds. In an embodiment, a linker sequence may comprise or consist of a sequence selected from the group consisting of GGGGSG (SEQ ID NO:11), GGSGG (SEQ ID NO:12), GGGGSGGGGS (SEQ ID NO:13), GGSGGGGSG (SEQ ID NO:14), GGSGGGGSGS (SEQ ID NO:15), GGSGGGGSGGGGS (SEQ ID NO:16), GGGGSGGGGSGGGG (SEQ ID NO:17), GGGGSGGGGSGGGGS (SEQ ID NO:18), ASTKGP (SEQ ID NO:19), ASTKGPSVFPLAP (SEQ ID NO:20), TVAAP (SEQ ID NO:21), RTVAAP (SEQ ID NO:22), TVAAPSVFIFPP (SEQ ID NO:23), RTVAAPSVFIFPP (SEQ ID NO:24), AKTTPKLEEGEFSEAR (SEQ ID NO:25), AKTTPKLEEGEFSEARV (SEQ ID NO:26), AKTTPKLGG (SEQ ID NO:27), SAKTTPKLGG (SEQ ID NO:28), SAKTTP (SEQ ID NO:29), RADAAP (SEQ ID NO:30), RADAAPTVS (SEQ ID NO:31), RADAAAAGGPGS (SEQ ID NO:32), RADAAAAGGGGSGGGGSGGGGSGGGGS (SEQ ID NO:33), SAKTTPKLEEGEFSEARV (SEQ ID NO:34), ADAAP (SEQ ID NO:35), ADAAPTVSIFPP (SEQ ID NO:36), QPKAAP (SEQ ID NO:37), QPKAAPSVTLFPP (SEQ ID NO:38), AKTTPP (SEQ ID NO:39), AKTTPPSVTPLAP (SEQ ID NO:40), AKTTAP (SEQ ID NO:41), AKTTAPSVYPLAP (SEQ ID NO:42), GENKVEYAPALMALS (SEQ ID NO:43), GPAKELTPLKEAKVS (SEQ ID NO:44), and GHEAAAVMQVQYPAS (SEQ ID NO:45).

The choice of linker sequences may be based on crystal structure analysis of several Fab molecules. There is a natural flexible linkage between the variable domain and the CH1/CL constant domain in Fab or antibody molecular structure. This natural linkage comprises approximately 10-12 amino acid residues, contributed by 4-6 residues from C-terminus of V domain and 4-6 residues from the N-terminus of CL/CH1 domain. DVD-Igs described herein can be generated using N-terminal 5-6 amino acid residues, or 11-12 amino acid residues, of CL or CH1 as linker in light chain and heavy chain of DVD-Ig, respectively. The N-terminal residues of CL or CH1 domains, particularly the first 5-6 amino acid residues, adopt a loop conformation without strong secondary structures, and therefore can act as flexible linkers between the two variable domains. The N-terminal residues of CL or CH1 domains are natural extension of the variable domains, as they are part of the Ig sequences, and therefore minimize to a large extent any immunogenicity potentially arising from the linkers and junctions.

Unless otherwise defined herein, scientific and technical terms used in connection with the present disclosure shall have the meanings that are commonly understood by those of ordinary skill in the art. The meaning and scope of such terms should be clear. However, in the event of any latent ambiguity, definitions provided herein take precedent over any dictionary or extrinsic definition. Further, unless otherwise required by context, singular terms shall include pluralities and plural terms shall include the singular. In this application, the use of the term "or" means "and/or" unless stated otherwise. Furthermore, the use of the term "including," as well as other forms, such as "includes" and "included," is not limiting. Also, terms such as "element" or "component" encompass both elements and components comprising one unit and elements and components that comprise more than one subunit unless specifically stated otherwise. All ranges shall be interpreted to include the endpoints of those ranges unless stated otherwise.

Generally, nomenclatures used in connection with, and techniques of, cell and tissue culture, molecular biology, immunology, microbiology, genetics, pathology, and protein and nucleic acid chemistry and hybridization described herein are those well-known and commonly used in the art unless stated otherwise. The methods and techniques of the present disclosure are generally performed according to conventional methods well known in the art and as described in various general and more specific references that are cited and discussed throughout the present specification unless otherwise indicated. Enzymatic reactions and purification techniques are performed according to manufacturers' specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the present disclosure may be more readily understood, select terms are defined below.

The term "polypeptide" means any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric. The term "polypeptide" encompasses fragments and variants (including fragments of variants) thereof, unless otherwise contradicted by context. For an antigenic polypeptide, a fragment of polypeptide optionally contains at least one contiguous or non-linear epitope of polypeptide. The precise boundaries of the at least one epitope fragment can be confirmed using ordinary skill in the art. The fragment comprises at least about 5 contiguous amino acids, such as at least about 10 contiguous amino acids, at least about 15 contiguous amino acids, or at least about 20 contiguous amino acids.

The term "isolated protein" or "isolated polypeptide" means a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" means the process of rendering a chemical species such as a polypeptide substantially free of naturally associated components by isolation, e.g., using protein purification techniques well known in the art.

The term "biological activity" means all inherent biological properties of a protein, e.g., for LRP-8, mediating one or any combination of endocytosis, transcytosis, signal transduction, brain localization, spinal cord localization, placental localization, testes localization and/or travel across the blood brain barrier (BBB), for example.

The terms "specific binding" or "specifically binding" in reference to the interaction of an antibody, a binding protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody. In certain embodiments, a binding protein that specifically binds to an antigen binds to that antigen with a $K_D$ greater than $10^{-6}$, $10^{-7}$, $10^{-8}$, $10^{-9}$, $10^{-10}$, $10^{-11}$, $10^{-12}$, $10^{-13}$ or $10^{-14}$ M. In other embodiments, a binding protein that specifically binds to an antigen binds to that antigen with a $K_D$ of between $10^{-6}$ and $10^{-7}$, $10^{-6}$ and $10^{-8}$, $10^{-6}$ and $10^{-9}$, $10^{-6}$ and $10^{-10}$, $10^{-6}$ and $10^{-11}$, $10^{-6}$ and $10^{-12}$, $10^{-6}$ and $10^{-13}$, $10^{-6}$ and $10^{-14}$, $10^{-9}$ and $10^{-10}$, $10^{-9}$ and $10^{-11}$, $10^{-9}$ and $10^{-12}$, $10^{-9}$ and $10^{-13}$ or $10^{-9}$ and $10^{-14}$ M.

The term "antibody" broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below.

In a full-length antibody, each heavy chain is comprised of a heavy chain variable domain (abbreviated herein as VH) and a heavy chain constant region. The heavy chain constant region is comprised of three domains: CH1, CH2, and CH3. Each light chain is comprised of a light chain variable domain (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "Fc region" is used to define the C-terminal region of an immunoglobulin heavy chain, which may be generated by papain digestion of an intact antibody. The Fc region may be a native sequence Fc region or a variant Fc region. The Fc region of an immunoglobulin generally comprises two constant domains, a CH2 domain, and a CH3 domain, and optionally comprises a CH4 domain. Replacements of amino acid residues in the Fc portion to alter antibody effector function are known in the art (U.S. Pat. Nos. 5,648,260 and 5,624,821). The Fc portion of an antibody mediates several important effector functions, for example, cytokine induction, ADCC, phagocytosis, complement dependent cytotoxicity (CDC), and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered. The term "antigen-binding portion" of an antibody refers to one or more fragments of an antibody that retain the ability to specifically bind to an antigen (e.g., hLRP-8). Antigen-binding functions of an antibody can be performed by fragments of a full-length antibody. Such antibody fragment embodiments may also be incorporated in bispecific, dual specific, or multi-specific formats such as a DVD-Ig format; specifically binding to two or more different antigens (e.g., h LRP-8 and a different antigen molecule). Examples of binding fragments encompassed within the term "antigen-binding portion" of an antibody include (i) a Fab fragment, a monovalent fragment consisting of the VL, VH, CL, and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) Nature, 341: 544-546; PCT Publication No. WO 90/05144), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, for example, Bird et al. (1988) Science 242:

423-426; and Huston et al. (1988) Proc. Natl. Acad. Sci. USA 85: 5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al. (1993) Proc. Natl. Acad. Sci. USA 90: 6444-6448; Poljak (1994) Structure 2: 1121-1123); Kontermann and Dubel eds., Antibody Engineering, Springer-Verlag, N.Y. (2001), p. 790 (ISBN 3-540-41354-5). In addition single chain antibodies also include "linear antibodies" comprising a pair of tandem Fv segments (VH-CH1-VH-CH1) which, together with complementary light chain polypeptides, form a pair of antigen binding regions (Zapata et al. (1995) Protein Eng. 8(10): 1057-1062; and U.S. Pat. No. 5,641,870).

An immunoglobulin constant (C) domain refers to a heavy (CH) or light (CL) chain constant domain. Murine and human IgG heavy chain and light chain constant domain amino acid sequences are known in the art.

The term "LRP-8 binding protein construct" (or "binding protein construct") refers to a polypeptide comprising one or more of the antigen binding portions of the disclosure linked to a linker or an immunoglobulin constant domain. A "linker polypeptide" comprises two or more amino acid residues joined by peptide bonds and are used to link one or more antigen binding portions. Such linker polypeptides are well known in the art (see e.g., Holliger et al. (1993) Proc. Natl. Acad. Sci. USA 90: 6444-6448; Poljak (1994) Structure 2: 1121-1123). An immunoglobulin constant domain refers to a heavy or light chain constant domain. Human IgG heavy chain and light chain constant domain amino acid sequences are known in the art and several are represented in Table 8. In various embodiments, the binding proteins and antibodies disclosed herein can comprise any of the constant domains listed in Table 8.

TABLE 8

Sequence of Human IgG Heavy Chain Constant Domain and Light Chain Constant Domain

| Protein | Sequence Identifier | Sequence 12345678901234567890123456 7890 |
|---|---|---|
| Ig gamma-1 constant region | SEQ ID NO: 197 | ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPELLGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK |
| Ig gamma-1 constant region 234, 235 mutant | SEQ ID NO: 198 | ASTKGPSVFPLAPSSKSTSGGTAALGCLVK DYFPEPVTVSWNSGALTSGVHTFPAVLQSS GLYSLSSVVTVPSSSLGTQTYICNVNHKPS NTKVDKKVEPKSCDKTHTCPPCPAPEAAGG PSVFLFPPKPKDTLMISRTPEVTCVVVDVS HEDPEVKFNWYVDGVEVHNAKTKPREEQYN STYRVVSVLTVLHQDWLNGKEYKCKVSNKA LPAPIEKTISKAKGQPREPQVYTLPPSREE MTKNQVSLTCLVKGFYPSDIAVEWESNGQP ENNYKTTPPVLDSDGSFFLYSKLTVDKSRW QQGNVFSCSVMHEALHNHYTQKSLSLSPGK |
| Ig Kappa constant region | SEQ ID NO: 199 | TVAAPSVFIFPPSDEQLKSGTASVVCLLNN FYPREAKVQWKVDNALQSGNSQESVTEQDS KDSTYSLSSTLTLSKADYEKHKVYACEVTH QGLSSPVTKSFNRGEC |
| Ig Lambda constant region | SEQ ID NO: 200 | QPKAAPSVTLFPPSSEELQANKATLVCLIS DFYPGAVTVAWKADSSPVKAGVETTTPSKQ SNNKYAASSYLSLTPEQWKSHRSYSCQVTH EGSTVEKTVAPTECS |

Still further, an LRP-8 binding protein, antibody, or antigen-binding portion thereof, may be part of a larger immunoadhesion molecule, formed by covalent or noncovalent association of the antibody antigen-binding portion with one or more other proteins or peptides. Examples of such immunoadhesion molecules include use of the streptavidin core region to make a tetrameric scFv molecule (Kipriyanov et al. (1995) Human Antibod. Hybridomas 6:93-101) and use of a cysteine residue, a marker peptide and a C-terminal polyhistidine tag to make bivalent and biotinylated scFv molecules (Kipriyanov et al. (1994) Mol. Immunol. 31:1047-1058). Antibody portions, such as Fab and F(ab')₂ fragments, can be prepared from whole antibodies using conventional techniques, such as papain or pepsin digestion, respectively, of whole antibodies. Moreover, antibodies, antigen-binding portions thereof, and immunoadhesion molecules can be obtained using standard recombinant DNA techniques. An LRP-8 binding protein, such as an antigen-binding portion of an antibody may also be part of a DVD-Ig.

An "isolated antibody" is intended to refer to an antibody that is substantially free of other antibodies having different antigenic specificities (e.g., an isolated antibody that specifically binds LRP-8 is substantially free of antibodies that specifically bind antigens other than LRP-8). An isolated antibody that specifically binds LRP-8 may, however, have cross-reactivity to other antigens, such as LRP-8 molecules from other species. Moreover, an isolated antibody may be substantially free of other cellular material and/or chemicals.

The term "monoclonal antibody" or "mAb" refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each mAb is directed against a single determinant on the antigen. The modifier "monoclonal" is not to be construed as requiring production of the antibody by any particular method.

The term "human antibody" includes antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody" does not include antibodies in which CDR sequences derived from the germline of another mammalian species, such as a mouse, have been grafted onto human framework sequences.

The term "recombinant human antibody" includes all human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes, or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "chimeric antibody" refers to antibodies that comprise heavy and light chain variable domain sequences from one species and constant region sequences from another species, such as antibodies having murine heavy and light chain variable domains linked to human constant regions.

The term "CDR-grafted antibody" refers to antibodies that comprise heavy and light chain variable domain sequences from one species but in which the sequences of one or more of the CDR regions of VH and/or VL are replaced with CDR sequences of another species, such as antibodies having murine heavy and light chain variable domains in which one or more of the murine CDRs (e.g., CDR3) has been replaced with human CDR sequences.

The term "CDR" refers to the complementarity determining region within antibody variable sequences. There are three CDRs in each of the variable domains of the heavy chain and the light chain, which are designated CDR1, CDR2 and CDR3, for each of the variable domains. The term "CDR set" as used herein refers to a group of three CDRs that occur in a single variable domain capable of binding the antigen. The exact boundaries of these CDRs have been defined differently according to different systems. The system described by Kabat (Kabat et al., Sequences of Proteins of Immunological Interest, National Institutes of Health, Bethesda, Md. (1987) and (1991)) not only provides an unambiguous residue numbering system applicable to any variable domain of an antibody, but also provides precise residue boundaries defining the three CDRs. These CDRs may be referred to as Kabat CDRs. Chothia and coworkers (Chothia et al. (1987) J. Mol. Biol. 196: 901-917; and Chothia et al. (1989) Nature 342: 877-883) found that certain sub-portions within Kabat CDRs adopt nearly identical peptide backbone conformations, despite having great diversity at the level of amino acid sequence. These sub-portions were designated as L1, L2, and L3 or H1, H2, and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan et al. ((1995) FASEB J. 9:133-139) and MacCallum et al. ((1996) J. Mol. Biol. 262(5):732-745). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although exemplary embodiments use Kabat or Chothia defined CDRs.

The terms "Kabat numbering", "Kabat definitions", and "Kabat labeling" are used interchangeably herein. These terms, which are recognized in the art, refer to a system of numbering amino acid residues which are more variable (i.e., hypervariable) than other amino acid residues in the heavy and light chain variable domains of an antibody, or an antigen binding portion thereof (Kabat et al. (1971) Ann. NY Acad. Sci. 190:382-391; and Kabat et al. (1991) Sequences of Proteins of Immunological Interest, Fifth Edition, U.S. Department of Health and Human Services, NIH Publication No. 91-3242). For the heavy chain variable domain, the hypervariable region ranges from amino acid positions 31 to 35 for CDR1, amino acid positions 50 to 65 for CDR2, and amino acid positions 95 to 102 for CDR3. For the light chain variable domain, the hypervariable region ranges from amino acid positions 24 to 34 for CDR1, amino acid positions 50 to 56 for CDR2, and amino acid positions 89 to 97 for CDR3.

The growth and analysis of extensive public databases of amino acid sequences of variable heavy and light regions over the past twenty years have led to the understanding of the typical boundaries between framework regions (FR) and CDR sequences within variable region sequences and enabled persons skilled in this art to accurately determine the CDRs according to Kabat numbering, Chothia numbering, or other systems. See, e.g., Martin, "Protein Sequence and Structure Analysis of Antibody Variable Domains,"

Chapter 31, In Antibody Engineering, (Kontermann and Dubel, eds.) (Springer-Verlag, Berlin, 2001), especially pages 432-433. A useful method of determining the amino acid sequences of Kabat CDRs within the amino acid sequences of variable heavy (VH) and variable light (VL) regions is provided below:

To identify a CDR-L1 amino acid sequence: Starts approximately 24 amino acid residues from the amino terminus of the VL region; Residue before the CDR-L1 sequence is always cysteine (C); Residue after the CDR-L1 sequence is always a tryptophan (W) residue, typically Trp-Tyr-Gln (W-Y-Q), but also Trp-Leu-Gln (W-L-Q), Trp-Phe-Gln (W-F-Q), and Trp-Tyr-Leu (W-Y-L); Length is typically 10 to 17 amino acid residues.

To identify a CDR-L2 amino acid sequence: Starts always 16 residues after the end of CDR-L1; Residues before the CDR-L2 sequence are generally Ile-Tyr (I-Y), but also Val-Tyr (V-Y), Ile-Lys (1-K), and Ile-Phe (1-F); Length is always 7 amino acid residues.

To identify a CDR-L3 amino acid sequence: Starts always 33 amino acids after the end of CDR-L2; Residue before the CDR-L3 amino acid sequence is always a cysteine (C); Residues after the CDR-L3 sequence are always Phe-Gly-X-Gly (F-G-X-G) (SEQ ID NO: 201), where X is any amino acid; Length is typically 7 to 11 amino acid residues.

To identify a CDR-H1 amino acid sequence: Starts approximately 31 amino acid residues from amino terminus of VH region and always 9 residues after a cysteine (C); Residues before the CDR-H1 sequence are always Cys-X-X-X-X-X-X-X-X (SEQ ID NO: 202), where X is any amino acid; Residue after CDR-H1 sequence is always a Trp (W), typically Trp-Val (W-V), but also Trp-Ile (W-I), and Trp-Ala (W-A); Length is typically 5 to 7 amino acid residues.

To identify a CDR-H2 amino acid sequence: Starts always 15 amino acid residues after the end of CDR-H1; Residues before CDR-H2 sequence are typically Leu-Glu-Trp-Ile-Gly (L-E-W-I-G) (SEQ ID NO: 203), but other variations also; Residues after CDR-H2 sequence are Lys/Arg-Leu/Ile/Val/Phe/Thr/Ala-Thr/Ser/Ile/Ala (K/R-L/I/V/F/T/A-T/S/I/A); Length is typically 16 to 19 amino acid residues.

To identify a CDR-H3 amino acid sequence: Starts always 33 amino acid residues after the end of CDR-H2 and always 3 after a cysteine (C)' Residues before the CDR-H3 sequence are always Cys-X-X (C-X-X), where X is any amino acid, typically Cys-Ala-Arg (C-A-R); Residues after the CDR-H3 sequence are always Trp-Gly-X-Gly (W-G-X-G) (SEQ ID NO: 204), where X is any amino acid; Length is typically 3 to 25 amino acid residues.

As used herein, the term "canonical" residue refers to a residue in a CDR or framework that defines a particular canonical CDR structure as defined by Chothia et al. ((1987) J. Mol. Biol. 196: 901-917); and Chothia et al. ((1992) J. Mol. Biol. 227: 799-817), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

An "affinity matured" antibody is an antibody with one or more alterations in one or more CDRs thereof which result in an improvement in the affinity of the antibody for a target antigen, compared to a parent antibody which does not possess the alteration(s). Exemplary affinity matured antibodies will have nanomolar or even picomolar affinities for the target antigen. A variety of procedures for producing affinity matured antibodies are known in the art. For example, Marks et al. (1992) BioTechnology 10: 779-783 describes affinity maturation by VH and VL domain shuffling. Random mutagenesis of CDR and/or framework residues is described by Barbas et al. (1994) Proc. Nat. Acad. Sci. USA 91: 3809-3813; Schier et al. (1995) Gene 169: 147-155; Yelton et al. (1995) J. Immunol. 155: 1994-2004; Jackson et al. (1995) J. Immunol. 154(7): 3310-3319; Hawkins et al. (1992) J. Mol. Biol. 226: 889-896. Selective mutation at selective mutagenesis positions and at contact or hypermutation positions with an activity enhancing amino acid residue is described in U.S. Pat. No. 6,914,128.

The term "multivalent binding protein" denotes a binding protein comprising two or more antigen binding sites. A multivalent binding protein may be engineered to have three or more antigen binding sites, and is generally not a naturally occurring antibody. The term "multispecific binding protein" refers to a binding protein capable of binding two or more related or unrelated targets.

In some embodiments, the binding protein is a single chain dual variable domain immunoglobulin protein. The terms "single chain dual variable domain immunoglobulin protein" or "scDVD-Ig protein" or scFvDVD-Ig protein" refer to the antigen binding fragment of a DVD molecule that is analogous to an antibody single chain Fv fragment. scDVD-Ig proteins are described in U.S. Ser. Nos. 61/746,659; 14/141,498; and 14/141,500, incorporated herein by reference in their entireties. In an embodiment, the variable domains of a scDVD-Ig protein are antibody variable domains. In an embodiment, the variable domains are non-immunoglobulin variable domains (e.g., receptor).

In some embodiments, the binding protein is a DVD-Fab. The terms "DVD-Fab" or fDVD-Ig protein" refer to the antigen binding fragment of a DVD-Ig molecule that is analogous to an antibody Fab fragment. fDVD-Ig proteins are described in U.S. Ser. Nos. 61/746,663; 14/141,498; and 14/141,501, incorporated herein by reference in their entireties.

In some embodiments, the binding protein is a receptor DVD-Ig protein. The terms "receptor DVD-Ig protein" constructs, or "rDVD-Ig protein" refer to DVD-Ig™ constructs comprising at least one receptor-like binding domain. rDVD-Ig proteins are described in U.S. Ser. Nos. 61/746,616; and 14/141,499, incorporated herein by reference in their entireties.

The term "receptor domain" (RD), or receptor binding domain refers to the portion of a cell surface receptor, cytoplasmic receptor, nuclear receptor, or soluble receptor that functions to bind one or more receptor ligands or signaling molecules (e.g., toxins, hormones, neurotransmitters, cytokines, growth factors, or cell recognition molecules).

The terms multi-specific and multivalent IgG-like molecules or "pDVD-Ig" proteins are capable of binding two or more proteins (e.g., antigens). pDVD-Ig proteins are described in U.S. Ser. No. 14/141,502, incorporated herein by reference in its entirety. In certain embodiments, pDVD-Ig™ proteins are disclosed which are generated by specifically modifying and adapting several concepts. These concepts include but are not limited to: (1) forming Fc heterodimer using CH3 "knobs-into-holes" design, (2) reducing light chain missing pairing by using CH1/CL cross-over, and (3) pairing two separate half IgG molecules at protein production stage using "reduction then oxidation" approach.

In certain embodiments, a binding protein disclosed herein is a "half-DVD-Ig" comprised of one DVD-Ig heavy chain and one DVD-Ig light chain. The half-DVD-Ig™ protein preferably does not promote cross-linking observed with naturally occurring antibodies which can result in antigen clustering and undesirable activities. See U.S. Patent Publication No. 20120201746 which is incorporated by reference herein in its entirety.

In some embodiments, the binding protein is a pDVD-Ig protein. In one embodiment, a pDVD-Ig construct may be created by combining two halves of different DVD-Ig molecules, or a half DVD-Ig protein and half IgG molecule.

In some embodiments, the binding protein is an mDVD-Ig protein. As used herein "monobody DVD-Ig protein" or "mDVD-Ig protein" refers to a class of binding molecules wherein one binding arm has been rendered non-functional. mDVD-Ig proteins are described in U.S. Ser. No. 14/141,503, incorporated herein by reference in its entirety.

The Fc regions of the two polypeptide chains that have a formula of VDH-(X1)n-C-(X2)n may each contain a mutation, wherein the mutations on the two Fc regions enhance heterodimerization of the two polypeptide chains. In one aspect, knobs-into-holes mutations may be introduced into these Fc regions to achieve heterodimerization of the Fc regions. See Atwell et al. (1997) J. Mol. Biol. 270:26-35.

In some embodiments, the binding protein is a cross-over DVD-Ig protein. As used herein "cross-over DVD-Ig" protein or "coDVD-Ig" protein refers to a DVD-Ig protein wherein the cross-over of variable domains is used to resolve the issue of affinity loss in the inner antigen-binding domains of some DVD-Ig molecules. coDVD-Ig proteins are described in U.S. Ser. No. 14/141,504, incorporated herein by reference in its entirety.

In certain embodiments, a binding protein that binds to LRP-8 (e.g., one or any combination of human, cynomolgus, mouse and rat LRP-8) is provided as part of a bispecific antibody. The term "bispecific antibody", as used herein, refers to full-length antibodies that are generated by quadroma technology (see Milstein et al. (1983) Nature 305: 537-540), by chemical conjugation of two different monoclonal antibodies (see Staerz et al. (1985) Nature 314: 628-631), or by knob-into-hole or similar approaches which introduces mutations in the Fc region (see Holliger et al. (1993) Proc. Natl. Acad. Sci. USA 90(14): 6444-6448), resulting in multiple different immunoglobulin species of which only one is the functional bispecific antibody. By molecular function, a bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen binding arms (in both specificity and CDR sequences), and is monovalent for each antigen it binds.

The term "dual-specific antibody", as used herein, refers to full-length antibodies that can bind two different antigens (or epitopes) in each of its two binding arms (a pair of HC/LC) (see PCT Publication No. WO 02/02773). Accordingly a dual-specific binding protein has two identical antigen binding arms, with identical specificity and identical CDR sequences, and is bivalent for each antigen to which it binds.

A "functional antigen binding site" of a binding protein is one that is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same.

As used herein, the terms "donor" and "donor antibody" refer to an antibody providing one or more CDRs. In an exemplary embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable domain minus the CDRs. Because the exact definition of a CDR sequence can be determined by different systems, the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable domain of a single, naturally occurring immunoglobulin chain. As used herein, a FR represents one of the four sub-regions, and FRs represents two or more of the four sub-regions constituting a framework region.

As used herein, the terms "acceptor" and "acceptor antibody" refer to the antibody providing or nucleic acid sequence encoding at least 80%, at least 85%, at least 90%, at least 95%, at least 98%, or 100% of the amino acid sequences of one or more of the framework regions. In some embodiments, the term "acceptor" refers to the antibody amino acid providing or nucleic acid sequence encoding the constant region(s). In yet another embodiment, the term "acceptor" refers to the antibody amino acid providing or nucleic acid sequence encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well known in the art, antibodies in development, or antibodies commercially available).

Human heavy chain and light chain acceptor sequences are known in the art. In one embodiment of the disclosure the human heavy chain and light chain acceptor sequences are selected from the sequences listed from V-base or from IMGT®, the international ImMunoGeneTics Information System®. In another embodiment of the disclosure the human heavy chain and light chain acceptor sequences are selected from the sequences described in Table 3 and Table 4 of U.S. Patent Publication No. 2011/0280800, incorporated by reference herein in their entireties.

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al. (2002) Crit. Rev. Immunol. 22(3): 183-200; Marchalonis et al. (2001) Adv. Exp. Med. Biol. 484:13-30). One of the advantages provided by various embodiments of the present disclosure stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable domain that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable domain and light chain variable domain, a residue within the Vernier zone, and a residue in the region that overlaps between the Chothia definition of a variable heavy chain CDR/and the Kabat definition of the first heavy chain framework.

The term "humanized antibody" refers to antibodies that comprise heavy and light chain variable domain sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. Also "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')₂, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

A humanized antibody may be selected from any class of immunoglobulins, including IgM, IgG, IgD, IgA and IgE, and any isotype including without limitation IgG1, IgG2, IgG3, and IgG4. The humanized antibody may comprise sequences from more than one class or isotype, and particular constant domains may be selected to optimize desired effector functions using techniques well known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In an exemplary embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, e.g., Winnaker, From Genes to Clones (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

With respect to constructing DVD-Ig or other binding protein molecules, a "linker" is used to denote a single amino acid or a polypeptide ("linker polypeptide") comprising two or more amino acid residues joined by peptide bonds and used to link one or more antigen binding portions. Such linker polypeptides are well known in the art (see, e.g., Holliger et al. (1993) Proc. Natl. Acad. Sci. USA 90: 6444-6448; Poljak (1994) Structure 2: 1121-1123).

As used herein, "Vernier" zone refers to a subset of framework residues that may adjust CDR structure and fine-tune the fit to antigen as described by Foote et al. (1992) J. Mol. Biol., 224: 487-499, which is incorporated herein by reference. Vernier zone residues form a layer underlying the CDRs and may impact on the structure of CDRs and the affinity of the antibody.

As used herein, the term "neutralizing" refers to neutralization of the biological activity of an antigen (e.g., LRP-8 or another antigen) when a binding protein specifically binds the antigen. A neutralizing binding protein described herein can bind to LRP-8 or another antigen resulting in the inhibition of a biological activity of the LRP-8 or other antigen. The neutralizing binding protein can bind LRP-8 or another antigen and reduce a biologically activity of the LRP-8 or other antigen by at least about 20%, 40%, 60%, 80%, 85%, or more. Inhibition of a biological activity of LRP-8 or other antigen by a neutralizing binding protein can be assessed by measuring one or more indicators of LRP-8 or other antigen biological activity well known in the art; for example, inhibition of endocytosis and/or transcytosis.

The term "activity" includes activities such as the binding specificity/affinity of a binding protein for an antigen, for example, a binding protein that specifically binds to an LRP-8 antigen and/or the neutralizing potency of an LRP-8 binding protein.

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by a binding protein. An epitope may be determined by obtaining an X-ray crystal structure of an antibody:antigen complex and determining which residues on the antigen (LRP-8) are within a specified distance of residues on the antibody of interest, wherein the specified distance is, 5 Å or less, e.g., 5 Å, 4 Å, 3 Å, 2 Å, 1 Å or any distance in between. In some embodiments, the epitope is defined as a stretch of 8 or more contiguous amino acid residues along the LRP-8 sequence in which at least 50%, 70% or 85% of the residues are within the specified distance of the antibody or binding protein in the X-ray crystal structure.

In certain embodiments, a binding protein is said to specifically bind an antigen when it preferentially recognizes its target antigen in a complex mixture of proteins and/or macromolecules. Binding proteins that bind to the same or similar epitopes will likely cross-compete (one prevents the binding or modulating effect of the other). Cross-competition, however, can occur even without epitope overlap, e.g., if epitopes are adjacent in three-dimensional space and/or due to steric hindrance.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). See also Jonsson U. et al., (1993) Ann. Biol. Clin., 51:19-26; Jonsson U. et al., (1991) BioTechniques, 11:620-627 (1991); Johnsson U. et al., (1995) J. Mol. Recognit., 8:125-131; and Johnsson U. et al., (1991) Anal. Biochem., 198:268-277.

The term "$K_{on}$" (also "Kon", "kon"), as used herein, is intended to refer to the on rate constant for association of a binding protein (e.g., a DVD-Ig) to an antigen to form an association complex, e.g., binding protein/antigen complex, as is known in the art. The "$K_{on}$" also is known by the terms "association rate constant", or "ka", as used interchangeably herein. This value indicates the binding rate of a binding protein to its target antigen or the rate of complex formation between an antibody and antigen as is shown by the equation below:

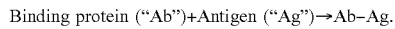

Binding protein ("Ab")+Antigen ("Ag")→Ab-Ag.

The term "$K_{off}$" (also "Koff", "koff"), as used herein, is intended to refer to the off rate constant for dissociation, or "dissociation rate constant", of a binding protein (e.g., an DVD-Ig) from an association complex (e.g., a binding protein/antigen complex) as is known in the art. This value indicates the dissociation rate of an antibody from its target antigen or separation of Ab-Ag complex over time into free binding protein and antigen as shown by the equation below:

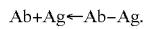

Ab+Ag←Ab-Ag.

The term "$K_D$" (also "$K_d$"), as used herein, is intended to refer to the "equilibrium dissociation constant", and refers to the value obtained in a titration measurement at equilibrium, or by dividing the dissociation rate constant (Koff) by the association rate constant (Kon). The association rate constant (Kon), the dissociation rate constant (Koff), and the equilibrium dissociation constant (K are used to represent the binding affinity of a binding protein to an antigen. Methods for determining association and dissociation rate constants are well known in the art. Using fluorescence-based techniques offers high sensitivity and the ability to examine samples in physiological buffers at equilibrium.

Other experimental approaches and instruments such as a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) can also be used.

The terms "label" and "detectable label" mean a moiety attached to a specific binding partner, such as a binding protein or an analyte, e.g., to render the reaction between members of a specific binding pair, such as a binding protein and an analyte, detectable. The specific binding partner, e.g., binding protein or analyte, so labeled is referred to as "detectably labeled." Thus, the term "labeled binding protein" as used herein, refers to a protein with a label incorporated that provides for the identification of the binding protein. In an embodiment, the label is a detectable marker that can produce a signal that is detectable by visual or instrumental means, e.g., incorporation of a radiolabeled amino acid or attachment to a polypeptide of biotinyl moieties that can be detected by marked avidin or streptavidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^3H$ $^{14}C$, $^{35}S$, $^{90}Y$, $^{99}Tc$, $^{111}In$, $^{125}I$, $^{131}I$, $^{177}Lu$, $^{166}Ho$, or $^{153}Sm$), chromogens, fluorescent labels (e.g., FITC, rhodamine, lanthanide phosphors), enzymatic labels (e.g., horseradish peroxidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), and magnetic agents (e.g., gadolinium chelates). Representative examples of labels commonly employed for immunoassays include moieties that produce light, e.g., acridinium compounds, and moieties that produce fluorescence, e.g., fluorescein. Other labels are described herein. In this regard, the moiety itself may not be detectably labeled but may become detectable upon reaction with yet another moiety. Use of the term "detectably labeled" is intended to encompass the latter type of detectable labeling.

The term "binding protein conjugate" refers to a binding protein described herein chemically linked to a second chemical moiety, such as a therapeutic or cytotoxic agent. The term "agent" is used herein to denote a chemical compound, a mixture of chemical compounds, a biological macromolecule, or an extract made from biological materials. Preferably the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. When employed in the context of an immunoassay, a binding protein conjugate may be a detectably labeled antibody, which is used as the detection antibody.

The terms "crystal" and "crystallized" as used herein, refer to a binding protein (e.g., a DVD-Ig), or antigen binding portion thereof, that exists in the form of a crystal. Crystals are one form of the solid state of matter that is distinct from other forms such as the amorphous solid state or the liquid crystalline state. Crystals are composed of regular, repeating, three-dimensional arrays of atoms, ions, molecules (e.g., proteins such as DVD-Igs), or molecular assemblies (e.g., antigen/binding protein complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege et al., Chapter 1, In Crystallization of Nucleic Acids and Proteins, a Practical Approach, 2nd ed., Ducruix and Giege (eds.), Oxford University Press, N. Y. (1999) p. 1-16.

The term "polynucleotide" means a polymeric form of two or more nucleotides, either ribonucleotides or deoxynucleotides or a modified form of either type of nucleotide. The term includes single and double stranded forms of DNA.

The term "isolated polynucleotide" shall mean a polynucleotide (e.g., of genomic, cDNA, or synthetic origin, or some combination thereof) that, by virtue of its origin, the "isolated polynucleotide" is not associated with all or a portion of a polynucleotide with which the "isolated polynucleotide" is found in nature; is operably linked to a polynucleotide that it is not linked to in nature; or does not occur in nature as part of a larger sequence.

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the disclosure is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences.

The term "recombinant host cell" (or simply "host cell"), is intended to refer to a cell into which exogenous DNA has been introduced. In an embodiment, the host cell comprises two or more (e.g., multiple) nucleic acids encoding antibodies, such as the host cells described in U.S. Pat. No. 7,262,028, for example. Such terms are intended to refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. In an embodiment, host cells include prokaryotic and eukaryotic cells selected from any of the Kingdoms of life. In another embodiment, eukaryotic cells include protist, fungal, plant and animal cells. In another embodiment, host cells include but are not limited to the prokaryotic cell line *Escherichia coli*; mammalian cell lines CHO, HEK 293, COS, NS0, SP2 and PER.C6; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., Molecular Cloning: A Laboratory Manual, 2nd ed., Cold Spring Harbor Laboratory Press, Cold Spring Harbor, N.Y., (1989).

The terms "regulate" and "modulate" are used interchangeably, and, as used herein, refer to a change or an alteration in the activity of a molecule of interest (e.g., the biological activity of LRP-8 or another antigen). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," as used herein, is a compound capable of changing or altering an activity or function of a molecule of interest (e.g., the biological activity of LRP-8 or another antigen). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in PCT Publication No. WO 01/83525.

The term "agonist," as used herein, refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, LRP-8 polypeptides, nucleic acids, carbohydrates, or any other molecule that binds to LRP-8.

The terms "antagonist" and "inhibitor," as used herein, refer to a modulator that, when contacted with a molecule of interest causes a decrease in the magnitude of a certain activity or function of the molecule compared to the magnitude of the activity or function observed in the absence of the antagonist. Particular antagonists of interest include those that block or modulate the biological or immunological activity of human LRP-8. Antagonists and inhibitors of human LRP-8 may include, but are not limited to, proteins, nucleic acids, carbohydrates, or any other molecules, which bind to human LRP-8.

As used herein, the term "effective amount" refers to the amount of a therapy that is sufficient to reduce or ameliorate the severity and/or duration of a disorder or one or more symptoms thereof; prevent the advancement of a disorder; cause regression of a disorder; prevent the recurrence, development, onset, or progression of one or more symptoms associated with a disorder; detect a disorder; or enhance or improve the prophylactic or therapeutic effect(s) of another therapy (e.g., prophylactic or therapeutic agent).

"Patient" and "subject" may be used interchangeably herein to refer to an animal, such as a mammal, including a primate (for example, a human, a monkey (e.g., a cynomolgus monkey), and a chimpanzee), a non-primate (for example, a cow, a pig, a camel, a llama, a horse, a goat, a rabbit, a sheep, a hamster, a guinea pig, a cat, a dog, a rat, a mouse or a whale), a bird (e.g., a duck or a goose), and a fish (e.g. zebrafish or a shark). Preferably, a patient or subject is a human, such as a human being treated or assessed for a disease, disorder or condition, a human at risk for a disease, disorder or condition, a human having a disease, disorder or condition, and/or human being treated for a disease, disorder or condition.

The term "sample," as used herein, is used in its broadest sense. A "biological sample," as used herein, includes, but is not limited to, any quantity of a substance from a living thing or formerly living thing. Such living things include, but are not limited to, humans, non-human primates, mice, rats, monkeys, dogs, rabbits and other animals. Such substances include, but are not limited to, blood (e.g., whole blood), plasma, serum, urine, amniotic fluid, synovial fluid, endothelial cells, leukocytes, monocytes, other cells, organs, tissues, bone marrow, lymph nodes and spleen.

"Control" refers to a composition known to not analyte ("negative control") or to contain analyte ("positive control"). A positive control can comprise a known concentration of analyte. "Control," "positive control," and "calibrator" may be used interchangeably herein to refer to a composition comprising a known concentration of analyte. A "positive control" can be used to establish assay performance characteristics and is a useful indicator of the integrity of reagents (e.g., analytes).

"Risk" refers to the possibility or probability of a particular event occurring either presently or at some point in the future. "Risk stratification" refers to an array of known clinical risk factors that allows physicians to classify patients into a low, moderate, high or highest risk of developing a particular disease, disorder or condition.

"Specific" and "specificity" in the context of an interaction between members of a specific binding pair (e.g., an antigen (or fragment thereof) and a binding protein (or antigenically reactive fragment thereof)) refer to the selective reactivity of the interaction. The phrase "specifically binds to" and analogous phrases refer to the ability of binding proteins to bind specifically to analyte (or a fragment thereof) and not bind specifically to other entities.

"Specific binding partner" is a member of a specific binding pair. A specific binding pair comprises two different molecules, which specifically bind to each other through chemical or physical means. Therefore, in addition to antigen and binding protein specific binding pairs of common immunoassays, other specific binding pairs can include biotin and avidin (or streptavidin), carbohydrates and lectins, complementary nucleotide sequences, effector and receptor molecules, cofactors and enzymes, enzyme inhibitors and enzymes, and the like. Furthermore, specific binding pairs can include members that are analogs of the original specific binding members, for example, an analyte-analog. Immunoreactive specific binding members include antigens, antigen fragments, and antibodies, including monoclonal and polyclonal antibodies as well as complexes, fragments, and variants (including fragments of variants) thereof, whether isolated or recombinantly produced.

"Variant" as used herein means a polypeptide that differs from a given polypeptide (e.g., binding proteins or LRP-8 polypeptide) in amino acid sequence by the addition (e.g., insertion), deletion, or conservative substitution of amino acids, but that retains one or more biological activity of the given polypeptide (e.g., a variant LRP-8 may compete with wild-type LRP-8 for binding to an anti-LRP-8 binding protein). A conservative substitution of an amino acid, i.e., replacing an amino acid with a different amino acid of similar properties (e.g., hydrophilicity and degree and distribution of charged regions) is recognized in the art as typically involving a minor change. These minor changes can be identified, in part, by considering the hydropathic index of amino acids, as understood in the art (see, e.g., Kyte et al. (1982) J. Mol. Biol. 157: 105-132). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids also can be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity (see, e.g., U.S. Pat. No. 4,554,101). Substitution of amino acids having similar hydrophilicity values can result in peptides retaining biological activity, for example immunogenicity, as is understood in the art. In one aspect, substitutions are performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to describe a polypeptide or fragment thereof that has been differentially processed, such as by proteolysis, phosphorylation, or other post-translational modification, yet retains its biological activity or antigen reactivity, e.g., the ability to bind to LRP-8. Use of "variant" herein is intended to encompass fragments of a variant unless otherwise contradicted by context.

Alternatively or additionally, a "variant" is to be understood as a polynucleotide or protein which differs in comparison to the polynucleotide or protein from which it is derived by one or more changes in its length or sequence. The polypeptide or polynucleotide from which a protein or nucleic acid variant is derived is also known as the parent polypeptide or polynucleotide. The term "variant" comprises "fragments" or "derivatives" of the parent molecule. Typically, "fragments" are smaller in length or size than the parent molecule, whilst "derivatives" exhibit one or more differences in their sequence in comparison to the parent molecule. Also encompassed are modified molecules such as but not limited to post-translationally modified proteins (e.g. glycosylated, biotinylated, phosphorylated, ubiquitinated, palmitoylated, or proteolytically cleaved proteins) and modified nucleic acids such as methylated DNA. Also mixtures of different molecules such as but not limited to RNA-DNA hybrids, are encompassed by the term "variant". Typically, a variant is constructed artificially, preferably by gene-technological means whilst the parent polypeptide or polynucleotide is a wild-type protein or polynucleotide. However, also naturally occurring variants are to be understood to be encompassed by the term "variant" as used herein. Further, the variants usable in the present disclosure may also be derived from homologs, orthologs, or paralogs of the parent molecule or from artificially constructed variant, provided that the variant exhibits at least one biological activity of the parent molecule, i.e. is functionally active.

Alternatively or additionally, a "variant" as used herein, can be characterized by a certain degree of sequence identity to the parent polypeptide or parent polynucleotide from which it is derived. More precisely, a protein variant in the context of the present disclosure exhibits at least 80% sequence identity to its parent polypeptide. A polynucleotide variant in the context of the present disclosure exhibits at least 80% sequence identity to its parent polynucleotide. The term "at least 80% sequence identity" is used throughout the specification with regard to polypeptide and polynucleotide sequence comparisons. This expression preferably refers to a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide.

The similarity of nucleotide and amino acid sequences, i.e. the percentage of sequence identity, can be determined via sequence alignments. Such alignments can be carried out with several art-known algorithms, preferably with the mathematical algorithm of Karlin and Altschul (Karlin et al. (1993) Proc. Natl. Acad. Sci. USA 90: 5873-5877), with hmmalign (HMMER package) or with the CLUSTAL algorithm (Thompson et al. (1994) Nucleic Acids Res. 22:4673-80) The grade of sequence identity (sequence matching) may be calculated using e.g. BLAST, BLAT or BlastZ (or BlastX). A similar algorithm is incorporated into the BLASTN and BLASTP programs of Altschul et al. (1990) J. Mol. Biol. 215: 403-410. BLAST polynucleotide searches are performed with the BLASTN program, score=100, word length=12, to obtain polynucleotide sequences that are homologous to those nucleic acids which encode mir-146a. BLAST protein searches are performed with the BLASTP program, score=50, word length-3, to obtain amino acid sequences homologous to mir-146a. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno et al. (2003) Bioinformatics, 19 Suppl 1: 154-162) or Markov random fields. When percentages of sequence identity are referred to in the present application, these percentages are calculated in relation to the full length of the longer sequence, if not specifically indicated otherwise.

I. Anti LRP-8 DVD-Ig Binding Proteins

In various embodiments, provided herein are DVD-Ig binding proteins that bind one or more epitopes of LRP-8 and/or another antigen other than an LRP-8 polypeptide. An exemplary embodiment of such DVD-Ig molecules comprises a heavy chain that comprises the structural formula VD1-(X1)n-VD2-C-(X2)n, wherein VD1 is a first heavy chain variable domain, VD2 is a second heavy chain variable domain, C is a heavy chain constant domain, X1 is a linker, X2 is an Fc region on the first polypeptide chain and X2 does not comprise an Fc region on the second polypeptide chain; n is independently 0 or 1 on the first and second chains; and a light chain that comprises the structural formula VD1-(X1)n-VD2-C-(X2)n, wherein VD1 is a first light chain variable domain, VD2 is a second light chain variable domain, C is a light chain constant domain, X1 is a linker, and X2 is an Fc region on the first polypeptide chain and X2 does not comprise an Fc region on the second polypeptide chain; n is independently 0 or 1 on the first and second chains. Such a DVD-Ig may comprise two such heavy chains and two such light chains, wherein each chain comprises variable domains linked in tandem without an intervening constant region between the variable domains, wherein a heavy chain and a light chain associate to form two tandem antigen binding sites, and a pair of heavy and light chains may associate with another pair of heavy and light chains to form a tetrameric binding protein with four antigen binding sites. In another embodiment, a DVD-Ig molecule may comprise heavy and light chains that each comprise three variable domains, e.g., VD1, VD2, VD3, linked in tandem without an intervening constant region between variable domains, wherein a pair of heavy and light chains may associate to form three antigen binding sites, and wherein a pair of heavy and light chains may associate with another pair of heavy and light chains to form a tetrameric binding protein with six antigen binding sites.

Each variable domain (VD) in a DVD-Ig may be obtained from one or more "parent" monoclonal antibodies that bind one or more desired antigens or epitopes, such as LRP-8 antigens or epitopes. General methods of making DVD-Ig and properties associated with DVD-Igs are described in U.S. Pat. No. 8,841,417, incorporated by reference herein in its entirety. Specific methods used with the DVD-Ig specifically presented herein are provided below.

II. Use of LRP-8 Binding Proteins in Various Diseases

In some embodiments, LRP-8 binding proteins of the disclosure are useful as therapeutic molecules to treat various diseases, particularly diseases in which crossing the BBB would be advantageous for treatment, e.g., in disorders of the brain and/or spinal cord. Such LRP-8 binding proteins may bind one or more targets involved in a specific disease. Examples of such targets in various diseases are described below. In some embodiments, a binding protein disclosed herein is administered to a patient in need of treatment. In some embodiments, the patient is one who would benefit from altered LRP-8 levels and/or function. In some embodiments, administration of a binding protein does not alter normal LRP-8 biologic function, but binding of the administered protein to LRP-8 allows for transport across the blood-brain barrier. In some embodiments, the binding protein comprises a second therapeutic agent (e.g., an agent acting on the nervous system) that is delivered across the blood-brain barrier by binding of the protein to LRP-8. In some embodiments, the binding protein is administered to a human patient. In some embodiments, the binding protein is administered to a non-human patient. In some embodiments, the binding protein exhibits cross-reactivity with LRP-8 in a non-human mammal (e.g., one or any combination of cynomolgus monkey, rat or mouse), allowing for binding and transport across the blood-brain barrier in any of these species. In certain embodiments, the binding protein comprises clone ML199.11H1.5B2, or the CDR and/or variable domains from that clone.

Altered expression of LRP-8 is associated with certain neurological diseases. Thus, in one aspect, an LRP-8 binding protein is used for treating a neurological disease or disorder. Neurological diseases include, but are not limited to a brain disorder, an autoimmune or inflammatory disease of the brain, an infectious disorder of the brain, a neurological disorder, a neurodegenerative disorder, a brain cancer, a brain metastasis, Huntington's chorea, Parkinson's disease, Alzheimer's disease, multiple sclerosis, stroke, mental disorders, depression, schizophrenia, acute pain, and chronic pain.

In various embodiments, the LRP-8 binding protein comprises a second binding domain or therapeutic agent targeting a brain antigen and which benefits from transport to the brain via binding of the LRP-8 binding domain to that antigen.

In an embodiment, a disorder that may be treated by administering to a subject an LRP-8 binding protein described herein includes, but is not limited to, diabetes; uveitis; neuropathic pain; osteoarthritic pain; inflammatory pain; rheumatoid arthritis; osteoarthritis; juvenile chronic arthritis; septic arthritis; Lyme arthritis; psoriatic arthritis; reactive arthritis; spondyloarthropathy; systemic lupus erythematosus (SLE); Crohn's disease; ulcerative colitis; inflammatory bowel disease; autoimmune diabetes; insulin dependent diabetes mellitus; thyroiditis; asthma; allergic diseases; psoriasis; dermatitis; scleroderma; graft versus host disease; organ transplant rejection; acute immune disease associated with organ transplantation; chronic immune disease associated with organ transplantation; sarcoidosis; atherosclerosis; disseminated intravascular coagulation (DIC); Kawasaki's disease; Grave's disease; nephrotic syndrome; chronic fatigue syndrome; Wegener's granulomatosis; Henoch-Schoenlein purpurea; microscopic vasculitis of the kidneys; chronic active hepatitis; autoimmune uveitis; septic shock; toxic shock syndrome; sepsis syndrome; cachexia; infectious diseases; parasitic diseases; acute transverse myelitis; Huntington's chorea; Parkinson's disease; Alzheimer's disease; stroke; primary biliary cirrhosis; hemolytic anemia; malignancies; heart failure; myocardial infarction; Addison's disease; sporadic polyglandular deficiency type I; polyglandular deficiency type II (Schmidt's syndrome); acute respiratory distress syndrome (ARDS); alopecia; alopecia areata; seronegative arthropathy; arthropathy; Reiter's disease; psoriatic arthropathy; ulcerative colitic arthropathy; enteropathic synovitis; chlamydia; *Yersinia* and *Salmonella* associated arthropathy; spondyloarthropathy; atheromatous disease/arteriosclerosis; atopic allergy; autoimmune bullous disease; pemphigus vulgaris; pemphigus foliaceus; pemphigoid; linear IgA disease; autoimmune haemolytic anemia; Coombs positive haemolytic anemia; acquired pernicious anemia; juvenile pernicious anemia; myalgic encephalitis/Royal Free disease; chronic mucocutaneous candidiasis; giant cell arteritis (GCA); primary sclerosing hepatitis; cryptogenic autoimmune hepatitis; acquired immunodeficiency syndrome (AIDS); acquired immunodeficiency related diseases; hepatitis B; hepatitis C; common varied immunodeficiency (common variable hypogammaglobulinaemia); dilated cardiomyopathy; female infertility; ovarian failure; premature ovarian failure; fibrotic lung disease; cryptogenic fibrosing alveolitis; postinflammatory interstitial lung disease; interstitial pneumonitis; connective tissue disease associated interstitial lung disease; mixed connective tissue disease associated lung disease; systemic sclerosis associated interstitial lung disease; rheumatoid arthritis associated interstitial lung disease; systemic lupus erythematosus associated lung disease; dermatomyositis/polymyositis associated lung disease; Sjorgren's disease associated lung disease; ankylosing spondylitis associated lung disease; vasculitic diffuse lung disease; haemosiderosis associated lung disease; drug-induced interstitial lung disease; fibrosis; radiation fibrosis; bronchiolitis obliterans; chronic eosinophilic pneumonia; lymphocytic infiltrative lung disease; postinfectious interstitial lung disease; gouty arthritis; autoimmune hepatitis; type-1 autoimmune hepatitis (classical autoimmune or lupoid hepatitis); type-2 autoimmune hepatitis (anti-LKM antibody hepatitis); autoimmune mediated hypoglycemia; type B insulin resistance with acanthosis nigricans; hypoparathyroidism; osteoarthritis; primary sclerosing cholangitis; psoriasis type 1; psoriasis type 2; idiopathic leucopenia; autoimmune neutropaenia; renal disease NOS; glomerulonephritides; microscopic vasculitis of the kidneys; Lyme disease; discoid lupus erythematosus; idiopathic male infertility; nitric oxide-associated male infertility; sperm autoimmunity; multiple sclerosis (all subtypes, including primary progressive, secondary progressive, relapsing remitting); sympathetic ophthalmia; pulmonary hypertension secondary to connective tissue disease; Goodpasture's syndrome; pulmonary manifestation of polyarteritis nodosa; acute rheumatic fever; rheumatoid spondylitis; Still's disease; systemic sclerosis; Sjorgren's syndrome; Takayasu's disease/arteritis; autoimmune thrombocytopenia (AITP); idiopathic thrombocytopenia; autoimmune thyroid disease; hyperthyroidism; goitrous autoimmune hypothyroidism (Hashimoto's disease); atrophic autoimmune hypothyroidism; primary myxoedema; phacogenic uveitis; primary vasculitis; vitiligo; acute liver disease; chronic liver disease; alcoholic cirrhosis; alcohol-induced liver injury; cholestasis; hypercholesterolemia; idiosyncratic liver disease; drug-induced hepatitis; non-alcoholic steatohepatitis; allergy; group B Streptococci (GBS) infection; mental disorders (e.g., depression and schizophrenia); Th2 Type and Th1 Type mediated diseases; acute and chronic pain (different forms of pain); cancer (such as lung, breast, stomach, bladder, colon, pancreas, ovarian, prostate, and rectal cancer); hematopoietic malignancies; leukemia; lymphoma; abetalipoproteinemia; acrocyanosis; acute and chronic parasitic or infectious processes; acute leukemia; acute lymphoblastic leukemia (ALL); T-cell ALL; FAB ALL; acute myeloid leukemia (AML); acute or chronic bacterial infection; acute pancreatitis; acute renal failure; adenocarcinomas; atrial ectopic beats; AIDS dementia complex; alcohol-induced hepatitis; allergic conjunctivitis; allergic contact dermatitis; allergic rhinitis; allograft rejection; alpha-1-antitrypsin deficiency; amyotrophic lateral sclerosis; anemia; angina pectoris; anterior horn cell degeneration; anti-CD3 therapy; antiphospholipid syndrome; anti-receptor hypersensitivity reactions; aortic and peripheral aneurysms; aortic dissection; arterial hypertension; arteriosclerosis; arteriovenous fistula; ataxia; atrial fibrillation (sustained or paroxysmal); atrial flutter; atrioventricular block; B cell lymphoma; bone graft rejection; bone marrow transplant (BMT) rejection; bundle branch block; Burkitt's lymphoma; burns; cardiac arrhythmias; cardiac stun syndrome; cardiac tumors; cardiomyopathy; cardiopulmonary bypass inflammation response; cartilage transplant rejection; cerebellar cortical degenerations; cerebellar disorders; chaotic or multifocal atrial tachycardia; chemotherapy associated disorders; chronic myelocytic leukemia (CML); chronic alcoholism; chronic inflammatory pathologies; chronic lymphocytic leukemia (CLL); chronic obstructive pulmonary disease (COPD); chronic salicylate intoxication; colorectal carcinoma; congestive heart failure; conjunctivitis; contact dermatitis; cor pulmonale; coronary artery disease; Creutzfeldt-Jakob disease; culture negative sepsis; cystic fibrosis; cytokine therapy associated disorders; dementia pugilistica; demyelinating diseases; dengue hemorrhagic fever; dermatitis; dermatologic conditions; diabetes mellitus; diabetic arteriosclerotic disease; diffuse Lewy body disease; dilated congestive cardiomyopathy; disorders of the basal ganglia; Down's syndrome in middle age; drug-induced movement disorders induced by drugs which block CNS dopamine receptors; drug sensitivity; eczema; encephalomyelitis; endocarditis; endocrinopathy; epiglottitis; Epstein-Barr virus infection; erythromelalgia; extrapyramidal and cerebellar disorders; familial hemophagocytic lymphohistiocytosis; fetal thymus implant rejection; Friedreich's ataxia; functional peripheral arterial disorders; fungal sepsis; gas gangrene; gastric ulcer; glomerular nephritis; graft rejection of any organ or tissue; gram negative sepsis; gram positive sepsis; granulomas due to intracellular organisms; hairy cell leukemia; Hallervorden-Spatz disease; Hashimoto's thyroiditis; hay fever; heart transplant rejection; hemochromatosis; hemodialysis; hemolytic uremic syndrome/thrombolytic thrombocytopenic purpura; hemorrhage; hepatitis A; His bundle arrhythmias; HIV infection/HIV neuropathy; Hodgkin's disease; hyperkinetic movement disorders; hypersensitivity reactions; hypersensitivity pneumonitis; hypertension; hypokinetic movement disorders; hypothalamic-pituitary-adrenal axis evaluation; idiopathic Addison's disease; idiopathic pulmonary fibrosis (IPF); antibody mediated cytotoxicity; asthenia; infantile spinal muscular atrophy; inflammation of the aorta; influenza a; ionizing radiation exposure; iridocyclitis/uveitis/optic neuritis; ischemia-reperfusion injury; ischemic stroke; juvenile rheumatoid arthritis; juvenile spinal muscular atrophy; Kaposi's sarcoma; kidney transplant rejection; *legionella*; leishmaniasis; leprosy; lesions of the corticospinal system; lipedema; liver transplant rejection; lymphedema; malaria; malignant lymphoma; malignant histiocytosis; malignant melanoma; meningitis; meningococcemia; metabolic syndrome migraine headache; idiopathic migraine headache; mitochondrial multisystem disorder; mixed connective tissue disease; monoclonal gammopathy; multiple myeloma; multiple systems degenerations (Menzel; Dejerine-Thomas; Shy-Drager; and Machado-Joseph); myasthenia gravis; *mycobacterium avium* intracellulare; *mycobacterium tuberculosis*; myelodysplastic syndrome; myocardial infarction; myocardial ischemic disorders; nasopharyngeal carcinoma; neonatal chronic lung disease; nephritis; nephrosis; neurodegenerative diseases; neurogenic I muscular atrophies; neutropenic fever; non-Hodgkin's lymphoma; occlusion of the abdominal aorta and its branches; occlusive arterial disorders; OKT3® therapy; orchitis/epididymitis; orchitis/vasectomy reversal procedures; organomegaly; osteoporosis; pancreas transplant rejection; pancreatic carcinoma; paraneoplastic syndrome/hypercalcemia of malignancy; parathyroid transplant rejection; pelvic inflammatory disease; perennial rhinitis; pericardial disease; peripheral atherosclerotic disease; peripheral vascular disorders; peritonitis; pernicious anemia; *pneumocystis carinii* pneumonia; pneumonia; POEMS syndrome (polyneuropathy, organomegaly, endocrinopathy, monoclonal gammopathy, and skin changes syndrome); post perfusion syndrome; post pump syndrome; post-MI cardiotomy syndrome; preeclampsia; progressive supra nucleo palsy; primary pulmonary hypertension; radiation therapy; Raynaud's phenomenon; Raynaud's disease; Refsum's disease; regular narrow QRS tachycardia; renovascular hypertension; reperfusion injury; restrictive cardiomyopathy; sarcomas; senile chorea; senile dementia of Lewy body type; seronegative arthropathies; shock; sickle cell anemia; skin allograft rejection; skin changes syndrome; small bowel transplant rejection; solid tumors; specific arrhythmias; spinal ataxia; spinocerebellar degenerations; streptococcal myositis; structural lesions of the cerebellum; subacute sclerosing panencephalitis; syncope; syphilis of the cardiovascular system; systemic anaphylaxis; systemic inflammatory response syndrome; systemic onset juvenile rheumatoid arthritis; telangiectasia; thromboangitis obliterans; thrombocytopenia; toxicity; transplants; trauma/hemorrhage; type III hypersensitivity reactions; type IV hypersensitivity; unstable angina; uremia; urosepsis; urticaria; valvular heart diseases; varicose veins; vasculitis; venous diseases; venous thrombosis; ventricular fibrillation; viral and fungal infections; viral encephalitis/aseptic meningitis; viral-associated hemophagocytic syndrome; Wernicke-Korsakoff syndrome; Wilson's disease; xenograft rejection of any organ or tissue; acute coronary syndromes; acute idiopathic polyneuritis; acute inflammatory demyelinating polyradiculoneuropathy; acute ischemia; adult Still's disease; alopecia areata; anaphylaxis; antiphospholipid antibody syndrome; aplastic anemia; arteriosclerosis; atopic eczema; atopic dermatitis; autoimmune dermatitis; autoimmune disorder associated with *Streptococcus* infection; autoimmune enteropathy; autoimmune hearing loss; autoimmune lymphoproliferative syndrome (ALPS); autoimmune myocarditis; autoimmune premature ovarian failure; blepharitis; bronchiectasis; bullous pemphigoid; cardiovascular disease; catastrophic antiphospholipid syndrome; celiac disease; cervical spondylosis; chronic ischemia; cicatricial pemphigoid; clinically isolated syndrome (CIS) with risk for multiple sclerosis; conjunctivitis; childhood onset psychiatric disorder; dacryocystitis; dermatomyositis; diabetic retinopathy; disk herniation; disk prolapse; drug induced immune hemolytic anemia; endocarditis; endometriosis; endophthalmitis; episcleritis; erythema multiforme; erythema multiforme major; gestational pemphigoid; Guillain-Barre syndrome (GBS); hay fever; Hughes syndrome; idiopathic Parkinson's disease; idiopathic interstitial pneumonia; IgE-mediated allergy; immune hemolytic anemia; inclusion body myositis; infectious ocular inflammatory disease; inflammatory demyelinating disease; inflammatory heart disease; inflammatory kidney disease; iritis; keratitis; keratojunctivitis sicca; Kussmaul disease or Kussmaul-Meier disease; Landry's paralysis; Langerhan's cell histiocytosis; livedo reticularis; macular degeneration; microscopic polyangiitis; Morbus Bechterev; motor neuron disorders; mucous membrane pemphigoid; multiple organ failure; myasthenia gravis; myelodysplastic syndrome; myocarditis; nerve root disorders; neuropathy; non-A non-B hepatitis; optic neuritis; osteolysis; pauciarticular JRA; peripheral artery occlusive disease (PAOD); peripheral vascular disease (PVD); peripheral artery; disease (PAD); phlebitis; polyarteritis nodosa (or periarteritis nodosa); polychondritis; polymyalgia rheumatica; poliosis; polyarticular JRA; polyendocrine deficiency syndrome; polymyositis; polymyalgia rheumatica (PMR); post-pump syndrome; primary Parkinsonism; secondary Parkinsonism; prostatitis; pure red cell aplasia; primary adrenal insufficiency; recurrent neuromyelitis optica; restenosis; rheumatic heart disease; SAPHO (synovitis, acne, pustulosis, hyperostosis, and osteitis); secondary amyloidosis; shock lung; scleritis; sciatica; secondary adrenal insufficiency; silicone associated connective tissue disease; Sneddon-Wilkinson dermatosis; spondylitis ankylosans; Stevens-Johnson syndrome (SJS); systemic inflammatory response syndrome; temporal arteritis; toxoplasmic retinitis; toxic epidermal necrolysis; transverse myelitis; TRAPS (tumor necrosis factor receptor type 1 (TNFR)-associated periodic syndrome); type B insulin resistance with acanthosis nigricans; type 1 allergic reaction; type II diabetes; urticaria; usual interstitial pneumonia (UIP); vernal conjunctivitis; viral retinitis; Vogt-Koyanagi-Harada syndrome (VKH syndrome); wet macular degeneration; wound healing; or *Yersinia* and *Salmonella* associated arthropathy.

Also disclosed herein are methods of treating pain in an individual (human or other mammal) comprising the step of administering to the individual a protein that binds LRP-8 in combination with a protein that binds a non-LRP-8 antigen. In an embodiment, the binding proteins are administered in combination, for example, in a mixture, by successive administration, or by concurrent administration. In another aspect, a method of treating pain in an individual comprises the step of administering to the individual a multispecific protein that comprises at least one antigen binding site that binds LRP-8 and at least one antigen binding site that binds a non-LRP-8 antigen.

III. Pharmaceutical Compositions

The disclosure also provides pharmaceutical compositions comprising one or more of the LRP-8 binding proteins LRP-8 of the disclosure and a pharmaceutically acceptable carrier. The pharmaceutical compositions comprising binding proteins of the disclosure are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies of the disclosure. In another embodiment, the pharmaceutical composition comprises one or more antibodies of the disclosure and one or more prophylactic or therapeutic agents other than antibodies of the disclosure for treating a disorder in which LRP-8 activity is detrimental or in which crossing the BBB, localizing to the brain and/or localizing to the spinal cord is advantageous. In an embodiment, the prophylactic or therapeutic agents are known to be useful for or having been or currently being used in the prevention, treatment, management, or amelioration of a disorder or one or more symptoms thereof. In accordance with these embodiments, the composition may further comprise of a carrier, diluent or excipient.

The LRP-8 binding proteins of the disclosure can be incorporated into pharmaceutical compositions suitable for administration to a subject. Typically, the pharmaceutical composition comprises a binding protein of the disclosure and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the binding protein.

Various delivery systems are known and can be used to administer one or more antibodies of the disclosure or the combination of one or more antibodies of the disclosure and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the binding protein, receptor-mediated endocytosis (see, e.g., Wu et al. (1987) J. Biol. Chem. 262: 4429-4432), construction of a nucleic acid as part of a retroviral or other vector. Methods of administering a prophylactic or therapeutic agent of the disclosure include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913 and 5,290,540; and PCT Publication Nos. WO 92/19244, WO 97/32572, WO 97/44013, WO 98/31346, and WO 99/66903, each of which is incorporated herein by reference their entireties. In one embodiment, a binding protein of the disclosure, combination therapy, or a composition of the disclosure is administered using Alkermes AIR® pulmonary drug delivery technology (Alkermes, Inc., Cambridge, Mass.). In a specific embodiment, prophylactic or therapeutic agents of the disclosure are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal, and intestinal mucosa, etc.) and may be administered together with other biologically active agents. Administration can be systemic or local.

In an embodiment, specific binding of antibody-coupled carbon nanotubes (CNTs) to tumor cells in vitro, followed by their highly specific ablation with near-infrared (NIR) light can be used to target tumor cells. For example, biotinylated polar lipids can be used to prepare stable, biocompatible, noncytotoxic CNT dispersions that are then attached to one or two different neutralite avidin-derivatized DVD-Igs directed against one or more tumor antigens (e.g., CD22) (Chakravarty et al. (2008) Proc. Natl. Acad. Sci. USA 105:8697-8702).

In a specific embodiment, it may be desirable to administer the prophylactic or therapeutic agents of the disclosure locally to the area in need of treatment; this may be achieved by, for example, and not by way of limitation, local infusion, by injection, or by means of an implant, the implant being of a porous or non-porous material, including membranes and matrices, such as sialastic membranes, polymers, fibrous matrices (e.g., Tissuel®), or collagen matrices. In one embodiment, an effective amount of one or more antibodies of the disclosure antagonists is administered locally to the affected area to a subject to prevent, treat, manage, and/or ameliorate a disorder or a symptom thereof. In another embodiment, an effective amount of one or more antibodies of the disclosure is administered locally to the affected area in combination with an effective amount of one or more therapies (e.g., one or more prophylactic or therapeutic agents) other than a binding protein of the disclosure of a subject to prevent, treat, manage, and/or ameliorate a disorder or one or more symptoms thereof.

In another embodiment, the prophylactic or therapeutic agent can be delivered in a controlled release or sustained release system. In one embodiment, a pump may be used to achieve controlled or sustained release (see Langer, supra; Sefton (1987) CRC Crit. Rev. Biomed. Eng. 14: 201-240; Buchwald et al. (1980) Surgery 88: 507-516; Saudek et al. (1989) N. Engl. J. Med. 321: 574-579). In another embodiment, polymeric materials can be used to achieve controlled or sustained release of the therapies of the disclosure (see, e.g., Goodson, J. M., Chapter 6, In Medical Applications of Controlled Release, Vol. II, Applications and Evaluation, Langer and Wise (eds.), CRC Press, Inc., Boca Raton (1984) p. 115-138; Langer and Peppas (1983) J. Macromol. Sci. Rev. Macromol. Chem. Phys. C23(1): 61-126; see also Levy et al. (1985) Science 228: 190-192; During et al. (1989) Ann. Neurol. 25: 351-356; Howard et al. (1989) J. Neurosurg. 71: 105-112); U.S. Pat. Nos. 5,679,377; 5,916,597; 5,912,015; 5,989,463; 5,128,326; PCT Publication Nos. WO 99/15154; and WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In an exemplary embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, p. 115-138 (1984)).

Controlled release systems are discussed in the review by Langer ((1990) Science, 249: 1527-1533). Any technique known to one of skill in the art can be used to produce sustained release formulations comprising one or more therapeutic agents of the disclosure. See, e.g., U.S. Pat. No. 4,526,938, PCT Publication Nos. WO 91/05548, WO 96/20698; Ning et al. (1996) Radiotherapy Oncol. 39: 179-189; Song et al. (1996) PDA J. Pharm. Sci. Technol. 50:372-377; Cleek et al. (1997) Proceed. Int'l. Symp. Control. Rel. Bioact. Mater. 24: 853-854; and Lam et al. (1997) Proceed. Int'l. Symp. Control Rel. Bioact. Mater. 24: 759-760, each of which is incorporated herein by reference in their entireties.

In a specific embodiment, where the composition of the disclosure is a nucleic acid encoding a prophylactic or therapeutic agent, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic®, DuPont), or coating with lipids or cell-surface receptors or transfecting agents, or by administering it in linkage to a homeobox-like peptide which is known to enter the nucleus (see, e.g., Joliot et al. (1991) Proc. Natl. Acad. Sci. USA 88: 1864-1868). Alternatively, a nucleic acid can be introduced intracellularly and incorporated within host cell DNA for expression by homologous recombination.

A pharmaceutical composition of the disclosure is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic, such as lignocaine, to ease pain at the site of the injection.

If the compositions of the disclosure are to be administered topically, the compositions can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as FREON®) or in a squeeze bottle. Moisturizers or humectants can also be added to pharmaceutical compositions and dosage forms if desired. Examples of such additional ingredients are well known in the art.

If the method of the disclosure comprises intranasal administration of a composition, the composition can be formulated in an aerosol form, spray, mist or in the form of drops. In particular, prophylactic or therapeutic agents for use according to the present disclosure can be conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the disclosure comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulfate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the disclosure may comprise pulmonary administration, e.g., by use of an inhaler or nebulizer, of a composition formulated with an aerosolizing agent. See, e.g., U.S. Pat. Nos. 6,019,968; 5,985,320; 5,985,309; 5,934,272; 5,874,064; 5,855,913; and 5,290,540; and PCT Publication Nos. WO 92/19244, WO 97/32572, WO 97/44013, WO 98/31346, and WO 99/66903, each of which is incorporated herein by reference their entireties. In a specific embodiment, a binding protein of the disclosure, combination therapy, and/or composition of the disclosure is administered using Alkermes AIR® pulmonary drug delivery technology (Alkermes, Inc., Cambridge, Mass.).

The method of the disclosure may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

The methods of the disclosure may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the disclosure encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachet indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the disclosure also provides that one or more of the prophylactic or therapeutic agents, or pharmaceutical compositions of the disclosure is packaged in a hermetically sealed container such as an ampoule or sachette indicating the quantity of the agent. In one embodiment, one or more of the prophylactic or therapeutic agents, or pharmaceutical compositions of the disclosure is supplied as a dry sterilized lyophilized powder or water free concentrate in a hermetically sealed container and can be reconstituted (e.g., with water or saline) to the appropriate concentration for administration to a subject. Preferably, one or more of the prophylactic or therapeutic agents or pharmaceutical compositions of the disclosure is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, at least 100 mg or at least 200 mg/mL. The lyophilized prophylactic or therapeutic agents or pharmaceutical compositions of the disclosure should be stored at between 2° C. and 8° C. in its original container and the prophylactic or therapeutic agents, or pharmaceutical compositions of the disclosure should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the disclosure is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml, at least 100 mg/ml or at least 200 mg/mL. The liquid form should be stored at between 2° C. and 8° C. in its original container.

The binding protein of the disclosure can be incorporated into a pharmaceutical composition suitable for parenteral administration. Preferably, the binding protein will be prepared as an injectable solution containing 0.1-250 mg/ml binding protein. The injectable solution can be composed of either a liquid or lyophilized dosage form in a flint or amber vial, ampoule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising a binding protein of the disclosure prepared as an injectable solution for parenteral administration, can further comprise an agent useful as an adjuvant, such as those used to increase the absorption, or dispersion of a therapeutic protein (e.g., DVD-Ig). A particularly useful adjuvant is hyaluronidase (such as Hylenex® recombinant human hyaluronidase). Addition of hyaluronidase in the injectable solution improves human bioavailability following parenteral administration, particularly subcutaneous administration. It also allows for greater injection site volumes (i.e., greater than 1 ml) with less pain and discomfort, and minimum incidence of injection site reactions (see, PCT Publication No. WO 2004/078140 and US Publication No. 2006/104968).

The compositions provided in this disclosure may be in a variety of forms. These include, for example, liquid, semisolid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In an exemplary embodiment, the binding protein is administered by intravenous infusion or injection. In another preferred embodiment, the binding protein is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., binding protein) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The binding proteins of the present disclosure can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Robinson, J. R. (ed.) Sustained and Controlled Release Drug Delivery Systems, Marcel Dekker, Inc., N.Y. (1978).

In certain embodiments, a binding protein of the disclosure may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the disclosure by other than parenteral administration, it may be necessary to coat the compound with, or co-administer the compound with, a material to prevent its inactivation.

Supplementary active compounds can also be incorporated into the compositions. In certain embodiments, a binding protein of the disclosure is coformulated with and/or coadministered with one or more additional therapeutic agents that are useful for treating disorders in which LRP-8 activity is detrimental. For example, an anti-human LRP-8 binding protein of the disclosure may be coformulated and/or coadministered with one or more additional antibodies that bind other targets (e.g., antibodies that bind other cytokines or that bind cell surface molecules). Furthermore, one or more antibodies of the disclosure may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, a binding protein to LRP-8 or fragment thereof is linked to a half-life extending vehicle known in the art. Such vehicles include, but are not limited to, the Fc domain, polyethylene glycol, and dextran. Such vehicles are described, e.g., in U.S. Pat. No. 6,660,843, which is hereby incorporated by reference for any purpose.

In a specific embodiment, nucleic acid sequences comprising nucleotide sequences encoding a binding protein of the disclosure or another prophylactic or therapeutic agent of the disclosure are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the disclosure, the nucleic acids produce their encoded binding protein or prophylactic or therapeutic agent of the disclosure that mediates a prophylactic or therapeutic effect.

Any of the methods for gene therapy available in the art can be used according to the present disclosure. Detailed descriptions of various methods of gene therapy are disclosed in US Publication No. 2005/0042664, which is incorporated herein by reference.

A binding protein of the disclosure also can be administered with one or more additional agents useful in the treatment of various diseases, or conjugated to one or more such agent. Binding proteins of the disclosure, can be used alone or in combination to treat such diseases. It should be understood that the binding proteins of the disclosure can be used alone or in combination with an additional agent, e.g., a therapeutic agent, the additional agent being selected by the skilled artisan for its intended purpose. For example, the additional agent can be a therapeutic agent art-recognized as being useful to treat the disease or condition being treated by the binding protein of the present disclosure. The additional agent also can be an agent that imparts a beneficial attribute to the therapeutic composition, e.g., an agent that affects the viscosity of the composition.

It should further be understood that the combinations which are to be included within this disclosure are those combinations useful for their intended purpose. The agents set forth below are illustrative for purposes and not intended to be limited. The combinations, which are part of this disclosure, can be the antibodies of the present disclosure and at least one additional agent selected from the lists below. The combination can also include more than one additional agent, e.g., two or three additional agents if the combination is such that the formed composition can perform its intended function.

Preferred combinations are non-steroidal anti-inflammatory drug(s) also referred to as NSAIDS which include drugs like ibuprofen. Other preferred combinations are corticosteroids including prednisolone; the well-known side-effects of steroid use can be reduced or even eliminated by tapering the steroid dose required when treating patients in combination with the anti-LRP-8 binding proteins of this disclosure. Non-limiting examples of therapeutic agents for rheumatoid arthritis with which a binding protein can be combined include, but are not limited to, the following: cytokine suppressive anti-inflammatory drug(s) (CSAIDs); antibodies to or antagonists of other human cytokines or growth factors, for example, TNF, LT, IL-1, IL-2, IL-3, IL-4, IL-5, IL-6, IL-7, IL-8, IL-15, IL-16, IL-18, IL-21, interferons, EMAP-II, GM-CSF, FGF, and PDGF. Antibodies of the disclosure, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the autoimmune and subsequent inflammatory cascade; preferred examples include TNF antagonists like chimeric, humanized or human TNF antibodies, D2E7, (PCT Publication No. WO 97/29131), CA2 (Remicade™), CDP 571, and soluble p55 or p75 TNF receptors, derivatives, thereof, (p75TNFR1gG (Enbrel™) or p55TNFR1gG (Lenercept), and also TNFα converting enzyme (TACE) inhibitors; similarly IL-1 inhibitors (Interleukin-1-converting enzyme inhibitors, IL-1RA etc.) may be effective for the same reason. Other preferred combinations include Interleukin 11. Yet another preferred combination are other key players of the autoimmune response which may act parallel to, dependent on or in concert with LRP-8 function. Yet another preferred combination are non-depleting anti-CD4 inhibitors. Yet other preferred combinations include antagonists of the co-stimulatory pathway CD80 (B7.1) or CD86 (B7.2) including antibodies, soluble receptors or antagonistic ligands.

The binding proteins of the disclosure may also be combined with agents, such as methotrexate, 6-MP, azathioprine sulphasalazine, mesalazine, olsalazine chloroquinine/hydroxychloroquine, pencillamine, aurothiomalate (intramuscular and oral), azathioprine, colchicine, corticosteroids (oral, inhaled and local injection), beta-2 adrenoreceptor agonists (salbutamol, terbutaline, salmeteral), xanthines (theophylline, aminophylline), cromoglycate, nedocromil, ketotifen, ipratropium and oxitropium, cyclosporin, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as TNF-α or IL-1 (e.g., IRAK, NIK, IKK, p38, or MAP kinase inhibitors), IL-1β converting enzyme inhibitors, TNFα converting enzyme (TACE) inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors and the derivatives p75TNFRIgG (Enbrel™ and p55TNFRIgG (Lenercept)), sIL-1RI, sIL-1RII, sIL-6R), anti-inflammatory cytokines (e.g., IL-4, IL-10, IL-11, IL-13 and TGFβ), celecoxib, folic acid, hydroxychloroquine sulfate, rofecoxib, etanercept, infliximab, naproxen, valdecoxib, sulfasalazine, methylprednisolone, meloxicam, methylprednisolone acetate, gold sodium thiomalate, aspirin, triamcinolone acetonide, propoxyphene napsylate/apap, folate, nabumetone, diclofenac, piroxicam, etodolac, diclofenac sodium, oxaprozin, oxycodone HCl, hydrocodone bitartrate/apap, diclofenac sodium/misoprostol, fentanyl, anakinra, human recombinant, tramadol HCl, salsalate, sulindac, cyanocobalamin/fa/pyridoxine, acetaminophen, alendronate sodium, prednisolone, morphine sulfate, lidocaine hydrochloride, indomethacin, glucosamine sulf/chondroitin, amitriptyline HCl, sulfadiazine, oxycodone HCl/acetaminophen, olopatadine HCl, misoprostol, naproxen sodium, omeprazole, cyclophosphamide, rituximab, IL-1 TRAP, MRA, CTLA4-IG, IL-18 BP, anti-IL-18, anti-IL15, BIRB-796, SCIO-469, VX-702, AMG-548, VX-740, Roflumilast, IC-485, CDC-801, and Mesopram. Preferred combinations include methotrexate or leflunomide and in moderate or severe rheumatoid arthritis cases, cyclosporine.

Non-limiting additional agents which can also be used in combination with a binding protein to treat rheumatoid arthritis (RA) include, but are not limited to, the following: non-steroidal anti-inflammatory drug(s) (NSAIDs); cytokine suppressive anti-inflammatory drug(s) (CSAIDs); CDP-571/BAY-10-3356 (humanized anti-TNFα antibody; Celltech/Bayer); cA2/infliximab (chimeric anti-TNFα antibody; Centocor); 75 kdTNFR-IgG/etanercept (75 kD TNF receptor-IgG fusion protein; Immunex; see e.g., Moreland et al., Abstract No. 813 (1994) Arthritis Rheum., 37:5295; Baumgartner et al., (1996) J. Invest. Med., 44(3):235A; 55 kdTNF-IgG (55 kD TNF receptor-IgG fusion protein; Hoffmann-LaRoche); IDEC-CE9.1/SB 210396 (non-depleting primatized anti-CD4 antibody; IDEC/SmithKline; see e.g., Kaine et al., Abstract No. 195 (1995) Arthritis Rheum., 38:5185); DAB 486-IL-2 and/or DAB 389-IL-2 (IL-2 fusion proteins; Seragen; see e.g., Sewell et al., (1993) Arthritis Rheum., 36(9):1223-1233); Anti-Tac (humanized anti-IL-2Rα; Protein Design Labs/Roche); IL-4 (anti-inflammatory cytokine; DNAX/Schering); IL-10 (SCH 52000; recombinant IL-10, anti-inflammatory cytokine; DNAX/Schering); IL-4; IL-10 and/or IL-4 agonists (e.g., agonist antibodies); IL-1RA (IL-1 receptor antagonist; Synergen/Amgen); anakinra (Kineret®/Amgen); TNF-bp/s-TNF (soluble TNF binding protein; see e.g., Evans et al., Abstract No. 1540 (1996) Arthritis Rheum., 39(9) (supplement):S284); Kapadia et al., (1995) Amer. J. Physiol. Heart and Circulatory Physiology, 268: H517-H525); RP73401 (phosphodiesterase Type IV inhibitor; see e.g., Chikanza et al., Abstract No. 1527 (1996) Arthritis Rheum., 39(9) (supplement):S282); MK-966 (COX-2 Inhibitor; see e.g., Erich et al., Abstract Nos. 328 and 329 (1996) Arthritis Rheum., 39(9)(supplement):S81); Iloprost (see e.g., Scholz P., Abstract No. 336 (1996) Arthritis Rheum., 39(9) (supplement):S82); methotrexate; thalidomide (see e.g., Lee et al., Abstract No. 1524 (1996) Arthritis Rheum., 39(9)(supplement):S282) and thalidomide-related drugs (e.g., Celgen); leflunomide (anti-inflammatory and cytokine inhibitor; see e.g., Finnegan et al., Abstract No. 627 (1996) Arthritis Rheum., 39(9)(supplement):S131); Thoss et al., (1996) Inflamm. Res., 45:103-107); tranexamic acid (inhibitor of plasminogen activation; see e.g., Ronday et al., Abstract No. 1541 (1996) Arthritis Rheum., 39(9)(supplement):S284); T-614 (cytokine inhibitor; see e.g., Hara et al., Abstract No. 1526 (1996) Arthritis Rheum., 39(9)(supplement):S282); prostaglandin E1 (see e.g., Moriuchi et al., Abstract No. 1528 (1996) Arthritis Rheum., 39(9)(supplement):S282); Tenidap (non-steroidal anti-inflammatory drug; see e.g., Guttadauria, M., Abstract No. 1516 (1996) Arthritis Rheum., 39(9)(supplement):S280); Naproxen (non-steroidal anti-inflammatory drug; see e.g., Fiebich et al., (1996) Neuro. Report, 7:1209-1213); Meloxicam (non-steroidal anti-inflammatory drug); Ibuprofen (non-steroidal anti-inflammatory drug); Piroxicam (non-steroidal anti-inflammatory drug); Diclofenac (non-steroidal anti-inflammatory drug); Indomethacin (non-steroidal anti-inflammatory drug); Sulfasalazine (see e.g., Farr et al., Abstract No. 1519 (1996) Arthritis Rheum., 39(9)(supplement):S281); Azathioprine (see e.g., Hickey et al., Abstract No. 1521 (1996) Arthritis Rheum., 39(9)(supplement):S281); ICE inhibitor (inhibitor of the enzyme interleukin-1β converting enzyme); zap-70 and/or lck inhibitor (inhibitor of the tyrosine kinase zap-70 or lck); VEGF inhibitor and/or VEGF-R inhibitor (inhibitors of vascular endothelial cell growth factor or vascular endothelial cell growth factor receptor; inhibitors of angiogenesis); corticosteroid anti-inflammatory drugs (e.g., SB203580); TNF-convertase inhibitors; anti-IL-12 antibodies; anti-IL-18 antibodies; interleukin-11 (see e.g., Keith Jr. et al., Abstract No. 1613 (1996) Arthritis Rheum., 39(9) (supplement):S296); interleukin-13 (see e.g., Bessis et al., Abstract No. 1681 (1996) Arthritis Rheum., 39(9)(supplement):S308); interleukin-17 inhibitors (see e.g., Lotz et al. Abstract No. 559 (1996) Arthritis Rheum., 39(9)(supplement):S120); gold; penicillamine; chloroquine; chlorambucil; hydroxychloroquine; cyclosporine; cyclophosphamide; total lymphoid irradiation; anti-thymocyte globulin; anti-CD4 antibodies; CD5-toxins; orally-administered peptides and collagen; lobenzarit disodium; Cytokine Regulating Agents (CRAs) HP228 and HP466 (Houghten Pharmaceuticals, Inc.); ICAM-1 antisense phosphorothioate oligo-deoxynucleotides (ISIS 2302; Isis Pharmaceuticals, Inc.); soluble complement receptor 1 (TP10; T Cell Sciences, Inc.); prednisone; orgotein; glycosaminoglycan polysulphate; minocycline; anti-IL2R antibodies; marine and botanical lipids (fish and plant seed fatty acids; see e.g., DeLuca et al., (1995) Rheum. Dis. Clin. North Am., 21:759-777); auranofin; phenylbutazone; meclofenamic acid; flufenamic acid; intravenous immune globulin; zileuton; azaribine; mycophenolic acid (RS-61443); tacrolimus (FK-506); sirolimus (rapamycin); amiprilose (therafectin); cladribine (2-chlorodeoxyadenosine); methotrexate; bcl-2 inhibitors (see Bruncko et al., (2007) J. Med. Chem., 50(4):641-662); antivirals and immune modulating agents.

In one embodiment, the binding protein described herein is administered in combination with one of the following agents for the treatment of rheumatoid arthritis (RA): small molecule inhibitor of KDR, small molecule inhibitor of Tie-2; methotrexate; prednisone; celecoxib; folic acid; hydroxychloroquine sulfate; rofecoxib; etanercept; infliximab; leflunomide; naproxen; valdecoxib; sulfasalazine; methylprednisolone; ibuprofen; meloxicam; methylprednisolone acetate; gold sodium thiomalate; aspirin; azathioprine; triamcinolone acetonide; propoxyphene napsylate/apap; folate; nabumetone; diclofenac; piroxicam; etodolac; diclofenac sodium; oxaprozin; oxycodone HCl; hydrocodone bitartrate/apap; diclofenac sodium/misoprostol; fentanyl; anakinra, human recombinant; tramadol HCl; salsalate; sulindac; cyanocobalamin/fa/pyridoxine; acetaminophen; alendronate sodium; prednisolone; morphine sulfate; lidocaine hydrochloride; indomethacin; glucosamine sulfate/chondroitin; cyclosporine; amitriptyline HCl; sulfadiazine; oxycodone HCl/acetaminophen; olopatadine HCl; misoprostol; naproxen sodium; omeprazole; mycophenolate mofetil; cyclophosphamide; rituximab; IL-1 TRAP; MRA; CTLA4-IG; IL-18 BP; IL-12/23; anti-IL 18; anti-IL 15; BIRB-796; SCIO-469; VX-702; AMG-548; VX-740; Roflumilast; IC-485; CDC-801; and mesopram.

Non-limiting examples of therapeutic agents for inflammatory bowel disease with which a binding protein of the disclosure can be combined include the following: budenoside; epidermal growth factor; corticosteroids; cyclosporin, sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β mAbs; anti-IL-6 mAbs; growth factors; elastase inhibitors; pyridinyl-imidazole compounds; antibodies to or antagonists of other human cytokines or growth factors, for example, TNF, LT, IL-1, IL-2, IL-6, IL-7, IL-8, IL-15, IL-16, IL-17, IL-18, EMAP-II, GM-CSF, FGF, and PDGF. Antibodies of the disclosure, or antigen binding portions thereof, can be combined with antibodies to cell surface molecules such as CD2, CD3, CD4, CD8, CD25, CD28, CD30, CD40, CD45, CD69, CD90 or their ligands. The binding proteins of the disclosure may also be combined with agents, such as methotrexate, cyclosporin, FK506, rapamycin, mycophenolate mofetil, leflunomide, NSAIDs, for example, ibuprofen, corticosteroids such as prednisolone, phosphodiesterase inhibitors, adenosine agonists, antithrombotic agents, complement inhibitors, adrenergic agents, agents which interfere with signaling by proinflammatory cytokines such as TNFα or IL-1 (e.g., IRAK, NIK, IKK, p38 or MAP kinase inhibitors), IL-1β converting enzyme inhibitors, TNFα converting enzyme inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors, sIL-1RI, sIL-1RII, sIL-6R) and anti-inflammatory cytokines (e.g., IL-4, IL-10, IL-11, IL-13 and TGFβ) and bcl-2 inhibitors.

Non-limiting examples of therapeutic agents for multiple sclerosis (MS) with which binding proteins of the disclosure can be combined include the following: corticosteroids;

prednisolone; methylprednisolone; azathioprine; cyclophosphamide; cyclosporine; methotrexate; 4-aminopyridine; tizanidine; interferon-β1a (AVONEX; Biogen); interferon-β1b (BETASERON; Chiron/Berlex); interferon α-n3) (Interferon Sciences/Fujimoto), interferon-α (Alfa Wassermann/J&J), interferon β1A-IF (Serono/Inhale Therapeutics), Peginterferon α2b (Enzon/Schering-Plough), Copolymer 1 (Cop-1; COPAXONE; Teva Pharmaceutical Industries, Inc.); hyperbaric oxygen; intravenous immunoglobulin; clabribine; antibodies to or antagonists of other human cytokines or growth factors and their receptors, for example, TNF, LT, IL-1, IL-2, IL-6, IL-7, IL-8, IL-23, IL-15, IL-16, IL-18, EMAP-II, GM-CSF, FGF, and PDGF. Binding proteins of the disclosure can be combined with antibodies to cell surface molecules such as CD2, CD3, CD4, CD8, CD19, CD20, CD25, CD28, CD30, CD40, CD45, CD69, CD80, CD86, CD90 or their ligands. Binding proteins of the disclosure, may also be combined with agents, such as methotrexate, cyclosporine, FK506, rapamycin, mycophenolate mofetil, leflunomide, NSAIDs, for example, ibuprofen, corticosteroids such as prednisolone, phosphodiesterase inhibitors, adensosine agonists, antithrombotic agents, complement inhibitors, adrenergic agents, agents which interfere with signaling by proinflammatory cytokines such as TNFα or IL-1 (e.g., IRAK, NIK, IKK, p38 or MAP kinase inhibitors), IL-1β converting enzyme inhibitors, TACE inhibitors, T-cell signaling inhibitors such as kinase inhibitors, metalloproteinase inhibitors, sulfasalazine, azathioprine, 6-mercaptopurines, angiotensin converting enzyme inhibitors, soluble cytokine receptors and derivatives thereof (e.g., soluble p55 or p75 TNF receptors, sIL-1RI, sIL-1RII, sIL-6R), anti-inflammatory cytokines (e.g., IL-4, IL-10, IL-13 and TGFβ) and bcl-2 inhibitors.

Examples of therapeutic agents for multiple sclerosis with which binding proteins of the disclosure can be combined include interferon-β, for example, IFNβ1a and IFNβ1b; copaxone; corticosteroids; caspase inhibitors, for example inhibitors of caspase-1; IL-1 inhibitors; TNF inhibitors; and antibodies to CD40 ligand and CD80.

The binding proteins of the disclosure, may also be combined with agents, such as alemtuzumab, dronabinol, Unimed, daclizumab, mitoxantrone, xaliproden hydrochloride, fampridine, glatiramer acetate, natalizumab, sinnabidol, a-immunokine NNSO3, ABR-215062, AnergiX.MS, chemokine receptor antagonists, BBR-2778, calagualine, CPI-1189, LEM (liposome encapsulated mitoxantrone), THC.CBD (cannabinoid agonist) MBP-8298, mesopram (PDE4 inhibitor), MNA-715, anti-IL-6 receptor antibody, neurovax, pirfenidone allotrap 1258 (RDP-1258), sTNF-R1, talampanel, teriflunomide, TGF-beta2, tiplimotide, VLA-4 antagonists (for example, TR-14035, VLA4 Ultrahaler, Antegran-ELAN/Biogen), interferon gamma antagonists, IL-4 agonists.

Non-limiting examples of therapeutic agents for angina with which binding proteins of the disclosure can be combined include the following: aspirin, nitroglycerin, isosorbide mononitrate, metoprolol succinate, atenolol, metoprolol tartrate, amlodipine besylate, diltiazem hydrochloride, isosorbide dinitrate, clopidogrel bisulfate, nifedipine, atorvastatin calcium, potassium chloride, furosemide, simvastatin, verapamil HCl, digoxin, propranolol hydrochloride, carvedilol, lisinopril, spironolactone, hydrochlorothiazide, enalapril maleate, nadolol, ramipril, enoxaparin sodium, heparin sodium, valsartan, sotalol hydrochloride, fenofibrate, ezetimibe, bumetanide, losartan potassium, lisinopril/hydrochlorothiazide, felodipine, captopril, bisoprolol fumarate.

Non-limiting examples of therapeutic agents for ankylosing spondylitis with which binding proteins of the disclosure can be combined include the following: ibuprofen, diclofenac and misoprostol, naproxen, meloxicam, indomethacin, diclofenac, celecoxib, rofecoxib, sulfasalazine, methotrexate, azathioprine, minocyclin, prednisone, etanercept, infliximab.

Non-limiting examples of therapeutic agents for asthma with which binding proteins of the disclosure can be combined include the following: albuterol, salmeterol/fluticasone, montelukast sodium, fluticasone propionate, budesonide, prednisone, salmeterol xinafoate, levalbuterol HCl, albuterol sulfate/ipratropium, prednisolone sodium phosphate, triamcinolone acetonide, beclomethasone dipropionate, ipratropium bromide, azithromycin, pirbuterol acetate, prednisolone, theophylline anhydrous, methylprednisolone sodium succinate, clarithromycin, zafirlukast, formoterol fumarate, influenza virus vaccine, methylprednisolone, amoxicillin trihydrate, flunisolide, allergy injection, cromolyn sodium, fexofenadine hydrochloride, flunisolide/menthol, amoxicillin/clavulanate, levofloxacin, inhaler assist device, guaifenesin, dexamethasone sodium phosphate, moxifloxacin HCl, doxycycline hyclate, guaifenesin/d-methorphan, p-ephedrine/cod/chlorphenir, gatifloxacin, cetirizine hydrochloride, mometasone furoate, salmeterol xinafoate, benzonatate, cephalexin, pe/hydrocodone/chlorphenir, cetirizine HCl/pseudoephed, phenylephrine/cod/promethazine, codeine/promethazine, cefprozil, dexamethasone, guaifenesin/pseudoephedrine, chlorpheniramine/hydrocodone, nedocromil sodium, terbutaline sulfate, epinephrine, methylprednisolone, metaproterenol sulfate.

Non-limiting examples of therapeutic agents for COPD with which binding proteins of the disclosure can be combined include the following: albuterol sulfate/ipratropium, ipratropium bromide, salmeterol/fluticasone, albuterol, salmeterol xinafoate, fluticasone propionate, prednisone, theophylline anhydrous, methylprednisolone sodium succinate, montelukast sodium, budesonide, formoterol fumarate, triamcinolone acetonide, levofloxacin, guaifenesin, azithromycin, beclomethasone dipropionate, levalbuterol HCl, flunisolide, ceftriaxone sodium, amoxicillin trihydrate, gatifloxacin, zafirlukast, amoxicillin/clavulanate, flunisolide/menthol, chlorpheniramine/hydrocodone, metaproterenol sulfate, methylprednisolone, mometasone furoate, p-ephedrine/cod/chlorphenir, pirbuterol acetate, p-ephedrine/loratadine, terbutaline sulfate, tiotropium bromide, (R,R)-formoterol, TgAAT, Cilomilast, Roflumilast.

Non-limiting examples of therapeutic agents for HCV with which binding proteins of the disclosure can be combined include the following: Interferon-alpha-2a, Interferon-alpha-2b, Interferon-alpha con1, Interferon-alpha-n1, PEGylated interferon-alpha-2a, PEGylated interferon-alpha-2b, ribavirin, Peginterferon alfa-2b+ribavirin, Ursodeoxycholic Acid, Glycyrrhizic Acid, Thymalfasin, Maxamine, VX-497 and any compounds that are used to treat HCV through intervention with the following targets: HCV polymerase, HCV protease, HCV helicase, HCV IRES (internal ribosome entry site).

Non-limiting examples of therapeutic agents for idiopathic pulmonary fibrosis with which binding proteins of the disclosure can be combined include the following: prednisone, azathioprine, albuterol, colchicine, albuterol sulfate, digoxin, gamma interferon, methylprednisolone sod succ, lorazepam, furosemide, lisinopril, nitroglycerin, spironolactone, cyclophosphamide, ipratropium bromide, actinomycin d, alteplase, fluticasone propionate, levofloxacin, metaproterenol sulfate, morphine sulfate, oxycodone hcl, potassium chloride, triamcinolone acetonide, tacrolimus anhydrous, calcium, interferon-alpha, methotrexate, mycophenolate mofetil, Interferon-gamma-1β.

Non-limiting examples of therapeutic agents for myocardial infarction with which binding proteins of the disclosure can be combined include the following: aspirin, nitroglycerin, metoprolol tartrate, enoxaparin sodium, heparin sodium, clopidogrel bisulfate, carvedilol, atenolol, morphine sulfate, metoprolol succinate, warfarin sodium, lisinopril, isosorbide mononitrate, digoxin, furosemide, simvastatin, ramipril, tenecteplase, enalapril maleate, torsemide, retavase, losartan potassium, quinapril HCl/mag carb, bumetanide, alteplase, enalaprilat, amiodarone hydrochloride, tirofiban HCl m-hydrate, diltiazem hydrochloride, captopril, irbesartan, valsartan, propranolol hydrochloride, fosinopril sodium, lidocaine hydrochloride, eptifibatide, cefazolin sodium, atropine sulfate, aminocaproic acid, spironolactone, interferon, sotalol hydrochloride, potassium chloride, docusate sodium, dobutamine HCl, alprazolam, pravastatin sodium, atorvastatin calcium, midazolam hydrochloride, meperidine hydrochloride, isosorbide dinitrate, epinephrine, dopamine hydrochloride, bivalirudin, rosuvastatin, ezetimibe/simvastatin, avasimibe, cariporide.

Non-limiting examples of therapeutic agents for psoriasis with which binding proteins of the disclosure can be combined include the following: small molecule inhibitor of KDR, small molecule inhibitor of Tie-2, calcipotriene, clobetasol propionate, triamcinolone acetonide, halobetasol propionate, tazarotene, methotrexate, fluocinonide, betamethasone diprop augmented, fluocinolone acetonide, acitretin, tar shampoo, betamethasone valerate, mometasone furoate, ketoconazole, pramoxine/fluocinolone, hydrocortisone valerate, flurandrenolide, urea, betamethasone, clobetasol propionate/emoll, fluticasone propionate, azithromycin, hydrocortisone, moisturizing formula, folic acid, desonide, pimecrolimus, coal tar, diflorasone diacetate, etanercept folate, lactic acid, methoxsalen, hc/bismuth subgal/znox/resor, methylprednisolone acetate, prednisone, sunscreen, halcinonide, salicylic acid, anthralin, clocortolone pivalate, coal extract, coal tar/salicylic acid, coal tar/salicylic acid/sulfur, desoximetasone, diazepam, emollient, fluocinonide/emollient, mineral oil/castor oil/na lact, mineral oil/peanut oil, petroleum/isopropyl myristate, psoralen, salicylic acid, soap/tribromsalan, thimerosal/boric acid, celecoxib, infliximab, cyclosporine, alefacept, efalizumab, tacrolimus, pimecrolimus, PUVA, UVB, sulfasalazine.

Non-limiting examples of therapeutic agents for psoriatic arthritis with which binding proteins of the disclosure can be combined include the following: methotrexate, etanercept, rofecoxib, celecoxib, folic acid, sulfasalazine, naproxen, leflunomide, methylprednisolone acetate, indomethacin, hydroxychloroquine sulfate, prednisone, sulindac, betamethasone diprop augmented, infliximab, methotrexate, folate, triamcinolone acetonide, diclofenac, dimethylsulfoxide, piroxicam, diclofenac sodium, ketoprofen, meloxicam, methylprednisolone, nabumetone, tolmetin sodium, calcipotriene, cyclosporine, diclofenac sodium/misoprostol, fluocinonide, glucosamine sulfate, gold sodium thiomalate, hydrocodone bitartrate/apap, ibuprofen, risedronate sodium, sulfadiazine, thioguanine, valdecoxib, alefacept, efalizumab and bcl-2 inhibitors.

Non-limiting examples of therapeutic agents for restenosis with which binding proteins of the disclosure can be combined include the following: sirolimus, paclitaxel, everolimus, tacrolimus, Zotarolimus, acetaminophen.

Non-limiting examples of therapeutic agents for sciatica with which binding proteins of the disclosure can be combined include the following: hydrocodone bitartrate/apap, rofecoxib, cyclobenzaprine HCl, methylprednisolone, naproxen, ibuprofen, oxycodone HCl/acetaminophen, celecoxib, valdecoxib, methylprednisolone acetate, prednisone, codeine phosphate/apap, tramadol HCl/acetaminophen, metaxalone, meloxicam, methocarbamol, lidocaine hydrochloride, diclofenac sodium, gabapentin, dexamethasone, carisoprodol, ketorolac tromethamine, indomethacin, acetaminophen, diazepam, nabumetone, oxycodone HCl, tizanidine HCl, diclofenac sodium/misoprostol, propoxyphene napsylate/apap, asa/oxycod/oxycodone ter, ibuprofen/hydrocodone bit, tramadol HCl, etodolac, propoxyphene HCl, amitriptyline HCl, carisoprodol/codeine phos/asa, morphine sulfate, multivitamins, naproxen sodium, orphenadrine citrate, temazepam.

Examples of therapeutic agents for SLE (lupus) with which binding proteins of the disclosure can be combined include the following: NSAIDS, for example, diclofenac, naproxen, ibuprofen, piroxicam, indomethacin; COX2 inhibitors, for example, Celecoxib, rofecoxib, valdecoxib; anti-malarials, for example, hydroxychloroquine; Steroids, for example, prednisone, prednisolone, budenoside, dexamethasone; cytotoxics, for example, azathioprine, cyclophosphamide, mycophenolate mofetil, methotrexate; inhibitors of PDE4 or purine synthesis inhibitor, for example Cellcept. Binding proteins of the disclosure, may also be combined with agents such as sulfasalazine, 5-aminosalicylic acid, olsalazine, Imuran and agents which interfere with synthesis, production or action of proinflammatory cytokines such as IL-1, for example, caspase inhibitors like IL-1β converting enzyme inhibitors and IL-1ra. Binding proteins of the disclosure may also be used with T cell signaling inhibitors, for example, tyrosine kinase inhibitors; or molecules that target T cell activation molecules, for example, CTLA-4-IgG or anti-B7 family antibodies, anti-PD-1 family antibodies. Binding proteins of the disclosure, can be combined with IL-11 or anti-cytokine antibodies, for example, fonotolizumab (anti-IFNg antibody), or anti-receptor receptor antibodies, for example, anti-IL-6 receptor antibody and antibodies to B-cell surface molecules. Antibodies of the disclosure or antigen binding portion thereof may also be used with LJP 394 (abetimus), agents that deplete or inactivate B-cells, for example, Rituximab (anti-CD20 antibody), lymphostat-B (anti-BlyS antibody), TNF antagonists, for example, anti-TNF antibodies, Adalimumab (PCT Publication No. WO 97/29131; HUMIRA®), CA2 (REMICADE®), CDP 571, TNFR-Ig constructs, (p75TNFRIgG (ENBREL®) and p55TNFRIgG (LENERCEPT®)) and bcl-2 inhibitors, because bcl-2 overexpression in transgenic mice has been demonstrated to cause a lupus like phenotype (see Marquina R. et al., (2004) J. Immunol., 172(11):7177-7185), therefore inhibition is expected to have therapeutic effects.

The pharmaceutical compositions of the disclosure may include a "therapeutically effective amount" or a "prophylactically effective amount" of a binding protein of the disclosure. A "therapeutically effective amount" refers to an amount effective, at dosages and for periods of time necessary, to achieve the desired therapeutic result. A therapeutically effective amount of the binding protein may be determined by a person skilled in the art and may vary according to factors such as the disease state, age, sex, and weight of the individual, and the ability of the binding protein to elicit a desired response in the individual. A therapeutically effective amount is also one in which any toxic or detrimental effects of the binding protein, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the disclosure are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

IV. Diagnostics

The disclosure herein also provides diagnostic applications. LRP-8 binding proteins of the disclosure may be employed in any of a variety of formats to detect LRP-8 in vivo, in vitro, or ex vivo (e.g., in cells or tissues that have been obtained from a living subject, subjected to a procedure, then returned to the subject). LRP-8 multispecific binding proteins of the disclosure offer the further advantage of being capable of binding to an epitope of LRP-8 as well as other antigens or epitopes in various diagnostic and detection assay formats.

In an aspect, the disclosure provides methods of determining the presence of at least one antigen or fragment thereof in a test sample by an immunoassay comprising the LRP-8 binding protein described herein. In another embodiment, the method further comprises: (i) contacting the test sample with the at least one LRP-8 binding protein, wherein the binding protein binds to an epitope on LRP-8 or fragment thereof so as to form a first complex; (ii) contacting the first complex with the at least one detectable label, wherein the detectable label binds to an epitope of the LRP-8 binding protein or an epitope on the antigen or fragment thereof that is not bound by the LRP-8 binding protein to form a second complex; and (iii) detecting the presence of LRP-8 or fragment thereof in the test sample based on the signal generated by the detectable label in the second complex, wherein the presence of LRP-8 or fragment thereof is identified or indicated by analyzing the signal generated by the detectable label.

In another embodiment, the method further comprises: (i) contacting the test sample with the at least one LRP-8 binding protein, wherein the LRP-8 binding protein binds to an epitope on LRP-8 the antigen or fragment thereof so as to form a first complex; (ii) contacting the first complex with the at least one detectable label, wherein the detectable label competes with LRP-8 or fragment thereof for binding to the LRP-8 binding protein so as to form a second complex; and (iii) detecting the presence of LRP-8 or fragment thereof in the test sample based on the signal generated by the detectable label in the second complex, wherein the presence of LRP-8 or fragment thereof is measured by analyzing the signal generated by the detectable label.

In one embodiment, the test sample is from a patient and the method further comprises diagnosing, prognosticating, or assessing the efficiency of therapeutic/prophylactic treatment of the patient, and optionally wherein if the method further comprises assessing the efficacy of therapeutic/prophylactic treatment of the patient, the method optionally further comprises modifying the therapeutic/prophylactic treatment of the patient as needed to improve efficacy. In another embodiment, the method is adapted for use in an automated system or a semi-automated system. In another embodiment, the method determines the presence of more than one antigen in the sample.

In one aspect, the disclosure provides a method of determining the amount or concentration of LRP-8 or fragment thereof in a test sample by an immunoassay, wherein the immunoassay (a) employs at least one agent and at least one detectable label and (b) comprises comparing a signal generated by the detectable label with a control or a calibrator comprising LRP-8 or fragment thereof, wherein the calibrator is optionally part of a series of calibrators in which each calibrator differs from the other calibrators in the series by the concentration of LRP-8 or fragment thereof, and wherein the at least one agent comprises a LRP-8 binding protein described herein.

In one embodiment, the method comprises: (i) contacting the test sample with the at least one LRP-8 binding protein, wherein the LRP-8 binding protein binds to an epitope on LRP-8 or fragment thereof so as to form a first complex; (ii) contacting the first complex with the at least one detectable label, wherein the detectable label binds to an epitope on LRP-8 or fragment thereof that is not bound by the LRP-8 binding protein to form a second complex; and (iii) determining the amount or concentration of the antigen or fragment thereof in the test sample based on the signal generated by the detectable label in the second complex, wherein the amount or concentration of the antigen or fragment thereof is identified by analyzing the signal generated by the detectable label.

V. Kits

A kit for assaying a test sample for the presence, amount, or concentration of an analyte (or a fragment thereof) in a test sample is also provided. The kit comprises at least one component for assaying the test sample for LRP-8 (or fragments thereof) and instructions for assaying the test sample for the analyte (or a fragment thereof). The at least one component for assaying the test sample for the analyte (or a fragment thereof) can include a composition comprising an anti-LRP-8 multispecific binding protein, such as a DVD-Ig (or a fragment, a variant, or a fragment of a variant thereof), as described herein and which is optionally immobilized on a solid phase.

It will be readily apparent to those skilled in the art that other suitable modifications and adaptations of the methods of the disclosure described herein are obvious and may be made using suitable equivalents without departing from the scope of the disclosure or the embodiments disclosed herein.

Having now described the binding proteins and methods of making and using them of the disclosure in detail, the same will be more clearly understood by reference to the following examples, which are included for purposes of illustration only and are not intended to be limiting of the disclosure.

EXAMPLES

The following examples are intended to be illustrative and in no way limit the scope of the disclosure.

Example 1. Materials and Methods

Example 1.1. Cynomolgus LRP-8 De Novo Cloning

Example 1.1.1. Cynomolgus LRP-8 (Isoform 1) De Novo Cloning

Five cynomolgus cDNAs from the NGS database that has 13 tissues from a 99F donor and limited data from 4 donors were set as a workstation. The predicted cynomolgus LRP8 (isoform 1) was obtained. The cDNA sequences were translated in silico and the protein sequences of all tissues were aligned. The brain sequences were from different animals (234B, 481B, 568B, 571B, and 99F-HIPO). The protein sequence of cynomolgus LRP-8 isoform 1 is shown in Table 1.

Example 1.1.2. Cynomolgus LRP-8 (Isoform 3) De Novo Cloning

Eight cynomolgus cDNAs were purchased from a commercial source (BioChain Institute, CA). The eight cDNAs were derived from eight different tissues from five different donors (Table 9). The taxon ID and subspecies of these tissues are unknown.

TABLE 9

List of Commercial Sources of Cynomolgus cDNA from Different Tissues

| Tissue | BioChain Cat # | Lot # | Donor # |
|---|---|---|---|
| Brain | C1534035-Cy | B412038 | S12822N |
| Kidney | C1534142-Cy | B509183 | S12495N |
| Testis | C1534260-Cy | B312050 | S12805N |
| Lung | C1534152-Cy | B509138 | S12805N |
| Heart | C1534122-Cy | B406122 | S12821N |
| Spleen | C1534246-Cy | B606234 | S12823N |
| Liver | C1534149-Cy | B603082 | S12495N |
| Small intestine | C1534226-Cy | B402223 | S12495N |

Primer sets located in the 5' and 3' UTRs were designed based on the human LRP-8 sequence (Accession # NP_059992). The cDNAs from all tissues were used as templates and standard PCR analyses were performed. Two out of eight tissues (brain and testis) produced the expected PCR products. The PCR products from those tissues were cloned into a TA cloning vector (Invitrogen, CA), and multiple subclones (approximately 25) were sequenced. The cDNA sequences were translated in silico and the amino acid sequences of all tissues were aligned. The testis and brain sequences were from different animals (Table 9). The cynomolgus (*Macaca fascicularis*, crab-eating macaque) amino acid sequences from all animals were identical to each other. The *Macaca fascicularis* amino acid sequences from brain and testis were aligned with the *Homo sapiens* (human) sequence.

Example 1.2. LRP-8 Stable Cell Line Generation

HEK293H and 3T12 cells were cultured in T25 culture flasks and incubated at 37° C., 5% $CO_2$, and cells were passaged every four to five days. On the day before transfection, cells were diluted to $2\times10^5$ cells in 2 ml/well in a 6 well plate at 99% cell viability. The *Homo sapiens* LRP-8 (isoform3) (Accession # NP_059992) amino acid sequence was identified from GenBank. The *Mus musculus* (mouse) LRP-8 (isoform2) (Accession # NP_001074395) amino acid sequence was identified from GenBank. Cynomolgus LRP-8 amino acid sequence was identified in house by de novo cloning according to Example 1.1. The LRP-8 cDNAs were each cloned into a pCMV vector.

HEK293H and 3T12 cells were pre-incubated in six wells plate (2 ml/well in Opti-MEM) at 37° C./5% $CO_2$. A mixture of 2.5 µg plasmid DNA and 10 µl Lipofectamine2000 (Invitrogen) in 500 µl Opti-MEM was incubated at room temperature (RT) for 20 minutes, and then added to the cells. The cells were incubated at 37° C./5% $CO_2$ for 4 hours. The cells were incubated in culture medium at 37° C./5% $CO_2$ overnight. On the day after transfection, 2 mls of selection media with 0.5 mg/ml G-418 (final concentration) was added to each well. Growth media were changed on the transfected cells every 4-5 days. Stable clonal cell lines were generated by serial dilution of the parental cells and subsequent expansion of isolated single cell colonies. For characterization of cell lines by FACS, the 3T12 transfected cells were dissociated using PBS-based Cell Dissociation Buffer (Invitrogen). HEK293 transfected cells were dissociated using growth medium, washed and re-suspended in cold PBS (pH 7.2)/2% FBS (FACS Buffer) to $1\times10^6$ cells/ml, incubated one hour at 4° C. with the primary antibodies, and analyzed using an Accuri C6 flow cytometer.

Example 1.3. Endocytosis Assay

HEK293 cells overexpressing human LRP-8 were collected and $0.3\times10^6$ cells were plated into each well. Cells were then blocked with 5% normal goat serum on ice for 1 hour. After three washes with PBS, cells were re-suspended in 50 µl primary antibody 3 µg/ml in 5% normal goat serum for one hour on ice. Unbound primary antibody was removed by three washes with PBS. Cells were then re-suspended in 50 µL PBS/2% FBS and incubated at 3° C. the indicated times. Cells were placed on ice after incubation and washed three times with PBS. External antibody signal was blocked with unconjugated secondary antibody at 20 µg/ml on ice for one hour. After three washes with PBS, dead cells were stained for thirty minutes with eFlour660 (eBioscience) on ice. After three washes with PBS, cells were fixed and made permeable with BD Fix/Perm solution as described by the manufacturer. The internalized antibody signal was detected using a FITC-conjugated secondary antibody at 2 µg/ml. Unbound secondary antibody was removed by washing the cells three times with PBS. Cells were re-suspended in PBS, and each plate was read using an EnVision (without eFlour660 staining) or FACS Accuri (with eFlour660 staining) flow cytometer.

Example 1.4. Transcytosis Assay

Human epithelial colorectal adenocarcinoma Caco-2 cells (ECACC) were cultured and maintained as recommended by the manufacturer. Cells ($2.5 \times 10^4$) suspended in 200 µl culture medium were plated on the top side of a transwell filter (Corning #3470). A one milliliter (ml) of culture medium was added to the bottom side of the transwell. Cells were then cultured at 37° C., 5% $CO_2$ for 21 days before the assay. 50% of the medium was refreshed every three to four days and transepithelial electrical resistance (TEER) was measured with EVOM and ENDOHM (World Precision Instruments). Antibodies were prepared as a 10× solution in PBS. A volume (20 µl) of a test sample was added to the top side of the transwell. After an indicated time, 100 µl of each sample was collected from the bottom side of the transwell. At the end of the transcytosis assay, the TEER of each transwell was measured to ensure the integrity of the monolayer.

Antibody concentrations in the samples were determined using an Electrochemiluminescence-Meso Scale Discovery (ECL-MSD) assay. The MSD plate (MSD Cat# L15XB-3/L11XB-3) was coated with an F(ab')2 fragment of Fc fragment-specific capture antibody overnight at 4° C. The plate was blocked with 3% MSD blocking buffer (MSD Cat#R93AA-01) for one hour at 25° C., and then washed with 1× Tris-Buffered Saline and Tween 20 (TTBS) wash buffer. Standards and samples were diluted in 1% MSD assay buffer or 0.1% serum containing 1% MSD assay buffer. Each antibody was used as an internal standard to quantify respective antibody concentrations. Each assay plate was incubated for two hours at 25° C. and bound antibody was detected using goat anti-human/mouse/rat Sulfo-TAG (MSD). Plate values were read/calculated using an MSD SECTOR Imager 6000 system. Each concentration was determined from the standard curve with a five-parameter nonlinear regression program using Excel Fit software (N=3 for each test article).

Example 1.5. Cell-Based FACS Assay

LRP-8 stable cells and parental cells were collected and incubated in FACS buffer (1×PBS/2% FCS) and an aliquot was removed for control wells. Parental cells were labeled with CFSE (5(6)-Carboxyfluorescein N-hydroxysuccinimidyl ester). $5 \times 10^4$ cells/well of equal numbers of CFSE labeled parental cells and un-labeled LRP-8 stable cells were mixed and centrifuged for ten minutes at 1200 rpm. After adding FACS buffer, cells were spun at 2000 rpm for three minutes and then incubated for 15 minutes at 4° C. with mAb from 30 µg/ml, with a 3-fold dilution across the plate. After three washes with FACS buffer, cells were incubated for 15 minutes at 4° C. with 50 µl of secondary Thermoscientific APC antibody diluted 1:500. Unbound secondary antibodies were removed by three washes with FACS buffer, and the cells were re-suspended in 50 µl of FACS buffer and analysed using a BD FACSCanto system (BD Biosciences, CA).

Example 1.6. Antibody Affinity Measurements (Cell-Based MSD Assay)

A cell-based ECL-MSD binding assay was used to determine antibody affinity. HEK293 cells overexpressing human, monkey or mouse LRP-8 were added onto MSD 96-well plate (MSD Cat# L15XB-3/L11XB-3) and incubated at 37° C. for one hour. Cells were blocked using 15% FBS (Hyclone, Thermo Scientific Cat# SH300700.03) at RT for 30 minutes with mild agitation. Plates were washed with DPBS three times and Abs or DVD-Ig binding proteins were added to the well. After incubation at RT for one hour, plates were washed with DPBS and goat anti-human or anti-mouse Sulfo TAG (MSD Cat#R32AJ-1) was added. Plates were incubated at RT for one hour, washed with DPBS and immersed in MSD read buffer (MSD Cat#R92TD-2) before reading on a MSD SECTOR Imager 6000. EC50 values were obtained using Xlfit4 software system.

Example 1.7. Measuring Antibody Concentration in Mouse Brain, Spinal Cord, and Serum Wild type C57Bl/6N or Balb/c mice 6-8 weeks were injected intravenously or intraperitoneally with antibodies. After the indicated time, mice were perfused using DPBS with Heparin (1000 units/L) at a rate of 2 ml/minute for ten minutes. The brain of each murine subject was extracted, vertically divided into equal halves and the half brains were homogenized using Bullet Blender Blue (NextAdvance BBX24B) and zirconium beads (NextAdvance ZROB05/ZROB10) in 1% NP-40 (Thermo Scientific Cat#28324) in PBS containing protease inhibitors (Roche Diagnostics Ref#06538304001). Homogenized brain samples were rotated at 4° C. for one hour before spinning at 14,000 rpm for 20 minutes. Supernatant material was isolated for brain antibody measurement. The spinal cord was collected in some instances for further analysis. An incision was made post axis and prior to hips. The spinal cord was puffed out using syringe containing PBS. A segment of spinal cord (0.06-0.08 g) was cut and placed in a cryogenic test tube and snap frozen. A second segment of spinal cord (0.06-0.08 g) was cut and placed flat on an IHC cassette and fixed in 4% PFA. Homogenization and antibody detection methods were the same as those used for brain tissue.

Whole blood was collected from tail nick or cardiac puncture (terminal). Whole blood from tail nick was diluted 1:5 in assay buffer with EDTA and was snap frozen. Whole blood from cardiac puncture was collected in serum separator microcontainer tubes (BD Diagnostics, Ref#365956), allowed to clot for 30 minutes, and spun down at 13 k rpm at RT for 8 minutes. Supernatant was isolated for antibody measurement in serum.

Antibody concentrations were measured with an ECL-MSD assay. MSD plates (MSD Cat# L15XB-3/L11XB-3) were coated with an F(ab')2 fragment of donkey anti-human IgG, Fc fragment-specific polyclonal antibody (Jackson ImmunoResearch Code#709-006-098), or donkey anti-mouse IgG (Jackson ImmunoResearch Code#) overnight at 4° C. Plates were blocked with 3% MSD blocking buffer (MSD Cat#R93AA-01) for 1 hour at 25° C. Plates were washed with 1×TTBS wash buffer. Standards and samples diluted in 1% MSD assay buffer or 0.1% serum containing 1% MSD assay buffer were added. Each antibody was used as an internal standard to quantify respective antibody concentrations. Plates were incubated for two hours at 25° C. and bound antibody was detected with goat anti-human Sulfo-TAG (MSD Cat#R32AJ-1). Plates were read on an MSD SECTOR Imager 6000 system. Antibody concentrations were determined from the standard curve with a five-parameter nonlinear regression program using Excel Fit software. Each group contained three animals unless otherwise indicated. Data were expressed as means+/−SD.

Example 1.8. Immunohistochemistry and Evaluation

Antibody treated mice were perfused and divided into equal halves as described above, and half brains were fixed in 4% paraformaldehyde for 6 hours. Following fixative, tissues were processed through a graded series RUSH protocol (Leica TP1050 Tissue Processor) of alcohol to xylene and then embedded in paraffin (Leica EG1150H). 5 µM brain sections were cut with a microtome (Microm, HM355S). Sections were de-paraffinized and rehydrated to water and placed into Tris with tween-20 buffer (Teknova Cat#T5155). Staining was performed on a Dako autostainer links 48 system. Briefly, the sections were blocked with 3% hydrogen peroxide plus methanol for 30 minutes, washed with wash buffer then incubated for 8 minutes with protease I (Ventana Ref#760-2018). Sections were blocked with a streptavidin and biotin blocking kit (Vector Laboratories Cat#SP-2002) for 8 minutes each, followed by Dako protein block for 30 minutes. The sections were incubated for 1 hour at RT with a biotinylated donkey anti-human IgG (H+L) F(ab') (Jackson ImmunoResearch Code#709-066-149) at 15 µg/ml followed by an R.T.U Vectastain Universal ABC Kit PK-7100 (Vector Labs, UK) for 30 minutes at RT. The sections were then reacted with diaminobenzidine (DAB) chromogen (Dako Ref#K3468) for 3 minutes to form a brown precipitate, washed with water, counterstained with Gill Modified Hematoxylin (EMD Harleco Ref#65065) for 30 seconds and bluing reagent (Richard-Allan Scientific Ref#7301), dehydrated and mounted for microscopic observation. Five sections from different regions of the brain were stained. Representative images from the cerebellum and cortex sections were captured. All settings (filters and light levels) for each image were kept constant throughout the experiment. Staining intensity of vasculature, parenchyma and neurons were visually scored under a microscope using 0 to 4 scale, where 0 is no staining; 1 is light staining at small portion of tissue; 2 is light staining at most tissue, 3 is moderate staining at most tissue; 4 is strong staining at most tissue. The data was evaluated in a blind manner. The average score of each group with at least three animals was reported.

Example 1.9. Aldevron cDNA Immunization and Antibody Generation

Human LRP-8 Extracellular domain (ECD) cDNA was subcloned into an Aldevron proprietary immunization vector. Genetic immunization introduces the cDNA encoding the target sequence into the skin of rat, the target protein was expressed, and an immune response was generated. The screening system developed using the GENOVAC Antibody Technology at Aldevron Freiburg is based on screening vectors expressing the target protein that are transiently transfected into mammalian cells. In this case, hLRP-8 and mLRP-8 were transiently expressed for screening. Bleeds and hybridoma supernatants were screened using flow cytometry.

Example 1.10. Epitope Binning

Example 1.10.1. Cell-Based Anti-LRP-8 Competition Assay

An anti-LRP-8 competition assay was based on a cell-based Electrochemiluminescence-Meso Scale Discovery Assay (ECL-MSD) binding assay HEK293 cells overexpressing mouse or cynomolgus monkey LRP-8 were added onto MSD 96-well plate (MSD Cat# L15XB-3/L11XB-3) and incubated at 37° C. for 1 hour. Cells were blocked using 15% FBS (Hyclone, Thermo Scientific Cat# SH300700.03) at RT for 30 minutes with mild agitation and plates were washed with DPBS 3 times. Competing LRP-8 antibodies with human Fc and mouse Fc domains were used in two competition combinations:

Example 1.10.2. Competition 1 (Competitor Ab with Mouse Fc)

A 1:1 mixture of fixed concentrated anti-LRP-8 human Fc Ab and a titer of competitor LRP8 mouse Fc Ab were added onto the plate and incubated at room temp for 1 hour. After washing, anti-human SULFO-TAG Ab was added on the plate and incubated for 1 hour.

Example 1.10.3. Competition 2 (Competitor Ab with Human Fc)

A 1:1 mixture of fixed concentrated anti-LRP-8 mouse Fc Ab and a titer of competitor LRP-8 human Fc Ab were added onto the plate and incubated at room temp for 1 hour. After washing, an anti-mouse SULFO-TAG Ab was added to the plate and incubated for 1 hour. Plates were washed with DPBS and immersed in MSD read buffer T surfactant free (MSD Cat# R92TD-2) before reading on an MSD SECTOR Imager 6000. Data were obtained and analyzed using a GraphPad Prism 6 software package (GraphPad Software, Inc., La Jolla, Calif.).

Example 1.11. Crystallographic Study of Anti-LRP-8 ML199.11H1.5B2 Fab in Complex with CR1 Peptide Fab fragment of LRP-8 11H1.5B2 was prepared by papain cleavage of the parent antibody, anti-LRP-8 ML199.11H1.5B2 [mu/hu IgG1/k] LALA chimeric antibody. Papain was activated with 50 mM cysteine in PBS, pH 7.4 buffer. Anti-LRP-8 ML199.11H1.5B2 chimeric antibody in PBS, pH 7.4 buffer was mixed with papain at 1:100 weight ratio of papain to the antibody and incubated for 1 hr at 37° C. The reaction was quenched with 5 mM iodoacetamide. The mixture was purified on 5 ml Mab SelectSure resin (GE Healthcare) where the Fab fragment was collected as flow through. The flow through was concentrated using an Ultrafree-15 Biomax 10 kDa molecular weight cut-off (MWCO) centrifugal device (Millipore). The concentrated mixture was purified on 2.6 cm×60 cm Sephacryl 200 HiPrep column (GE Healthcare) pre-equilibrated in 50 mM HEPES, 50 mM NaCl, pH 7.5 buffer.

CR1 peptide was dissolved with the protein buffer from the last purification step (50 mM NaCl, 50 mM HEPES, pH 7.5) to a final concentration of 100 mM. The peptide was added to the LPR-8 Fab sample (29.4 mg/ml) to a final molar ratio (peptide over protein) of 8:1. Sitting drop vapor diffusion method was used by mixing equal volume of LRP-8-peptide complex and the crystallization reagent of 25% PEG 4000, 0.2 M Ammonium Sulfate, 0.1 M Sodium acetate/HCl, pH 4.6. Thin stacking plate crystals were initially found with 2-3 days and continued to grow to their full size within one week. Single plate crystals were separated and flash frozen into liquid nitrogen using 20% propylene glycol plus the crystallization solution as the cryoprotectant. Diffraction data were collected at a temperature of 100 K using beamline XALOC (BL13) at ALBA synchrotron, Spain.

Diffraction data for the complex crystal structure were processed using the program autoPROC from Global Phasing Ltd. The Fab fragment and CR1 peptide complex dataset was processed in the space group P21 with the following unit cell dimensions: a=41.3 b=79.8 c=67.1, β=95.5. A maximum likelihood molecular replacement solution was determined using the program PHASER using an Fab search model reported previously (Protein Data Bank entry 1VPO). Coordinates for 1 Fab molecule were found based on the molecular replacement solution. Preliminary refinement of the resulting solution was conducted using REFMAC and the program BUSTER. The model for CR1 peptide and edits to the Fab scaffold were built manually using the program COOT and examination of 2Fo-Fc and Fo-Fc electron-density maps. Refinement concluded with the addition of water molecules using BUSTER. Final refinement statistics reported Rfree/Rwork values of 0.23/0.20.

The contacts between the Fab fragment and CR1 peptide involve both critical hydrogen bond and hydrophobic interactions which stabilize the interface. A list of molecular contacts (measuring within a 4.0 Å range) were generated using the program NCONT in the CCP4 suite of programs. The contacts were measured between the peptide and the corresponding light and heavy chains of the Fab fragment.

Example 1.12. Binding Studies of Mutant Peptides to Delineate Residues Implicated in Binding

Example 1.12.1. Mutagenesis of CR1 and CR2 Peptides

Cyclic peptides CR1 and CR2, based on loop sequences from LRP-8, were designed and used as tools for antibody generation and binding studies for the generated antibodies.

```
3A7Q  GSGPAKECEKDQFQCRNERCIPSVWRCDEDDDCLDHSDEDDCPK

CR1   -------CEKDQFQSRNERCIPSVWRC [cyc (1, 13)]

CR2   -------CADSDFTSDNGHCIHERWKC [cyc (1 = 13)]

(SEQ ID NOS 205 and 5-6, respectively, in order of
appearance)
```

These peptides were shown by Biacore studies to bind several subsequently generated antibodies, including anti-LRP-8 ML199-11H1.5B2 antibody. Based on the aligned sequence of CR1 and CR2 peptide, the sequence FxSxN appeared to be common in both binding peptides, and therefore likely important for the binding epitope. Note that the serine in the CR1 and CR2 peptide sequences was already changed from the parent LRP-8 protein sequence, removing an unpaired cysteine. Modified forms of cyclic peptide CR1, containing the following changes were synthesized, and examined for binding to chimeric anti-LRP-8 ML199-11H1.5B2 antibody ([hu IgG1/k] LALA) by both BIACORE and direct ELISA assays.

```
CR1   [cyc(1, 13)] H2N-CEKDQFQSRNERCIPSVWR(KAoa)-
amide

CR1.1 [cyc(1, 13)] H2N-CEKDQAQSRNERCIPSVWR(KAoa)-
amide

CR1.2 [cyc(1, 13)] H2N-CEKDQFQARNERCIPSVWR(KAoa)-
amide

CR1.3 [cyc(1, 13)] H2N-CEKDQFQSRAERCIPSVWR(KAoa)-
amide

CR1.4 [cyc(1, 13)] H2N-CEKDQAQARAERCIPSVWR(KAoa)-
amide (SEQ ID NOS 206-210, respectively, in order of
appearance)
```

In both assays, peptides CR1.2 and CR1.3 bound with affinity similar that of the unmodified CR1, whereas peptides CR1.1 & CR1.4, both containing the F→A substitution, did not bind. This indicated that the phenylalanine in the sequence -FQSRN- (SEQ ID NO: 211) is required for antibody binding, and thus a key residue in the epitope.

Example 1.12.2. CR1/CR2 Peptide Anti-LRP-8 Binding ELISA

High binding MSD plates (MSD Cat# L15XB-3/L11XB-3) were coated with 1 µg/ml of CR1 or CR2 peptide overnight at 4° C. The next day, the plate was blocked with 3% MSD blocking buffer (MSD Cat# R93AA-01) for 1 hour at RT. The plates were washed with TTBS buffer (20 mM Tris; 0.5% Tween, 150 mM sodium chloride; pH 7.5) three times and a titer of anti-LRP-8 human Fc Ab was added. After incubating for 1 hour at RT, plate was washed and anti-human SULFO-TAG Ab was added to the plate and incubated for 1 hour. The plates were washed and immersed in MSD read buffer T with surfactant (MSD Cat# R92TC-1) before reading on an MSD SECTOR Imager 6000. Data were obtained and analyzed using a GraphPad Prism 6 software package (GraphPad Software, Inc., La Jolla, Calif.).

Example 2. Generation of Anti-LRP-8 Antibodies Based on LRP-8 Peptides

Example 2.1. Design of LRP-8 Peptides as Immunogen

LRP-8 contains complement-like repeat regions (CR) in its sequence and these were used as antigenic peptides. A high resolution structure of CR7 from LRP was solved to 1.8 Å resolution as presented previously (Simonovic et al. (2001) Biochem. 40(50):15127-34). This structure shows a loop/turn motif that is stabilized by a disulfide linkage (FIG. 1A). When examining two complement-like repeat regions in LRP-8 (CR1 and CR2), this loop/motif was predicted by sequence as compared to the protein x-ray structure of LRP (Protein Data Bank ID: 1J8E). This sequence is outlined in FIG. 1B. Due to an internal Cys in the sequence, this residue was mutated to serine (Ser; shown in FIG. 1B in bold) to increase peptide stability and improve peptide aggregation. The peptide was cyclized to mimic the beta turn as displayed by the structure 1J8E. The resulting designed peptides are shown below (KLH—keyhole limpet hemocyanin).

```
CR1:
                                    (SEQ ID NO: 206)
[Cyc (1, 13)]H2N-CEKDQFQSRNERCIPSVWR(KAoa)-
amide 10 mgs, >90% Purity (5 mgs uncoupled,
5 mgs to KLH via Aoa)

CR2:
                                    (SEQ ID NO: 212)
[Cyc (1, 13)]H2N-CADSDFTSDNGHCIHERWK(KAoa)-
amide 10 mgs, >90% Purity (5 mgs uncoupled,
5 mgs to KLH via Aoa)
```

Figure 2D:
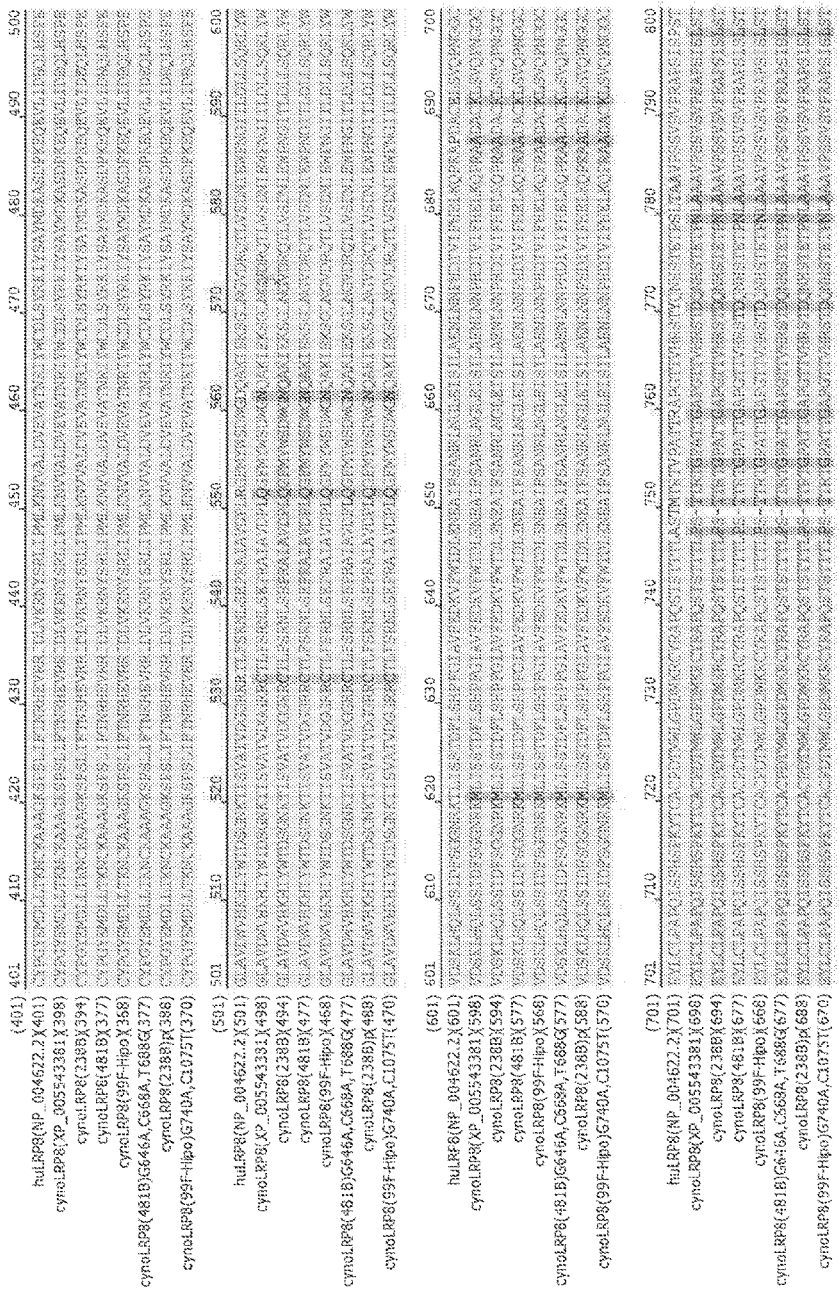
Figure 2E:
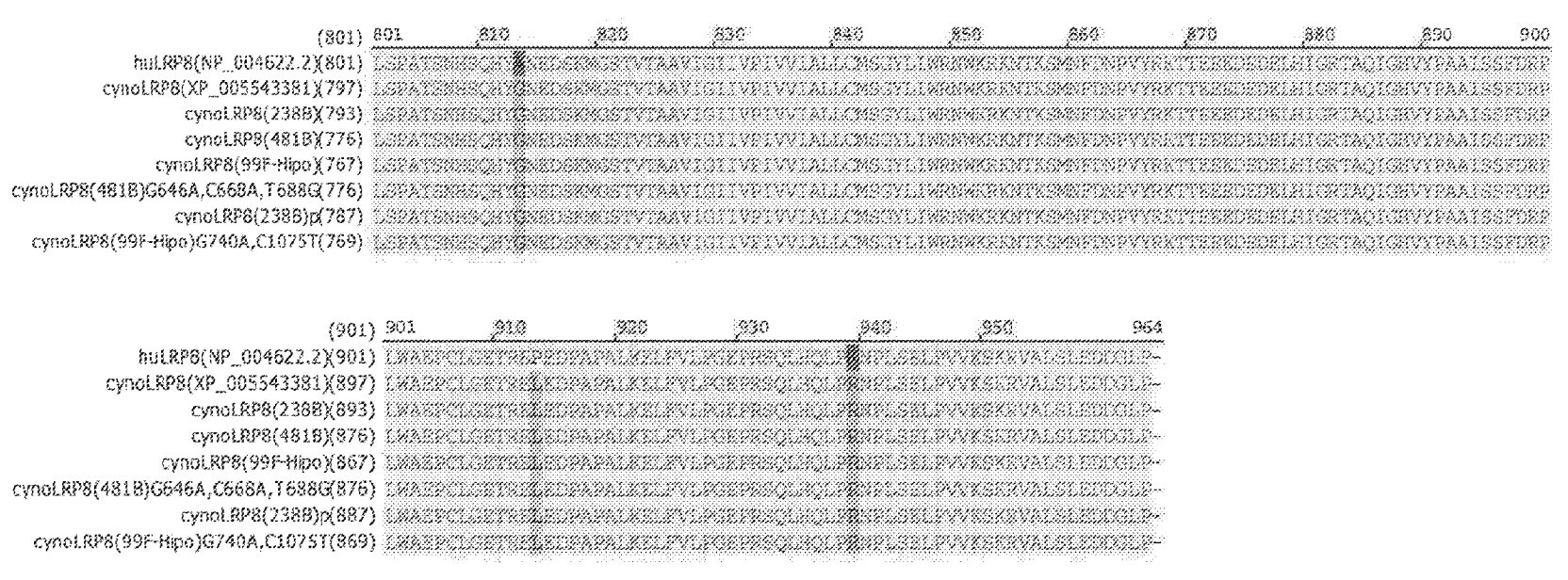

Sequence analysis shows that CR1 and CR2 peptides share sequence similarities (FIG. 1B), and are identical in the analyzed cynomolgus and human samples shown in FIGS. 2A and 2B. FIGS. 2C, 2D, and 2E show the alignment between human and cyno LRP-8 isoform 3.

Example 2.2. Antibody Generation and Screening

KLH-conjugated CR1 and CR2 peptides were synthesized by New England Peptide (Gardner, Mass.). Equal amounts of CR1 and CR2 (50 µg) were mixed for immunization and were injected in mice subcutaneously every three weeks for four times before the mouse spleens were harvested. Lymphocytes were isolated and fused with NS0 cells with a well-established protocol. Hybridoma supernatant (SN) was used for cell-based FACS with hLRP-8-HEK293 stable cells and HEK293 parental cells. Supernatants (SN) that bind to hLRP-8-HEK293 stable cells, but not to HEK293 parental cells were selected. All positive SNs were tested against the 3T12-LRP-8 cells to further confirm binding. Two fusions (ML199 and ML201) were generated and about six positively binding hybridomas were selected. Three monoclonal antibodies (ML201-2B4.2B1.2H10; ML201-8F3.3D7; and ML199-11H1.5B2) were subcloned.

Example 2.3. Anti-LRP-8 and Mu/Hu Chimeric Antibody Generation

Anti-LRP-8 antibodies were produced at AbbVie Bioresearch Center. The antibody variable domain DNAs were codon optimized and cloned into expression vectors to produce mouse or human IgG proteins. The antibody constructs were expressed in HEK293 cells and purified according to established methods. Expression yield was measured with a Nanodrop spectrophotometer. Percentile of monomer was determined by size exclusion chromatography (SEC). Heavy chain and light chain variable regions of three monoclonal antibodies (ML201-2B4.2B1.2H10; ML201-8F3.3D7; and ML199-11H1.5B2) are summarized in Tables 2 and 5.

Example 2.4. Murine Anti-LRP-8 Antibody Analysis

Figure 3A:
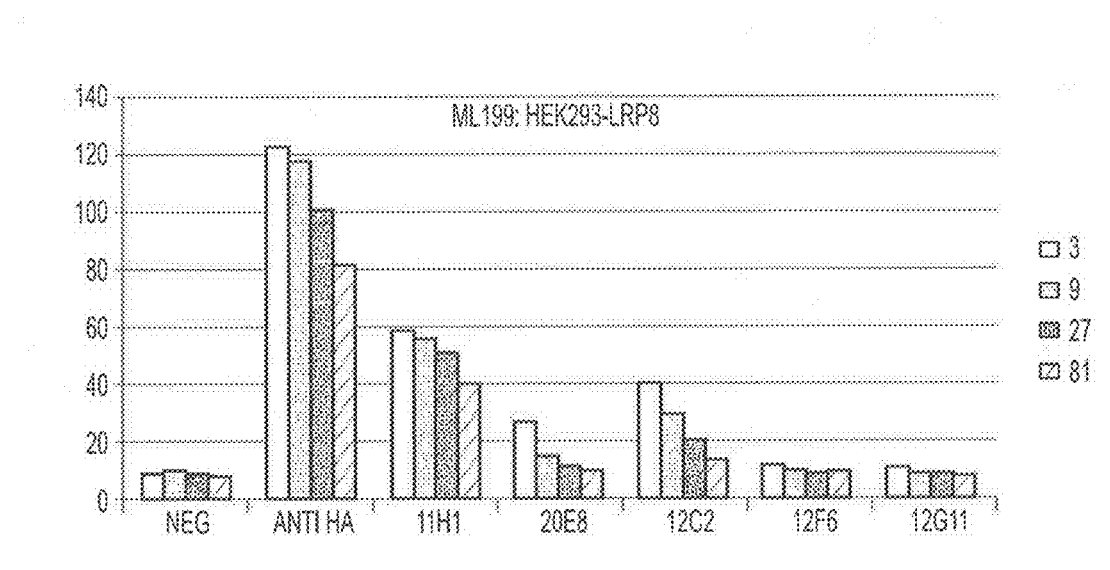
FIG. 3A shows FACS binding analysis of LRP-8 expressing HEK293 cells (ordinate) to ML199 antibodies from mice immunized using CR1 and CR1. The antibodies clones analyzed were 11H1, 20E8, 12C2, 12F6 and 12G11 (abscissa). An HA-Tag antibody was used as a control.
Figure 3B:
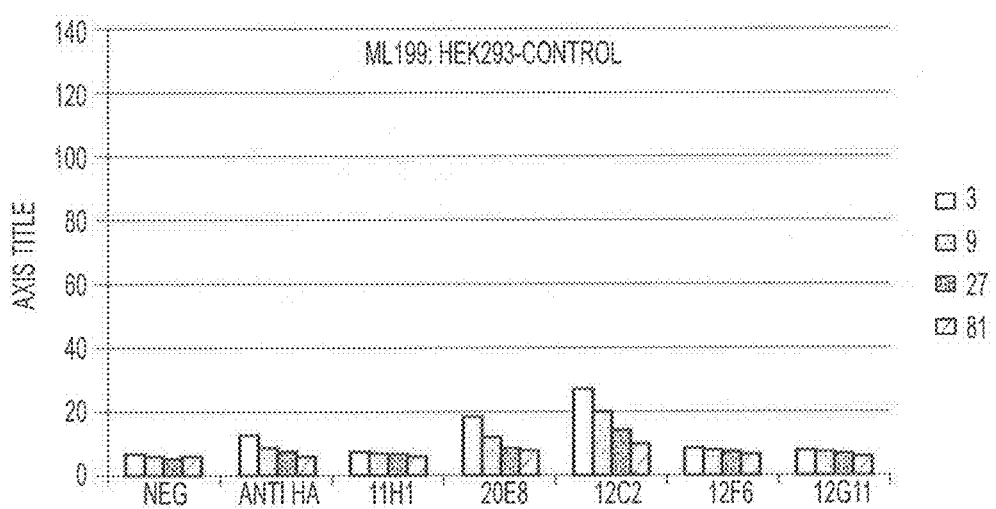
FIG. 3B shows FACS binding analysis of HEK293 cells that do not express LRP-8 (ordinate) to ML199 antibodies. The antibodies clones analyzed were 11H1, 20E8, 12C2, 12F6 and 12G11 (abscissa). An HA-Tag antibody was used as a control.
Figure 4A:
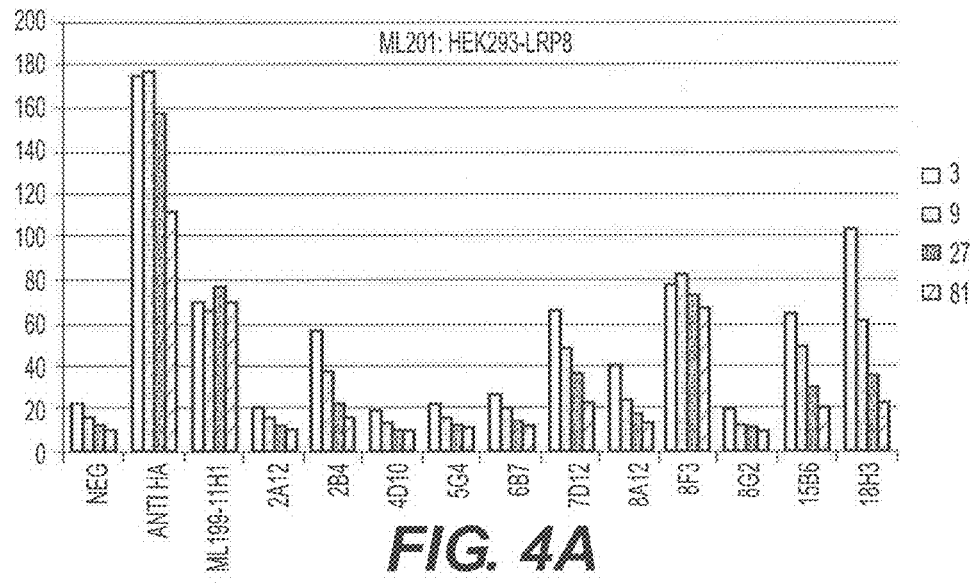
FIG. 4A shows FACS binding analysis of LRP-8 expressing HEK293 cells (ordinate) to ML199-11H1 antibody and ML201 antibodies (abscissa). An HA-Tag antibody was used as a control.
Figure 4B:
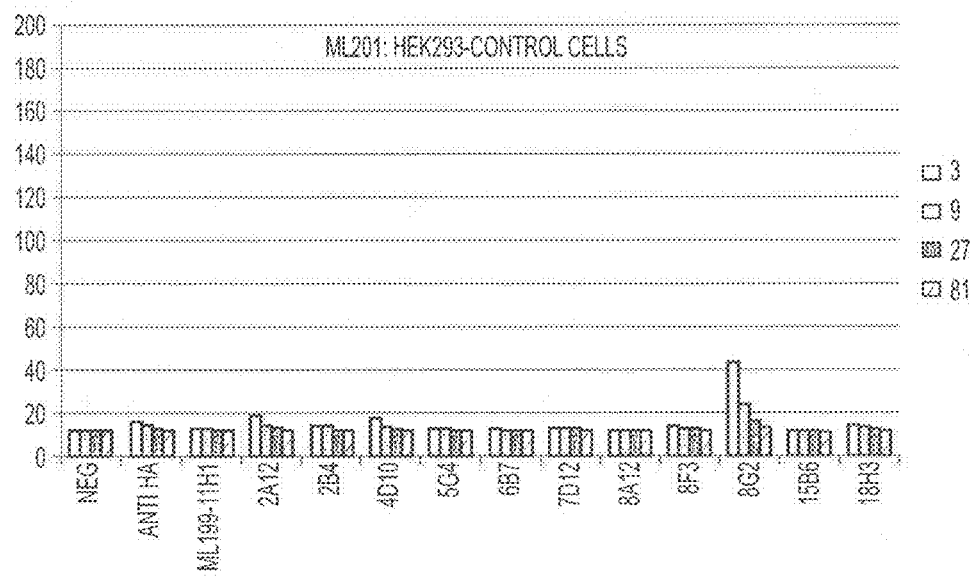
FIG. 4B shows FACS binding of HEK293 cells that do not express LRP-8 (ordinate) to ML199-11H1 antibody and ML201 antibodies (abscissa). An HA-Tag antibody was used as a control.

The ML199 and ML201 antibodies were analyzed for binding to LRP-8 transfected HEK293 cells and control HEK293 cells (FIGS. 3 and 4). Data showed that the ML199-11H1, ML201-8F3, and ML201-2B4 clones effectively bound human, mouse, and cyno LRP-8 (Tables 10-12).

TABLE 10

Binding Data For anti-LRP-8 M199-11H1.5B2 Antibody

| Clone | huLRP-8 cell based EC50 (nM) | Reactivity | Endocytosis (fold-over Ig) | Transcytosis (folder-over Ig) |
|---|---|---|---|---|
| anti-LRP-8,11H1.5B2 | 0.4 | hu, cyno, mu | 1.7 | 2.0 |

TABLE 11

ECL-MSD Binding with 10 µg/Ml Abs (Data Re-Expressed as Fold over mIgG Control)

| | human_LRP-8_HEK293 | cyno-LRP-8-HEK293 | mouse-LRP-8-HEK293 | HEK293 parental |
|---|---|---|---|---|
| ab58216 mFc | 17.3* | 1.2 | 19.2* | 0.9 |
| ML199-11H1-5B2 muFc | 15.1* | 7.0** | 23.1* | 1.0 |
| ML201-8F3-3D7 muFc | 13.6* | 5.2** | 21.1* | 1.0 |
| ML201-2B4.2B1.2H10 muFc | 14.2* | 2.8*** | 1.2 | 0.9 |

TABLE 12

Endocytosis and Transcytosis Data (Data Expressed as Fold over IgG Control)

| | Endocytosis hLRP-8-HEK293 (FACS-based) | Transcytosis Caco-2_hLRP-8 |
|---|---|---|
| ab58216 mFc | 2.6*** | 1.53 |
| ML199-11H1-5B2 muFc | 1.7 | 2.0*** |
| ML201-8F3-3D7 muFc | 1.6 | 1.08 |
| ML201-2B4.2B1.2H10 muFc | 1.8 | 1.44 |

*More than 10 fold; more than 5-10 fold; *more than 2-5 fold

Example 2.5. Chimeric Anti-LRP-8 Antibody Analysis

Figure 5:
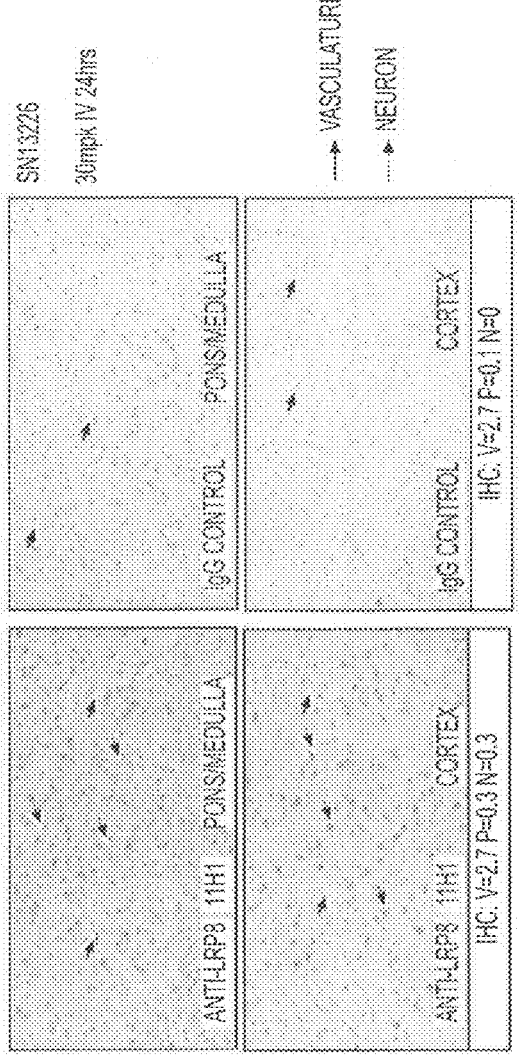
FIG. 5 shows immunohistochemistry (IHC) data from a mouse in vivo pharmacokinetics (PK) study using an anti-LRP-8 antibody, ML199.11H1.5B2 mu/hu IgG1 m/k. The data show enhanced uptake into the brain 24 hours after 30 mg/kg (mpK) intravenous (IV) dosing. Positive IHC staining is observed in parenchyma and neuronal cells.
Figure 6:
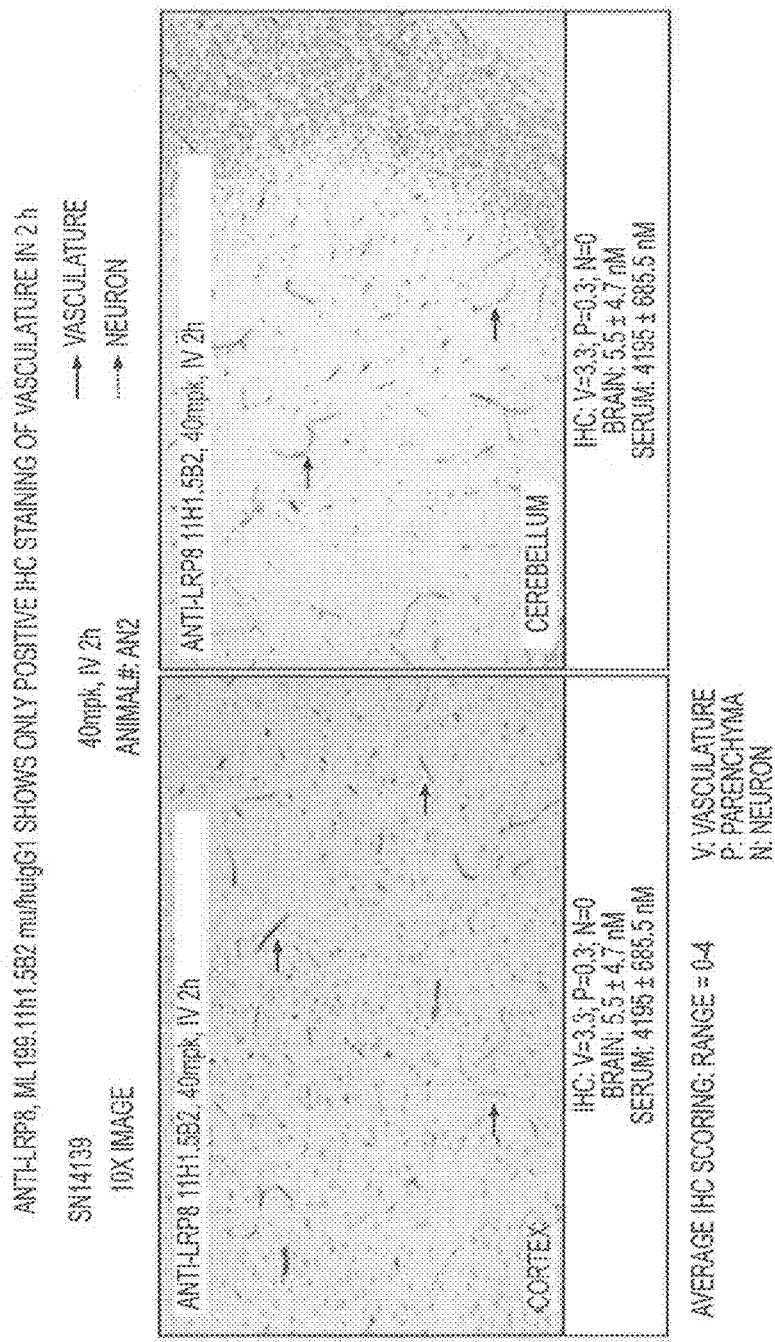
FIG. 6 shows IHC data from a mouse in vivo pharmacokinetics PK study using an anti-LRP-8 antibody, ML199.11H1.5B2 mu/hu IgG1 m/k. The data confirm that anti-LRP-8, ML199.11h1.5B2 mu/huIgG1 shows positive IHC staining of vasculature two hours after 40 mpK IV dosing of the anti-LRP-8 antibody.
Figure 7:
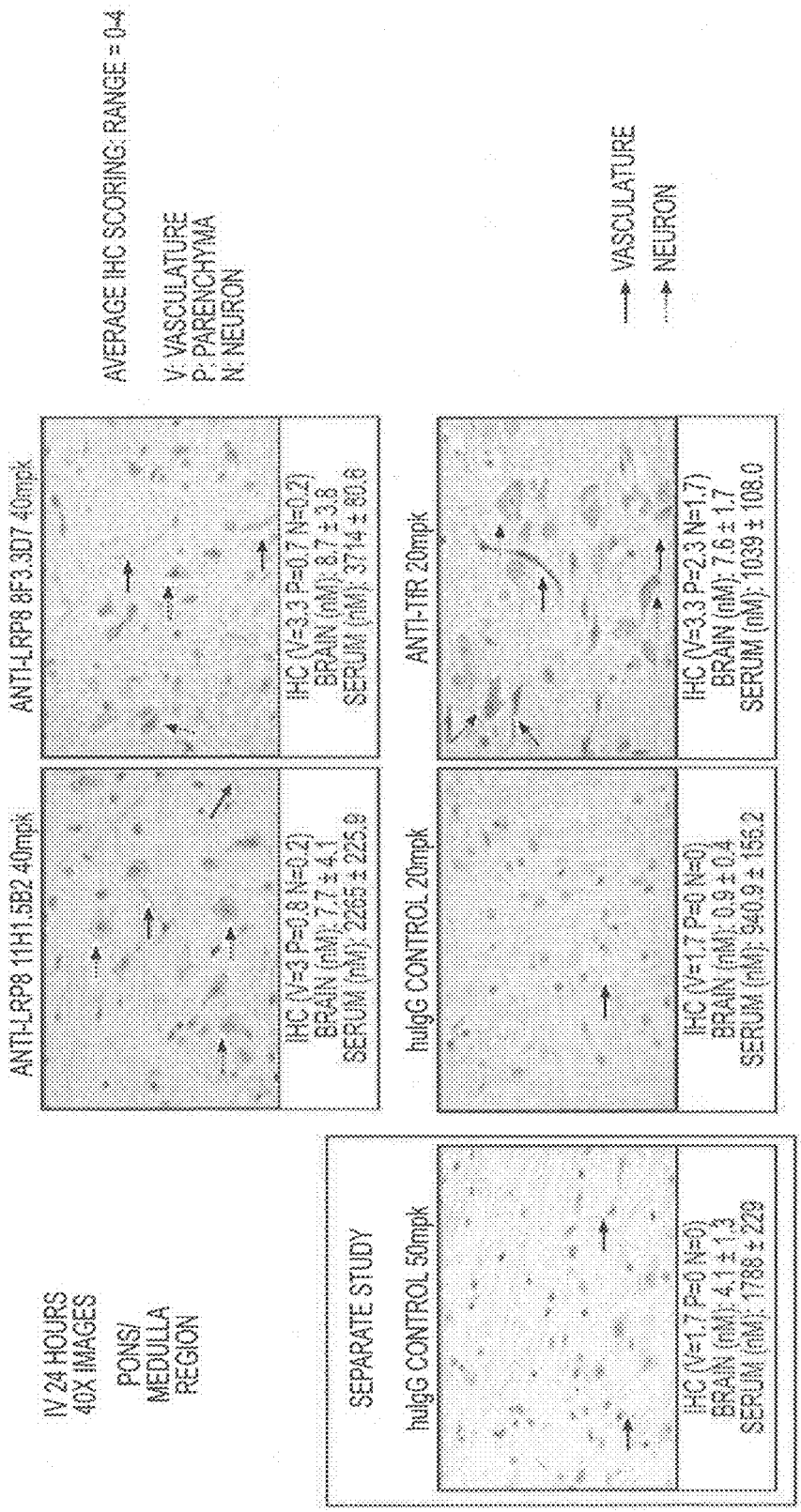
FIG. 7 shows a set of photographs from a mouse in vivo staining study using anti-LRP-8 antibodies, ML199.11H1.5B2 and 8F3.3D7, and an anti-TfR antibody as a positive control (20 mpk or 40 mpk IV dosing). A human IgG antibody was used as a negative control. Staining data show that the anti-LRP-8 antibodies had enhanced uptake into brain 24 hours after dosing. The photographs show positive IHC staining of parenchyma and neuronal cells.

Chimeric anti-LRP-8 antibody (ML199.11H1.5B2 mu/hu IgG1 m/k) was intravenously administered to subjects and analyzed for IHC staining. Mouse in vivo PK study data using an intravenous dose (30 mpk) of anti-LRP-8, ML199.11H1.5B2 mu/hu IgG1 m/k antibody showed enhanced uptake into brain in 24 hours (FIG. 5). Clear positive IHC staining was parenchyma and neuronal cells. Anti-LRP-8, ML199.11h1.5B2 mu/huIgG1 at an intravenous dose of 40 mpk also produced positive IHC staining of vasculature in two hours (FIG. 6). As shown in FIG. 7, anti-LRP-8 antibodies (i.e., anti-LRP-8 ML199.11H1.5B2 and anti-LRP-8 8F3.3D7 40 mpk) and control Tfr antibody had enhanced uptake into brain in 24 hours. Positive IHC staining of parenchyma and neuronal cells was observed. Tables 13 and 14 show anti-LRP-8 PK study IHC score and data for antibody concentration detected in brain, spinal cord, and serum samples (e.g., homogenates). V, P, and N in Tables 13 and 14 refer to vasculature, parenchyma, and neuron, respectively.

TABLE 13

MSD Data for LRP-8 Antibodies

| SN14139 ANIMAL # | Test Article | Treatment (Single/IV) | Conc, nM Brain | Conc, nM Spinal Cord | Conc, nM Serum | % Ab/serum Brain | % Ab/serum Spinal Cord | Mean Conc, nM Brain | Mean Conc, nM Spinal Cord | Mean Conc, nM Serum | IHC score V | IHC score P | IHC score N | IHC score-average V | IHC score-average P | IHC score-average N |
|---|---|---|---|---|---|---|---|---|---|---|---|---|---|---|---|---|
| 1 | anti-LRP-8 | 2 hr/ | 10.91 | 2.08 | 3419.40 | 0.32 | 0.06 | | | | 4 | 0 | 0 | 3.3 | 0.3 | 0.0 |
| 2 | (ML199.11H1.5B2) | 40 mpk | 3.98 | 1.31 | 4443.69 | 0.09 | 0.03 | | | | 3 | 0.5 | 0 | | | |
| 3 | hFc | | 1.76 | 2.13 | 4720.77 | 0.04 | 0.05 | 5.5 ± 4.7 | 1.8 ± 0.4 | 4195 ± 685.5 | 3 | 0.5 | 0 | | | |
| 4 | Lot2194993 | 4 hr/ | 3.89 | 0.98 | 2717.01 | 0.14 | 0.04 | | | | 4 | 0 | 0 | 3.7 | 0.0 | 0.0 |
| 5 | | 40 mpk | 10.93 | 1.37 | 3261.31 | 0.33 | 0.04 | | | | 4 | 0 | 0 | | | |
| 6 | | | 2.20 | 1.65 | 2044.51 | 0.11 | 0.08 | 5.6 ± 4.6 | 1.3 ± 0.3 | 2674 ± 609.5 | 3 | 0 | 0 | | | |
| 7 | | 24 hr/ | 12.52 | 5.82 | 2420.83 | 0.52 | 0.24 | | | | 4 | 1 | 0 | 3.0 | 0.8 | 0.2 |
| 8 | | 40 mpk | 5.56 | 2.68 | 2005.72 | 0.28 | 0.13 | | | | 3 | 1 | 0.5 | | | |
| 9 | | | 5.15 | 4.30 | 2367.86 | 0.22 | 0.18 | 7.76 ± 4.1 | 4.2 ± 1.5 | 2265 ± 225.9 | 2 | 0.5 | 0 | | | |
| 10 | anti-LRP-8 | 24 hr/ | 12.76 | | 37.91 | 0.34 | | | | | 4 | 0.5 | 0.5 | 3.3 | 0.7 | 0.2 |
| 11 | (ML201.8F3.3D7) | 40 mpk | 8.11 | | 3630.11 | 0.22 | | | | | 3 | 0.5 | 0 | | | |
| 12 | hFc LOT2193691 | | 5.23 | | 3721.20 | 0.14 | | 8.7 ± 3.8 | | 3714 ± 80.6 | 3 | 1 | 0 | | | |
| 34 | hIgG1/K mut | 24 hr/ | 1.43 | 0.94 | 848.40 | 0.17 | 0.11 | | | | 3 | 0 | 0 | 1.7 | 0.0 | 0.0 |
| 35 | (234,235) | 20 mpk | 0.77 | 0.28 | 1121.18 | 0.07 | 0.02 | | | | 1 | 0 | 0 | | | |
| 36 | Lot2140396 | | 0.61 | 0.30 | 853.10 | 0.07 | 0.04 | 0.9 ± 0.4 | 0.5 ± 0.3 | 940.9 ± 156.2 | 1 | 0 | 0 | | | |
| 37 | (TfR) | 24 hr/ | 9.5 | | 1085.95 | 0.87 | | | | | 4 | 3 | 2 | 3.3 | 2.3 | 1.7 |
| 38 | hFc | 20 mpk | 7.23 | | 1114.89 | 0.65 | | | | | 3 | 2 | 1 | | | |
| 39 | Lot1892291 | | 6.09 | | 915.12 | 0.67 | | 7.6 ± 1.7 | | 1039 ± 108.0 | 3 | 2 | 2 | | | |

LLD for anti-LRP-8 (ML199.11H1.5B2): Brain/Spine = 4.12 ng/mL & Serum = 0.02 ng/mL
LLD for anti-LRP-8 (ML201.8F3.3D7)): Brain/Spine = 4.12 ng/mL & Serum = 0.05 ng/mL
LLD for IgG: Brain/Spine = 0.46 ng/mL & Serum = 0.05 ng/mL
LLD for (TfR): Brain/Spine = 0.46 ng/mL & Serum = 0.05 ng/mL

TABLE 14

Anti-LRP-8 PK Study IHC Score and Concentration in Brain Homogenates and Serum

| SN14166 Balb/C, C57, SJL Male 8 Wk Mice Animal # | Group | Timepoint/ ROUTE/Dose | Male Animal | IHC Brain score (0-4) V | IHC Brain score (0-4) P | IHC Brain score (0-4) N | IHC Brain average score V | IHC Brain average score P | IHC Brain average score N | IHC Spinal Cord score (0-4) V | IHC Spinal Cord score (0-4) P | IHC Spinal Cord score (0-4) N |
|---|---|---|---|---|---|---|---|---|---|---|---|---|
| 1-3 | anti-LRP-8 (ML199.11H1.5B2) hFc Lot2194993 | 28 hr/IV/50 mpk (Multiple) | Balb/C | 3 | 1 | 0.5 | 3.0 | 1.0 | 0.5 | 3 | 1 | 2 |
| | | | | 3 | 1 | 0.5 | | | | 4 | 1 | 2 |
| | | | | 3 | 1 | 0.5 | | | | 4 | 1 | 2 |
| 4-6 | | | C57B1/6N | 4 | 1 | 1 | 4.0 | 0.8 | 1.0 | | | |
| | | | | 4 | 1 | 1 | | | | | | |
| | | | | 4 | 0.5 | 1 | | | | | | |
| 7-9 | anti-LRP-8 (ab58216) hFc Lot2196879 | 2 h/IV/45 mpk (single) | Balb/C | 3 | 0.5 | 0.5 | 3.0 | 0.2 | 0.2 | | | |
| | | | | 3 | 0 | 0 | | | | | | |
| | | | | 3 | 0 | 0 | | | | | | |
| 10-12 | | 28 hr/IV/45 mpk (Multiple) | Balb/C | 4 | 1 | 1 | 3.3 | 0.7 | 0.8 | 4 | 0.5 | 1 |
| | | | | 3 | 0.5 | 1 | | | | 3 | 0.5 | 1 |
| | | | | 3 | 0.5 | 0.5 | | | | 3 | 0.5 | 1 |
| 13-15 | | 2 hr/IV/45 mpk (single) | C57B1/6N | 3.5 | 0 | 0 | 3.2 | 0.2 | 0.0 | | | |
| | | | | 3 | 0 | 0 | | | | | | |
| | | | | 3 | 0.5 | 0 | | | | | | |
| 16-18 | | 28 hr/IV/45 mpk (Multiple) | C57B1/6N | 4 | 0.5 | 0 | 4.0 | 0.7 | 0.2 | | | |
| | | | | 4 | 1 | 0.5 | | | | | | |
| | | | | 4 | 0.5 | 0 | | | | | | |
| 25-27 | hIgG1/K mut (234,235) Lot2140396 | 24 hr/IV/50 mpk (Single) | Balb/C | 2 | 0 | 0 | 1.7 | 0.0 | 0.0 | 1 | 0 | 0 |
| | | | | 1 | 0 | 0 | | | | 2 | 0 | 0 |
| | | | | 2 | 0 | 0 | | | | 1 | 0 | 0 |
| 28-30 | | 24 hr/IV/50 mpk (Single) | C57B1/6N | 4 | 0.5 | 0 | 3.3 | 0.3 | 0.0 | | | |
| | | | | 3 | 0.5 | 0 | | | | | | |
| | | | | 3 | 0 | 0 | | | | | | |

TABLE 14-continued

Anti-LRP-8 PK Study IHC Score and Concentration in Brain Homogenates and Serum

| | | | | | | | | | | | |
|---|---|---|---|---|---|---|---|---|---|---|---|
| 31-33 | | 24 hr/IV/50 mpk (Single) | SJL | 2 | 0 | 0 | 2.3 | 0.0 | 0.0 | 2 | 0 | 0 |
| | | | | 2 | 0 | 0 | | | | 2 | 0 | 0 |
| | | | | 3 | 0 | 0 | | | | 3 | 0 | 0 |
| 34-36 | (TfR) Lot 1892324 | 24 hr/IV/50 mpk (Single) | C57B1/6N | 3 | 1.5 | 1.5 | 3.7 | 1.7 | 1.7 | | | |
| | | | | 4 | 1.5 | 1.5 | | | | | | |
| | | | | 4 | 2 | 2 | | | | | | |

SN14166

Balb/C, C57, SJL Male 8 Wk Mice

| Animal # | Group | Timepoint/ ROUTE/Dose | Male Animal | IHC Spinal Cord average score V | P | N | MSD-Brain Conc, nM Brain | Serum | % Ab/ serum | Mean Conc, nM Brain | Serum |
|---|---|---|---|---|---|---|---|---|---|---|---|
| 1-3 | anti-LRP-8 (ML199.11H1.5B2) hFc Lot2194993 | 28 hr/IV/50 mpk (Multiple) | Balb/C | 3.7 | 1.0 | 2.0 | 11.88 | 8134.46 | 0.15 | | |
| | | | | | | | 12.55 | 7071.87 | 0.18 | | |
| | | | | | | | 13.37 | 8156.77 | 0.16 | 12.6 ± 0.74 | 7788 ± 620 |
| 4-6 | | | C57B1/6N | | | | 15.70 | 612.04 | 0.26 | | |
| | | | | | | | 25.77 | 7145.26 | 0.36 | | |
| | | | | | | | 11.75 | 4506.15 | 0.26 | 16.7 ± 7.2 | 5924 ± 1330 |
| 7-9 | anti-LRP-8 (ab58216) hFc Lot2196879 | 2 h/IV/45 mpk (single) | Balb/C | | | | | | | | |
| 10-12 | | 28 hr/IV/45 mpk (Multiple) | Balb/C | 3.3 | 0.5 | 1.0 | | | | | |
| 13-15 | | 2 hr/IV/45 mpk (single) | C57B1/6N | | | | | | | | |
| 16-18 | | 28 hr/IV/45 mpk (Multiple) | C57B1/6N | | | | | | | | |
| 25-27 | hIgG1/K mut (234,235) Lot2140396 | 24 hr/IV/50 mpk (Single) | Balb/C | 1.3 | 0.0 | 0.0 | 3.96 | 2009.17 | 0.20 | | |
| | | | | | | | 3.38 | 1894.86 | 0.18 | | |
| | | | | | | | 4.11 | 1626.76 | 0.25 | 3.8 ± 0.38 | 1844 ± 196 |
| 28-30 | | 24 hr/IV/50 mpk (Single) | C57B1/6N | | | | 3.27 | 1803.69 | 0.18 | | |
| | | | | | | | 5.64 | 1550.47 | 0.36 | | |
| | | | | | | | 3.63 | 2008.74 | 0.18 | 4.1 ± 1.27 | 1788 ± 229 |
| 31-33 | | 24 hr/IV/50 mpk (Single) | SJL | 2.3 | 0.0 | 0.0 | | | | | |
| 34-36 | (TfR) Lot 1892324 | 24 hr/IV/50 mpk (Single) | C57B1/6N | | | | 2.08 | 1754.41 | 0.12 | | |
| | | | | | | | 2.57 | 2203.72 | 0.12 | | |
| | | | | | | | 2.23 | 2403.59 | 0.09 | 2.3 ± 0.25 | 2121 ± 332 |

Figure 8:
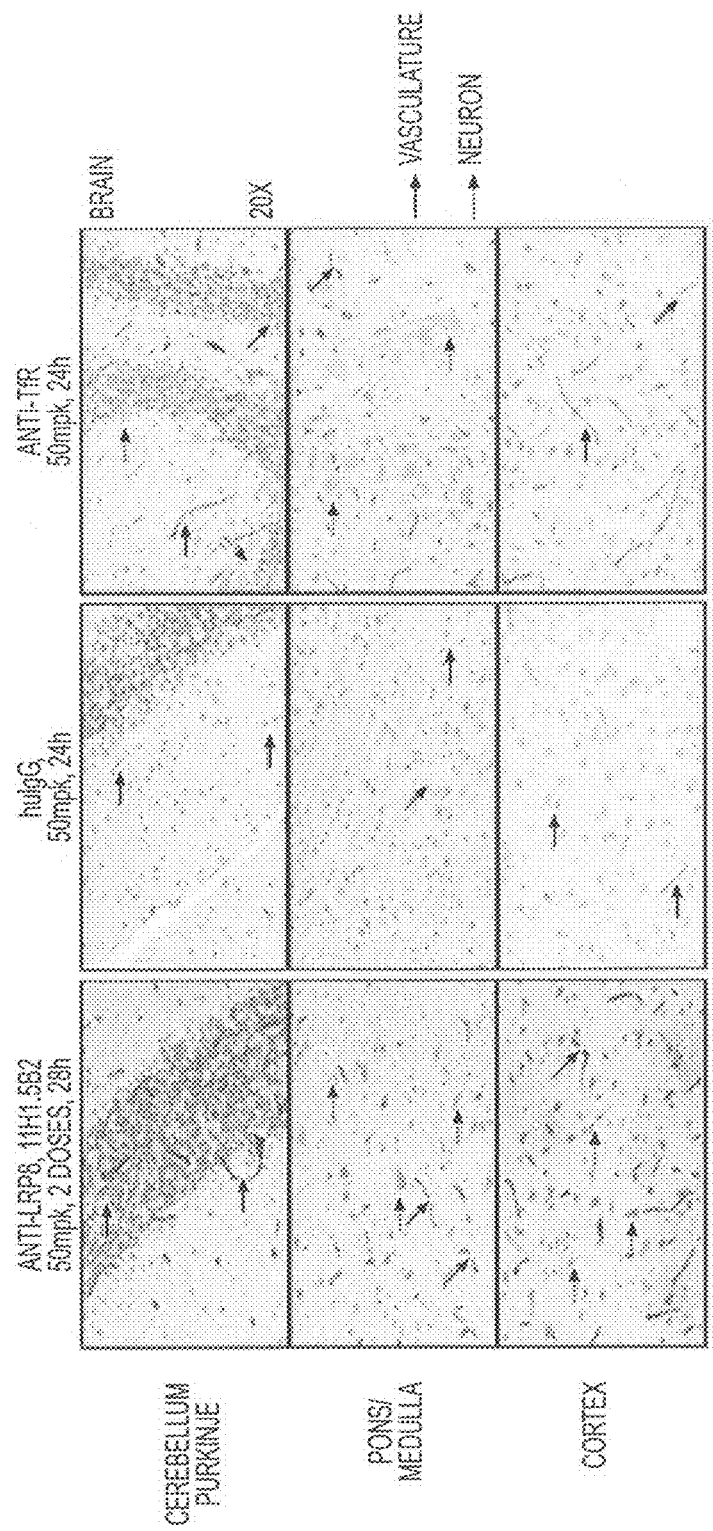
FIG. 8 shows a set of photographs from a mouse in vivo staining study using anti-LRP-8 antibodies ML199.11H1.5B2 and an anti-TfR antibody as a positive control (50 mpk IV dose). The staining data show enhanced uptake of anti-LRP-8 antibody, ML199.11H1.5B2, into brain at 24 hours after IV dosing. A human IgG antibody was used as a control. The photographs (cerebellum/purkinje cells: first row; pons/medulla: second row; cortex: third row) show positive staining of parenchyma and neurons.
Figure 9:
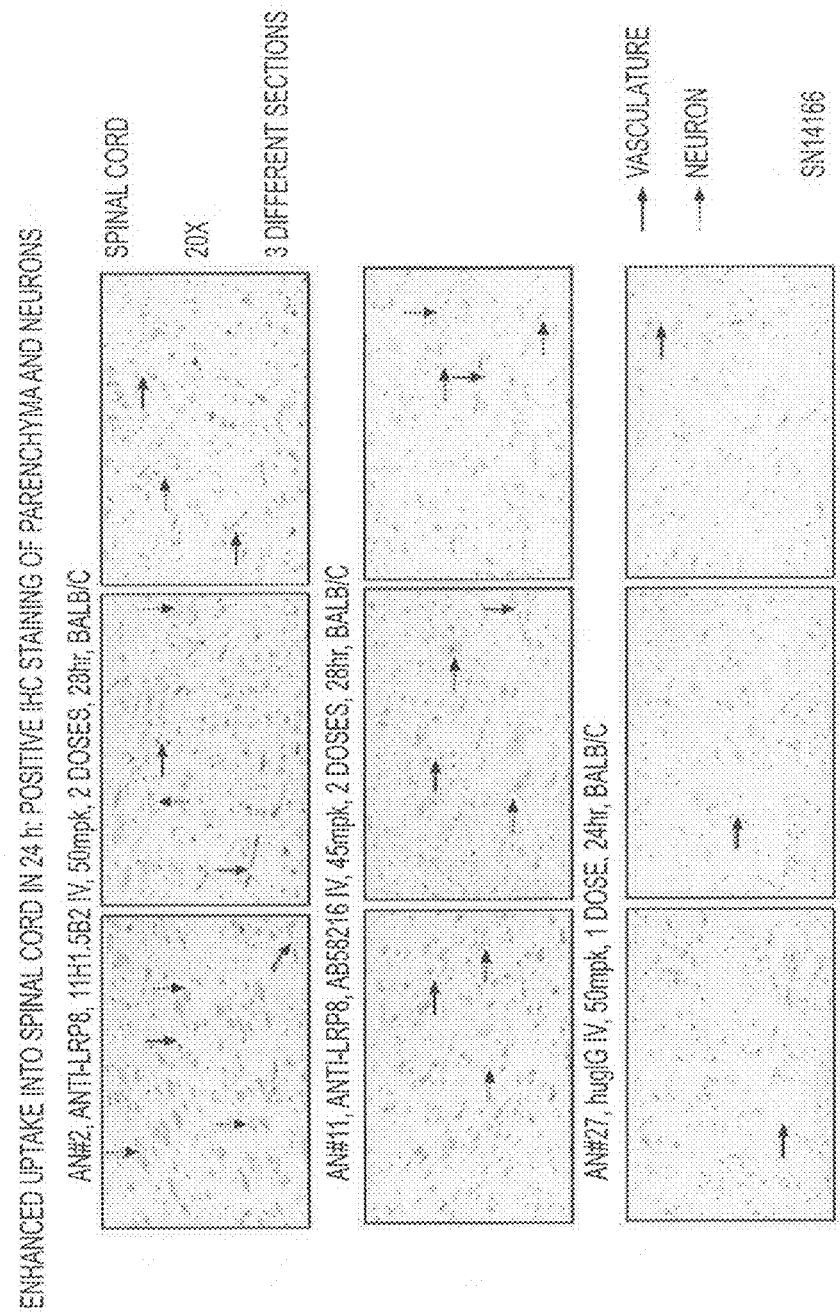
FIG. 9 shows a set of photographs from a mouse in vivo staining study of the spinal cord using anti-LRP-8 antibodies ML.199.11H1.5B2 and ab58216 (45 mpk or 50 mpk IV dose). The data show enhanced uptake of anti-LRP-8 antibody, ML199.11H1.5B2 into the spinal cord 24 hours after IV administration. The photographs show positive IHC staining of parenchyma and neurons.

Additional data show enhanced uptake of anti-LRP-8.ML199.11H1.5B2 antibody into brain at 24 hours with positive staining of parenchyma and neurons (FIG. 8). Enhanced uptake into the spinal cord was observed at 24 hours for LRP-8 antibody intravenously administered 24 hours earlier. Positive IHC staining of parenchyma and neurons were observed (FIG. 9). Data showed that the administered LRP-8 effectively crossed the blood-brain-barrier.

Example 2.6. Anti-LRP-8, ML199-11H1-5B2 Humanization

Variable domain sequences for anti-LRP-8 antibody, ML199-11H1-5B2 were obtained by cDNA cloning using well-established methods. Variable region residues were annotated according to the Kabat numbering system. The canonical structures of the CDRs were determined according to Huang et al. (2005) Methods 36:35-42. Canonical structure was assigned: ML199-11H1-5B2 VH: 1-3. A search of vh.1-3.fasta for VH acceptor human framework found that the FR4 region sequence of hIGHJ6*01 has the highest similarity to that of ML199-11H1-5B2 VH sequence. IGHJ6*01 was used as the acceptor sequence. All other hJH FR4 sequences are also possible acceptor sequences. By calculating the structural important VH position, IGHV3-21*01 was chosen as a human acceptor framework sequence. For light chain humanization, using the same method, IGKV2-28*01 was chosen as a likely human acceptor framework sequence. IGKV2-30*01 may also be used as an acceptor for humanization in other embodiments. Variable domain sequences of humanized variants of anti-LRP-8 antibody ML199-11H1-5B2 are shown in Tables 2 and 5. Humanized variants of anti-LRP-8 antibody ML199-11H1-5B2 either showed lower binding to LRP-8 and/or yielded lower expression in HEK 293 cells (Table 15).

TABLE 15

Binding Affinity and Production Yield of Humanized Variant Antibodies

| Clone | Light Chain | Heavy Chain | mLRP8 cell binding EC50 (nM) | Yield (mg/ml) |
|---|---|---|---|---|
| ML199-11H1.5B2VH.1/VL.1 | VL.1 | VH.1 | 22.45 | 2.84 |

TABLE 15-continued

Binding Affinity and Production Yield of Humanized Variant Antibodies

| Clone | Light Chain | Heavy Chain | mLRP8 cell binding EC50 (nM) | Yield (mg/ml) |
|---|---|---|---|---|
| ML199-11H1.5B2VH.1/VL.1a | VL.1a | VH.1 | 13.44 | 0.10 |
| ML199-11H1.5B2VH.1/VL.1b | VL.1b | VH.1 | 7.92 | 0.74 |
| ML199-11H1.5B2VH.1a/VL.1 | VL.1 | VH.1a | 6.83 | 6.01 |
| ML199-11H1.5B2VH.1a/VL.1a | VL.1a | VH.1a | 41.84 | 1.57 |
| ML199-11H1.5B2VH.1a/VL.1b | VL.1b | VH.1a | 19.65 | 3.14 |
| ML199-11H1.5B2 | chimeric VL | chimeric VH | 0.95 | 0.38 |

Example 2.7. Anti-LRP-8, ML199-11H1-5B2VH1/VL1a Liability Free Variants

Protein liability motifs were found in HCDR2 and LCDR1 of humanized anti-LRP-8 antibody, ML199-11H1-5B2VH1/VL1a. Firstly, 59 variants using the combination VH1/VL1a as template and introducing mutations in each liability on HCDR2 and LCDR1 were made as shown below:

hML199-11H1-5B2VH.1 (SEQ ID NOS 70 and 213-214, respectively, in order of appearance)

EVQLVESGGGLVKPGGSLRLSCAASrftfsnygmsWVRQAPGKGLEWVStissg grytyypdsvkgRFTISRDNAKNSLYLQMNSLRAEDTAVYYCARdylyamdyWGQGTTV

TVSS xs (15 variants)

dz (14 variants)

hML199-11H1-5B2VL.1a (SEQ ID NOS 134 and 215-216, respectively, in order of appearance)

DVVMTQSPLSLPVTPGEPASISCrsscislvysngntylhWYLQKPGQSPQVLMY kvsnr xg (15 variants)

nz (15 variants)

fsGVPDRFSGSGSGTDFTLKISRVEAEDVGVYFCsqsthvpltFGQGTKLEIK where,
  x=Any amino acid but: M, C, N, D or Q.
  z=Any amino acid but: M, C, G, S or N. No P in VH1.

Heavy chain and light chain variable domains of the liability free variants of anti-LRP-8 ML199-11H1-5B2VH1/VL1a antibody are shown in Tables 2 and 5.

Figure 10:
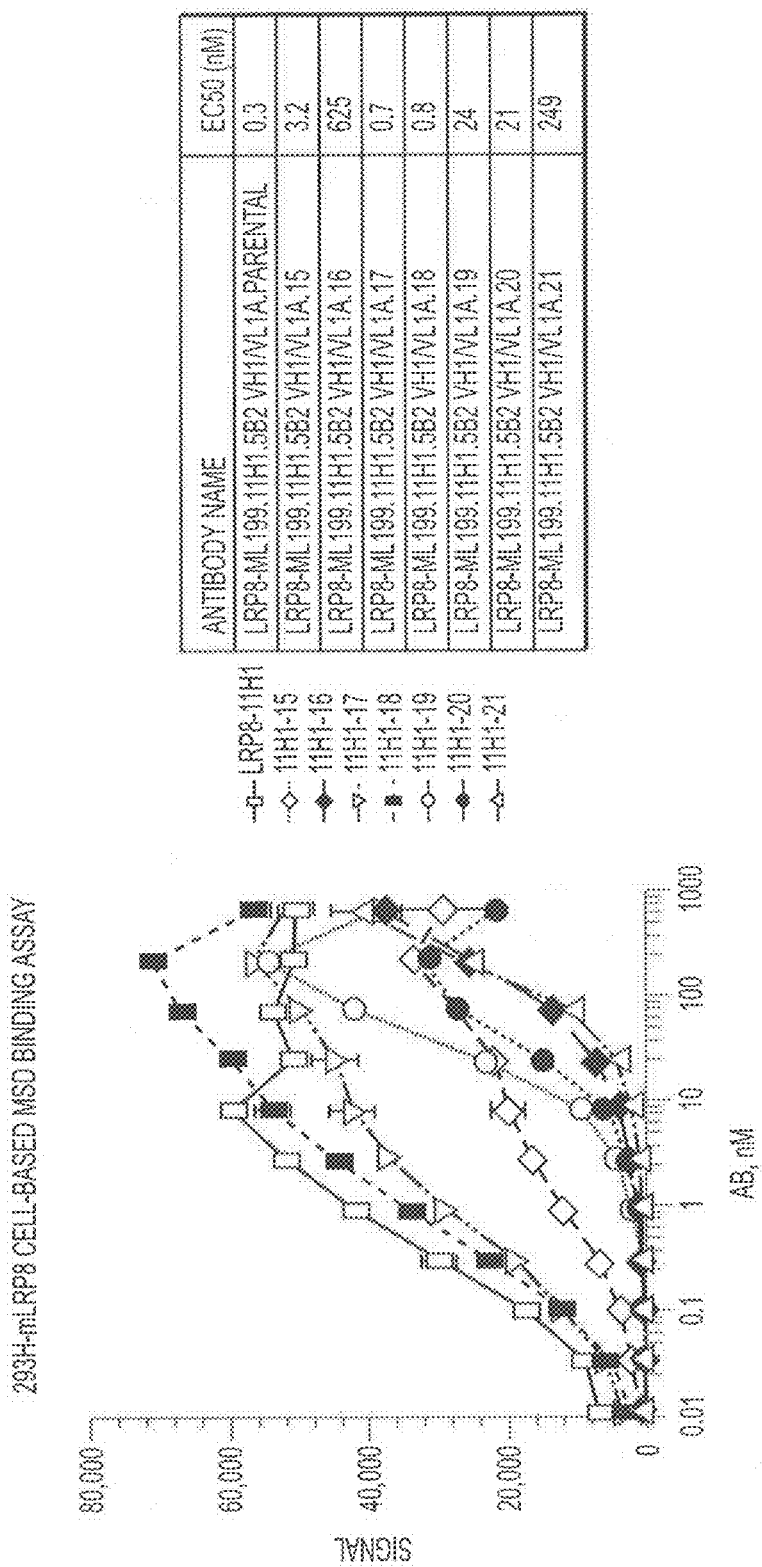
FIG. 10 shows binding of anti-LRP-8 parental antibody ML199.11H1.5B2 and variants to mLRP-8 expressing HEK293 cells in an MSD-ECL assay.

Supernatants from each variant were tested for expression and binding to LRP-8. Selected liability free variants were purified (Table 16) and their affinity was determined by cell-based ECL-MSD binding assay (FIG. 10). Removal of liability sequences yielded variants with either lower binding affinity to LRP-8 and/or yielded lower expression in HEK 293 cells.

TABLE 16

Structural Information and Production Yield of hML199-11H1.5B2 VH/VL1a Variants

| Protein name | hML199-11H1.5B2 VH/VL1a | | |
|---|---|---|---|
| | VH mutation | VL mutation | Yield (mg/L) |
| CL-73742 hCg1 LALA/k (ML199.11H1.5B2 1A.15) | S62H | G29E | 0.64 |
| CL-73743 hCg1 LALA/k (ML199.11H1.5B2 1A.16) | S62H | N28T | 0.68 |
| CL-73744 hCg1 LALA/k (ML199.11H1.5B2 1A.17) | S62H | G29L | 0.54 |
| CL-73745 hCg1 LALA/k (ML199.11H1.5B2 1A.18) | S62H | G29K | 0.46 |
| CL-73746 hCg1 LALA/k (ML199.11H1.5B2 1A.19) | S62H | N28R | 1.30 |
| CL-73747 hCg1 LALA/k (ML199.11H1.5B2 1A.20) | S62H | N28W | 0.68 |
| CL-73748 hCg1 LALA/k (ML199.11H1.5B2 1A.21) | S62H | N28P | 5.92 |

Example 3. Generation of Anti-LRP-8 Antibodies Based on GENOVAC™ Technology

Example 3.1. Aldevron cDNA Immunization and Antibody Generation

Figures 11A, 11B:
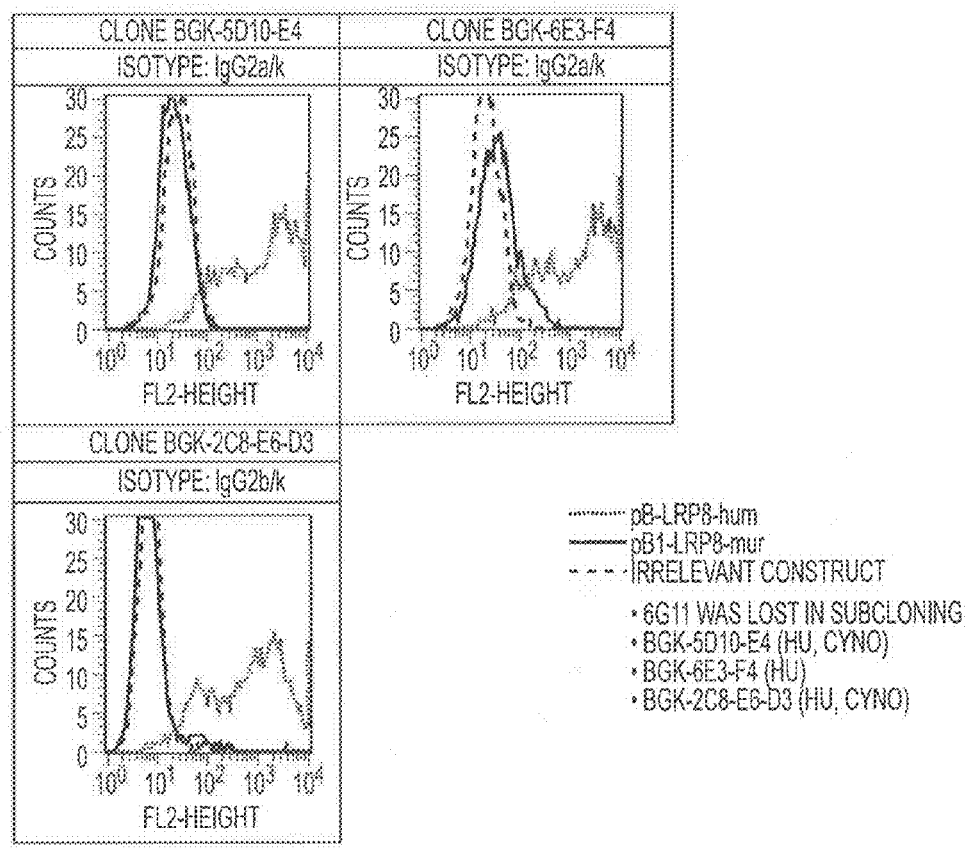
FIG. 11A shows flow cytometry relative cell count (ordinate) as compared with FL2-height (PI staining) for hLRP-8 and mLRP-8 using antibodies BGK-5D10-E4, BGK-6E3-F4 and BGK-2C8-E6-D3.
FIG. 11B shows binding data (folder over isotype control) for anti-LRP-8 antibodies described herein.

Additional anti-LRP-8 antibodies were generated by using genetic immunization with GENOVAC™ antibody technology by Aldevron Freiburg as described above. In this Example, FL_hLRP-8 cDNA was used and 108 positive binders were collected and analyzed using mouse cross reactivity assays and endocytosis assays. Twenty five candidates were selected for scale up using cyno cross-reactivity assays, endocytosis assays, and transcytosis assays (Table 17). Data in Table 17 shows effective binding of the antibodies to LRP-8 (see also FIG. 11).

anti-LRP-8 antibodies in a cell-based binding assay. Most of the tested antibodies showed the ability to cross-react with cynomolgus LRP-8. Table 18 also shows the percentage of monomer of each antibody tested in this assay as determined by size exclusion chromatography (SEC).

TABLE 17

Cell-Based MSD Binding (Fold Over IgG Control) and FACS Data for the LRP-8 Antibodies Developed Using GENOVAC ™ Antibody Technology

| clone name | human_LRP8_HEK293 | | | cyno-LRP8-HEK293 | | | mouse-LRP8-HEK293 | | | HEK293 parental | | | Endocytosis | Transcytosis |
|---|---|---|---|---|---|---|---|---|---|---|---|---|---|---|
| | 1 to 5 | 1 to 25 | 1 to 125 | 1 to 5 | 1 to 25 | 1 to 125 | 1 to 5 | 1 to 25 | 1 to 125 | 1 to 5 | 1 to 25 | 1 to 125 | hLRP8-293 fold over-IgG | Caco-2_hLRP8 fold over-IgG |
| BGK-2C8 | 5.3 | 4.9 | 4.0 | 15.3 | 15.0 | 11.2 | 9.2 | 8.5 | 3.2 | 0.4 | 0.3 | 0.2 | 5.76 | 2.29 |
| BKG-5D10 | 28.9 | 27.2 | 22.9 | 27.6 | 28.9 | 29.2 | 0.8 | 1.4 | 1.6 | 0.3 | 0.2 | 0.2 | 6.33 | 2.33 |
| BGK-6B5 | 5.3 | 3.8 | 3.1 | 5.6 | 5.8 | 5.2 | 0.3 | 0.6 | 0.8 | 0.3 | 0.2 | 0.2 | 2.34 | 1.08 |
| BGK-6E3 | 8.7 | 7.3 | 6.7 | 3.1 | 2.2 | 1.8 | 0.9 | 1.0 | 0.9 | 1.1 | 0.5 | 0.3 | 4.76 | 3.06 |
| BGK-7F7 | 5.0 | 5.2 | 5.0 | 2.0 | 1.9 | 1.8 | 3.5 | 6.0 | 5.3 | 0.4 | 0.3 | 0.2 | 5.18 | 2.17 |
| BGK-9D10 | 7.9 | 6.7 | 6.0 | 2.4 | 1.7 | 1.6 | 1.7 | 1.4 | 1.1 | 0.8 | 0.4 | 0.2 | 5.09 | 0.96 |

Example 3.2. Anti-LRP-8 and Mu/Hu Chimeric Antibody Generation and Murine Anti-LRP-8 Antibody Analysis Anti-LRP-8 antibody variable domain DNAs were codon optimized and cloned into expression vectors to produce mouse or human IgG proteins. The antibody constructs were expressed in HEK293 cells and purified according to established methods. Expression yield was measured with a Nanodrop spectrophotometer. Percentage of monomer was determined by size exclusion chromatography (SEC).

Nine (9) monoclonal antibodies were obtained (BGK-2C8.E6.D3; BGK-5D10-E4; BGK-6E3-F4; BGK-2C8.8C; BGK-2H4; BGK-7A11; BGK-7F7; BGK-9D10-2; BGK-6B5-2). Tables 2 and 5 show heavy chain and light chain variable region sequences for the 10 monoclonal LRP-8 antibodies that were constructed using this method.

Using a cell-based MSD assay, anti-LRP-8 BGK-2C8.8C antibody reacted with both human LRP-8 (hLRP-8) and cyno LRP-8 (cLRP-8) (FIG. 12).

Example 4. In Vitro and In Vivo Analysis of Anti-LRP-8 Antibodies

Example 4.1. In Vitro Cell-Based Assay for Cross-Reactivity

Figure 13A:
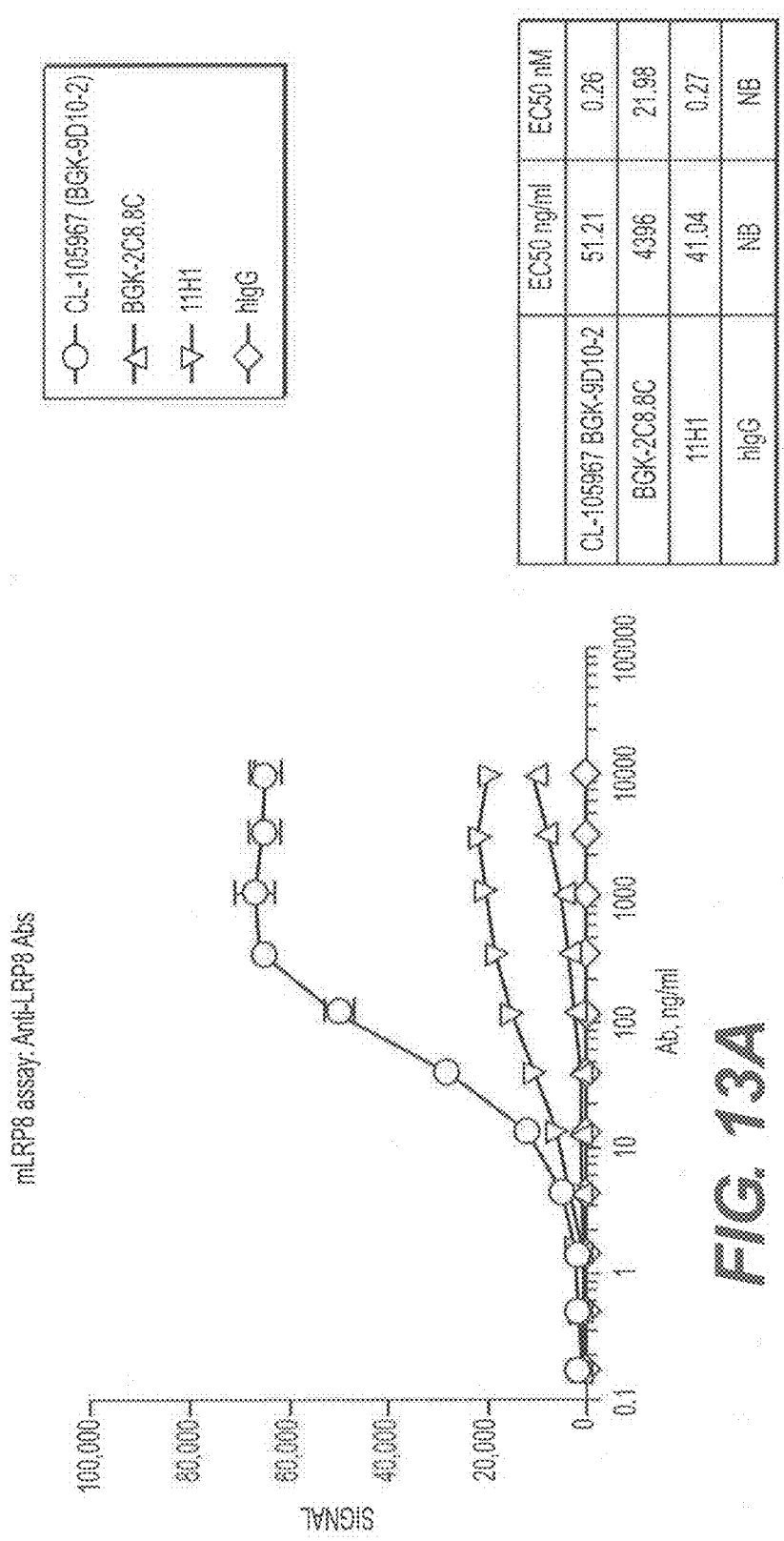
FIG. 13A shows binding of LRP-8 antibodies ML1991.11H1.5B2, BGK-2C8.8C, and BGT-9D10-2 to cells overexpressing mouse LPR-8 variant 1 in a MSD-ECL assay.
Figure 13B:
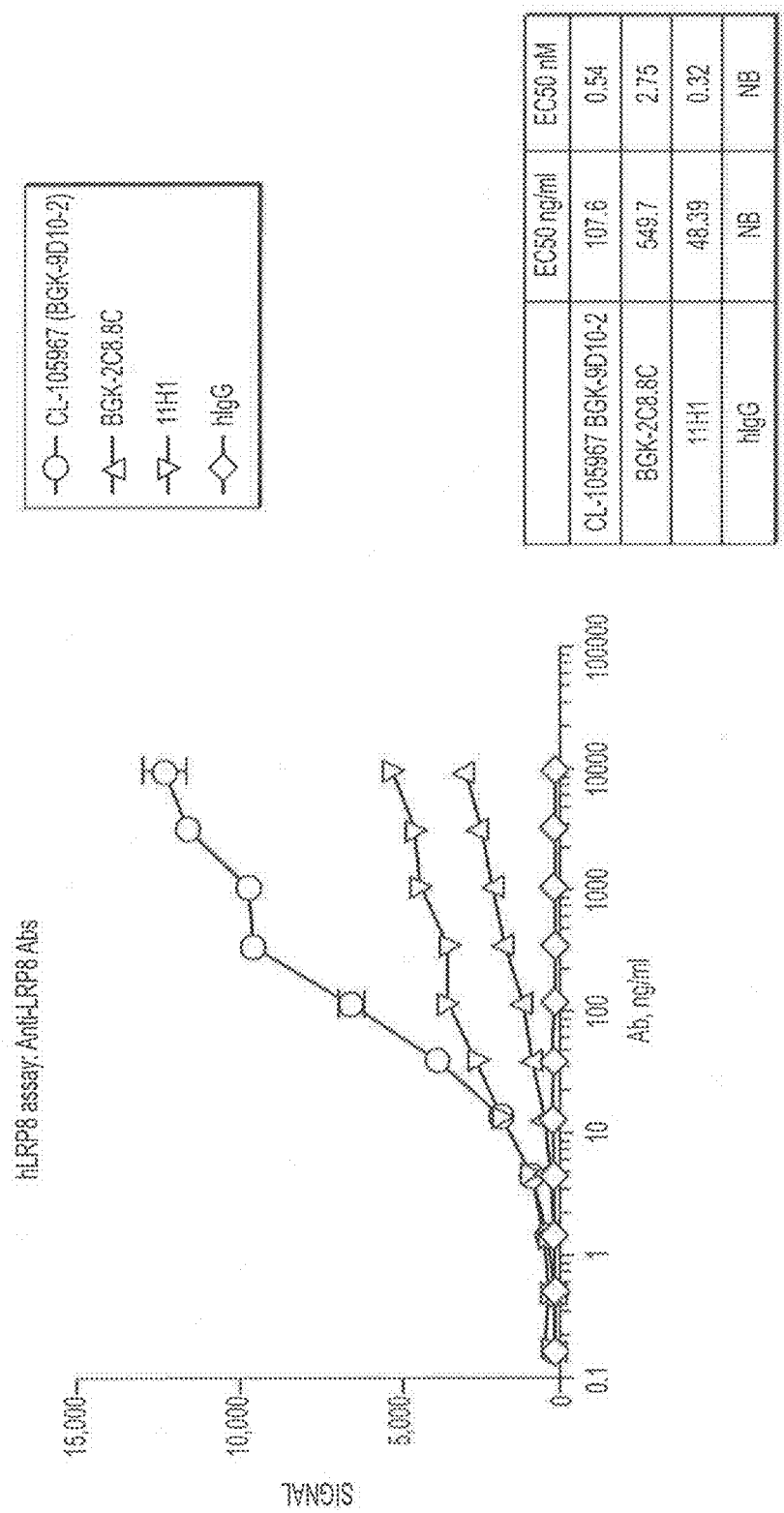
FIG. 13B shows binding of LRP-8 antibodies ML1991.11H1.5B2, BGK-2C8.8C, and BGT-9D10-2 to cells overexpressing human LRP-8 variant 3 in a MSD-ECL assay.

Anti-LRP-8 antibodies generated in Examples 2 and 3 were further analyzed for cross-reactivity in a cell-based binding assay using cynomolgus LRP-8, mouse LRP-8, and human LRP-8. FIG. 13 shows representative data obtained from four monoclonal anti-LRP-8 antibodies, CL-105967 (BGK-9D10-2), BGK-2C8.8C, and ML199-11H1.5B2, demonstrating that all of those antibodies were capable of cross-reacting with LRP-8 from mouse, cynomolgus, and human. Table 18 summarizes the results obtained from the

TABLE 18

Binding Data and Percentage of Monomer of Chimeric anti-LRP-8 Antibodies

| Clone | SEC % Monomer | Binding hLRP8 $EC_{50}$ (nM) | Binding cynoLRP8 $EC_{50}$ (nM) | Binding mLRP8 $EC_{50}$ (nM) |
|---|---|---|---|---|
| ML199-11H1.5B2 | 100 | 0.22 | 0.21 | 0.32 |
| ML201-8F3.3D7 | 100 | 0.16 | NT** | NT |
| BGK-2C8.8C | 100 | 2.62 | 0.82 | 21.98 |
| BGK-9D10-2 | 100 | 2.29 | 0.64 | 0.43 |
| BGK-7F7 | 100 | 0.11 | 0.35 | 3.92 |
| BGK-6B5-2 | 100 | 0.15 | 0.51 | 41.8 |
| BGK-7A11 | 98 | 0.12 | 0.53 | 27.63 |
| BGK-2H4 | 100 | 0.21 | 1.08 | NB* |
| BGK.2C8.E6.D3 [r/m IgG2a/K] | 99 | 0.1 | 0.31 | NB |
| BGK.5D10.E4 [r/m IgG2a/K] | 95 | 0.24 | 0.77 | NB |
| BGK.6E3.F4 [r/m IgG2a/K] | 100 | 0.11 | 0.25 | NB |
| hIgG1/K mut control | — | NB | NB | NB |

*NB: No binding observed
**NT: No test data available

Figure 14:
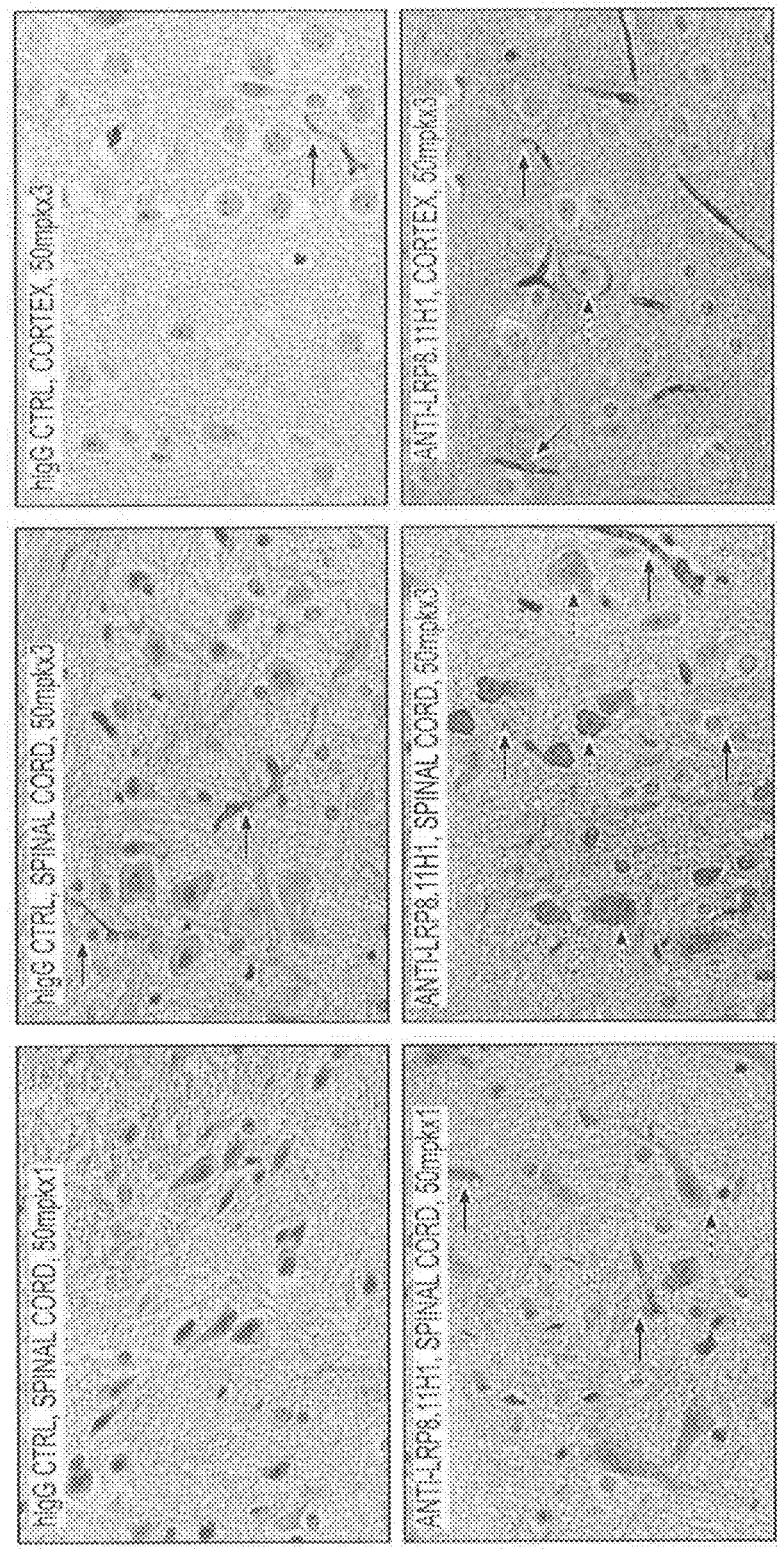
FIG. 14 shows a set of photographs from a mouse in vivo staining study using anti-LRP-8 antibody 11H1.5B2 and an hIgG antibody as a positive control.
Figure 15:
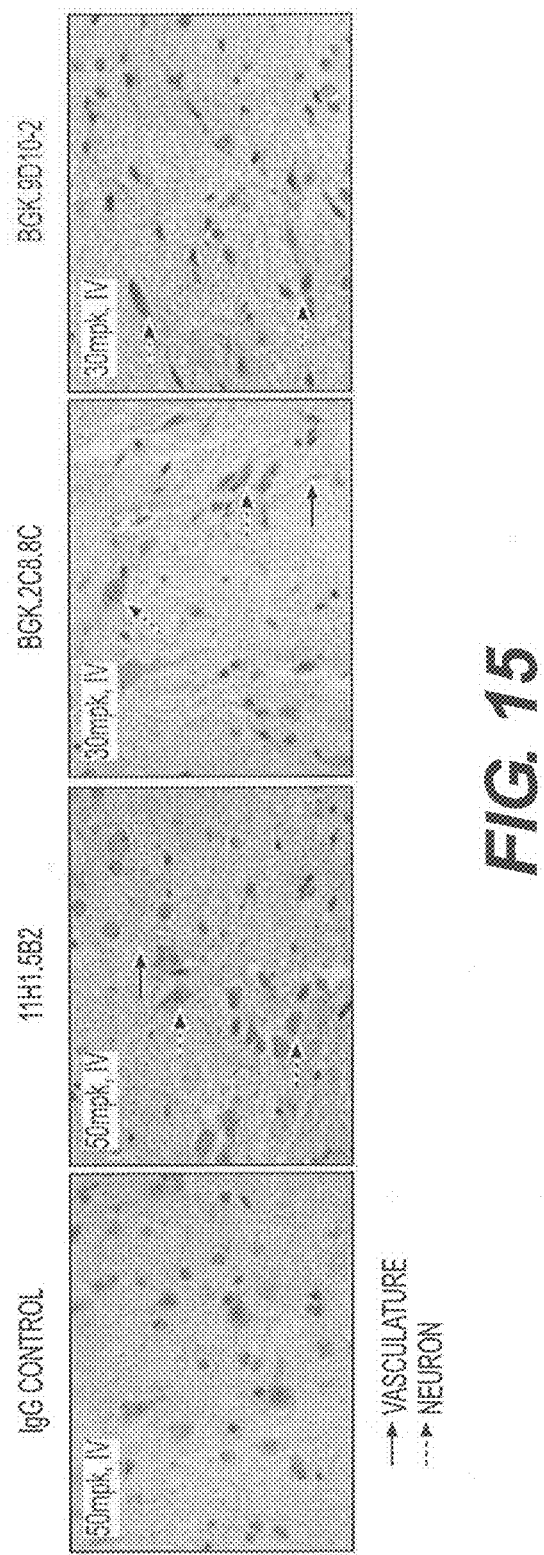
FIG. 15 shows a set of photographs from a mouse spinal cord in vivo staining study using anti-LRP-8 antibodies 11H1.5B2, BGK.2C8.8C, BGK.9D10-2, and an hIgG antibody as a positive control.

Example 4.2. Anti-LRP-8 PK Study IHC Score and Concentration in Brain Homogenates and Serum Anti-LRP-8 antibodies were administered to mice through an intravenous or intraperitoneal route in order to quantitatively measure their capacities to cross the blood brain barrier in the subjects. As can be seen in FIG. 14, with a single intravenous injection or three consecutive intravenous (IV) injections of anti-LRP-8 ML199.11H1.5B2 antibody (50 mpk×1 or 50 mpk×3), clear vasculature IHC staining in all brain regions as well as neuronal staining in pons, medulla, spinal cord, and cortex was observed. With anti-LRP-8 ML199.11H1.5B2 antibody administration, enhanced parenchyma staining in all brain regions was observed as compared with control IgG administration. FIG. 15 shows the results obtained from anti-LRP-8 antibodies, ML199.11H1.5B2, BGK-2C8.8C, and BGK-9D10-2 (administered intravenously, 30-50 mpk) from IHC staining in spinal cord.

Table 19 shows anti-LRP-8 PK study IHC assessment and mouse in vivo PK study data including antibody concentration detected in brain, spinal cord, and serum samples (e.g., homogenates). Table 19 also summarizes the initial assessment of stability of the tested antibodies based on serum exposure, with 4 antibodies (ML199.11H1.5B2, ML201-8F3.3D7, BGK-2C8.8C, and BGK-9D10-2) showing enhanced brain uptake in mice.

TABLE 19

Anti-LRP-8 PK Study IHC Assessment and Concentration in Brain Homogenates and Serum

| Clone Name | Serum exposure (24 h in vivo) | IHC | Mouse brain uptake Brain, nM | spinal cord, nM | IV/IP Dose |
|---|---|---|---|---|---|
| ML199-11H1.5B2 | Good | Yes | 7.9 ± 1.1 | 1.2 ± 0.7 | 50 mpk IV |
|  | Good | Yes | 6.9 ± 2.5 | 1.0 ± 0.6 | 50 mpk IP |
| ML201-8F3.3D7 | Good | Yes | 8.7 ± 3.8 | — | 40 mpk IV |
| BGK-2C8.8C | Good | Yes | 2.5 ± 0.5 | 1.1 ± 0.4 | 50 mpk IP |
| BGK-9D10-2 | reduced | Yes | 8.1 ± 2.6 | 1.1 ± 0.5 | 50 mpk IV |
|  | Good | Yes | 2.7 ± 0.9 | 1.1 ± 0.3 | 50 mpk IP |
| BGK-7F7 | low | No | — | — | 50 mpk IV |
| BGK-6B5-2 | low | No | — | — | 50 mpk IV |
| BGK-7A11 | low | No | — | — | 50 mpk IV |
| BGK-2H4 | — | — | — | — | — |
| BGK.2C8.E6.D3 [r/m IgG2a/K] | — | — | — | — | — |
| BGK.5D10.E4 [r/m IgG2a/K] | — | — | — | — | — |
| BGK.6E3.F4 [r/m IgG2a/K] | — | — | — | — | — |
| hIgG1/K mut control | Good | No | 3.05 ± 1.4 | 0.27 ± 0.1 | 50 mpk IV |
|  | Good | No | 4.8 ± 4.0 | 1.3 ± 0.5 | 50 mpk IP |

Example 4.3. Antibodies Generated by a Yeast Display Method

Additional anti-LRP-8 antibodies were generated by a yeast-display method. Heavy chain and light chain variable domains of the additional antibodies are shown in Tables 2 and 5. Those antibodies were also tested in a cell-based binding assay and shown to bind cyno LRP-8 as well as mouse LRP-8 (Table 20).

TABLE 20

Binding of Anti-LRP-8 Antibodies to Cyno and Mouse LRP8

| Clone | ELISA using CR1 Peptide (OD450) | cyno LRP8 FACS (ratio +/−) | mouse LRP8 FACS (ratio +/−) |
|---|---|---|---|
| ML199.11H1.5B2 | 4.00 | 141.2 | 282.6 |
| CL-134994 | 0.37 | 19.4 | 10.0 |
| CL-135325 | 0.17 | 16.5 | 21.2 |
| CL-135359 | 0.10 | 12.6 | 7.3 |
| Negative IgG control | 0.08 | 0.8 | 1.0 |

Example 4.4. Epitope Binning

Anti-LRP-8 antibodies were tested in a label-free cell-based competition assay in order to determine which antibodies are capable of binding to LRP-8 simultaneously. If antibodies were not able to bind LRP-8 simultaneously (therefore possibly competing for the same or substantially similar epitope), those antibodies were assigned to the same "epitope bin." If antibodies were capable of binding to LRP-8 simultaneously and therefore did not compete for binding to LRP-8, those antibodies were assigned to a different "epitope bin."

Figure 16A:
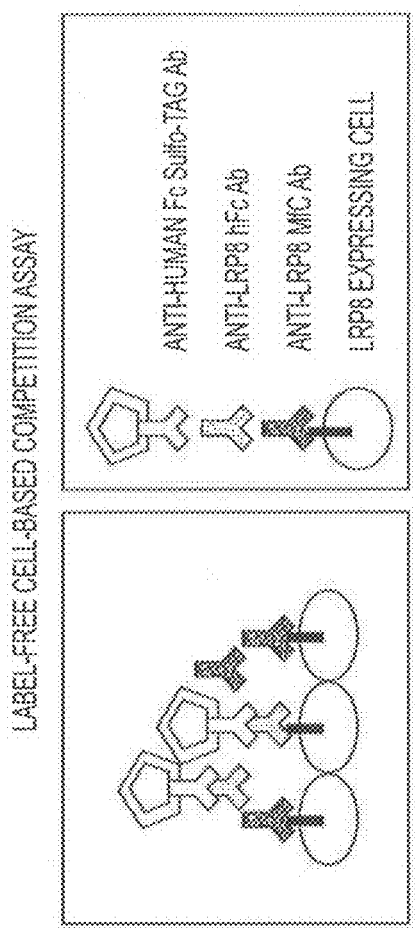
FIG. 16A is a schematic showing a procedure for an epitope binning assay using anti-LRP-8 antibodies.
Figure 16B:
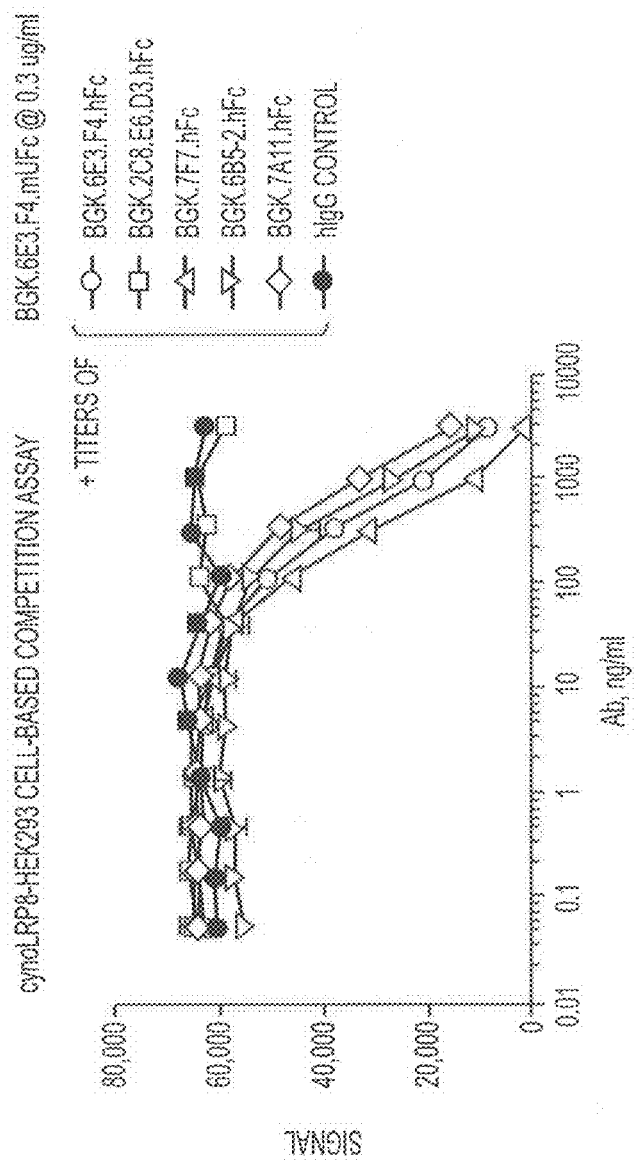
FIG. 16B shows a representative epitope binning assay using anti-LRP-8 antibodies.

FIG. 16A shows a schematic assay procedure. FIG. 16B shows representative data obtained from the competition assay using cyno LRP-8-HEK 293 stable cells. In this representative experiment, 30 μg/ml of anti-LRP-8 BGK.6E3.F4 antibody was incubated with varying amounts of antibodies including chimeric anti-LRP-8 antibodies, BGK.2C8.E6D3, BGK.7F7, BGK.6B5-2, BGK.7A11, or a negative control, hIgG. As a positive control, chimeric anti-LRP-8 BGK.6E3.F4 antibody was used to demonstrate the degree of self-competition.

As shown in FIG. 16B, the competition between anti-LRP-8 BGK.6E3.F4 antibody and the subset of antibodies including BGK.7F7, BGK.6B5-2, BGK.7A11 was observed, and therefore those antibodies were assigned to the same epitope bin. There was no competition observed between anti-LRP-8 BGK.6E3.F4 and BGK.2C8.E6D3 antibodies, and therefore these two antibodies were assigned to a different epitope bin. Table 21 summarizes the exemplary epitope binning assignments based on the cyno LRP-8-HEK293 cell-based competition assay (antibodies capable of binding human and cyno LRP-8 are listed in bold; antibodies capable of binding human, mouse, and cyno LRP-8 are underlined; and antibodies that demonstrated brain penetration in mice are listed in italic).

TABLE 21

Epitope Binning

| Bin 1 | Bin 2 | Bin 3 | Bin 4 |
|---|---|---|---|
| ML199-11H1.5B2 | BGK.2C8.8C | BGK.6E3.F4 | BGK.9D10.2 |
| ML201-8F3.3D7 | | BGK.7F7 | BGK.2H4 |
| CL-134994 | | BGK.7A11 | BGK.2C8.E6.D3 |
| CL-135325 | | BGK.6B5.2 | BGK.5D10.E4 |
| CL-135359 | | | |

Antibodies with significant sequence homology to the CDR sequences of anti-LRP-8-ML199-11H1.5B2 antibody would be expected to bind to the same or substantially similar epitope of anti-LRP-8-ML199-11H1.5B2 antibody, and therefore compete for binding to LRP-8 in a competition assay. Those competing antibodies would exhibit desirable biological properties of anti-LRP-8-ML199-11H1.5B2 antibody when evaluated in in vitro and/or in vivo assays described herein and known in the art.

Example 4.5. Mutagenesis Analysis

Figure 17B:
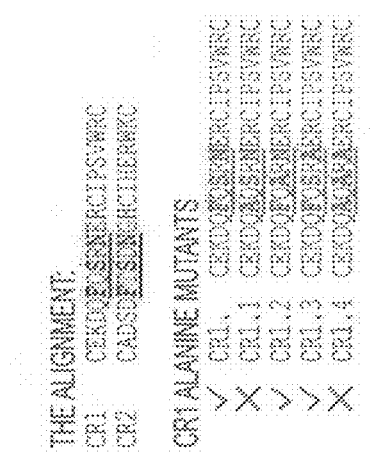

In order to determine the key residues involved in the interaction between anti-LRP-8 antibodies and LRP-8 protein, a mutagenesis analysis was performed based on CR1 peptide that was used as an immunogen for generating the ML199 and ML201 antibodies. Anti-LRP-8 ML199-11H1.5B2 antibody was capable of binding CR1 and CR2 peptides with similar affinity. Affinity of Anti-LRP-8 ML199-11H1.5B2 to CR1 and CR2 is 1.5 nM and 2.1 nM respectively (FIG. 17A). This, indicates that the antibody may recognize residues shared by the peptides. The sequence alignment between CR1 and CR2 peptides shows that residues including F6, S8, and N10 are conserved between CR1 and CR2 (FIG. 17B). Based on the alignment, variants of CR1 peptide were generated by mutating the conserved residues to alanine (CR1.1, CR1.2, CR1.3, and CR1.4; see also Table 1).

Figure 17C:
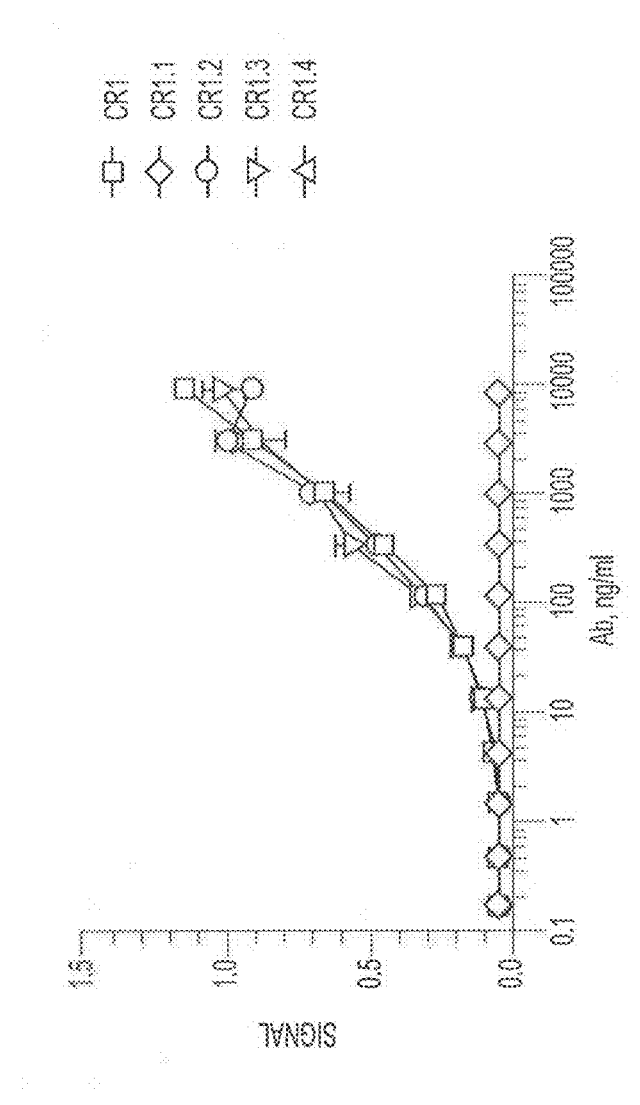
FIG. 17C shows binding of anti-LRP-8 ML199.11H1.5B2 antibody to CR1, CR1.1, CR1.2, CR1.3, and CR1.4 peptides.

As shown in FIG. 17C, in an ELISA binding assay, anti-LRP-8 ML199-11H1.5B2 antibody was not able to bind CR1 variants of which F6 was mutated to alanine (CR1.1. and CR1.4) while the mutation of other residues did not affect the interaction between the antibody and the peptide (CR1.2, and CR1.3). The similar result was also obtained based on a BIACORE kinetic binding assay. These experiments demonstrate that F6 of CR1 peptide is a part of the key binding site of anti-LRP-8 ML199-11H1.5B2 antibody.

Example 4.6. Crystal Structure of Anti-LRP-8 Antibody with CR1 Peptide

Figure 18A:
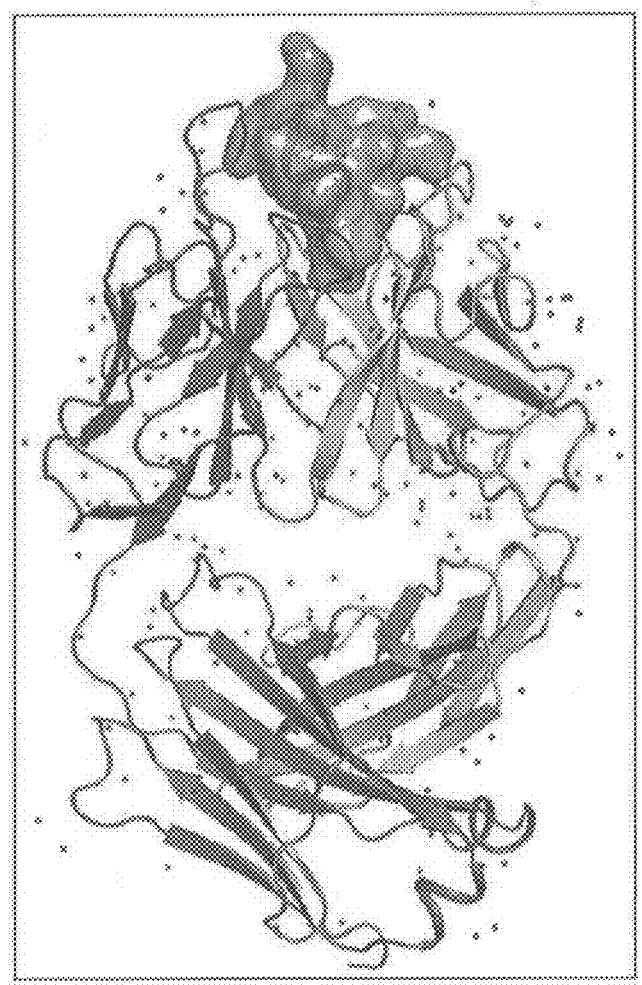
FIG. 18A shows one view of a crystal structure for anti-LRP-8.11H1.5B2 antibody in complex with the CR1 peptide, determined at 1.72 Å resolution.

In order to determine the conformational epitope recognized by anti-LRP-8 ML199-11H1.5B2 antibody, the crystal structure of anti-LRP-8 ML199-11H1.5B2 antibody Fab fragment complexed with CR1 peptide was determined at 1.72 Å resolution. FIG. 18A. The last 5 residues of the peptide are not seen in the crystal structure because those 5 residues were not resolved in electron density, indicating those residues do not make contact with the Fab fragment and are most likely flexible, thus not contributing to the epitope. The Fab fragment and the peptide were co-crystallized at an 8:1 molar ratio. The structure was determined by molecular replacement method ($R_{free}/R_{work}$=0.23/0.20).

Figure 18B:
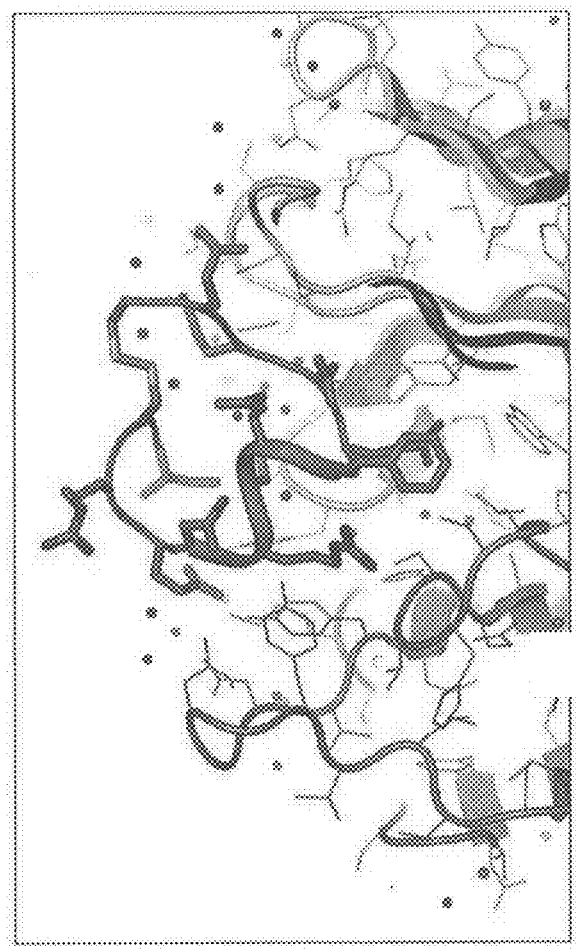
FIG. 18B shows another view of a crystal structure of anti-LRP-8.11H1.5B2 antibody in complex with the CR1 peptide, determined at 1.72 Å resolution.

The detailed structural analysis confirms that anti-LRP-8 ML199-11H1.5B2 antibody makes significant contacts with CR1 peptide (FIG. 18B). Using NCONT (ccp4 suite) program, 175 atomic contacts were identified within a 4.0 Å range. Based on the analysis, the region of CR1 peptide indicated in bold [CEKDQFQSRNERCIPSVWRC] (SEQ ID NO: 5) was identified as a part of the comprehensive conformational epitope recognized by anti-LRP-8 ML199-11H1.5B2 antibody. Antibodies that bind to the same conformational epitope of anti-LRP-8 ML199-11H1.5B2 antibody would be expected to possess similar biological properties of anti-LRP-8 ML199-11H1.5B2 antibody.

Example 4.7. Pharmacokinetic Analysis of Antibodies

The pharmacokinetics of anti-LRP-8 antibody was evaluated in male CD-1 mice. Groups of mice were dosed intravenously at a dose of 0.2, 1, or 5 mg/kg (5 mice per dose level). Serial blood samples were collected by tail vein puncture from 1 to 504 hours post-dose. Samples were diluted in assay buffer and analyzed using an anti-human IgG immunoassay to quantify the plasma concentration of anti-LRP-8. Pharmacokinetic parameters were estimated by non-compartmental analysis using WinNonlin (Certara, Princeton, N.J.).

Figure 19:
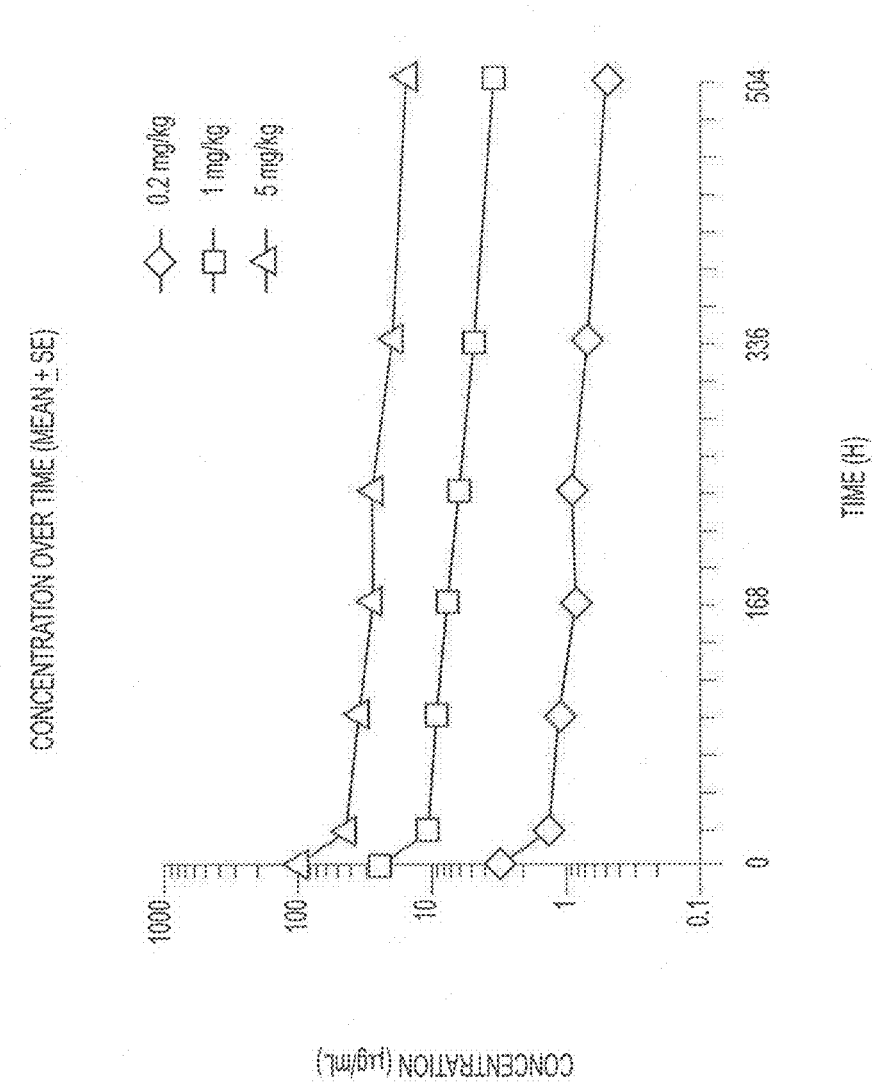
FIG. 19 shows the results of a pharmacokinetic study with IV dose-ranging of chimeric anti-LRP-8 ML199.11H1.5B2 antibody in CD1 mice.

Upon IV dosing, chimeric anti-LRP-8 ML199.11H1.5B2 antibody ([hu IgG1/k] LALA) exhibited typical bi-phasic pattern of distribution and elimination in CD-1 mice, with a volume of distribution of 85 to 135 mL/kg and clearance of 0.2 to 0.3 mL/h/kg (FIG. 19). Terminal half-life of anti-LRP-8 antibody was approximately 312 to 335 hours. There was no indication of target-mediated disposition and no apparent change in elimination over time. PK was dose-linear across 0.2 to 5 mg/kg and exposure is approximately dose-proportional. Table 22 summarizes the pharmacokinetic parameters measured with chimeric anti-LRP-8 ML199.11H1.5B2 antibody ([hu IgG1/k] LALA) at various doses.

TABLE 22

Pharmacokinetic Parameters

| Dose (mg/kg) | Route | N | $AUC_{0-t}$ (h*µg/ml) | $AUC_{INF}$ (h*µg/ml) | $V_{ss}$ (mL/kg) | CL (mL/h/kg) | $t_{1/2}$ (h)* |
|---|---|---|---|---|---|---|---|
| 0.2 | IV | 3 | 459 ± 8 | 686 ± 49 | 135 ± 5.7 | 0.294 ± 0.02 | 315 |
| 1 | IV | 4 | 3500 ± 120 | 5110 ± 240 | 84.6 ± 18 | 0.197 ± 0.01 | 312 |
| 5 | IV | 4 | 15300 ± 900 | 23900 ± 1140 | 106 ± 11 | 0.211 ± 0.01 | 335 |

*$t_{1/2}$ reported as harmonic mean without variance

Figure 20A:
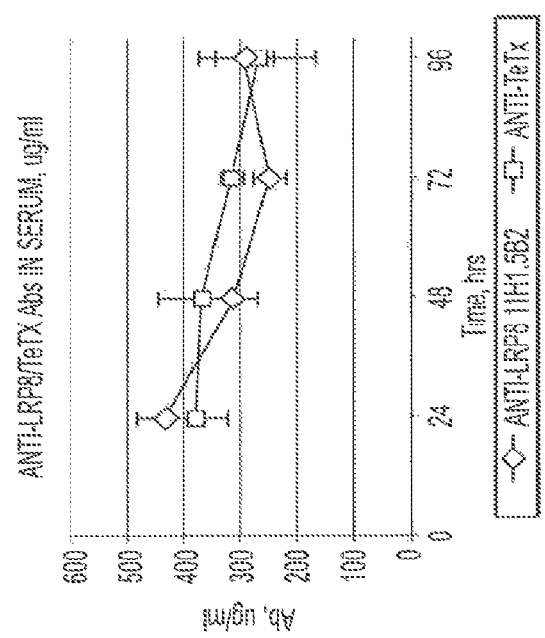
FIGS. 20A, 20B, and 20C show the results of a pharmacokinetic study with chimeric anti-LRP-8.M199.11H1.5B2 antibody in a 4 day period after a single dose administration (35 mg/kg). The serum PK of anti-LRP-8 was comparable to control IgG (FIG. 20A), and significant brain (FIG. 20B) and spinal cord (FIG. 20C) uptake was shown at 24 hours compared to control IgG.
Figures 20B, 20C:
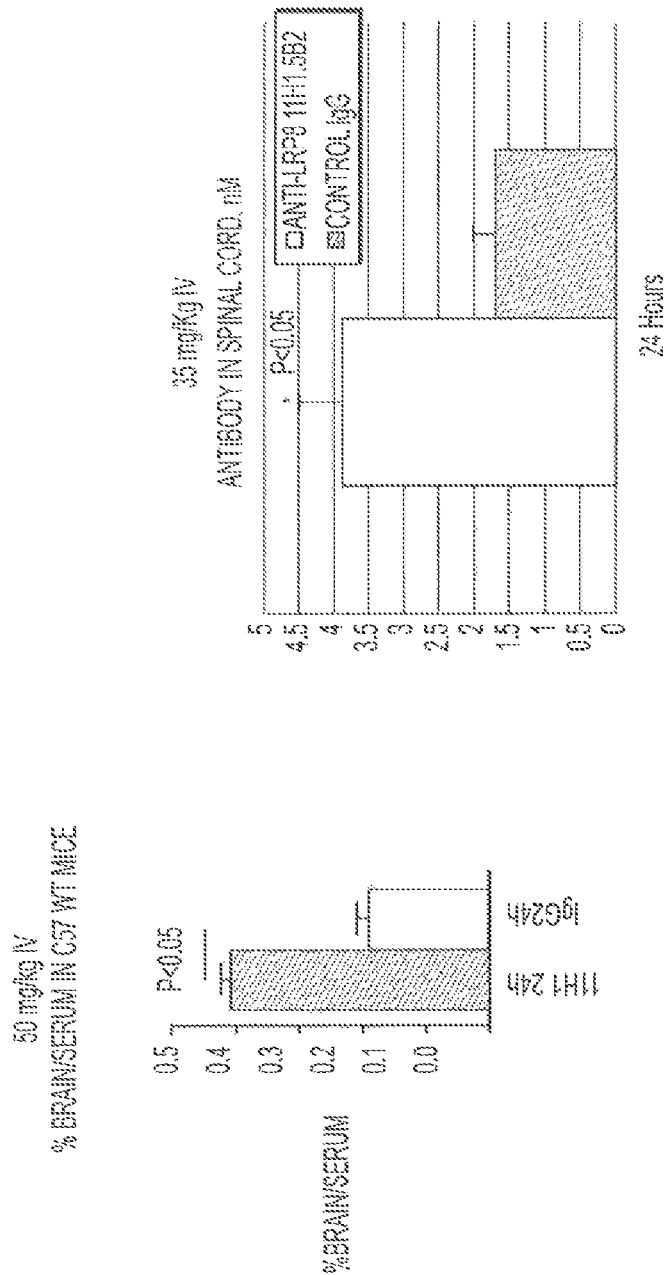

High dose (35 mg/kg) PK was examined by a single IV dosing in 8 week male C57Bl/6 mice. Three mice were dosed for each group. Antibody concentration in serum was determined by ECL-MSD assay (FIG. 20A).

Example 4.8. Reelin Binding and ML199.11H1.5B2 Reelin Competition

Example 4.8.1. CR1/CR2 Peptide Ligand Binding Assay

High binding MSD plates (MSD Cat# L15XB-3/L11XB-3) were coated with 1 µg/ml of CR1 or CR2 peptide overnight at 4° C. The next day, the plate was blocked with 3% MSD blocking buffer (MSD Cat# R93AA-01) for 1 hour at RT. The plates were washed with TTBS buffer (20 mM Tris; 0.5% Tween, 150 mM sodium chloride; pH 7.5) 3 times and the titer of reelin-HIS FLAG was added. After incubating for 1 hour at RT, the plate was washed and Anti-HIS (C-Term) Ab (Invitrogen Ref#46-0693) was used to detect reelin. After incubating for 1 hour at RT, the plate was washed, and an anti-mouse SULFO-TAG Ab was added to the plate and incubated for 1 hour. The plates were washed and immersed in MSD read buffer T with surfactant (MSD Cat# R92TC-1) before reading on an MSD SECTOR Imager 6000. Data were obtained and analyzed using a GraphPad Prism 6 software package (GraphPad Software, Inc., La Jolla, Calif.).

Example 4.8.2. Cell-Based Reelin-Anti-LRP8 Competition Assay

Anti-LRP8 competition assay was based on a cell-based Electrochemiluminescence-Meso Scale Discovery Assay (ECL-MSD) binding assay. HEK293 cells overexpressing cynomolgus monkey LRP-8 were added to the MSD 96-well plate (MSD Cat# L15XB-3/L11XB-3) and incubated at 37° C. for 1 hour. Cells were blocked using 15% FBS (Hyclone, Thermo Scientific Cat# SH300700.03) at RT for 30 minutes with mild agitation, plates were washed with DPBS 3 times. Anti-LRP-8 antibody with a human Fc and reelin-HIS-FLAG were used in two competition combinations:

Competition 1 (Competitor Anti-LRP8 Ab):

A 1:1 mixture of fixed concentrated reelin-HIS-FLAG and a titer of competitor LRP-8 were added to the plate and incubated at RT for 1 hour. After washing, reelin was detected with anti-HIS Ab for 1 hour followed by incubation with anti-mouse SULFO-TAG Ab for 1 hour.

Competition 2 (Competitor Reelin):

A 1:1 mixture of fixed concentrated anti-LRP8 human Fc Ab and a titer of competitor reelin were added to the plate and incubated at RT for 1 hour. After washing, an anti-human SULFO-TAG Ab was added to the plate and incubated for 1 hour. The plates were washed with DPBS and immersed in MSD read buffer T surfactant free (MSD Cat# R92TD-2) before reading on an MSD SECTOR Imager 6000. Data were obtained and analyzed using a GraphPad Prism 6 software package (GraphPad Software, Inc., La Jolla, Calif.).

Figure 21B:
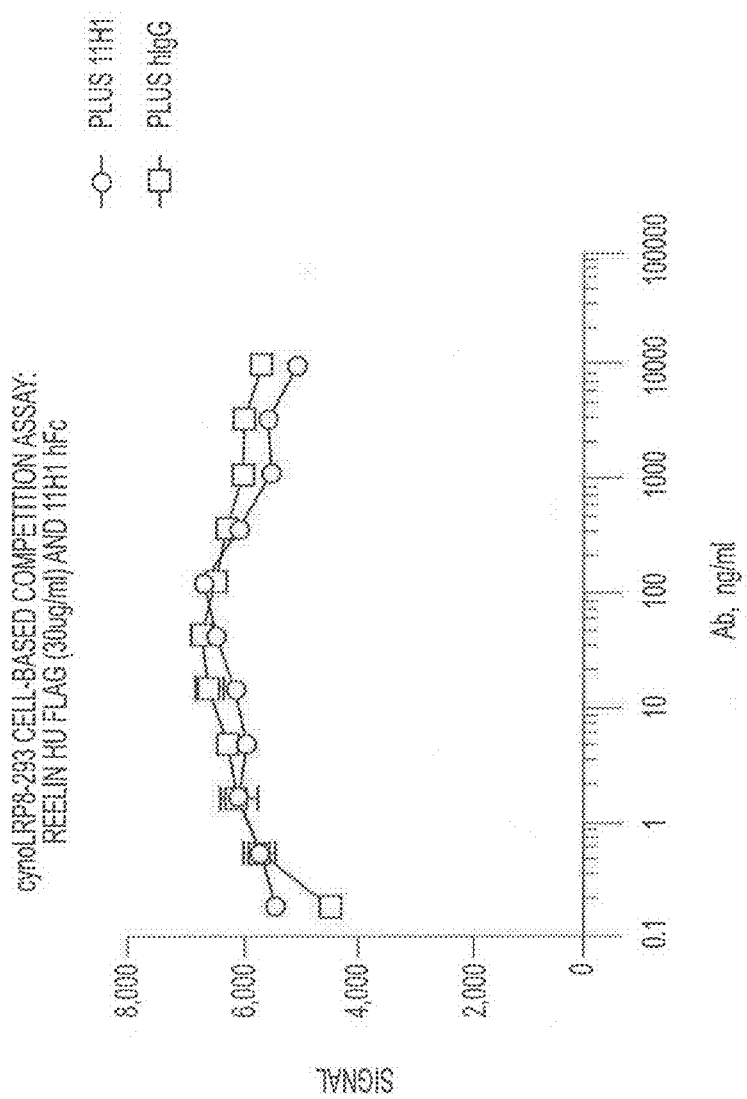
FIG. 21B shows the results of cell-based competition assay using cynoLRP8-293 cells and a reelin HU-flag.

As shown in FIG. 21A, reelin was capable of binding HEK293 cells overexpressing cynomolgus monkey LRP-8 in a dose-dependent manner. When the cells were incubated with 30 ug/ml of reelin and various amounts of either anti-LRP-8 ML199.11H1.5B2 antibody or human IgG as a negative control, neither anti-LRP-8 ML199.11H1.5B2 antibody nor human IgG blocked the interaction between reelin and cynomolgus LRP-8-HEK293 stable cells (FIG. 21B).

INCORPORATION BY REFERENCE

The present disclosure incorporates by reference in their entirety techniques well known in the field of molecular biology, drug delivery, immunology, molecular biology and cell biology. These techniques include, but are not limited to, techniques described in the following publications: Ausubel et al. (eds.) (1993) Current Protocols in Molecular Biology, John Wiley & Sons, NY; Ausubel et al. (eds.) (1999) Short Protocols In Molecular Biology John Wiley & Sons, NY (ISBN 0-471-32938-X); Smolen and Ball (eds.) (1984) Controlled Drug Bioavailability Drug Product Design and Performance, Wiley, NY; Giege and Ducruix (1999) Crystallization of Nucleic Acids and Proteins, a Practical Approach, 2nd ed., pp. 20 1-16, Oxford University Press, NY; Goodson (1984) Medical Applications of Controlled Release, vol. 2, pp. 115-138; Hammerling et al. (1981) Monoclonal Antibodies and T-Cell Hybridomas 563-681 (Elsevier, N.Y.; Harlow et al. (1988) Antibodies: A Laboratory Manual, (Cold Spring Harbor Laboratory Press, 2nd ed.; Kabat et al. (1987) Sequences of Proteins of Immunological Interest (National Institutes of Health, Bethesda, Md.; Kabat et al. (1991) Sequences of Proteins of Immunological Interest, Fifth Edition, U.S. Department of Health and Human Services, NIH Publication No. 91-3242; Kontermann and Dubel (eds.) (2001) Antibody Engineering Springer-Verlag, NY 790 pp. (ISBN 3-540-41354-5); Kriegler (1990) Gene Transfer and Expression, A Laboratory Manual, Stockton Press, NY; Lu and Weiner (eds.) (2001) Cloning and Expression Vectors for Gene Function Analysis BioTechniques Press. Westborough, Mass. 298 pp. (ISBN 1-881299-21-X); Langer and Wise (eds.) (1974) Medical Applications of Controlled Release, CRC Pres., Boca Raton, Fla.; Old and Primrose (1985) Principles of Gene Manipulation: An Introduction To Genetic Engineering (3d Ed.) Blackwell Scientific Publications, Boston, Mass. Studies in Microbiology; V.2:409 pp. (ISBN 0-632-01318-4); Sambrook et al. (eds.) (1989) Molecular Cloning: A Laboratory Manual (2d Ed.) Cold Spring Harbor Laboratory Press, NY, Vols. 1-3 (ISBN 0-87969-309-6); Robinson (ed.) (1978) Sustained and Controlled Release Drug Delivery Systems, Marcel Dekker, Inc., NY; Winnacker (1987) from Genes To Clones: Introduction To Gene Technology; VCH Publishers, NY (translated by Horst Ibelgaufts), 634 pp. (ISBN 0-89573-614-4).

EQUIVALENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein.

The invention claimed is:

1. A dual variable domain immunoglobulin (DVD-Ig) binding protein capable of binding low density lipoprotein receptor-related protein 8 (LRP-8), comprising a heavy chain variable domain comprising a set of three heavy chain complementarity determining regions (CDRs) (CDR-H1, CDR-H2, and CDR-H3), and a light chain variable domain comprising a set of three light chain CDRs (CDR-L1, CDR-L2, and CDR-L3), wherein the heavy chain CDRs are:
(a) CDR-H1: RFTFSNX$_1$GMS (SEQ ID NO: 9), wherein X$_1$ is F or Y, or GFTVSDYYMA (SEQ ID NO: 53);
(b) CDR-H2: TISSGGRYTYYPDX$_2$VKG (SEQ ID NO: 10), wherein X$_2$ is S or H, or SISYEGSSTYYGDSVKG (SEQ ID NO: 54); and
(c) CDR-H3: DYLYAMDY (SEQ ID NO: 46) or PLRYYGYNYRFAY (SEQ ID NO: 55), and the light chain CDRs are:
(d) CDR-L1: RSSQSLVYSX$_3$X$_4$NTYLH (SEQ ID NO: 47), wherein X$_3$ is N, T, R, W or P, and wherein X$_4$ is G, E, L or K, or KASQNIHKNLD (SEQ ID NO: 56);
(e) CDR-L2: KVSNRFS (SEQ ID NO: 48) or YTDNLQT (SEQ ID NO: 57); and
(f) CDR-L3: SQSTHVPLT (SEQ ID NO: 49) or YQYNSGPT (SEQ ID NO: 58).

2. The DVD-Ig binding protein of claim 1, wherein the set of three heavy chain CDRs is selected from the group consisting of:
(a) SEQ ID NO: 88, SEQ ID NO: 89, SEQ ID NO: 90;
(b) SEQ ID NO: 91, SEQ ID NO: 89, SEQ ID NO: 90;
(c) SEQ ID NO: 92, SEQ ID NO: 93, SEQ ID NO: 46;
(d) SEQ ID NO: 92, SEQ ID NO: 94, SEQ ID NO: 46; and
(e) SEQ ID NO: 107, SEQ ID NO: 108, SEQ ID NO: 109;
wherein the set of three light chain CDRs is selected from the group consisting of:
(i) SEQ ID NO: 157, SEQ ID NO: 48, SEQ ID NO: 49;
(ii) SEQ ID NO: 158, SEQ ID NO: 48, SEQ ID NO: 49;
(iii) SEQ ID NO: 159, SEQ ID NO: 48, SEQ ID NO: 49;
(iv) SEQ ID NO: 160, SEQ ID NO: 48, SEQ ID NO: 49;
(v) SEQ ID NO: 161, SEQ ID NO: 48, SEQ ID NO: 49;
(vi) SEQ ID NO: 162, SEQ ID NO: 48, SEQ ID NO: 49;
(vii) SEQ ID NO: 163, SEQ ID NO: 48, SEQ ID NO: 49;
(viii) SEQ ID NO: 164, SEQ ID NO: 48, SEQ ID NO: 49; and
(xi) SEQ ID NO: 56, SEQ ID NO: 57, SEQ ID NO: 58.

3. The DVD-Ig binding protein of claim 1, wherein:
(a) the heavy chain variable domain comprises an amino acid sequence of EVQLVESGGDLVKPGGSLKLSCAASRFTFSNFGMSWVRQTPDKRLEWVATISSGGRYTYYPDX$_1$VKGRFTISRDNAKNTLYLQMSSLRSEDTAMYYCARDYLYAMDYWGQGTSVTVSS (SEQ ID NO: 50), or EVQLVESGGDLVKPGGSLKLSCAASRFTFSNYGMSWVRQTPDKRLEWV ATISSGGRYTYYPDX$_1$VKGRFTISRDNAKNTLYLQMSSLRSEDTAMYYCARDYLYAMDYWGQGTSVTVSS (SEQ ID NO: 51), wherein X$_1$ is S or H; or EVQLVESGGGINQPGRSLKLSCAASGFTVSDYYMAWVRQAPKKGLEWV ASISYEGSSTYYGDSVKGRFTISRDNAKSILYLQMNSLRSEDTATYYC ARPLRYYGYNYRFAYWGQGTLVTVSS (SEQ ID NO: 59), and/or
(b) the light chain variable domain comprises an amino acid sequence of DVVMTQTPLSLPVSLGDQASISCRSSQSLVYSX$_2$X$_3$NTYLHWYLQKPG QSPKVLMYKVSNRFSGVSDRFSGSGSGTDFTLKISRVEAEDLGVYFCS QSTHVPLTFGAGTKLELK (SEQ ID NO: 52) wherein X$_2$ is N, T, R, W or P and X$_3$ is G, E, L or K; or DIQMSQSPPVLSASVGDRVILSCKASQNIHKNLDWYQQKHGEAPKLLI IYYTDNLQTGIPSRFSGSGSGTDYTLTISSLQPEDVATYYCYQYNSGP TFGAGTKLELQ (SEQ ID NO: 60).

4. The DVD-Ig binding protein of claim 1, wherein the binding protein comprises a heavy chain CDR set of:

(a) CDR-H1: RFTFSNYGMS (SEQ ID NO: 92);
(b) CDR-H2: TISSGGRYTYYPDSVKG (SEQ ID NO: 93); and
(c) CDR-H3: DYLYAMDY (SEQ ID NO: 46),
and a light chain CDR set of:
(d) CDR-L1: RSSQSLVYSNGNTYLH (SEQ ID NO: 157);
(e) CDR-L2: KVSNRFS (SEQ ID NO: 48); and
(f) CDR-L3: SQSTHVPLT (SEQ ID NO: 49).

5. The DVD-Ig binding protein of claim 1, wherein the binding protein comprises
(a) a heavy chain variable domain of:

```
                                           (SEQ ID NO: 62)
EVQLVESGGDLVKPGGSLKLSCAARSRFTFSNYGMSWVRQTPDKRLEWVA

TISSGGRYTYYPDSVKGRFTISRDNAKNTLYLQMSSLRSEDTAMYYCARD

YLYAMDYWGQGTSVTVSS;
``` and a light chain variable domain of:

```
                                           (SEQ ID NO: 63)
DVVMTQTPLSLPVSLGMASISCRSSQSLVYSNGNTYLHWYLQKPGOSPKV

LMYKVSNRFSGVSDRFSGSGSGTDFTLKISRVEAEDLGVYFCSQSTHVPL

TFGAGTKLELK;
```

(b) a heavy chain variable domain of:

```
                                           (SEQ ID NO: 59)
EVQLVESGGGLVQPGRSLKLSCAASGFTVSDYYMAWVRQAPKKGLEWVAS

ISYEGSSTYYGDSVKGRFTISRDNAKSILYLQMNSLRSEDTATYYCARPL

RYYGYNYRFAYWGQGTLVTVSS;
``` and a light chain variable domain of:

```
                                           (SEQ ID NO: 60)
DIQMSQSPPVLSASVGDRVTLSCKASQNIHKNLDWYQQKHGEAPKLLIYY

TDNLQTGIPSRFSGSGSGTDYTLTISSLQPEDVATYYCYQYNSGPTFGAG

TKLELQ;
```

(c) a heavy chain variable domain of:

```
                                           (SEQ ID NO: 61)
EVQLVESGGDLVKPGGSLKLSCAASRFTFSNFGMSWVRQTPDKRLEWVAT

ISSGGRYTYYPDSVKGRFTISRDNAKNTLYLQMSSLRSEDTAMYYCARDY

LYAMDYWGQGTSVTVSS;
and
``` and
a light chain variable domain of:

```
                                           (SEQ ID NO: 63)
DVVMTQTPLSLPVSLGDQASISCRSSQSLVYSNGNTYLHWYLQKPGQSPK

VLMYKVSNRFSGVSDRFSGSGSGTDFTLKISRVEAEDLGVYFCSQSTHVP

LTFGAGTKLELK.
```

6. The DVD-Ig binding protein of claim 1, wherein the binding protein is also capable of binding a second antigen target in the brain or spinal cord other than LRP-8.

7. The DVD-Ig binding protein of claim 1, wherein the binding protein binds human LRP-8 and is cross-reactive with at least one of cynomolgus monkey, rat, and mouse LRP-8.

8. The DVD-Ig binding protein of claim 1, wherein the binding protein
   (a) binds to human LRP-8 with an EC50 of at most about 2.62 nM, or at most about 2.29 nM, or at most about 0.88 nM, or at most about 0.24 nM;
   (b) undergoes endocytosis by HEK293 cells expressing LRP-8 at a rate between 1.5 and 2.5 times the endocytosis of control IgG into HEK293 cells expressing LRP-8;
   (c) undergoes transcytosis across a Caco-2 cell monolayer expressing LRP-8 at a rate between 1.5 and 2.0 times the transcytosis of control IgG across a Caco-2 cell monolayer expressing LRP-8; and/or
   (d) is able to cross the blood-brain barrier after binding to LRP-8.

9. The DVD-Ig binding protein of claim 1, further comprising a wild-type human lambda or kappa light chain constant region, and a wild-type human IgG1 heavy chain constant region or a variant of a human IgG1 heavy chain constant region.

10. The DVD-Ig binding protein of claim 9, wherein the variant comprises a leucine (L) to alanine (A) mutation at amino acid positions 234 and 235 of human IgG1.

11. The DVD-Ig binding protein of claim 1, further comprising a heavy chain constant region selected from the group consisting of IgG1, IgG2, IgG3, IgG4, IgA, IgM, IgE, and IgD, or a variant thereof.

12. The DVD-Ig binding protein of claim 1, wherein the heavy chain variable domain comprises an amino acid sequence at least about 80%, 90%, 95%, or 98% homologous to any of those selected from SEQ ID NOs: 59, 61, 62, and 70-72, and/or wherein the light chain variable domain comprises an amino acid sequence at least about 80%, 90%, 95%, or 98% homologous to any of those selected from SEQ ID NOs: 60, 63, and 133-142.

13. The DVD-Ig binding protein of claim 1, wherein the heavy chain variable domain comprises an amino acid sequence selected from SEQ ID NOs: 59, 61, 62, and 70-72 and/or wherein the light chain variable domain comprises an amino acid sequence selected from SEQ ID NOs: 60, 63, and 133-142.

14. A conjugate comprising the DVD-Ig binding protein of claim 1 and a second agent, wherein the second agent acts on the nervous system and is capable of being transported across the blood-brain barrier when the conjugate binds to LRP-8.

15. A pharmaceutical composition comprising the DVD-Ig binding protein of claim 1, and a pharmaceutically acceptable carrier.

16. The pharmaceutical composition of claim 15, further comprising at least one additional agent, wherein the additional agent acts on the nervous system, or is an imaging agent, a cytotoxic agent, an angiogenesis inhibitor, a kinase inhibitor, a co-stimulation molecule blocker, an adhesion molecule blocker, an anti-cytokine antibody or functional fragment thereof, a detectable label or reporter, an antirheumatic, a muscle relaxant, a narcotic, a non-steroid anti-inflammatory drug (NSAID), an analgesic, an anesthetic, a sedative, a neuromuscular blocker, an antimicrobial, an antipsoriatic, a corticosteriod, an anabolic steroid, an erythropoietin, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, or a cytokine antagonist.

17. A method of detecting the presence, amount, or concentration of LRP-8 or a fragment of LRP-8 in a test sample by an immunoassay, comprising contacting the test sample with at least one binding protein and at least one detectable label, and wherein the at least one binding protein comprises the DVD-Ig binding protein of claim 1.

18. A dual variable domain immunoglobulin (DVD-Ig) binding protein that binds to human low density lipoprotein receptor-related protein 8 (LRP-8) at an epitope comprising amino acid residues 47-66 of human LRP-8 (SEQ ID NO:1).

19. The DVD-Ig binding protein of claim 18, wherein the binding protein binds to human LRP-8 at an epitope comprising amino acid residues 47(C), 52(F), 56(N), 59(C), 60(I), 64(W), and 66(C) of human LRP-8 (SEQ ID NO:1).

20. A monoclonal antibody that binds to human low density lipoprotein receptor-related protein 8 (LRP-8) at an epitope comprising amino acid residues 47-66 of human LRP-8 (SEQ ID NO:1).

21. The antibody of claim 20, wherein the antibody binds to human LRP-8 at an epitope comprising amino acid residues 47(C), 52(F), 56(N), 59(C), 60(I), 64(W), and 66(C) of human LRP-8 (SEQ ID NO:1).

22. A monoclonal antibody capable of binding low density lipoprotein receptor-related protein 8 (LRP-8), comprising a heavy chain variable domain comprising a set of three heavy chain complementarity determining regions (CDRs) (CDR-H1, CDR-H2, and CDR-H3), and a light chain variable domain comprising a set of three light chain CDRs (CDR-L1, CDR-L2, and CDR-L3), wherein the heavy chain CDRs are:
   (a) CDR-H1: RFTFSNX$_1$GMS (SEQ ID NO: 9), wherein X$_1$ is F or Y, or GFTVSDYYMA (SEQ ID NO: 53);
   (b) CDR-H2: TISSGGRYTYYPDX$_2$VKG (SEQ ID NO: 10), wherein X$_2$ is S or H, or SISYEGSSTYYGDSVKG (SEQ ID NO: 54); and
   (c) CDR-H3: DYLYAMDY (SEQ ID NO: 46) or PLRYYGYNYRFAY (SEQ ID NO: 55),
   and the light chain CDRs are:
   (d) CDR-L1: RSSQSLVYSX$_3$X$_4$NTYLH (SEQ ID NO: 47), wherein X$_3$ is N, T, R, W or P, and wherein X$_4$ is G, E, L or K, or KASQNIHKNLD (SEQ ID NO: 56);
   (e) CDR-L2: KVSNRFS (SEQ ID NO: 48) or YTDNLQT (SEQ ID NO: 57); and
   (f) CDR-L3: SQSTHVPLT (SEQ ID NO: 49) or YQYNSGPT (SEQ ID NO: 58).

23. The antibody of claim 22, wherein the antibody comprises a heavy chain CDR set of:
   (a) CDR-H1: RFTFSNYGMS (SEQ ID NO: 92);
   (b) CDR-H2: TISSGGRYTYYPDSVKG (SEQ ID NO: 93); and
   (c) CDR-H3: DYLYAMDY (SEQ ID NO: 46),
   and a light chain CDR set of:
   (d) CDR-L1: RSSQSLVYSNGNTYLH (SEQ ID NO: 157);
   (e) CDR-L2: KVSNRFS (SEQ ID NO: 48); and
   (f) CDR-L3: SQSTHVPLT (SEQ ID NO: 49).

24. The antibody of claim 22, wherein the antibody is a humanized antibody.

25. The antibody of claim 23, wherein the antibody is a humanized antibody.

* * * * *